(12) United States Patent
Wong et al.

(10) Patent No.: US 7,943,330 B2
(45) Date of Patent: May 17, 2011

(54) TAILORED GLYCOPROTEOMIC METHODS FOR THE SEQUENCING, MAPPING AND IDENTIFICATION OF CELLULAR GLYCOPROTEINS

(75) Inventors: Chi-Huey Wong, La Jolla, CA (US); Tsui-Ling Hsu, Taipei (TW); Sarah R Hanson, San Diego, CA (US)

(73) Assignee: Academia Sinica, Taipei (TW)

( * ) Notice: Subject to any disclaimer, the term of this patent is extended or adjusted under 35 U.S.C. 154(b) by 431 days.

(21) Appl. No.: 12/079,157

(22) Filed: Mar. 24, 2008

(65) Prior Publication Data
US 2008/0299595 A1    Dec. 4, 2008

Related U.S. Application Data

(60) Provisional application No. 60/896,777, filed on Mar. 23, 2007, provisional application No. 60/896,787, filed on Mar. 23, 2007.

(51) Int. Cl.
*G01N 33/53* (2006.01)
*G01N 31/00* (2006.01)

(52) U.S. Cl. ............ 435/7.21; 435/7.1; 436/1; 436/501; 436/518; 424/9.1; 424/520; 422/1; 422/50; 530/300; 530/350

(58) Field of Classification Search .................. None
See application file for complete search history.

(56) References Cited

OTHER PUBLICATIONS

Hsu TL, Hanson SR, Kishikawa K, Wang SK, Sawa M, Wong CH, Alkynyl sugar analogs for the labeling and visualization of glycoconjugates in cells, (2007) Proc Natl Acad Sci 104:2614-2619.
Varki A, Cummings R, Esko JD, Freeze H, Hart GW, Marth J (1999) in Essentials of Glycobiology (Cold Spring Harbor Lab Press, Cold Spring Harbor, NY), pp. 1-635.
Axford JS, Glycosylation and rheumatic disease, (1999) Biochim Biophys Acta 1455:219-229.
Dube, D. H. & Bertozzi, C. R., Glycans in cancer and inflammation—potential for therapeutics and diagnostics, (2005) Nat. Rev. Drug Discov. 4, 477-488.
Mackiewicz A, Mackiewicz K, Glycoforms of serum a1-acid glycoprotein as markers of inflammation and cancer, (1995) Glycoconj J 12:241-247.
Meezan E, Wu HC, Black PH, Robbins PW, Comparative Studies on the Carbohydrate-Containing Membrane Components of Normal and Virus-Transformed Mouse Fibroblasts. II. Separation of Glycoproteins and Glycopeptides by Sephadex Chromatography, (1969) Biochemistry 8:2518-2524.
Turner GA, N-Glycosylation of serum proteins in disease and its investigation using lectins, (1992) Clin Chim Acta 208:149-171.
Orntoft TF, Vestergaard EM, Clinical aspects of altered glycosylation of glycoproteins in cancer, (1999) Electrophoresis 20:362-371.
Sell S, Cancer-Associated Carbonhydrates Identified by Monoclonal Antibodies, (1990) Hum Pathol 21:1003-1019.
Taylor-Papadimitriou J, Epenetos AA, Exploiting altered glycosylation patterns in cancer: progress and challenges in diagnosis and therapy, (1994) Trends Biotechnol 12:227-233.
Zhang S, Cordon-Cardo C, Zhang HS, Reuter VE, Adluri S, Hamilton WB, Lloyd KO, Livingston PO, Selection of tumor antigens as targets for immune attack using immunohistochemistry: I. Focus on gangliosides, (1997) Int J Cancer 73:42-49.
Zhang S, Zhang HS, Cordon-Cardo C, Reuter VE, Singhal AK, Lloyd KO, Livingston PO, Selection of tumor antigens as targets for immune attack using immunohistochemistry: II. Blood group-related antigens, (1997) Int J Cancer 73:50-56.
Mahal LK, Yarema KJ, Bertozzi CR, Engineering Chemical Reactivity on Cell Surfaces Through Oligosaccharide Biosynthesis, (1997) Science 276:1125-1128.
Tai HC, Khidekel N, Ficarro SB, Peters EC, Hsieh-Wilson LC, Parallel Identification of O-GlcNAc-Modified Proteins from Cell Lysates, (2004) J Am Chem Soc 126:10500-10501.
Saxon E, Bertozzi CR, Cell Surface Engineering by a Modified Staudinger Reaction, (2000) Science 287:2007-2010.
Sampathkumar SG, Li AV, Jones MB, Sun Z, Yarema KJ, Metabolic installation of thiols into sialic ads modulates adhesion and stem cell biology, (2006) Nat Chem Biol 2:149-152.
Agard NJ, Baskin JM, Prescher JA, Lo A, Bertozzi CR, A Comparative Study of Bioorthogonal Reactions with Azides, (2006) ACS Chem Biol 1:644-648.
Agard NJ, Prescher JA, Bertozzi CR, A Strain-Promoted [3 + 2] Azide-Alkyne Cycloaddition for Covalent Modification of Biomolecules in Living Systems, (2004) J Am Chem Soc 126:15046-15047.
Rabuka D, Hubbard SC, Laughlin ST, Argade SP, Bertozzi CR, A Chemical Reporter Strategy to Probe Glycoprotein Fucosylation, (2006) J Am Chem Soc 128:12078-12079.
Sawa M., Hsu T. L., Itoh T., Sugiyama M., Hanson S. R. , Vogt P. K. , Wong C. H. , Glycoproteomic probes for fluorescent imaging of fucosylated glycansin vivo, (2006) Proc. Natl. Acad. Sci. USA 103, 12371-12376.
Dube DH, Prescher JA, Quang CN, Bertozzi CR, Probing mucin-type O-linked glycosylation in living animals, (2006) Proc Natl Acad Sci USA 103:4819-4824.
Hang HC, Yu C, Kato DL, Bertozzi CR, A metabolic labeling approach toward proteomic analysis of mucin-type O-linked glycosylation, (2003) Proc Natl Acad Sci USA 100:14846-14851.
Becker, D. J. & Lowe, J. B., Fucose: biosynthesis and biological function in mammals, (2003) Glycobiology 13, 41R-53R.
Keppler OT, Horstkorte R, Pawlita M, Schmidt C, Reutter W, Fucose: biosynthesis and biological function in mammals, (2001) Glycobiology 11:11R-18R.

(Continued)

*Primary Examiner* — Lisa V Cook
(74) *Attorney, Agent, or Firm* — Eckman Basu LLP

(57) ABSTRACT

The present disclosure relates to tailored glycoproteomic methods, and more particularly to methods for the sequencing, mapping and identification of cellular glycoproteins using saccharide-selective bioorthogonal probes. A method is disclosed for saccharide-selective glycoprotein identification (ID) and glycan mapping (GIDmap) that generates glycoproteins tailored with bioorthogonally tagged alkynyl saccharides that can be selectively isolated, allowing for glycoprotein ID and glycan mapping via mass spectromic proteomics, including liquid chromatography-tandmen mass spectroscopy (LC-MS$^2$). LC-MS$^2$ may be used to identify cellular glycans, and more specifically cancer-related glycoproteins.

34 Claims, 41 Drawing Sheets

OTHER PUBLICATIONS

Rostovtsev W, Green LG, Fokin VV, Sharpless KB, A Stepwise Huisgen Cycloaddition Process: Copper(I)-Catalyzed Regioselective "Ligation" of Azides and Terminal Alkynes**, (2002) Angew Chem Int Ed Engl 41:2596-2599.

Wang Q, Chan TR, Hilgraf R, Fokin VV, Sharpless KB, Finn MG, Bioconjugation by Copper(I)-Catalyzed Azide-Alkyne [3 + 2] Cycloaddition, (2003) J Am Chem Soc 125:3192-3193.

Jacobs CL, Yarema KJ, Mahal LK, Nauman DA, Charters NW, Bertozzi CR, Metabolic Labeling of Glycoproteins with Chemical Tags through Unnatural Sialic Acid Biosynthesis, (2000) Methods Enzymol 327:260-275.

Sarkar AK, Fritz TA, Taylor WH, Esko JD, Disaccharide uptake and priming in animal cells: Inhibition of sialyl Lewis Xby acetylated Galll1-4GlcNAcl3-Onaphthalenemethanol, (1995) Proc Natl Acad Sci USA 92:3323-3327.

Sivakumar K, Xie F, Cash BM, Long S, Barnhill HN, Wang Q, A Fluorogenic 1,3-Dipolar Cycloaddition Reaction of 3-Azidocoumarins and Acetylenes, (2004) Org Lett 6:4603-4606.

Yarema KJ, Mahal LK, Bruehl RE, Rodriguez EC, Bertozzi CR, Metabolic Delivery of Ketone Groups to Sialic Acid Residues, (1998) J Biol Chem 273:31168-31179.

Speers AE, Cravatt BF, Profiling Enzyme Activities In Vivo Using Click Chemistry Methods, (2004) Chem Biol 11:535-546.

Hanson S, Best M, Bryan MC, Wong CH, Chemoenzymatic synthesis of oligosaccharides and glycoproteins (2004) Trends Biochem Sci 29:656-663.

Luchansky SJ, Bertozzi CR, Azido Sialic Acids Can Modulate Cell-Surface Interactions, (2004) Chembiochem 5:1706-1709.

Fujihashi M, Peapus DH, Kamiya N, Nagata Y, Miki K, Crystal Structure of Fucose-Specific Lectin from Aleuria aurantia Binding Ligands at Three of Its Five Sugar Recognition Sites, (2003) Biochemistry 42:11093-11099.

Wimmerova M, Mitchell E, Sanchez JF, Gautier C, Imberty A, Crystal Structure of Fungal Lectin, (2003) J Biol Chem 278:27059-27067.

Simanek EE, McGarvey GJ, Jablonowski JA, Wong CH, Selectin-Carbohydrate Interactions: From Natural Ligands to Designed Mimics, (1998) Chem Rev 98:833-862.

Yang L, McRae R, Henary MM, Patel R, Lai B, Vogt S, Fahmi CJ, Imaging of the intracellular topography of copper with a fluorescent sensor and by synchrotron x-ray fluorescence microscopy, (2005) Proc Natl Acad Sci USA 102:11179-11184.

Apweiler, R., Hermjakob, H. & Sharon, N., On the frequency of protein glycosylation, as deduced from analysis of the SWISS-PROT database, (1999) Biochim. Biophys. Acta 1473, 4-8.

Staudacher, E., α 1,3-Fucosyltransferases, (1996) Trends Glycosci. Glycotechnol. 8, 391-408.

Sears, P. & Wong, C.-H., Enzyme action in glycoprotein synthesis, (1998) Cell. Mol. Life Sci. 54, 223-252.

Haltiwanger, R. S. & Lowe, J. B., Role of glycosylation in development, (2004) Annu. Rev. Biochem. 73, 491-537.

Hirabayashi, J., Lectin-based structural glycomics: Glycoproteomics and glycan profiling, (2004) Glycoconj. J. 21, 35-40.

Shriver, Z., Raguram, S. & Sasisekharan, R., Glycomics: a pathway to a class of new and improved therapeutics, (2004) Nat. Rev. Drug Discov. 3, 863-873.

Khidekel, N., Ficarro, S. B., Peters, E. C. & Hsieh-Wilson, L. C., Exploring the O-GlcNAc proteome: Direct identification ofO-GlcNAc-modified proteins from the brain, (2004) Proc. Natl. Acad. Sci. USA 101, 13132-13137.

Ratner, D. M., Adams, E. W., Disney, M. D. & Seeberger, P. H., Tools for Glycomics: Mapping Interactions of Carbohydrates in Biological Systems, (2004) ChemBioChem 5, 1375-1383.

Prescher, J. A. & Bertozzi, C. R., Chemistry in living systems, (2005) Nat. Chem. Biol. 1, 13-21.

Raman, R., Raguram, S., Venkataraman, G., Paulson, J. C. & Sasisekharan, R., Glycomics: an integrated systems approach to structure-function relationships of glycans, (2005) Nat. Methods 2, 817-824.

Chudakov, D. M., Lukyanov, S. & Lukyanov, K. A., Fluorescent proteins as a toolkit for in vivo imaging, (2005) Trends Biotechnol. 23, 605-613.

Kolb, H. C. & Sharpless, K. B., The growing impact of click chemistry on drug discovery, (2003) Drug Discov. Today 8, 1128-1137.

Zhou, Z. & Fahmi, C. J., A Fluorogenic Probe for the Copper(I)-Catalyzed Azide-Alkyne Ligation Reaction: Modulation of the Fluorescence Emission via 3 (n,δ*)-1(δ,δ*) Inversion, (2004) J. Am. Chem. Soc. 126, 8862-8863.

de Silva, A. P., Gunaratne, H. Q. N. & Gunnlaugsson, T., Flourescent PET(Photoinduced Electron Transfer) Reagents for Thiols, (1998) Tetrahedron Lett. 39, 5077-5080.

McAdam, C. J., Morgan, J. L., Murray, R. E., Robinson, B. H. & Simpson, J., Synthesis and Flourescence Properties of New Enaminenaphthalimides, (2004) Aust. J. Chem. 57, 525-530.

Tonetti, M., Sturla, L., Bisso, A., Zanardi, D., Benatti, U. & De Flora, A., The metabolism of 6-deoxyhexoses in bacterial and animal cells, (1998) Biochimie 80, 923-931.

Zeitler, R., Danneschewski, S., Lindhorst, T., Thiem, J. & Reutter, W., Inhibition of L-fucokinase from rat liver by L-fucose analogues in vitro, (1997) J. Enzyme Inhib. 11, 265-273.

Yurcheno, P. D. & Atkinson, P. H., Fucosyl-Glycoprotein and Precursor Pools in HeLa Cells, (1975) Biochemistry 14, 3107-3114.

Yurcheno, P. D. & Atkinson, P. H., Equilibration of Fucosyl Glycoprotein Pools in HeLa Cells, (1977) Biochemistry 14, 944-953.

Dube, D. H. & Bertozzi, C. R., Metabolic oligosaccharide engineering as a tool for glycobiology, (2003) Curr. Opin. Chem. Biol. 7, 616-625.

Du ffels, A., Green, L. G., Lenz, R., Ley, S. V., Vincent, S. P. & Wong, C.-H., Chemoenzymatic Synthesis of L-Galactosylated Dimeric Sialyl Lewis X Structures Employing-1,3-Fucosyltransferase V, (2000) Bioorg. Med. Chem. 8, 2519-2525.

Srivastava, G., Kaur, K. J., Hindsgaul, O. & Palcic, M. M., Enzymatic Transfer of a Preassembled Trisaccharide Antigen to Cell Surfaces Using a Fucosyltransferase, (1992) J. Biol. Chem. 267, 22356-22361.

Vogel, C., Bergemann, C., Ott, A.-J., Lindhorst, T. K., Thiem, J., Dahlhoff, W. V., Ha Ilgren C., Palcic, M. M. & Hindsgaul, O., Synthesis of Carbon-Backbone-Elongated GDP-L-Fucose Derivatives as Substartes for Fucosyltransferase-Catalysed Reactions, (1997) Liebigs Ann. 601-612.

Binch, H., Stangier, K. & Thiem, J., Chemical synthesis of GDP-L-galactose and analogues, (1998) Carbohydr. Res. 306, 409-419.

Gilbert, J. C. & Weerasooriya, U., Diazoethenes: their attempted synthesis from akehydes and aromatic ketones by way of the Horner-Emmons modification of the Wittig reaction. A facile synthesis of Alkynes1-3, (1982) J. Org. Chem. 47, 1837-1845.

Huisgen, R., 1,3-Dipolar Cycloadditions Past and Future, (1963) Angew. Chem. Int. Ed. Engl. 2, 565-632.

Chan, T. R., Hilgraf, R., Sharpless, K. B. & Fokin, V. V., Polytriazoles as Copper(I)-Stabilizing Ligands in Catalysis, (2004) Org. Lett. 6, 2853-2855.

Lewis, W. G., Magallon, F. G., Fokin, V. V. & Finn, M. G., Discovery and Characterization of Catalysts for Azide-Alkyne Cycloaddition by Fluorescence Quenching, (2004) J. Am. Chem. Soc. 126, 9152-9153.

Wittmann, V. & Wong, C.-H., 1H-Tetrazole as Catalyst in Phosphomorpholidate Coupling Reactions: Efficient Synthesis of GDP-Fucose, GDP-Mannose, and UDP-Galactose, (1997) J. Org. Chem. 62, 2144-2147.

Fazio, F., Bryan, M. C., Blixt, O., Paulson, J. C. & Wong, C.-H., Synthesis of Sugar Arrays in Microtiter Plate, (2002) J. Am. Chem. Soc. 124, 14397-14402.

Bryan, M. C., Lee, L. V. & Wong, C.-H., High-throughput identification of fucosyltransferase inhibitors using carbohydrate microarrays, (2004) Bioorg. Med. Chem. Lett. 14, 3185-3188.

Ryde n, I., Påhlsson, P. & Lindgren, S., Diagnostic Accuracy of a1-Acid Glycoprotein Fucosylation for Liver Cirrhosis in Patients Undergoing Hepatic Biopsy, (2002) Clin. Chem. 48, 2195-2201.

Hashimoto, S., Asao, T., Takahashi, J., Yagihashi, Y., Nishimura, T., Saniabadi, A. R., Poland, D. C., van Dijk, W., Kuwano, H., Kochibe, N. & Yazawa, S., a1-Acid Glycoprotein Fucosylation as a Marker of Carcinoma Progression and Prognosis, (2004) Cancer 101, 2825-2836.

Link, A. J. Vink, M. K. S. & Tirrell, D. A., Presentation and Detection of Azide Functionality in Bacterial Cell Surface Proteins, (2004) J. Am. Chem. Soc. 126, 10598-10602.

Walz, G., Aruffo, A., Kolanus, W., Bevilacqua, M. & Seed, B., Recognition by ELAM-1 of the Sialyl-Lex Determinant on Myeloid and Tumor Cells, (1990) Science 250, 1132-1135.

Taniguchi, N., Ekuni, A., Ko, J. H., Miyoshi, E., Ikeda, Y., Ihara, Y., Nishikawa, A., Honke, K. & Takahashi, M., A glycomic approach to the identification and characterization of glycoprotein function in cells transfected with glycosyltransferase genes, (2001) Proteomics 1, 239-247.

Kannagi, R., Izawa, M., Koike, T., Miyazaki, K. & Kimura, N., Carbohydrate-mediated cell adhesion in cancer metastasis and angiogenesis, (2004) Cancer Sci. 95, 377-384.

Miyoshi, E., Noda, K., Yamaguchi, Y., Inoue, S., Ikeda, Y., Wang, W., Ko, J. H., Uozumi, N., Li, W. & Taniguchi, N., The a1-6-fucosyltransferase gene and its biological significance, (1999) Biochim. Biophys. Acta 1473, 9-20.

Hakomori, S. & Zhang, Y., Glycosphingolipid antigens and cancer therapy, (1997) Chem. Biol. 4, 97-104.

Kannagi, R., Levery, S. B., Ishigami, F., Hakomori, S. I., Shevinsky, L. H., Knowles, B. B. & Solter, D., New Globoseries Glycosphingolipids in Human Teratocarcinoma Reactive with the Monoclonal Antibody Directed to a Developmentally Regulated Antigen, Stage-specific Embryonic Antigen 3, (1983) J. Biol. Chem. 258, 8934-8942.

Huang, C.-Y., Thayer, D. A., Chang, A. Y., Best, M. D., Hoffmann, J., Head, S. & Wong, C.-H., Carbohydrate microarray for profiling the antibodies interacting with Globo H tumor antigen, (2006) Proc. Natl. Acad. Sci. USA 103, 15-20.

Schottelius, A. J., Hamann, A. & Asadullah, K., Role of fucosyltransferases in leukocyte trafficking: major impact for cutaneous immunity, (2003) Trends Immunol. 24, 101-104.

Javaud, C., Dupuy, F., Maftah, A., Julien, R. & Petit, J. M., The fucosyltransferase gene family: an amazing summary of the underlying mechanisms of gene evolution, (2003) Genetica 118, 157-170.

Roos, C., Kolmer, M., Mattila, P. & Renkonen, R., Composition of Drosophila melanogaster Proteome Involved in Fucosylated Glycan Metabolism, (2002) J. Biol. Chem. 277, 3168-3175.

Baboval, T. & Smith, F. I., Compatison of human and mouse Fuc-TX and Fuc-TXI genes, and expression studies in the mouse, (2002) Mamm. Genome 13, 538-541.

Oriol, R., Mollicone, R., Cailleau, A., Balanzino, L. & Breton, C., Divergent evolution of fucosyltransferase genes from vertebrates, invertebrates, and bacteria, (1999) Glycobiology 9, 323-334.

Staudacher, E., Altmann, F., Wilson, I. B. H. & Ma rz, L., Fucose in N-glycans: from plant to man, (1999) Biochim. Biophys. Acta 1473, 216-236.

Piller, V., Piller, F. & Fukuda, M., Biosynthesis of Truncated 0-Glycans in the T Cell Line Jurkat, (1990) J. Biol. Chem. 265, 9264-9271.

Mitchell, M. L., Tian, F., Lee, L. V. & Wong, C.-H., Synthesis and Evaluation of Transition-State Analogue Ingibitors of a-1,3-Fucosyltransferase, (2002), Angew. Chem. Int. Ed. Engl. 41, 3041-3044.

Lee, L. V., Mitchell, M. L., Huang, S.-J., Fokin, V. V., Sharpless, K. B. & Wong, C.-H., A Potent and Highly Selective Inhibitor of Human r-1,3-Fucosyltransferase via Click Chemistry, (2003) J. Am. Chem. Soc. 125, 9588-9589.

Hanson S. R., Hsu T. L., Weerapana E., Kishikawa K., Simon G. M., Cravatt B. F., Wong C. H., Tailored glycoproteomics and glycan site mapping using saccharide-selective bioorthogonal probes (2007) J Am Chem Soc. 129, 7266-7267.

Lowe, JB; Marth, JD., A Genetic Approach to Mammalian Glycan Funciton, Annu Rev Biochem. 2003;72:643-91.

Sears, P; Wong, CH. Toward Automated Synthesis of Oligosaccharides and Glycoproteins,Science. 2001;291:2344-50.

Grogan, MJ; Hanson, S; Best, M; Bryan, MC; Wong, CH., Chemoenzymatic synthesis of oligosaccharides and glycoproteins, Trend Biochem Sci. 2004;29:656-63.

Brik, A; Ficht, S; Wong, CH. Strategies for the preparation of homogenous glycoproteins, Cur Opin Chem Biol. 2006;10:638-44.

Bond, MR; Kohler, JJ. Chemical methods for glycoprotein discovery, Curr Opin Chem Biol. 2007;11:52-8.

Morelle, W; Canis, K; Chirat, F; Faid, V; Michalski, JC. The use of mass spectrometry for the proteomic analysis of glycosylation, Proteomics. 2006;6:3993-4015.

Prescher, JA; Bertozzi, CR. Chemical Technologies for Probing Glycans, Cell. 2006;126:851-854.

Laughlin, ST; Agard, NJ; Baskin, JM; Carrico, IS; Chang, PV; Ganguli, AS; Hangauer, MJ; Lo, A; Prescher, JA; Bertozzi, CR; Minoru, F., Metabolic Labeling of Glycans with Azido Sugars for Visualization and Glycoproteometics, Meth Enzym. vol. 415. Academic Press; 2006. pp. 230-250.

Speers, AE; Cravatt, BF., A Tandem Orthogonal Proteolysis Strategy for High-Content Chemical Proteomics, J Am Chem Soc. 2005;127:10018-9.

Zhang, H; Li, XJ; Martin, DB; Aebersold, R., A Tandem Orthogonal Proteolysis Strategy for High-Content Chemical Proteomics, Nat Biotech. 2003;21:660-6.

Kaji, H; Saito, H; Yamauchi, Y; Shinkawa, T; Taoka, M; Hirabayashi, J; Kasai, K; Takahashi, N; Isobe, T., A Tandem Orthogonal Proteolysis Strategy for High-Content Chemical Proteomics, Nat Biotech. 2003;21:667-72.

Kaji, H; Isobe, T., Large-Scale Analysis of Glycoproteins by LC-MS Method, Trend Glycosci Glycotech. 2006;18:313-22.

Eng, JK; McCormack, AL; Yates, JR., An approach to correlate tandem mass spectral data of peptides with amino acid sequences in a protein database, J Amer Soc Mass Spec. 1994;5:976-89.

Washburn, MP; Wolters, D; Yates, JR., Large-scale analysis of the yeast proteome by multidimensional protein identification technology, 3rd Nat Biotech. 2001;19:242-7.

Lewandrowski, U; Moebius, J; Walter, U; Sickmann, A., Elucidation of N-Glycosylation Sites on Human Platelet Proteins, Mol Cell Proteomics. 2006;5:226.

Ramachandran, P; Boontheung, P; Xie, YM; Sondej, M; Wong, DT; Loo, JA., Identification of N-Linked Glycoproteins in Human Saliva by Glycoprotein Capture and Mass Spectrometry, J Proteome Res. 2006;5:1493.

Liu, T; Qian, WJ; Gritsenko, MA; Campli, DG; Monroe, ME; Moore, RJ; Smith, RD., Human Plasma N-Glycoproteome Analysis by Immunoaffinity Subtraction, Hydrazide Chemistry, and Mass Spectrometry, J Prot Res. 2005;4:2070.

Roth, J., Protein N-Glycosylation along the Secretory Pathway: Relationship to Organelle Topography and Function, Protein Quality Control, and Cell Interactions, Chem Rev. 2002;102:285-304.

Shiraki, K; Takase, K; Tameda, Y; Hamada, M; Kosaka, Y; Nakano, T., A clinical study of lectin-reactive alpha-fetoprotein as an early indicator of hepatocellular carcinoma in the follow-upof cirrhotic patients, Hepatology. 1995;22:802-7.

Comunale, MA; Lowman, M; Long, RE; Krakover, J; Philip, R; Seeholzer, S; Evans, AA; Hann, HWL; Block, TM; Mehta, AS., Proteomic analysis of serum associated fucosylated glycoproteins in the development of primary hepatocellular carcinoma, J Proteome Res. 2006;5:3108-15.

Wells, L; Vosseller, K; Cole, RN; Cronshaw, JM; Matunis, MJ; Hart, GW., Mapping Sites of O-GlcNAc Modification Using Affinity Tags for Serine and Threonine Post-translational Modifications, Mol Cell Proteomics. 2002;1:791-804.

Vosseller, K; Trinidad, JC; Chalkley, RJ; Specht, CG; Thalhammer, A; Lynn, AJ; Snedecor, JO; Guan, S; Medzihradszky, KF; Maltby, DA; Schoepfer, R; Burlingame, AL., O-Linked N-Acetylglucosamine Proteomics of Postsynaptic Density Preparations Using Lectin Weak Affinity Chromatography and Mass Spectrometry, Mol Cell Proteomics. 2006;5:923-34.

FIG. 4-2
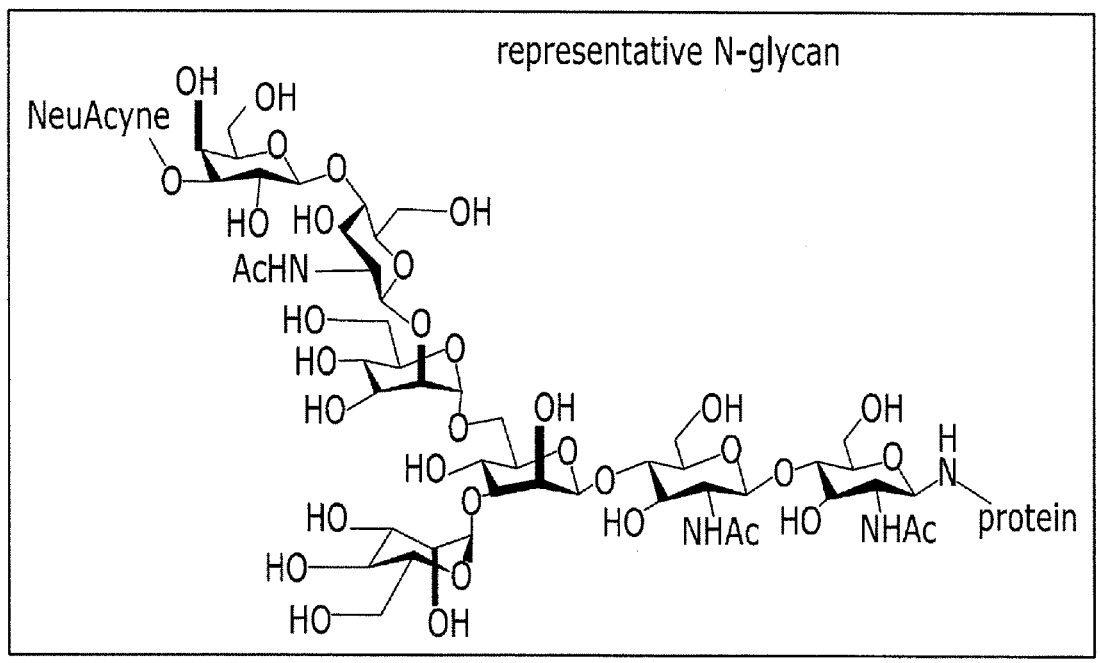
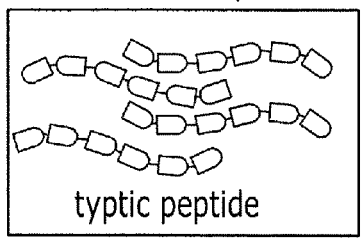
protein ID
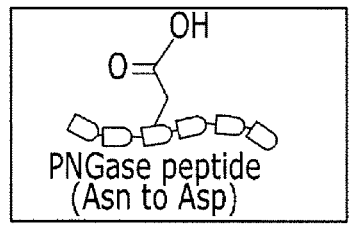
"PNGase mass signature"
+1Da
glycosylation site mapping

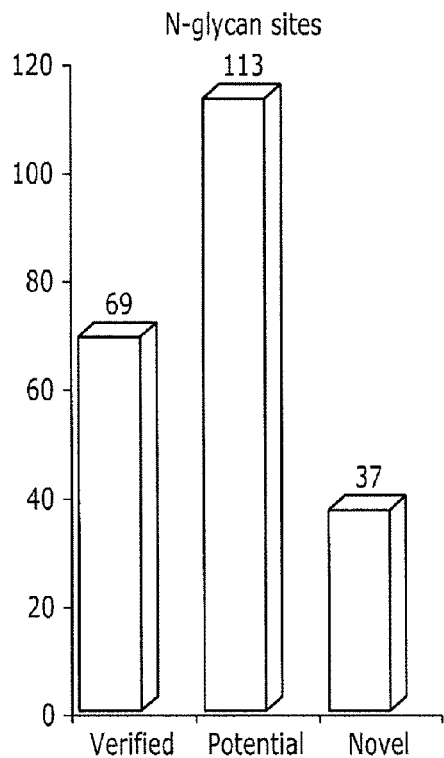
*FIG. 6A*
*FIG. 6B* function
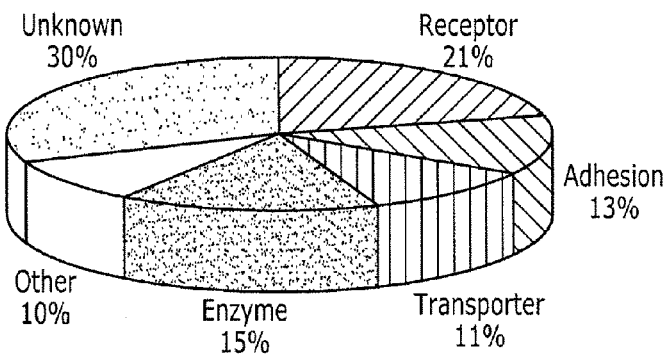
*FIG. 6C* location
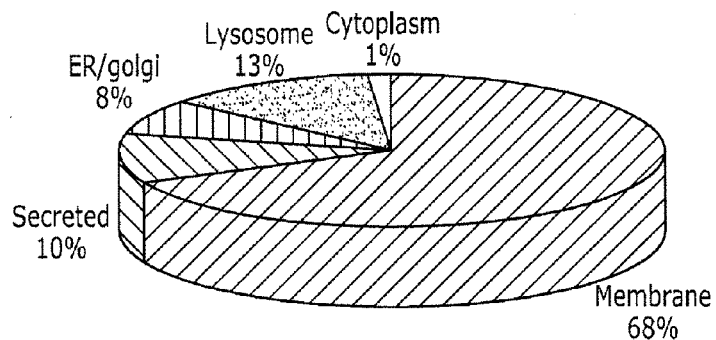

FIG. 7A-1

| # | IPI number & Description | 1t | 1p | 2t | 2p | 3t | 3p | Peptide | site | AP | N | SEQ ID NO. |
|---|---|---|---|---|---|---|---|---|---|---|---|---|
| 1 | IPI00221224-Aminopeptidase N | 204 | 5 | 321 | 14 | 212 | 8 | KLN*YTLSQGHR | 128 | 5 | 0 | 1 |
|   |   | 204 | 0 | 321 | 28 | 212 | 0 | AEFN*TTLIHPK | 234 |   |   | 2 |
|   |   | 204 | 2 | 321 | 3 | 212 | 0 | GPSTPLPEDPNWN*VTEFHTTPK | 265 |   |   | 3 |
|   |   | 204 | 0 | 321 | 183 | 212 | 9 | GPSTPLPEDPN*WN*VTEFHTTPK | 265 |   |   | 4 |
|   |   | 204 | 0 | 321 | 1 | 212 | 0 | VPVTLALN*N*TLFLIEER | 681 |   |   | 5 |
|   |   | 204 | 1 | 321 | 1 | 212 | 0 | N*ATLVNEADKLR | 818 |   |   | 6 |
|   |   | 204 | 0 | 321 | 1 | 212 | 0 | N*ATLVNEADKLR | 818 |   |   | 6 |
| 2 | IPI00022462-Transferrin receptor protein 1 | 205 | 81 | 380 | 68 | 119 | 38 | DFEDLYTPVN*GSIVIVR | 681 | 1 | 0 | 7 |
|   |   | 205 | 0 | 380 | 223 | 119 | 0 | KDFEDLYTPVN*GSIVIVR | 818 |   |   | 8 |
|   |   | 205 | 1 | 380 | 0 | 119 | 0 | LTTDFGN*AEKTDR | 818 |   |   | 9 |
| 3 | IPI00645194-Integrin beta 1 isoform 1A precursor | 75 | 3 | 189 | 1 | 124 | 1 | NPCTSEQN*CTSPFSYK | 128 | * | 4 | 10 |
|   |   | 75 | 0 | 189 | 2 | 124 | 0 | SCGECIQAGPNCGWCTN*STFLQEGMPTSAR | 234 |   |   | 11 |
|   |   | 75 | 0 | 189 | 9 | 124 | 6 | LRN*PCTSEQN*CTGPFSYK | 265 |   |   | 12 |
|   |   | 75 | 0 | 189 | 0 | 124 | 1 | LRNPCTSEQN*CTSPFSYK | 265 |   |   | 13 |
|   |   | 75 | 0 | 189 | 0 | 124 | 2 | N*PCTSEQN*CTSPFSYK | 681 |   |   | 14 |
|   |   | 75 | 0 | 189 | 1 | 124 | 0 | KEN*SSEICSNN*GECVCGQCVCR | 818 |   |   | 15 |
|   |   | 75 | 4 | 189 | 5 | 124 | 20 | DTCTQECSYFN*ITK | 818 |   |   | 16 |
|   |   | 75 | 0 | 189 | 14 | 124 | 42 | KDTCTQECSYFN*ITK | 818 |   |   | 17 |
| 4 | IPI00013744-Integrin alpha-2 precursor | 95 | 16 | 179 | 7 | 43 | 0 | LNLQTSTSIPN*VTEMK | 105 | 1 | 6 | 18 |
|   |   | 95 | 0 | 179 | 3 | 43 | 0 | LN*LQTSTSIPN*VTEMK | 105 |   |   | 19 |
|   |   | 95 | 5 | 179 | 0 | 43 | 0 | TN*MSLGLILTR | 112 |   |   | 20 |
|   |   | 95 | 30 | 179 | 73 | 43 | 0 | YFFN*VSDEAALLEK | 343 |   |   | 21 |
|   |   | 95 | 0 | 179 | 1 | 43 | 0 | AN*YTGQIVLYSVN*EN*GNITVIQAHR | 460 |   |   | 22 |
|   |   | 95 | 6 | 179 | 15 | 43 | 11 | TASCSN*VTCWLK | 1057 |   |   | 23 |
|   |   | 95 | 1 | 179 | 0 | 43 | 0 | GEYFVN*VTTR | 1074 |   |   | 24 |
|   |   | 95 | 0 | 179 | 1 | 43 | 0 | AN*YTGQIVLYSVN*EN*GN*ITVIQAHR | 460,475 |   |   | 25 |

| | | | | | | | | | | | SEQ ID |
|---|---|---|---|---|---|---|---|---|---|---|---|
| 5 | IPI00002478-Isoform B of Endothelin-converting enzyme | 52 | 4 | 94 | 3 | 89 | 2 | HLLEN*STASVSEAER | 166 | 1 | 0 | 26 |
| | | 52 | 1 | 94 | 0 | 89 | 1 | HLLEN*STASVSEAERK | 166 | 5 | | 27 |
| | | 52 | 27 | 94 | 17 | 89 | 0 | LGGWN*ITGPWAK | 210 | | | 28 |
| | | 52 | 6 | 94 | 0 | 89 | 9 | DYYLN*KTENEK | 270 | | | 29 |
| | | 52 | 6 | 94 | 7 | 89 | 0 | EYLEQISTLIN*TTDR | 383 | | | 30 |
| | | 52 | 6 | 94 | 9 | 89 | 0 | FFN*FSWR | 539 | | | 31 |
| | | 52 | 1 | 94 | 0 | 89 | 0 | N*SSVEAFKR | 632 | | | 32 |
| 6 | IPI00215995-Isoform Alpha-3A of Integrin alpha-3 precursor | 43 | 1 | 95 | 0 | 89 | 4 | ELAVPDGYTN*R | 86 | 0 | 0 | 33 |
| | | 43 | 0 | 95 | 0 | 89 | 1 | DDCERMN*ITVK | 107 | 6 | | 34 |
| | | 43 | 4 | 95 | 3 | 89 | 5 | N*ITIVTGAPR | 265 | | | 35 |
| | | 43 | 2 | 95 | 0 | 89 | 0 | N*ITLAYTLEADR | 511 | | | 36 |
| | | 43 | 0 | 95 | 1 | 89 | 0 | RN*ITLAYTLEADRDR | 511 | | | 37 |
| | | 43 | 0 | 95 | 2 | 89 | 0 | N*ITLAYTLEADRDR | 511 | | | 38 |
| | | 43 | 0 | 95 | 1 | 89 | 0 | AHCVWLECPIPDAPVVTN*VTVK | 926 | | | 39 |
| | | 43 | 0 | 95 | 6 | 89 | 0 | VN*GWATLFLR | 951 | | | 40 |
| | | 43 | 0 | 95 | 2 | 89 | 0 | TSIPTINMEN*K | 969 | | | 41 |
| 7 | IPI00414717-golgi apparatus protein 1 | 30 | 0 | 98 | 4 | 91 | 3 | LN*LTTDPK | 165 | * | * | 2 | 42 |
| | | 30 | 0 | 98 | 3 | 91 | 0 | GN*ITEYQCHQYITK | 210 | | | | 43 |

| # | IPI number & Description | 1t | 1p | 2t | 2p | 3t | 3p | Peptide | site | A | P | N | SEQ ID NO. |
|---|---|---|---|---|---|---|---|---|---|---|---|---|---|
| 8 | IPI00297160-CD44 antigen isoform 4 precursor | 45 | 20 | 0 | 0 | 109 | 0 | AFN*STLPTMAQMEK | 57 | 1 | 0 | 0 | 44 |
|   |   | 45 | 8 | 0 | 0 | 109 | 0 | LVINSGN*GAVEDR | 688 |   |   |   | 45 |
| 9 | IPI00022048-Prostaglandin F2 receptor negative regulator precursor | 46 | 13 | 66 | 6 | 39 | 10 | AAVPKN*VSVAEGK | 286 | 0 | 4 | 0 | 46 |
|   |   | 46 | 5 | 66 | 4 | 39 | 8 | ELDLTCN*TTTDR | 300 |   |   |   | 47 |
|   |   | 46 | 0 | 66 | 1 | 39 | 0 | VAEAVSSPAGVGVTWLEPDYQVYLN*ASK | 413 |   |   |   | 48 |
|   |   | 46 | 1 | 66 | 0 | 39 | 1 | LEN*WTDASR | 618 |   |   |   | 49 |
| 10 | IPI00021-Ephrin type-A receptor 2 precursor | 36 | 4 | 64 | 4 | 18 | 1 | TASVSIN*QTEPPK | 435 | 0 | 1 | 0 | 50 |
|   |   | 36 | 9 | 64 | 0 | 18 | 1 | TASVSIN*QTEPPKVR | 435 |   | 3 | 1 | 51 |
| 11 | IPI00152540-Isoform 1 of CD109 antigen precursor | 28 | 11 | 51 | 29 | 38 | 0 | TASN*LTVSVLEAEGVFEK | 68 |   |   |   | 52 |
|   |   | 28 | 6 | 51 | 6 | 38 | 9 | TQDEILFSN*STR | 118 |   |   |   | 53 |
|   |   | 28 | 2 | 51 | 0 | 38 | 1 | N*YTEYWSGSNSGNQK | 397 |   |   |   | 54 |
|   |   | 28 | 0 | 51 | 2 | 38 | 0 | IN*YTVPQSGTFK | 419 |   |   |   | 55 |
| 12 | IPI00027505-Integrin alpha-V precursor | 23 | 4 | 42 | 2 | 50 | 5 | AN*TTQPGIVEGGQVLK | 74 | 0 | 2 | 0 | 56 |
|   |   | 23 | 2 | 42 | 10 | 50 | 7 | ISSLQTTEKN*DTVAGQGER | 874 |   |   |   | 57 |
| 13 | IPI00018274-Isoform 1 of Epidermal growth factor receptor precursor | 11 | 0 | 41 | 1 | 40 | 0 | EFVEN*SECIQCHPECLPQAMN*ITCTGR | 568 | 2 | 0 | 0 | 58 |
|   |   | 11 | 0 | 41 | 0 | 40 | 6 | TCPAGVMGEN*NTLVWK | 603 |   |   |   | 59 |
|   |   | 11 | 0 | 41 | 0 | 40 | 3 | TCPAGVMGEN*N*TLVWK | 603 |   |   |   | 60 |
|   |   | 28 | 1 | 30 | 2 | 18 | 0 | N*ATYGYVLDDPDPDDGFNYK | 131 | 0 | 1 | 0 | 61 |
| 15 |   | 21 | 3 | 36 | 4 | 18 | 0 | LSAVNSIFLSHN*NTK | 453 | 0 | 4 | 0 | 62 |
|   |   | 21 | 0 | 36 | 1 | 18 | 2 | GDKN*VTMGQSSAR | 371 |   |   |   | 63 |
|   | IPI00299412-Isoform 2 of CD97 antigen precursor | 21 | 0 | 36 | 2 | 18 | 0 | RLSAVNSIFLSHN*NTK | 453 |   |   |   | 64 |
|   |   | 21 | 0 | 36 | 2 | 18 | 0 | LSAVN*SIFLSHN*NTK | 453 |   |   |   | 65 |
|   |   | 21 | 0 | 36 | 1 | 18 | 0 | LSAVN*SIFLSHN*N*TK | 453 |   |   |   | 66 |
|   |   | 21 | 0 | 36 | 1 | 18 | 6 | WCPQN*SSCVN*ATACR | 33, 38 |   |   |   | 67 |
| 16 | IPI00296099-Thrombospondin-1 precursor | 9 | 14 | 28 | 14 | 35 | 20 | VVN*STTGPGEHLR | 1067 | 1 | 0 | 0 | 68 |

| | | | | | | | | | | |
|---|---|---|---|---|---|---|---|---|---|---|
| 17 | IPI00398435-PREDICTED similar to Plexin-B2 precursor | 6 | 1 | 28 | 0 | 34 | 1 | ALSN*ISLR | 127 | 3 | 0 | 69 |
| | | 6 | 0 | 28 | 2 | 34 | 2 | SCVAVTSAQPQN*MSR | 528 | | 0 | 70 |
| | | 6 | 0 | 28 | 2 | 34 | 0 | LSHDAN*ETLPLHLYVK | 733 | | 0 | 71 |
| 18 | IPI00027078-Carboxypeptidase D precursor | 17 | 4 | 27 | 1 | 22 | 4 | FANEYPN*TTR | 522 | 1 | 2 | 72 |
| | | 17 | 0 | 27 | 1 | 22 | 0 | LLN*TTDVYLLPSLNPDGFER | 172 | | 0 | 73 |
| | | 17 | 0 | 27 | 1 | 22 | 0 | LLN*TTDVYLLPSLN*PDGFER | 172 | | 0 | 74 |
| | | 17 | 0 | 27 | 0 | 22 | 1 | RFAN*EYPN*TTR | 522 | | 0 | 75 |
| | | 17 | 2 | 27 | 1 | 22 | 0 | GYNPVTKN*VTVK | 855 | | 0 | 76 |
| 19 | IPI00023673-Galectin-3-binding protein precursor | 14 | 14 | 30 | 10 | 21 | 14 | ALGFEN*ATQALGR | 69 | 6 | 0 | 77 |
| | | 14 | 0 | 30 | 0 | 21 | 1 | DAGVVCTN*ETR | 125 | | | 78 |
| | | 14 | 0 | 30 | 3 | 21 | 0 | EPGSN*VTMSVDAECVPMVR | 192 | | | 79 |
| | | 14 | 13 | 30 | 15 | 21 | 7 | GLN*LTEDTYKPR | 398 | | | 80 |
| | | 14 | 5 | 30 | 3 | 21 | 3 | AAIPSALDTN*SSK | 551 | | | 81 |
| | | 14 | 8 | 30 | 13 | 21 | 0 | TVIRPFYLTN*SSGVD | 580 | | | 82 |
| 20 | IPI00022810-Dipeptidyl-peptidase 1 precursor | 11 | 0 | 21 | 1 | 29 | 0 | ILTNN*SQTPILSPQEVVSCSQYAQGCEGGFPYLIAGK | 276 | 2 | 0 | 83 |
| | | 11 | 0 | 21 | 0 | 29 | 1 | DVN*CSVMGPQEK | 53 | | | 84 |
| | | 11 | 0 | 21 | 1 | 29 | 0 | ILTN*NSQTPILSPQEVVSCSQYAQGCEGGFPYLIAGK | 276 | | | 85 |
| | | 11 | 0 | 21 | 4 | 29 | 0 | ILTN*N*SQTPILSPQEVVSCSQYAQGCEGGFPYLIAGK | 276 | | | 86 |
| 21 | IPI00003802-Alpha-mannosidase 2 | 13 | 2 | 37 | 3 | 9 | 0 | DSVIN*LSESVEDGPK | 78 | 1 | 0 | 87 |
| | IPI00003802-Isoform 1 of Nicastrin precursor | 12 | 0 | 26 | 4 | 16 | 5 | RPN*QSQPLPPSSLQR | 417 | 0 | 1 | 88 |
| 23 | IPI00296215-Tumor-associated calcium signal transducer 1 precursor | 14 | 2 | 26 | 0 | 11 | 0 | TQN*DVDIADVAYYFEK | 295 | 0 | 1 | 89 |
| | | 14 | 0 | 26 | 3 | 11 | 0 | FITSILYENNVITIDLVQN*SSQK | 198 | 0 | 0 | 90 |

| # | IPI number & Description | 1t | 1p | 2t | 2p | 3t | 3p | Peptide | site | A | P | N | SEQ ID NO. |
|---|---|---|---|---|---|---|---|---|---|---|---|---|---|
| 24 | IPI00009629-CMP-N-acetylneuraminat-beta-galactosamide-alpha-2,3-sialyltransferase | 15 | 8 | 26 | 12 | 9 | 0 | ELGDN*VSMILVPFK | 201 | 0 | 3 | 0 | 91 |
|  |  | 15 | 0 | 26 | 1 | 9 | 0 | FN*QTMQPLLTAQN*ALLEDDTYR | 79 |  |  |  | 92 |
|  |  | 15 | 0 | 26 | 1 | 9 | 0 | FN*QTMQPLLTAQNALLEDDTYR | 79 |  |  |  | 93 |
|  |  | 15 | 0 | 26 | 0 | 9 | 1 | EKKPNNLN*DTIK | 114 |  |  |  | 94 |
|  |  | 15 | 0 | 26 | 18 | 9 | 0 | TGVHDADFESN*VTATLASINK | 323 |  |  |  | 95 |
|  |  | 15 | 0 | 26 | 2 | 9 | 0 | TGVHDADFESN*VTATLASIN*K | 323 |  |  |  | 96 |
| 25 | IPI00306604-Integrin alpha-5 precursor | 4 | 2 | 16 | 0 | 29 | 0 | GNLTYGYVTILN*GSDIR | 307 | 0 | 3 | 0 | 97 |
|  |  | 4 | 1 | 16 | 0 | 29 | 0 | VTGLN*CTTNHPINPK | 868 |  |  |  | 98 |
|  |  | 4 | 0 | 16 | 9 | 29 | 0 | GN*LTYGYVTILN*GSDIR | 297, 307 |  |  |  | 99 |
| 26 | IPI00103175-Isoform 1 of Soluble calcium-activated nucleotidase 1 | 13 | 28 | 22 | 0 | 13 | 0 | LGQAPANWYN*DTYPLSPPQR | 88 | 0 | 1 | 0 | 100 |
|  |  | 13 | 0 | 22 | 5 | 13 | 0 | LGQAPAN*WYN*DTYPLSPPQR | 88 |  |  |  | 101 |
| 27 | IPI00030847-Transmembrane 9 superfamily protein member 3 precursor | 26 | 11 | 20 | 7 | 2 | 7 | IVDVN*LTSEGK | 174 | 0 | 1 | 0 | 102 |
| 28 | IPI00747849-Isoform 1 of Sodium/potassium-transporting ATPase sununit beta-1 | 10 | 2 | 12 | 0 | 22 | 0 | LEWLGN*CSGLNDETYGYK | 158 | 2 | 0 | 0 | 103 |
|  |  | 10 | 0 | 12 | 1 | 22 | 0 | YLQPLLAVQFTN*LTMDTEIR | 265 |  |  |  | 104 |
|  | IPI00747849-Neutral amino acid transporter B(0) | 10 | 8 | 24 | 3 | 8 | 4 | SYSTTYEERN*ITGTR | 212 | 0 | 1 | 0 | 105 |
| 30 | IPI00021807-Isoform Long of Glucosylceramidase precursor | 12 | 2 | 24 | 2 | 5 | 4 | DLGPTLAN*STHHNVR | 309 | 2 | 0 | 0 | 106 |
|  |  | 12 | 0 | 24 | 7 | 5 | 0 | TYTYADTPDDFQLHN*FSLPEEDTK | 185 |  |  |  | 107 |
| 31 | IPI00008494-Intercellular adhesion molecule 1 precursor | 7 | 3 | 12 | 2 | 20 | 0 | AN*LTVLLR | 145 | 2 | 0 | 0 | 108 |
|  |  | 7 | 9 | 12 | 2 | 20 | 7 | LNPTVTYGN*DSFSAK | 267 |  |  |  | 109 |
| 32 | IPI00293088-106 KDa protein | 13 | 2 | 14 | 1 | 11 | 0 | GVFITN*ETGQPLIGK | 470 | * | * | 1 | 110 |
| 33 | IPI00005107-Niemann-Pick C1 protein precursor | 10 | 3 | 20 | 0 | 8 | 0 | QSQFLNVTATEDYVDPVTN*QTK | 135 | 0 | 1 | 3 | 111 |
|  |  | 10 | 0 | 20 | 1 | 8 | 0 | NYKNPN*LTISFTAER | 598 |  |  |  | 112 |
|  |  | 10 | 0 | 20 | 5 | 8 | 0 | VDN*ITDQFCN*ASVDPACVR | 961, 968 |  |  |  | 113 |

| # | Protein | | | | | | | Peptide | | | | | SEQ ID |
|---|---|---|---|---|---|---|---|---|---|---|---|---|---|
| 34 | IPI00028931-desmoglein 2 preproprotein | 5 | 0 | 13 | 1 | 20 | 0 | DTGELN*VTSILDR | 111 | 1 | 1 | | 114 |
| | | 5 | 0 | 13 | 1 | 20 | 2 | YVQN*GTYTVK | 461 | 1 | 0 | 0 | 115 |
| 35 | IPI00009030-Isoform LAMP-2A of Lysome-associated membrane glycoprotein 2 precursor | 4 | 13 | 33 | 2 | 0 | 32 | WQMN*FTVR | 49 | 6 | 0 | 0 | 116 |
| | | 4 | 0 | 33 | 0 | 0 | 1 | YETTN*KTYK | 58 | | | | 117 |
| | | 4 | 0 | 33 | 4 | 0 | 1 | TVTISDHGTVTYN*GSICGDDQN*GPK | 75 | | | | 118 |
| | | 4 | 0 | 33 | 0 | 0 | 1 | TVTISDHGTVTYN*GSICGDDQNGPK | 75 | | | | 119 |
| | | 4 | 0 | 33 | 2 | 0 | 0 | IAVQFGPGFSWIAN*FTK | 101 | | | | 120 |
| | | 4 | 8 | 33 | 0 | 0 | 1 | VASVININPN*TTHSTGSCR | 257 | | | | 121 |
| | | 4 | 0 | 33 | 0 | 0 | 1 | VASVININ*PN*TTHSTGSCR | 257 | | | | 122 |
| | | 4 | 2 | 33 | 0 | 0 | 3 | VQPFN*VTQGK | 356 | | | | 123 |
| 36 | IPI00004503-lyosomal-associated membrane protein 1 | 7 | 2 | 13 | 0 | 16 | 0 | NMTFDLPSDATVVLN*R | 75 | 4 | 0 | 0 | 124 |
| | | 7 | 2 | 13 | 19 | 16 | 44 | SSCGKEN*TSDPSLVIAFGR | 83 | | | | 125 |
| | | 7 | 0 | 13 | 2 | 16 | 2 | LLNINPN*K | 260 | | | | 126 |
| | | 7 | 0 | 13 | 3 | 16 | 0 | N*MTFDLPSDATVVLN*R | 61, 75 | | | | 127 |
| 37 | IPI00299758-Carbohydrate sulfotransferase 12 | 11 | 1 | 12 | 2 | 12 | 3 | GFCAN*SSLAFPTK | 134 | 0 | 2 | 0 | 128 |
| | | 11 | 3 | 12 | 2 | 12 | 3 | LYAN*HTSLPASAR | 280 | | | | 129 |
| 38 | IPI00217766-Lysosome membrane protein 2 | 5 | 6 | 17 | 0 | 13 | 0 | NKANIQFGDN*GTTISAVSNK | 105 | 0 | 3 | 0 | 130 |
| | | 5 | 11 | 17 | 1 | 13 | 0 | ANIQFGDN*GTTISAVSNK | 105 | | | | 131 |
| | | 5 | 0 | 17 | 1 | 13 | 0 | AN*IQFGDN*GTTISAVSNK | 105 | | | | 132 |
| | | 5 | 0 | 17 | 4 | 13 | 9 | NGTN*DGDYVFLTGEDSYLN*FTK | 224 | | | | 133 |
| | | 5 | 0 | 17 | 4 | 13 | 0 | N*GTNDGDYVFLTGEDSYLN*FTK | 206, 224 | | | | 134 |
| | IPI00217766-Lysosome membrane protein 2 precursor | 6 | 3 | 0 | 0 | 28 | 6 | EN*STDYLYPEQLK | 322 | 1 | 0 | 0 | 135 |
| 40 | IPI00013302-ADAM 15 precursor | 5 | 0 | 17 | 6 | 10 | 0 | YRDFQHLLN*R | 237 | 0 | 2 | 0 | 136 |
| | | 5 | 0 | 17 | 1 | 10 | 1 | DFQHLLN*R | 237 | | | | 137 |
| | | 5 | 0 | 17 | 2 | 10 | 0 | TCIMEASTDFLPGLNFSN*CSR | 392 | | | | 138 |

| # | IPI number & Description | 1t | 1p | 2t | 2p | 3t | 3p | Peptide | site | A | P | N | SEQ ID NO |
|---|---|---|---|---|---|---|---|---|---|---|---|---|---|
| 41 | IPI00009507-Isoform 1 of Synaptophysin-like protein 1 | 2 | 2 | 20 | 0 | 9 | 0 | GQTEIQVNCPPAVTEN*K | 71 | 0 | 1 | 0 | 139 |
|  |  | 2 | 0 | 20 | 3 | 9 | 2 | GQTEIQVN*CPPAVTEN*K | 71 |  |  |  | 140 |
|  |  | 2 | 2 | 20 | 1 | 9 | 0 | LNEASFQPPPGVN*ICDVNWK | 96 |  |  |  | 141 |
|  |  | 2 | 0 | 20 | 1 | 9 | 0 | LN*EASFQPPPGVN*ICDVN*WK | 85, 96, 101 |  |  |  | 142 |
| 42 | IPI00290039-Isoform 1 of CUB domain-containing protein 1 precursor | 7 | 0 | 13 | 2 | 11 | 4 | IGTFCSN*GTVSR | 180 | 0 | 5 | 1 | 143 |
|  |  | 7 | 0 | 13 | 0 | 11 | 1 | ESN*ITVLIK | 39 |  |  |  | 144 |
|  |  | 7 | 0 | 13 | 0 | 11 | 1 | N*VSGFSIANR | 205 |  |  |  | 145 |
|  |  | 7 | 0 | 13 | 4 | 11 | 0 | ASVSFLNFN*LSNCER | 270 |  |  |  | 146 |
|  |  | 7 | 0 | 13 | 2 | 11 | 0 | LQFQVLVQHPQN*ESNK | 339 |  |  |  | 147 |
|  |  | 7 | 0 | 13 | 3 | 11 | 4 | TCSSN*LTLTSGSK | 386 |  |  |  | 148 |
| 43 | IPI00022649-Isoform 1 of Solute carrier family 12 member 2 | 11 | 1 | 19 | 0 | 0 | 0 | DATGNVNDTIVTELTN*CTSAACK | 562 | * | * | 2 | 149 |
|  |  | 11 | 0 | 19 | 1 | 0 | 0 | DATGNVN*DTIVTELTN*CTSAACK | 553, 562 |  |  |  | 150 |
| 44 | IPI00303401-UNCHARACTERIZED PROTEIN C1ORF75 | 7 | 1 | 16 | 0 | 6 | 0 | INYTDPFSN*QTVK | 162 | * | * | 2 | 151 |
|  |  | 7 | 0 | 16 | 6 | 6 | 8 | IN*YTDPFSN*QTVK | 155, 162 |  |  |  | 152 |
| 45 | IPI00303401-Type I transmembrane receptor precursor | 5 | 0 | 8 | 1 | 15 | 7 | IVSPEPGGAVGPN*LTCR | 303 | * | * | 1 | 153 |
| 46 | IPI00001922-Suppressor of tumorigenicity protein 14 | 3 | 4 | 17 | 0 | 6 | 0 | ITNENFVDAYENSN*STEFVSLASK | 109 | 0 | 2 | 0 | 154 |
|  |  | 3 | 1 | 17 | 0 | 6 | 0 | ITNENFVDAYEN*SNSTEFVSLASK | 109 |  |  |  | 155 |
|  |  | 3 | 0 | 17 | 2 | 6 | 0 | ITNENFVDAYEN*SN*STEFVSLASK | 109 |  |  |  | 156 |
|  |  | 3 | 1 | 17 | 0 | 6 | 0 | VIN*QTTCENLLPQQITPR | 772 |  |  |  | 157 |
|  |  | 3 | 0 | 17 | 1 | 6 | 0 | VIN*QTTCEN*LLPQQITPR | 772 |  |  |  | 158 |
| 47 | IPI00020470-glycosyltransferase 8 domain containing 1 | 9 | 3 | 11 | 1 | 5 | 3 | RQN*ITNQLEK | 257 | * | * | 2 | 159 |
|  |  | 9 | 0 | 11 | 1 | 5 | 0 | SNVIFYIVTLN*N*TADHLR | 103 |  |  |  | 160 |
|  |  | 9 | 0 | 11 | 0 | 5 | 1 | QN*ITNQLEK | 257 |  |  |  | 161 |

| | | | | | | | | | | | | |
|---|---|---|---|---|---|---|---|---|---|---|---|---|
| 48 | IPI00030273-Isoform RON of Macrophage-stimulating protein receptor precursor | 3 | 3 | 14 | 2 | 8 | 7 | DPQGWVAGN*LSAR | 841 | 0 | 2 | 162 |
| | | 3 | 0 | 14 | 3 | 8 | 0 | AVLVN*GTECLLAR | 720 | 0 | 0 | 163 |
| 49 | ipi00277728-High-affinity cationic amino acid transporter 1 | 4 | 4 | 9 | 2 | 5 | 2 | NWQLTEEDFGN*TSGR | 226 | 0 | 2 | 164 |
| | | 4 | 0 | 9 | 0 | 5 | 2 | LCLN*N*DTK | 235 | 0 | 0 | 165 |
| | IPI00277728-Neutrophil gelatinase-associated lipocalin precursor | 3 | 4 | 8 | 9 | 6 | 6 | SYN*VTSVLFR | 85 | 1 | 0 | 166 |
| | IPI00277728-Isofrom 1 of Ephrin type-B receptor 2 precursor | 4 | 0 | 10 | 1 | 3 | 1 | AGFEAVEN*GTVCR | 265 | 0 | 1 | 167 |
| | | 2 | 0 | 8 | 4 | 5 | 3 | DLCGPDAGPIGN*ATGQADCK | 56 | * | * | 168 |
| | IPI00277728-solute carrier family 43, member 3 | | | | | | | | | | | |
| 53 | IPI00441344-Beta-galactosidase precursor | 0 | 5 | 7 | 4 | 8 | 12 | NNVITLN*ITGK | 464 | 0 | 1 | 169 |
| | | 0 | 0 | 7 | 0 | 8 | 1 | N*NVITLN*ITGK | 464 | | | 170 |
| | IPI00441344-Beta-galactosidase precursor | 0 | 0 | 7 | 0 | 8 | 1 | NN*VITLN*ITGK | 464 | | | 171 |
| | IPI00441344-Alpha-1,6-mannosylglycoprotein 6-beta-N-acetylglucosaminyltransferase V | 4 | 6 | 0 | 5 | 9 | 0 | VEDEGN*YTCLFVTFPQGSR | 120 | 1 | 0 | 172 |
| | | 2 | 1 | 5 | 1 | 6 | 1 | RQN*QSLVYGK | 447 | 0 | 1 | 173 |
| 56 | IPI00022284-Major prion protein precursor | 2 | 1 | 10 | 0 | 0 | 2 | QHTVTTTKGEN*FTETDVK | 197 | 1 | 0 | 174 |
| | | 2 | 0 | 10 | 2 | 0 | 2 | GEN*FTETDVK | 197 | 0 | 0 | 175 |
| 57 | IPI00025049-Cation-dependent mannose-6-phosphate receptor precursor | 4 | 11 | 0 | 3 | 8 | 18 | EAGN*HTSGAGLVQINK | 83 | 0 | 2 | 176 |
| | | 4 | 0 | 0 | 0 | 8 | 1 | EAGN*HTSGAGLVQIN*K | 83, 94 | | | 177 |
| 58 | IPI00217481-Developmentally regulated G-protein-coupled receptor beta 1 | 3 | 0 | 5 | 4 | 4 | 0 | IDLN*STSHVN*ITTR | 667, 673 | 0 | 3 | 178 |
| | | 3 | 0 | 5 | 0 | 4 | 1 | LLKN*N*ESLDEGLR | 505 | | | 179 |

| # | IPI number & Description | 1t | 1p | 2t | 2p | 3t | 3p | Peptide | site | A | P | N | SEQ ID NO. |
|---|---|---|---|---|---|---|---|---|---|---|---|---|---|
| 59 | IPI00056478-Isoform 1 of Immunoglobulin superfamily member 8 precursor | 0 | 2 | 6 | 6 | 6 | 0 | GETASLLCN*ISVR | 463 | 0 | 1 | 1 | 180 |
|  |  | 0 | 0 | 6 | 3 | 6 | 0 | IGPGEPLELLCN*VSGALPPAGR | 327 |  | * |  | 181 |
|  | IPI00056478-64 kDa protein | 5 | 1 | 3 | 0 | 3 | 2 | TMFN*STDIK | 68 | * |  | 1 | 182 |
|  | IPI00056478-tumor necrosis factor, alpha-induced protein 9 | 4 | 5 | 5 | 1 | 0 | 0 | LGN*LTVTQAILK | 323 | * | * | 1 | 183 |
|  | IPI00056478-Equillbrative nucleoside transporter 1 | 3 | 3 | 3 | 10 | 0 | 0 | LDMSQN*VSLVTAELSK | 48 | 0 | 1 |  | 184 |
| 63 |  | 2 | 1 | 2 | 0 | 2 | 0 | QQMENYPKNN*HTASILDR | 130 | 1 | 2 | 0 | 185 |
|  |  | 2 | 2 | 2 | 0 | 2 | 2 | NN*HTASILDR | 130 |  |  |  | 186 |
|  |  | 2 | 0 | 2 | 0 | 2 | 2 | N*NHTASILDR | 130 |  |  |  | 187 |
|  |  | 2 | 0 | 2 | 0 | 2 | 3 | N*N*HTASILDR | 130 |  |  |  | 188 |
|  | IPI00215998-CD63 antigen | 2 | 1 | 2 | 2 | 2 | 8 | CCGAAN*YTDWEK | 150 |  |  |  | 189 |
|  |  | 2 | 0 | 2 | 1 | 2 | 0 | NRVPDSCCIN*VTVGCGIN*FNEK | 172 |  |  |  | 190 |
|  |  | 2 | 0 | 2 | 5 | 2 | 0 | N*RVPDSCCIN*VTVGCGINFNEK | 172 |  |  |  | 191 |
|  |  | 2 | 0 | 2 | 1 | 2 | 0 | VPDSCCIN*VTVGCGIN*FNEK | 172 |  |  |  | 192 |
|  | IPI00215998-Isoform 1 of Mucolipin-1 | 2 | 6 | 4 | 6 | 0 | 1 | GGGDPWTN*GSGLALCQR | 159 | * |  | 1 | 193 |
| 65 | IPI00414231-Isoform 1 of Low-density lipoprotein receptor-related protein 10 precursor | 2 | 2 | 0 | 2 | 3 | 0 | TSPAN*CTWLILGSK | 56 | 0 | 2 | 0 | 194 |
|  |  | 2 | 1 | 0 | 0 | 3 | 0 | GFN*ATYHVR | 299 |  |  |  | 195 |
| 66 | IPI00000735-Tetraspanin-13 | 0 | 3 | 2 | 3 | 3 | 4 | SVNPN*DTCLASCVK | 137 | 0 | 1 | 0 | 196 |
|  |  | 0 | 0 | 2 | 0 | 3 | 2 | SVN*PN*DTCLASCVK | 137 |  |  |  | 197 |
| 67 | IPI00290826-Transmembrane protein 157 | 2 | 1 | 2 | 0 | 0 | 0 | GSEGGN*GSNPVAGLETDDHGGK | 83 | 0 | 1 | 0 | 198 |
|  |  | 2 | 0 | 2 | 1 | 0 | 3 | GSEGGN*GSN*PVAGLETDDHGGK | 83 |  |  |  | 199 |

B. Mostly in PNGase

| | | 1t | 1p | 2t | 2p | 3t | 3p | Peptide | site | A | P | N | SEQ ID NO. |
|---|---|---|---|---|---|---|---|---|---|---|---|---|---|
| 68 |  | 0 | 16 | 0 | 34 | 102 | 0 | DASSFLAEWQN*ITK | 264 | 3 | 0 | 0 | 200 |
|  |  | 0 | 0 | 0 | 2 | 102 | 0 | DIENLKDASSFLAEWQN*ITK | 264 |  |  |  | 201 |
|  | IPI00027493-4F2 cell-surface antigen heavy chain | 0 | 0 | 0 | 3 | 102 | 0 | LLIAGTN*SSDLQQILSLLESNK | 280 |  |  |  | 202 |
|  |  | 0 | 0 | 0 | 1 | 102 | 0 | LLIAGTN*SSDLQQILSLLESN*K | 280 |  |  |  | 203 |

| # | Protein | | | | | | | | Peptide | | | | | SEQ ID |
|---|---|---|---|---|---|---|---|---|---|---|---|---|---|---|
| 69 | IPI00032292-Metalloproteinase Inhibitor 1 precursor | 0 | 28 | 0 | 0 | 21 | 102 | 35 | SLVTQYLN*ATGNR | 323 | | | | 204 |
|  |  | 0 | 0 | 0 | 0 | 5 | 102 | 0 | SLVTQYLN*ATGN*R | 323 | 1 | 0 | 0 | 205 |
|  | IPI00032292-INOSITOL MONOPHOSPHATASE DOMAIN-CONTAINING PROTEIN 1 | 0 | 1 | 14 | 0 | 0 | 0 | 0 | AKFVGTPEVN*QTTLYQR | 53 | * | * |  | 206 |
|  |  | 0 | 14 | 14 | 15 | 8 | 2 |  | FVGTPEVN*QTTLYQR | 53 |  |  |  | 207 |
| 71 | IPI00101374-Transmembrane 9 superfamily protein member 1 precursor | 8 | 14 | 0 | 13 | 0 | 0 | 0 | QVALQTFGN*QTTIPAGGAGYK | 259 | 0 | 1 | 0 | 208 |
|  |  | 0 | 3 | 8 | 3 |  | 0 | 0 | IIFAN*VSVR | 178 | 0 | 1 | 0 | 209 |
| 72 | IPI00293074-Isoform 2 of choline transporter-like protein 2 | 7 | 2 | 0 | 0 | 0 | 0 | 0 | N*ITDLVEGAK | 200 | 0 | 3 | 0 | 210 |
|  |  | 7 | 0 | 2 | 2 | 0 | 0 | 0 | GVLMVGN*ETTYEDGHGSR | 187 |  |  |  | 211 |
|  |  | 7 | 0 | 0 | 1 | 0 | 0 | 0 | KN*ITDLVEGAK | 200 |  |  |  | 212 |
|  |  | 7 | 2 | 0 | 1 | 0 | 0 | 0 | TCNPETFPSSN*ESR | 417 |  |  |  | 213 |
| 73 | IPI00024929-adipocyte-specific adhesion molecule | 0 | 0 | 7 | 1 | 0 | 0 | 0 | HVYNN*LTEEQK | 74 | * | * | 1 | 214 |
|  |  | 0 | 0 | 7 | 0 | 0 | 0 | 1 | HVYN*N*LTEEQK | 74 |  |  |  | 215 |
|  | IPI00024929-CD59 glycoprotein precursor | 0 | 1 | 5 | 59 | 0 | 0 | 23 | TAVN*CSSDFDACLITK | 43 | 1 | 0 | 0 | 216 |
|  | IPI00024929-Isoform 1 of Myelin protein zero-like protein 1 precursor | 0 | 6 | 4 | 3 | 0 | 0 | 4 | EIFVAN*GTQGK | 50 | 0 | 0 | 1 | 217 |
|  | IPI00024929-Isoform 1 of ICOS ligan precursor | 0 | 3 | 0 | 2 | 0 | 0 | 6 | LFN*VTPQDEQK | 102 | 0 | 1 | 0 | 218 |
| 77 | IPI00029723-Follistatin-related protein 1 precursor | 0 | 1 | 0 | 0 | 0 | 3 | 0 | FVEQNETAIN*ITTYPDQENNK | 180 | 1 | 1 | 0 | 219 |
|  |  | 0 | 0 | 0 | 0 | 0 | 3 | 4 | GSN*YSEILDK | 144 |  |  |  | 220 |
| 78 | IPI00018901-Isoform 1 of Gamma-glutamyltranspeptidase 1 precursor | 0 | 4 | 0 | 1 | 3 | 0 | 0 | LAFATMFN*SSEQSQK | 120 | 0 | 1 | 0 | 221 |

| # | IPI number & Description | 1t | 1p | 2t | 2p | 3t | 3p | Peptide | site | A | P | N | SEQ ID NO. |
|---|---|---|---|---|---|---|---|---|---|---|---|---|---|
| 79 | IPI00337612-Discoidin, CUB and LCCL domain-containing protein 1 precursor | 0 | 0 | 0 | 3 | 3 | 1 | ELLLN*TSEVTVR | 124 | 0 | 1 | 0 | 222 |
| 80 | IPI00465259-Peptie/histidine transporter | 0 | 3 | 0 | 1 | 2 | 3 | LLN*CTAPGPDAAAR | 140 | * | 1 | 0 | 223 |
| 81 | | 0 | 1 | 0 | 3 | 0 | 0 | LNLSEN*YTLSISNAR | 95 | 5 | 1 | 0 | 224 |
| | | 0 | 6 | 0 | 6 | 0 | 8 | LGDCISEDSYPDGN*ITWYR | 167 | | | | 225 |
| | | 0 | 5 | 0 | 0 | 0 | 2 | NAIKEGDN*ITLK | 265 | | | | 226 |
| | | 0 | 0 | 0 | 0 | 0 | 3 | EGDN*ITLK | 265 | | | | 227 |
| | IPI00015102-CD166 antigen precursor | 0 | 5 | 0 | 0 | 0 | 10 | N*ATVWMK | 361 | | | | 228 |
| | | 0 | 18 | 0 | 4 | 0 | 0 | IIISPEEN*VTLTCTAENQLER | 480 | | | | 229 |
| | | 0 | 0 | 0 | 4 | 0 | 0 | IIISPEEN*VTLTCTAEN*QLER | 480 | | | | 230 |
| | | 0 | 1 | 0 | 0 | 0 | 0 | TVNSLN*VSAISIPEHDEADEISDENR | 499 | | | | 231 |
| | | 0 | 0 | 0 | 16 | 0 | 0 | TVNSLN*VSAISIPEHDEADEISDEN*R | 499 | | | | 232 |
| | | 0 | 0 | 0 | 1 | 0 | 0 | TVSNLN*VSAISIPEHDEADEISDEN*REK | 499 | | | | 233 |
| 82 | | 0 | 16 | 0 | 14 | 0 | 33 | LFQN*CSELFK | 127 | 0 | 4 | 0 | 234 |
| | | 0 | 0 | 0 | 1 | 0 | 0 | FDGEPCDLSLN*ITWYLK | 79 | | | | 235 |
| | | 0 | 1 | 0 | 0 | 0 | 0 | EN*GTNLTFIGDK | 157 | | | | 236 |
| | IPI00106689-TMEM87A protein | 0 | 5 | 0 | 0 | 0 | 0 | QEAKENGTN*LTFIGDK | 160 | | | | 237 |
| | | 0 | 2 | 0 | 0 | 0 | 0 | ENGTN*LTFIGDK | 160 | | | | 238 |
| | | 0 | 0 | 0 | 11 | 0 | 23 | QEAKEN*GTN*LTFIGDK | 157, 160 | | | | 239 |
| | | 0 | 0 | 0 | 0 | 0 | 3 | EN*GTN*LTFIGDK | 157, 160 | | | | 240 |
| 83 | | 0 | 34 | 0 | 292 | 0 | 62 | ILLTCSLN*DSATEVTGHR | 160 | 2 | 0 | 0 | 241 |
| | IPI00019905-Isoform 2 of Basigin precursor | 0 | 43 | 0 | 6 | 0 | 15 | ITDSEDKALMN*GSESR | 268 | | | | 242 |
| | | 0 | 10 | 0 | 6 | 0 | 9 | ALMN*GSESR | 268 | | | | 243 |
| 84 | IPI00216516-CD47 antigen Isoform 3 precursor | 0 | 2 | 0 | 0 | 0 | 0 | DIYTFDGALN*K | 73 | 2 | 0 | 0 | 244 |
| | | 0 | 3 | 0 | 11 | 0 | 5 | SDAVSHTGN*YTCEVTELTR | 111 | | | | 245 |
| 85 | IPI00019275-Isoform 2 of CD276 antigen precursor | 0 | 17 | 0 | 25 | 0 | 0 | TALFPDLLAQGN*ASLR | 104 | 0 | 2 | 0 | 246 |
| | | 0 | 5 | 0 | 14 | 0 | 4 | VVLGAN*GTYSCLVR | 215 | | | | 247 |

| # | Protein | | | | | Peptide | | | | | SEQ ID |
|---|---|---|---|---|---|---|---|---|---|---|---|
| 86 | IPI00184474-Isoform 3 of Protein GPR107 precursor | 0 | 0 | 0 | 0 | VLGQSQEPNVNPASAGN*QTQK | 169 | 0 | 2 | 0 | 248 |
| 87 | IPI00165438-Muscle type neuropilin 1 | 0 | 5 | 0 | 0 | DGYMVVN*VSSLSIN*EPEDKDVTIGFSLDR | 70 | * | * | 4 | 249 |
| | | 0 | 6 | 0 | 0 | 17 RGPECSQN*YTTPSGVIK | 150 | | | | 250 |
| | | 0 | 1 | 0 | 0 | 4 GPECSQN*YTTPSGVIK | 150 | | | | 251 |
| | | 0 | 14 | 20 | 0 | 0 EGFSAN*YSVLQSSVSEDFK | 261 | | | | 252 |
| | | 0 | 0 | 0 | 0 | 1 IGYSN**N*GSDWK | 522 | | | | 253 |
| 88 | IPI00024811-Epithelia V-like antigen 1 precursor | 0 | 7 | 4 | 0 | 5 VLEAVN*GTDAR | 39 | 0 | 1 | 0 | 254 |
| 89 | IPI00013449-Tetraspanin-6 | 0 | 7 | 0 | 0 | 6 ALKQYN*STGDYR | 134 | 0 | 1 | 0 | 255 |
| 90 | IPI00788962-Protein | 0 | 3 | 4 | 0 | 0 GN*LTFTAQYLSYR | 136 | * | * | 1 | 256 |
| 91 | IPI00221240-Isoform 2 of Leucyl-cystinyl aminopeptidase | 0 | 1 | 0 | 0 | 0 N*QSIGLIQPFATNGK | 145 | 0 | 3 | 0 | 257 |
| | | 0 | 3 | 0 | 0 | 0 EETLLYDSN*TSSMADRK | 448 | | | | 258 |
| | | 0 | 0 | 13 | 0 | 0 SGVIN*LTEEVLWVK | 682 | | | | 259 |
| | | 0 | 7 | 5 | 0 | 8 EETLLYDSN*TSSMADR | 448 | | | | 260 |
| 92 | IPI00151036-RING finger protein 13 | 0 | 6 | 4 | 0 | 0 DN*SSGTFIVLIR | 88 | * | 1 | 1 | 261 |
| 93 | IPI00514585-CHROMOSOME 1 OPEN READING FRAME 85 | 0 | 8 | 6 | 0 | 18 TFAN*GSLAFR | 101 | * | * | 1 | 262 |
| 94 | IPI00006097-Tumor nicrosts factor receptor superfamily | 0 | 2 | 2 | 0 | 2 AGHFQN*TSSPSAR | 177 | 0 | 1 | 0 | 263 |
| 95 | IPI00043307-Lysosome-associated membrane glycoprotein 3 precursor | 0 | 1 | 1 | 0 | 1 TGIYQVLN*GSR | 232 | 1 | 2 | 0 | 264 |
| | | 0 | 0 | 1 | 0 | 0 YFNIDPN*ATQASGNCGTR | 266 | | | | 265 |
| 96 | IPI00043883-Isoform 1 of Heme carrier protein 1 | 0 | 4 | 0 | 0 | 4 FSADLGYN*GTR | 58 | 0 | 1 | 0 | 266 |
| 97 | IPI00027011-Sodium-and chloride-dependent neutral and basic amino acid tranporter B(0+) | 0 | 2 | 3 | 0 | 0 SPIVTHCN*VSTVNK | 174 | 0 | 1 | 0 | 267 |
| 98 | IPI00298702-Isoform 1 of Zinc transporter SLC39A6 precursor | 0 | 1 | 0 | 0 | 0 YGEN*NSLSVEGFRK | 67 | 0 | 1 | 0 | 268 |
| | | 0 | 0 | 0 | 0 | 2 YGEN*N*SLSVEGFR | 67 | | | | 269 |
| 99 | IPI00025276-Isoform XB of Tenascin-X precursor | 0 | 4 | 2 | 0 | 0 GPN*LTSPASITFTGLEAPR | 3965 | 1 | 0 | 0 | 270 |
| 100 | IPI00002541-CD44 antigen isoform 5 precursor | 0 | 0 | 11 | 0 | 27 AFN*STLPTMAQMEK | 57 | * | * | 1 | 271 |

| # | IPI number & Description | 1t | 1p | 2t | 2p | 3t | 3p | Peptide | site | A | P | N | SEQ ID NO. |
|---|---|---|---|---|---|---|---|---|---|---|---|---|---|
| 101 | IPI00472151-HLA class I histocompatibility antigen, A-23 alpha chain precursor | 34 | 0 | 76 | 51 | 25 | 0 | YYN*QSEAGSHTLQMMFGCDVGSDGR | 110 | 0 | 1 | 0 | 272 |
| 102 | IPI00026569-HLA class I histocompatibility antigen, A-1 alpha chain precursor | 31 | 0 | 69 | 26 | 19 | 0 | GYYN*QSEDGSHTIQIMYGCDVGPDGR | 110 | 0 | 1 | 0 | 273 |
| 103 | IPI00009111-Trophoblast glycoprotein precursor | 10 | 0 | 17 | 1 | 25 | 0 | N*LTEVPTDLPAYVR | 81 | 0 | 2 | 0 | 274 |
|  |  | 10 | 0 | 17 | 8 | 25 | 0 | VLHN*GTLAELQGLPHIR | 275 | 0 | 0 | 0 | 275 |
| 104 | IPI00297910-Tumor-associated calcium signal transducer 2 precursor | 2 | 0 | 26 | 79 | 23 | 0 | HRPTAGAFN*HSDLDAELR | 168 | 0 | 1 | 0 | 276 |
|  |  | 2 | 0 | 26 | 1 | 23 | 0 | HRPTAGAFN*HSDLDAELRR | 168 | 0 | 0 | 0 | 277 |
| 105 | IPI00220194-Solute carrier family 2, facilitated glucose transporter member 1 | 9 | 0 | 12 | 264 | 21 | 0 | VIEEFYN*QTWVHR | 45 | 1 | 0 | 0 | 278 |
| 106 | IPI00015756-Receptor-type tyrosine-protein phosphatase kappa precursor | 10 | 0 | 13 | 1 | 14 | 0 | LGDVEVN*AGQN*ATFQCIATGR | 211 | 0 | 2 | 0 | 279 |
|  |  | 10 | 0 | 13 | 5 | 14 | 0 | IAVDWESLGYN*ITR | 416 | 0 | 0 | 0 | 280 |
| 107 | IPI00010676-Isoform 1 Urokinase plasminogen activator surface receptor precursor | 0 | 0 | 23 | 25 | 8 | 0 | GN*STHGCSSEETFLIDCR | 222 | 0 | 1 | 0 | 281 |
| 108 | IPI00023542-transmembrane emp24 protein transport domain containing 9 | 8 | 0 | 8 | 68 | 7 | 0 | FIFTSHTPGEHQICLHSN*STK | 104 | 1 | 0 | 0 | 282 |
|  |  |  |  |  |  |  |  | TOTAL | | 69 | 113 | 37 | |

FIG. 8A

GIDmap of prostate cells (PNGase phase)

| Prostate cell | Protein No. | Unique | Common |
|---|---|---|---|
| RWPE-1 (normal) | 76 | 7 (9%) | 69 (91%) |
| PC-3 (cancer) | 134 | 65 (49%) | 69 (51%) |

FIG. 8B

Characterization of unique PC-3 sialylated N-glycoproteins

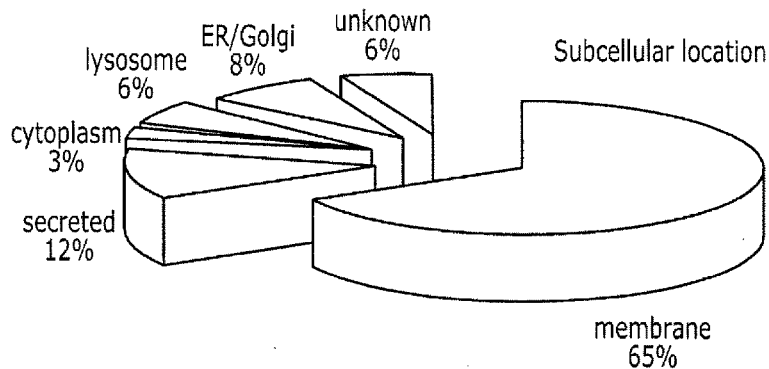

Subcellular location:
- membrane 65%
- secreted 12%
- ER/Golgi 8%
- unknown 6%
- lysosome 6%
- cytoplasm 3%

| Function | Percentage |
|---|---|
| Binding | 46% |
| Catalytic activity | 28% |
| Enzyme regulator activity | 5% |
| Molecular transducer activity | 17% |
| Transporter activity | 14% |
| Unknown | 31% |

| Process | Percentage |
|---|---|
| Biological adhesion | 14% |
| Biological regulation | 20% |
| Cellular process | 62% |
| Developmental process | 23% |
| Establishment of localization | 18% |
| Growth | 8% |
| Immune system process | 3% |
| Metabolic process | 35% |
| Multicellular organismal process | 23% |
| Reproductive process | 5% |
| Response to stimulus | 18% |
| Unknown | 26% |

FIG. 9A

GIDmap of lung cancer cells (PNGase phase)

| Lung cancer | Protein No. | Unique | Common |
|---|---|---|---|
| CL1 | 87 | 13 (15%) | 74 (85%) |
| CL1-5 (aggressive) | 144 | 70 (49%) | 74 (51%) |

FIG. 9B

Characterization of unique CL1-5 sialylated N-glycoproteins

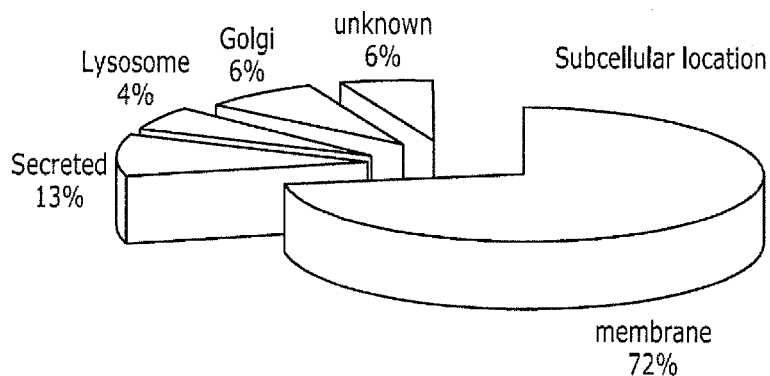

Subcellular location: Lysosome 4%, Golgi 6%, unknown 6%, Secreted 13%, membrane 72%

| Function | Percentage |
|---|---|
| Binding | 58% |
| Catalytic activity | 30% |
| Enzyme regulator activity | 6% |
| Molecular transducer activity | 32% |
| Transporter activity | 6% |
| Unknown | 25% |

| Process | Percentage |
|---|---|
| Biological adhesion | 17% |
| Biological regulation | 32% |
| Cellular process | 55% |
| Developmental process | 39% |
| Establishment of localization | 15% |
| Growth | 8% |
| Immune system process | 18% |
| Metabolic process | 34% |
| Multicellular organismal process | 38% |
| Reproductive process | 8% |
| Response to stimulus | 27% |
| Unknown | 30% |

Peptide counts of ECE-1

| RWPEI tryptic | RWPEI png | PC3 tryptic | PC3 png |
|---|---|---|---|
| 4.3 | 0 | 92.0 | 23.0 |

Peptide counts of NRP-1

| RWPEI tryptic | RWPEI png | PC3 tryptic | PC3 png |
|---|---|---|---|
| 0 | 0 | 0 | 20.8 |

IP: MALII

RWPE1　PC3

IB: anti-ECE-1

— 130KD

— 90KD

IB: anti-NRP-1

| No. | IPI number | | Cancer Association |
|---|---|---|---|
| 1 | IPI00002478 | PC3-unique protein | unknown |
| 2 | IPI00165438 | Isoform B of Endothelin-converting enzyme 1 | unknown |
| 3 | IPI00297910 | Muscle type neuropilin 1 | related |
| 4 | IPI00023542 | Tumor-associated calcium signal transducer 2 precursor | unknown |
| 5 | IPI00010676 | transmembrane emp24 protein transport domain containing 9 | unknown |
| 6 | IPI00299412 | Isoform 1 of Urokinase plasminogen activator surface receptor precursor | related |
| 7 | IPI00452161 | Isoform 2 of CD97 anitgen precursor | unknown |
| 8 | IPI00299547 | Isoform 1 of Mucolipin-1 | unknown |
| 9 | IPI00441344 | Neutrophil gelatinase-associated lipocalin precursor | unknown |
| 10 | IPI00303401 | Beta-galactosidase precursor | unknown |
| 11 | IPI00013449 | FLJ10874 protein | unknown |
| 12 | IPI00018276 | Tetraspanin-6 | unknown |
| 13 | IPI00293074 | Type I transmembrane receptor precursor | unknown |
| 14 | IPI00030273 | Isoform 2 of Choline transporter-like protein 2 | unknown |
| 15 | IPI00185191 | Isoform RON of Macrophage-stimulating protein receptor precursor | unknown |
| 16 | IPI00550382 | 42 kDa protein | unknown |
| 17 | IPI00219131 | Equilibrative nucleoside transporter 1 | unknown |
| 18 | IPI00056478 | Isoform 1 of ICOS ligand precursor | unknown |
| 19 | IPI00013302 | Isoform 1 of immunoglobulin superfamily member 8 precursor | unknown |
| 20 | IPI00151036 | ADAM 15 precursor | unknown |
| 21 | IPI00009111 | RING finger protein 13 | related |
| 22 | IPI00296180 | Trophoblast glycoprotein precursor | related |
| 23 | IPI00301100 | Urokinase-type plasminogen activator precursor | unknown |
| 24 | IPI00039680 | solute carrier family 43, member 3 | unknown |
| 25 | IPI00465259 | Isoform 2 of Solute carrier organic anion transporter family member 4A1 | unknown |
| 26 | IPI00028931 | Peptide/histidine transporter | unknown |
| 27 | IPI00029723 | desmoglein 2 preproprotein | unknown |
| 28 | IPI00006097 | Follistatin-related protein 1 precursor | unknown |
| 29 | IPI00043883 | Tumor necrosis factor receptor superfamily member 3 precursor | unknown |
| 30 | IPI00290826 | Isoform 1 Heme carrier protein 1 | unknown |
| | | Transmembrane protein 157 | |

FIG. 12B-1

| No. | IPI number | Protein | Cancer Association |
|---|---|---|---|
| 31 | IPI00788962 | PC3-unique protein | unknown |
| 32 | IPI00018305 | Insulin-like growth factor-binding protein 3 precursor | unknown |
| 33 | IPI00040900 | Isoform 2 of Heparan sulfate 2-O-sulfotransferase 1 | unknown |
| 34 | IPI00015756 | Receptor-type tyrosine-protein phoshatase kappa precursor | related |
| 35 | IPI00001922 | Suppressor of tumorigenicity protein 14 | related |
| 36 | IPI00217481 | Developmentally regulated G-protein-coupled receptor beta 1 | unknown |
| 37 | IPI00745161 | tumor necrosis factor, alpha-induced protein 9 | unknown |
| 38 | IPI00101374 | Transmembrane 9 superfamily protein member 1 precursor | unknown |
| 39 | IPI00018901 | Isoform 1 of Gamma-glutamyltranspeptidase 1 precursor | unknown |
| 40 | IPI00337612 | Discoidin, CUB and LCCL domain-containing protein 1 precursor | unknown |
| 41 | IPI00332887 | signal-regulatory protein alpha precursor | unknown |
| 42 | IPI00296215 | Tumor-associated calcium signal transducer 1 precursor | related |
| 43 | IPI00011662 | Kunitz-type protease inhibitor 2 precursor | unknown |
| 44 | IPI00414231 | Isoform 1 of Low-density lipoprotein receptor-related protein 10 precursor | unknown |
| 45 | IPI00298702 | Isoform 1 of Zinc transporter SLC39A6 precursor | related |
| 46 | IPI00014537 | Isoform 1 of Calumenin precursor | unknown |
| 47 | IPI00216273 | CMP-NeuAc-beta-galactosamide-alpha-2,3-sialyltransferase | unknown |
| 48 | IPI00009456 | 5'-nucleatidase precursor | unknown |
| 49 | IPI00064382 | 64 kDa protein | unknown |
| 50 | IPI00027011 | Na-and CL-dependent nutral and basic amino acid transporter B(0+) | unknown |
| 51 | IPI00004307 | Lysosome-associated membrane glycoprotein 3 precursor | related |
| 52 | IPI00334453 | Similar to RIKEN cDNA 1810059G22 | unknown |
| 53 | IPI00293088 | Alpha-glucosidase | unknown |
| 54 | IPI00171411 | Golgi phosphoprotein 2 | unknown |
| 55 | IPI00020407 | Alpha-1,6-mannosylglycoprotein 6-beta-GlcNAc transferase V | unknown |
| 56 | IPI00024929 | adipocyte-specific adhesion molecule | unknown |

| 58 | IPI00016627 | isoform 4 of Uncharacterized protein C1orf159 precursor | unknown |
| 59 | IPI00021275 | Isoform 1 of Ephrin type-B receptor 2 precursor | related |
| 60 | IPI00017529 | Isoform 1 of Lymphocyte function-associated antigen 3 precursor | unknown |
| 61 | IPI00072743 | Isoform 1 of Claudin domain-containing protein 1 | unknown |
| 62 | IPI00397393 | PREDICTED: similar to K06A9. 1b isoform 2 | unknown |
| 63 | IPI00025846 | Isoform 2A fo Desmocollin-2 precursor | unknown |
| 64 | IPI00030941 | Tetraspanin-3 | unknown |
| 65 | IPI00008901 | Epithelial membrane protein 3 | unknown |

| No. | IPI number | | Glycoprotein |
|---|---|---|---|
| 1 | IPI00002541 | CL1-5 specific protein | Yes |
| 2 | IPI00008494 | CD44 antigen isoform 5 precursor | Yes |
| 3 | IPI00009456 | Intercellular adhesion molecule 1 precursor | Potential |
| 4 | IPI00010338 | NT5E 5'-nucleotidase precursor | Potential |
| 5 | IPI00010676 | Tissue factor precursor | Yes |
| 6 | IPI00010737 | Urokinase plasminogen activator surface receptor precursor | Potential |
| 7 | IPI00012023 | Thrombomodulin precursor | Yes |
| 8 | IPI00013744 | Amphiregulin precursor | Yes |
| 9 | IPI00020446 | Integrin alpha-2 precursor | Potential |
| 10 | IPI00031713 | CD82 antigen | Potential |
| 11 | IPI00032292 | CD70 antigen | Yes |
| 12 | IPI00152540 | Metalloproteinase inhibitor 1 precursor | Yes |
| 13 | IPI00215995 | CD109 antigen precursor | Potential |
| 14 | IPI00216514 | Alpha-3A of Integrin alpha-3 precursor | Yes |
| 15 | IPI00221224 | Leukocyte surface antigen CD47 precursor | Yes |
| 16 | IPI00290039 | Aminopeptidase N | Potential |
| 17 | IPI00419724 | CUB domain-containing protein 1 precursor | Yes |
| 18 | IPI00552671 | Semaphorin 4B precursor | Potential |
| 19 | IPI00018274 | Plexin A- precursor | Yes |
| 20 | IPI00026941 | Epidermal growth factor receptor precursor | Potential |
| 21 | IPI00028150 | Serine protease 23 precursor | Potential |
| 22 | IPI00030431 | Neurotensin receptor type 1 | Yes |
| 23 | IPI00099650 | Anthrax toxin receptor 1 precursor | Potential |
| 24 | IPI00165438 | Jagged-1 precursor | Yes |
| 25 | IPI00337612 | Neuropilin 1 | Potential |
| 26 | IPI00644759 | Discoidin, CUB and LCCL domain-containing protein 1 precursor | Yes |
| | | 33 KDa protein | |

| | | | |
|---|---|---|---|
| 27 | IPI00026270 | Carboxypeptidase M precursor | Yes |
| 28 | IPI00289849 | Leucine-rich repeat and fibronectin type-III domain-containing protein 6 precursor | Potential |
| 29 | IPI00291262 | Clusterin precursor | Yes |
| 30 | IPI00296180 | Urokinase-type plasminogen activator precursor | Yes |
| 31 | IPI00396658 | Integrin alpha FG-GAP repeat containing 3 | Protein |
| 32 | IPI00465259 | Solute carrier family 15 member 4 | unknown |
| 33 | IPI00002406 | Lutheran blood group glycoprotein precursor (basal cell adhesion molecule) | Yes |
| 34 | IPI00008880 | Epithelial membrane protein 1 | Potential |
| 35 | IPI00009111 | Trophoblast glycoprotein precursor | Potential |
| 36 | IPI00011229 | Cathepsin D precursor | Potential |

| No. | IPI number | | Glycoprotein |
|---|---|---|---|
| 37 | IPI00012877 | CL1-5 specific protein | Potential |
| 38 | IPI00012989 | Interferon-alpha/beta receptor alpha chain precursor | Yes |
| 39 | IPI00013897 | Lysosomal alpha-mannosidase precursor | Yes |
| 40 | IPI00015102 | ADAM metallopeptidase domain 10 | Yes |
| 41 | IPI00015476 | CD166 antigen precursor | Potential |
| 42 | IPI00019381 | Neutral amino acid transporter A | Potential |
| 43 | IPI00020007 | Cell cycle control protein 50A | Potential |
| 44 | IPI00020431 | LMBR1 domain-containing protein 1 | Potential |
| 45 | IPI00022674 | TGF-beta receptor type-2 precursor | Potential |
| 46 | IPI00023814 | Oncostatin-M specific receptor subunit beta precursor | Yes |
| 47 | IPI00029273 | Neogenin precursor | Potential |
| 48 | IPI00029723 | Hepatocyte growth factor receptor precursor (et proto-oncogene) | Yes |
| 49 | IPI00056478 | Follistatin-related protein 1 precursor | Potential |
| 50 | IPI00157687 | Immunoglobulin superfamily member 8 precursor | Potential |
| 51 | IPI00217343 | Platelet endothelial cell adhesion molecule precursor | Unknown |
| 52 | IPI00235003 | CD302 antigen precursor | Potential |
| 53 | IPI00293088 | Tumor necrosis factor receptor superfamily, member 6 (Fas) | Unknown |
| 54 | IPI00296869 | 106 kDa protein | Potential |
| 55 | IPI00297124 | Proteinase-activated receptor 1 precursor (coagulation factor II (thrombin) receptor) | Potential |
| 56 | IPI00299116 | Interleukin-6 receptor sunbunit beta precursor | Potential |
| 57 | IPI00306835 | Podocalyxin-like protein 1 precursor | Potential |
| 58 | IPI00328263 | Fukutin | Yes |
| 59 | IPI00332887 | Membrane-bound transcription factor site-2 protease | Yes |
| 60 | IPI00334453 | Signal-regulatory protein alpha precursor | Unknown |
| 61 | IPI00334934 | Transmembrane protein 179B(LOC374395 Similar to RIKEN cDNA 1810059G22) | Potential |
| | | Solute carrier family 36 member 4 (28 kDa protein) | |

| 62 | IPI00375879 | Hypothetical protein LOC57613 | Unknown |
| 63 | IPI00553238 | Tweety homolog 3 (Drosophila) (CDNA FLJ42617 fis, clone BRACE3014807) | Potential |
| 64 | IPI00644618 | Myelin protein zero-like protein 1 precursor | Potential |
| 65 | IPI00844210 | Sodium/potassium-transporting ATPase subunit beta-1 | Yes |
| 66 | IPI00003802 | Alpha-mannosidase 2 | Yes |
| 67 | IPI00556655 | LAMP1 protein | Yes |
| 68 | IPI00024929 | Adipocyte adhesion molecule precursor | Potential |
| 69 | IPI00181391 | Meningioma expressed antigen 5 (hyaluronidase) (Bifunctional protein NCOAT) | Unknown |
| 70 | IPI00220350 | Integrin beta-3 precursor (CD61) | Yes |

| No. | IPI number | Name | Classification | Glycoprotein |
|---|---|---|---|---|
| 1 | IPI00235622 | CDCP1 Isoform 3 of CUB domain-containing protein 1 precursor | FucT4 | Potential |
| 2 | IPI00456589 | GALNT11 Isoform 1 of Polypeptide N-acetylgalactosaminyltransferase 11 | FucT4 | Potential |
| 3 | IPI00004962 | GOLIM4 Golgi integral membrane protein 4 | FucT4 | YES |
| 4 | IPI00009198 | TFPI2 Tissue factor pathway inhibitor 2 precursor | FucT4 | Potential |
| 5 | IPI00745220 | HLA-C;LOC730410;HLA-A;HLA-B;HLA-A29.1;MICA HLA class I histocompatibility antigen,A-25 alpha chain precursor | FucT4 | Potential |
| 6 | IPI00002478 | ECE1 Isoform B of Endothelin-converting enzyme 1 | FucT6 | YES |
| 7 | IPI00018274 | EGFR Isoform 1 of Epidermal growth factor receptor precursor | FucT6 | YES |
| 8 | IPI00151036 | RNF13 RING finger protein 13 | FucT6 | unknown |
| 9 | IPI00154588 | SPPL2A Signal peptide peptidase-like 2A | FucT6 | unknown |
| 10 | IPI00216514 | CD47 Isoform OA3-293 of Leukocyte surface antigen CD47 precursor | FucT6 | YES |
| 11 | IPI00328243 | PLD3 Phospholipase D3 | FucT6 | Potential |
| 12 | IPI00009111 | TPBG Trophoblast glycoprotein precursor | FucT6 | Potential |
| 13 | IPI00010338 | F3 Tissue factor precursor | FucT6 | Potential |
| 14 | IPI00018276 | SEZ6L2 Type I transmembrane receptor precursor | FucT6 | unknown |
| 15 | IPI00019472 | SLC1A5 Neutral amino acid transporter B | FucT6 | Potential |
| 16 | IPI00020557 | LRP1 Prolow-density lipoprotein receptor-related protein 1 precursor | FucT6 | YES |
| 17 | IPI00023868 | ABCC2 Canalicular multispecific organic anion transporter 1 | FucT6 | Potential |
| 18 | IPI00027745 | GUSB Isoform Long of Beta-glucuronidase precursor | FucT6 | YES |
| 19 | IPI00029273 | MET Isoform 1 of Hepatocyte growth factor receptor precursor | FucT6 | Potential |
| 20 | IPI00031456 | SLC29A2 Isoform 1 of Equilibrative nucleoside transporter 2 | FucT6 | YES |
| 21 | IPI00151710 | TMEM16F Transmembrane protein 16F | FucT6 | Potential |
| 22 | IPI00165438 | NRP1 Muscle type neuropilin 1 | FucT6 | YES |
| 23 | IPI00169285 | P76 LAMA-like protein 2 precursor | FucT6 | Potential |
| 24 | IPI00176427 | CADM4 Cell adhesion molecule 4 precursor | FucT6 | Potential |

| | | | |
|---|---|---|---|
| 25 | IPI00215995 | ITGA3 Isoform Alpha-3A of Integrin alpha-3 precursor | FucT6 | Potential |
| 26 | IPI00217481 | GPR126 Developmentally regulated G-protein coupled receptor beta 1 | FucT6 | YES |
| 27 | IPI00220530 | SPPL2B Isoform 3 of Signal peptide peptidase-like 2B | FucT6 | unknown |
| 28 | IPI00221240 | LNPEP Isoform 2 of Leucyl-cystinyl aminopeptidase | FucT6 | Potential |
| 29 | IPI00290328 | PTPRJ Receptor-type tyrosine-protein phosphatase eta precursor | FucT6 | YES |
| 30 | IPI00306604 | ITGA5 Integrin alpha-5 precursor | FucT6 | Potential |
| 31 | IPI00332887 | SIRPA signal-regulatory protein alpha precursor | FucT6 | YES |
| 32 | IPI00334934 | SLC36A4 28 kDa protein | FucT6 | unknown |
| 33 | IPI00394808 | EMB Embigin precursor | FucT6 | Potential |
| 34 | IPI00552671 | PLXNA1 Plexin-A1 precursor | FucT6 | Potential |
| 35 | IPI00807403 | ALCAM Isoform 2 of CD166 anitgen precursor | FucT6 | Potential |
| 36 | IPI00853369 | PLXNB2 Plexin-B2 precursor | FucT6 | YES |
| 37 | IPI00012503 | PSAP Isoform Sap-mu-0 of Proactivator polypeptide precursor | FucT6 | YES |
| 38 | IPI00018901 | GGT1 Isoform 1 of Gamma-glutamyltranspeptidase 1 precursor | FucT6 | YES |
| 39 | IPI00045928 | SLC9A7 Sodium/hydrogen exchanger 7 | FucT6 | unknown |
| 40 | IPI00441344 | GLB1 Beta-galactosidase precursor | FucT6 | Potential |

| No. | IPI number | Name | Classification | Glycoprotein |
|---|---|---|---|---|
| 41 | IPI00002103 | TMEM181 similar to G protein-coupled receptor 178 | FucT6 | unknown |
| 42 | IPI00011241 | GPR39 Probable G-protein coupled receptor 39 | FucT6 | Potential |
| 43 | IPI00013449 | TSPAN6 Tetraspanin-6 | FucT6 | Potential |
| 44 | IPI00020007 | LMBRD1 Isoform 1 of LMBR1 domain-containing protein 1 | FucT6 | Potential |
| 45 | IPI00020431 | TGFBR2 Isoform 1 of TGF-beta receptor typ-2 precursor | FucT6 | Potential |
| 46 | IPI00021302 | SUSD2 Sushi domain-containing protein 2 precursor | FucT6 | YES |
| 47 | IPI00022462 | TFRC Transferrin receptor protein 1 | FucT6 | YES |
| 48 | IPI00165064 | ODZ3 Uncharacterized protein ODZ3 | FucT6 | Potential |
| 49 | IPI00293074 | SLC44A2 Isoform 2 of Choline transporter-like protein 2 | FucT6 | Potential |
| 50 | IPI00297124 | IL6ST Isoform 1 of Interleukin-6 receptor subunit beta precursor | FucT6 | YES |
| 51 | IPI00329054 | OSTM1 Osteopetrosis-associated transmembrane protein 1 precursor | FucT6 | unknown |
| 52 | IPI00397229 | CD97 Isoform 1 of CD97 antigen precursor | FucT6 | Potential |
| 53 | IPI00452161 | MCOLN1 Isoform 1 of Mucolipin-1 | FucT6 | unknown |
| 54 | IPI00000736 | TSPAN15 Tetraspanin-15 | FucT6 | Potential |
| 55 | IPI00008148 | GFRA1 Isoform 1 of GDNF family receptor alpha-1 precursor | FucT6 | Potential |
| 56 | IPI00012545 | TGOLN2 Isoform TGN51 of Trans-Golgi network integral membrane protein 2 precursor | FucT6 | Potential |
| 57 | IPI00017232 | SLC24A6 Uncharacterized protein SLC24A6 | FucT6 | unknown |
| 58 | IPI00017529 | CD58 Isoform 1 of lymphocyte function-associated antigen 3 precursor | FucT6 | YES |
| 59 | IPI00021384 | FucT6 Isoform 1 of Alpha-(1,3)-fucosyltransferase | FucT6 | Potential |
| 60 | IPI00023814 | NEO1 Isoform 1 of Neogenin precursor | FucT6 | YES |
| 61 | IPI00029606 | ADAM17 Isoform B of ADAM 17 precursor | FucT6 | Potential |
| 62 | IPI00044600 | SORCS2 VPS10 domain-containing receptor SorCS2 precursor | FucT6 | Potential |
| 63 | IPI00217766 | SCARB2 Lysosome membrane protein 2 | FucT6 | YES |
| 64 | IPI00337495 | PLOD2 Isoform 2 of Procollagen-lysine,2-oxoglutarate 5-dioxygenase 2 precursor | FucT6 | Potential |

| | | | | |
|---|---|---|---|---|
| 65 | IPI00398020 | ODZ3 Teneurin-3 | FucT6 | Potential |
| 66 | IPI00550382 | SLC29A1 Equilibrative nucleoside transporter 1 | FucT6 | YES |
| 67 | IPI00844210 | ATP1B1 Isoform 1 of Sodium/potassium-transporting ATPase subunit beta-1 | FucT6 | YES |
| 68 | IPI00019275 | CD276 Isoform 2 of CD276 antigen precursor | FucT6 | Potential |
| 69 | IPI00289819 | IGF2R Cation-independent mannose-6-phosphate receptor precursor | FucT6 | YES |
| 70 | IPI00411750 | LOC728226 Uncharacterized protein ENSP00000341691 | FucT6 | unknown |
| 71 | IPI00227493 | LOC442497;SLC3A2 4F2 cell-surface antigen heavy chain | FucT4&FucT6 | YES |
| 72 | IPI00019906 | BSG Isoform 2 of Basigin precursor | FucT4&FucT6 | YES |
| 73 | IPI00003813 | CADM1 Isoform 1 of Cell adhesion molecule 1 precursor | FucT4&FucT6 | YES |
| 74 | IPI00004503 | LAMP1 lysosomal-associated membrane protein 1 | FucT4&FucT6 | YES |
| 75 | IPI00106689 | TMEM87A Isoform 2 of Transmembrane protein 87A precursor | FucT4&FucT6 | Potential |
| 76 | IPI00152540 | CD109 Isoform 1 of CD109 antigen precursor | FucT4&FucT6 | YES |
| 77 | IPI00465259 | SLC15A4 Solute carrier family 15 member 4 | FucT4&FucT6 | unknown |
| 78 | IPI00219421 | EPHB2 Isoform 2 of Ephrin type-B receptor 2 precursor | FucT4&FucT6 | Potential |
| 79 | IPI00337612 | DCBLD1 Discoidin, CUB and LCCL domain-containing protein 1 precursor | FucT4&FucT6 | Potential |
| 80 | IPI00012102 | GNS N-acetylglucosamine-6 sulfatase precursor | FucT4&FucT6 | YES |

| No. | IPI number | Name | Classification | Glycoprotein |
|---|---|---|---|---|
| 81 | IPI00043883 | SLC46A1 isoform 1 of Proton-coupled folate transporter | FucT4&FucT6 | unknown |
| 82 | IPI00015102 | ALCAM isoform 1 of CD166 antigen precursor | FucT4&FucT6 | YES |
| 83 | IPI00216620 | PPAP2C Lipid phosphate phosphohydrolase 2 | FucT4&FucT6 | Potential |
| 84 | IPI00002541 | CD44 CD44 antigen isoform 5 precursor | FucT4&FucT6 | YES |
| 85 | IPI00009507 | SYPL1 Isoform 1 of Synaptophysin-like protein 1 | FucT4&FucT6 | Potential |
| 86 | IPI00005707 | MRC2 Macrophage mannose receptor 2 precursor | FucT4&FucT6 | YES |
| 87 | IPI00011229 | CTSD Cathepsin D precursor | FucT4&FucT6 | YES |
| 88 | IPI00022810 | CTSC Dipeptidyl-peptidase 1 precursor | FucT4&FucT6 | YES |
| 89 | IPI00026941 | PRSS23 Serine protease 23 precursor | FucT4&FucT6 | Potential |
| 90 | IPI00029751 | CNTN1 Isoform 1 of Contactin-1 precursor | FucT4&FucT6 | YES |
| 91 | IPI00030941 | TSPAN3 Tetraspanin-3 | FucT4&FucT6 | Potential |
| 92 | IPI00152418 | CD55 Decay-accelerating factor splicing variant 4 | FucT4&FucT6 | YES |
| 93 | IPI00220194 | SLC2A1 Solute carrier family 2, facilitated glucose transporter member 1 | FucT4&FucT6 | YES |
| 94 | IPI00025869 | GLA Alpha-galactosidase A precursor | FucT4&FucT6 | YES |
| 95 | IPI00396658 | ITFG3 Isoform 2 of Protein ITFG3 | FucT4&FucT6 | Potential |
| 96 | IPI00003909 | SLC2A3 Solute carrier family 2, facilitated glucose transporter member 3 | FucT4&FucT6 | Potential |
| 97 | IPI00021267 | EPHA2 Ephrin type-A receptor 2 precursor | FucT4&FucT6 | Potential |
| 98 | IPI00027728 | SLC7A1 High affinity cationic amino acid transporter 1 | FucT4&FucT6 | Potential |
| 99 | IPI00290826 | TMEM157 Transmembrane protein 157 precursor | FucT4&FucT6 | Potential |
| 100 | IPI00184474 | GPR107 Isoform 3 of Protein GPR107 precursor | FucT4&FucT6 | Potential |
| 101 | IPI00291262 | CLU Clusterin precursor | FucT4&FucT6 | YES |
| 102 | IPI00009030 | LAMP2 Isoform LAMP-2A of Lysosome-associated membrane glycoprotein 2 precursor | FucT4&FucT6 | YES |
| 103 | IPI00011578 | NPTN Isoform 1 of Neuroplastin precursor | FucT4&FucT6 | Potential |
| 104 | IPI00011662 | SPINT2 Kunitz-type protease inhibitor 2 precursor | FucT4&FucT6 | YES |

| | | | | |
|---|---|---|---|---|
| 105 | IPI00027078 | CPD Carboxypeptidase D precursor | FucT4&FucT6 | YES |
| 106 | IPI00028931 | DSG2 Desmoglein-2 precursor | FucT4&FucT6 | YES |
| 107 | IPI00030431 | ANTXR1 Isoform 1 of Anthrax toxin receptor 1 precursor | FucT4&FucT6 | Potential |
| 108 | IPI00032292 | TIMP1 Metalloproteinase inhibitor 1 precursor | FucT4&FucT6 | unknown |
| 109 | IPI00215998 | CD63 CD63 antigen | FucT4&FucT6 | YES |
| 110 | IPI00217345 | B3GNT2 isoform 2 of UDP-GlcNAc:betaGal beta-1,3-N-acetylglucosaminyltransferase 2 | FucT4&FucT6 | YES |
| 111 | IPI00290039 | CDCP1 Isoform 1 of CUB domain-containing protein 1 precursor | FucT4&FucT6 | Potential |
| 112 | IPI00298702 | SLC39A6 solute carrier family 39 (zinc transporter), member 6 isoform 1 | FucT4&FucT6 | YES |
| 113 | IPI00644759 | GLG1 33 kDa protein | FucT4&FucT6 | YES |
| 114 | IPI00022558 | MPZL1 isoform 1 of Myelin protein zero-like protein 1 precursor | FucT4&FucT6 | YES |
| 115 | IPI00029741 | ITGB5 Integrin beta-5 precursor | FucT4&FucT6 | Potential |
| 116 | IPI00008303 | NAGPA Isoform 1 of N-acetylglucosamine-1-phosphodiester alpha-N-acetylglucosaminidase precursor | FucT4&FucT6 | Potential |
| 117 | IPI00009629 | ST3GAL1 CMP-N-acetylneuraminate-beta-galactosamide-alpha-2,3-sialyltransferase | FucT4&FucT6 | Potential |
| 118 | IPI00168812 | PTK7 PTK7 protein tyrosine kinase 7 isoform d precursor | FucT4&FucT6 | YES |
| 119 | IPI00303401 | C1orf75 Transmembrane protein C1orf75 | FucT4&FucT6 | unknown |
| 120 | IPI00101374 | TM9SF1 Transmembrane 9 superfamily protein member 1 precursor | FucT4&FucT6 | Potential |

*FIG. 14C-2*

TAILORED GLYCOPROTEOMIC METHODS FOR THE SEQUENCING, MAPPING AND IDENTIFICATION OF CELLULAR GLYCOPROTEINS

RELATED APPLICATIONS

This application claims priority to U.S. Ser. No. 60/896,777, filed on Mar. 23, 2007, titled "Pro-alkynyl sugar analogs for the labeling and visualization of glycoconjugates in vivo" and U.S. Ser. No. 60/896,787, filed on Mar. 23, 2007, titled "Pro-glycoproteomic probes for fluorescent imaging of fucosylated glycans in vivo," the entirety of these applications hereby incorporated by reference.

GOVERNMENT SUPPORT

This disclosure was supported, in whole or in part, by U.S. Public Health Service grants CA087660 and GM44154 from the National Institutes of Health.

SEQUENCE LISTING

This application contains a sequence listing, submitted in both paper via EFS and Computer Readable Form (CRF) and filed electronically via EFS. The computer readable copy has the file name "07395-050800-ST25.txt," is 86,339 bytes in size (measured in Windows XP), and was created Jul. 14, 2008.

FIELD OF THE DISCLOSURE

The present disclosure relates to tailored glycoproteomic methods, and more particularly to methods for the sequencing, mapping and identification of cellular glycoproteins using saccharide-selective bioorthogonal probes.

BACKGROUND

Glycans are integral components of biological systems with far reaching activities, many of which are only beginning to be understood. Glycans constitute the most abundant and diverse class of biomolecules found in natural systems, consisting of oligosaccharide chains that are present as independent polysaccharides (e.g., cellulose, an important structural component in plants; and heparin sulfate, an import factor of blood clotting in mammals) or as glycoconjugates with lipids (glycolipids), proteins (glycoproteins, proteoglycans), and small molecule natural products (e.g., antibiotics such as erythromycin, vancomycin, and teicoplanin).

Glycans play a role in almost every aspect of cellular activity. Most glycans in higher eukaryotes are produced in the secretory pathway by glycosylation events, which entail the enzymatic transfer of saccharides or oligosaccharide chains onto lipids and proteins. Protein glycosylation is a complex co- or post-translational process that modifies the majority of the human proteome and serves a vast array of biological functions. Protein glycosylation exerts intrinsic effects on structure, from mediating folding and oligimerization, to increasing stability, solubility, and circulation time. Inside of the cell, glycans affect recognition, binding, targeting, and cellular distribution. At the cell surface, glycans are prominently displayed where they are involved in a host of molecular recognition events that modulate important physiological processes, such as cell-cell adhesion, inflammation, angiogenesis, coagulation, embryogenesis, differentiation, communication, and a myriad of other cellular signaling pathways.

Cell surface glycans have also been associated with physiological dysfunctions such as bacterial and viral infection, rheumatoid arthritis, and tumor progression. In the latter case, several types of oncofetal and aberrant glycans have been established to correlate with malignancy, invasiveness, inflammation and cancer metastasis. In particular, altered terminal fucosylation and sialylation, which are believed to result from changes in expression locations and levels of fucosyltransferases (an enzyme that transfers a fucose from a donor substrate to an acceptor substrate, a glycoconjugate or glycan) and sialyltransferases (an enzyme that transfers a sialic acid from a donor substrate to an acceptor substrate, a glycoconjugate or glycan) respectively, are associated with tumor malignancy. For example, glycan determinants like Lewis y, Lewis x, sialyl Lewis x, sialyl Lewis a, sialyl Tn, Globo H, fucosyl GM1, and polysialic acid are expressed at elevated levels in neoplastic tissues. For this reason, these epitopes are promising and eagerly pursued targets for glycan-based vaccines. Additionally, several congenital glycosylation disorders, lysosomal storage disorders, and immunological diseases have been linked with dysregulation of glycan catabolism/metabolism. Although known to be involved in physiological and pathophysiological events, the identification of many glycan structures and delineation of their mode of action at the molecular level has been complicated by their underpinning complexity.

Glycan complexity results from many factors. They are synthesized in a non-templated, post-translational process, which means that sites of glycoconjugate glycosylation and structures within them have proven, thus far, to be minimally predictable. This also means that glycans cannot be genetically manipulated in a similar fashion to DNA and proteins. Glycans are synthesized in the secretory pathway by a suite of enzymes that are subject to multifaceted controls. The end glycan products can have enormous structural complexity (many possible glycan structures, the diversity of which is also a function of the sugar building blocks), structural microheterogeneity (multiple different glycan structures attached to a glycoconjugate at the same position), and structural macro-heterogeneity (multiple sites and types of glycan attachment; for example, glycoproteins can be N-linked at Asn residues, or O-linked at Ser/Thr resides). Heterogeneity in glycan structures appears to be dynamically regulated and functionally significant, governing multivalent interactions the cell surface. Heterogeneity and multivalentcy complicate structure-function studies and the isolation of homogenous glycans in meaningful amounts from natural sources is nearly impossible. For the procurement of homogenous glycoconjugates/glycans synthesis is the only viable route, but remains one of the most formidable challenges in glycobiology.

The link between glycan activity and complexity has presented major challenges to deciphering their activities on an individual protein, let alone, proteomic scale. Among the challenges facing global analysis are development of general methods for isolating glycans from complex proteomes; determining saccharide composition, site of protein modification, and fraction occupancy; and understanding the direct roles of glycans in cellular function and dysfunction.

Specific glycan-tagging systems provide a powerful method for probing the structure of heterogeneous glycans. The key to glycan tagging entails incorporating modified sugars derivatized with chemical reporting groups into cellular glycans (typically via the normal biosynthetic pathways, a process known as metabolic oligosaccharide engineering, or MOE) and then detecting the tagged-glycans by labeling their chemical reporting groups with a complementary probe that chemically reacts with them in a specific manner. Many selective chemical probing techniques have been used for performing chemistry with chemical reporting group-tagged glycoconjugates in cells. These methods include bioorthogonal reactions such as ketoneaminooxy/hydrazide ligation, Staudinger ligation, Michael addition, and the strain-promoted, and Cu(I)-catalyzed [3+2] azide-alkyne cycloaddition (CuAAC). Several chemical reporting groups are tolerated and successfully incorporated into glycoconjugates using MOE, including ketones, thiols, photoreactive groups, azides, and alkynes. These reporting sugars have been labeled with tags such as FLAG peptides, biotin, and fluorescent or fluorogenic molecules. The strength of these systems is that the labeled glycan products have the potential to be manipulated for specific glycan studies involving: enrichment and glycoproteomic analysis by means of mass spectrometry detection and/or quantitation by flow cytometry or visualization through microscopy to obtain information about glycan localization, trafficking, and dynamics.

The incorporation of exogenous natural or unnatural sugars into glycans has been achieved by cellular biosynthetic pathways. These processes involve multistep enzymatic transformations that render free sugars in the cytosol into nucleotide-donor sugars, the substrates for glycosyltransferases. In the case of fucose (Fuc), a salvage pathway consisting of Fuc kinase and GDP-Fuc (guanosine diphosphate fucose) pyrophosphorylase contributes to the production of GDP-Fuc, which is then exploited by fucosyltransferases (FucTs) located in the Golgi apparatus to add Fuc onto glycoconjugates. Modifications at the 6-position of Fuc are tolerated by the salvage pathway and FucTs. In the sialic acid (NeuAc) biosynthetic pathway, the precursor N-acetylmannosamine (ManNAc) is derived from GlcNAc or UDP-GlcNAc through specific epimerases, then sequentially converted to sialic acid by the cytosolic enzymes ManNAc 6-kinase, sialic acid-9-phosphate synthase, and sialic acid-9-phosphate phosphatase. CMP-NeuAc is subsequently formed in the nucleus, and transported to the Golgi apparatus for glycan elaboration by sialyltransferases. Studies on metabolic delivery of N-acetylmannosamine (ManNAc) analogs show that N-acyl chains up to five carbon atoms long and bulky aromatic groups are tolerated by the sialic acid biosynthetic pathway.

Prior glycoprotein probes have limited utility due to issues of cellular toxicity. The incorporation of exogenous natural or unnatural sugars comprising non-toxic probes into glycans by cellular biosynthetic pathways is important to study aberrant glycosylation. Further understanding of the molecular details and correlations between altered glycosylation and pathological status is of great interest and is likely to provide useful information for diagnosis and disease prognosis, in addition to unveiling new therapeutic targets.

SUMMARY OF THE DISCLOSURE

Details concerning method for metabolic oligosaccharide engineering (MOE) which allows cellular glycans to be tagged with chemical reporting groups in vivo, through the incorporation of chemically modified building block analogs/precursors that closely resemble natural sugars are detailed in U.S. Ser. No. 60/896,787. The above-mentioned tagged cellular glycans in some instances may be labeled based on the Cu(I)-catalyzed [3+2] azide-alkyne cycloaddition (CuAAC) probe, which is rapid, versatile, and provides specific covalent labeling. The CuAAC probe includes one of a visual probe and a fluorogenic probe. The visual probe may comprise a biotin azide group and the fluorogenic probe may comprise a coumarin group. In some instances the CuAAC probe includes a biotin azide group as detailed in U.S. Ser. No. 60/896,777.

According to aspects illustrated herein, there is provided a method of harvesting peptide fragments that includes: presenting an alkynyl-derivatized sugar to a cell, wherein the alkynyl-derivatized sugar has an alkynyl functional group, and wherein the cell is capable of producing a glycoprotein; incorporating the alkynyl-derivatized sugar into the cell, wherein the alkynyl-derivatized sugar is subsequently used by the cell to produce a tagged glycoprotein, and wherein the tagged glycoprotein includes a glycan portion, a peptide portion, and the alkynyl functional group; reacting the tagged glycoprotein with a probe to produce a labeled glycoprotein, wherein the labeled glycoprotein includes the glycan portion, the peptide portion, the alkynyl functional group and the probe; capturing the labeled glycoprotein onto a solid support, wherein the solid support is labeled with a binding moiety capable of binding to the probe of the labeled glycoprotein; and washing the solid support with an enzyme digestion to remove peptide fragments from the peptide portion of the labeled glycoprotein, resulting in the peptide fragments being harvested.

According to aspects illustrated herein, there is provided a method for identifying peptide fragments from an entire peptide portion of a glycoprotein that includes: presenting an alkynyl-derivatized sugar to a cell, wherein the alkynyl-derivatized sugar has an alkynyl functional group, and wherein the cell is capable of producing a glycoprotein; incorporating the alkynyl-derivatized sugar into the cell, wherein the alkynyl-derivatized sugar is subsequently used by the cell to produce a tagged glycoprotein, and wherein the tagged glycoprotein includes a glycan portion, a peptide portion, and the alkynyl functional group; reacting the tagged glycoprotein with a probe to produce a labeled glycoprotein, wherein the labeled glycoprotein includes the glycan portion, the peptide portion, the alkynyl functional group and the probe; capturing the labeled glycoprotein onto a solid support, wherein the solid support is labeled with a binding moiety capable of binding to the probe of the labeled glycoprotein; washing the solid support with an enzyme digestion to remove peptide fragments from the peptide portion of the labeled glycoprotein; harvesting the peptide fragments; and analyzing the peptide fragments using mass spectrometry-based proteomics, resulting in the peptide fragments being identified.

According to aspects illustrated herein, there is provided a method for determining a site of glycosylation on a glycoprotein that includes: presenting an alkynyl-derivatized sugar to a cell, wherein the alkynyl-derivatized sugar has an alkynyl functional group, and wherein the cell is capable of producing a glycoprotein; incorporating the alkynyl-derivatized sugar into the cell, wherein the alkynyl-derivatized sugar is subsequently used by the cell to produce a tagged glycoprotein, and wherein the tagged glycoprotein includes a glycan portion, a peptide portion, and the alkynyl functional group; reacting the tagged glycoprotein with a probe to produce a labeled glycoprotein, wherein the labeled glycoprotein includes the glycan portion, the peptide portion, the alkynyl functional group and the probe; capturing the labeled glycoprotein onto a solid support, wherein the solid support is labeled with a binding moiety capable of binding to the probe of the labeled glycoprotein; washing the solid support with an enzyme digestion to remove peptide fragments from the peptide portion of the labeled glycoprotein; harvesting the peptide fragments; and analyzing the peptide fragments using mass spectrometry-based proteomics, resulting in the site of glycosylation on the glycoprotein being determined.

According to aspects illustrate herein, there is provided a method of determining whether sites of glycosylation found on a glycoprotein from an abnormal cell are present in a proteome of a healthy cell that includes: presenting an alkynyl-derivatized sugar to the abnormal cell, wherein the alkynyl-derivatized sugar has an alkynyl functional group, and wherein the abnormal cell is capable of producing a glycoprotein; incorporating the alkynyl-derivatized sugar into the abnormal cell, wherein the alkynyl-derivatized sugar is subsequently used by the abnormal cell to produce a tagged glycoprotein, and wherein the tagged glycoprotein includes a glycan portion, a peptide portion, and the alkynyl functional group; reacting the tagged glycoprotein with a probe to produce a labeled glycoprotein, wherein the labeled glycoprotein includes the glycan portion, the peptide portion, the alkynyl functional group and the probe; capturing the labeled glycoprotein onto a solid support, wherein the solid support is labeled with a binding moiety capable of binding to the probe of the labeled glycoprotein; washing the solid support with an enzyme digestion to remove peptide fragments of the glycoprotein from the abnormal cell; harvesting the peptide fragments of the glycoprotein from the abnormal cell; analyzing the peptide fragments of the glycoprotein from the abnormal cell using mass spectrometry-based proteomics, resulting in the sites of glycosylation on the glycoprotein from the abnormal cell being determined; presenting an alkynyl-derivatized sugar to the healthy cell, wherein the alkynyl-derivatized sugar has an alkynyl functional group, and wherein the healthy cell is capable of producing a proteome; incorporating the alkynyl-derivatized sugar into the healthy cell, wherein the alkynyl-derivatized sugar is subsequently used by the healthy cell to produce a tagged proteome, and wherein the tagged proteome includes at least one of a glycan portion, a peptide portion, and the alkynyl functional group; reacting the tagged proteome with a probe to produce a labeled proteome, wherein the labeled proteome includes the glycan portion, the peptide portion, the alkynyl functional group and the probe; capturing the labeled proteome onto a solid support, wherein the solid support is labeled with a binding moiety capable of binding to the probe of the labeled proteome; washing the solid support with an enzyme digestion to remove peptide fragments from the peptide portion of the labeled proteome from the healthy cell; harvesting the peptide fragments of the proteome from the healthy cell; analyzing the peptide fragments of the proteome from the healthy cell using mass spectrometry-based proteomics, resulting in the peptide fragments being identified; and determining whether sites of glycosylation found on the glycoprotein from the abnormal cell are present in the proteome of the healthy cell.

In an exemplary implementation, the alkynyl-derivatized saccharide is selected from the group consisting of an alkynyl-derivatized fucose analog, an alkynyl-derivatized sialic acid analog and an alkynyl-derivatized sialic acid precursor. For example, the alkynyl-derivatized fucose analog may be 1,2,3,4-tetraacetyl alkynyl fucose. For example, the alkynyl-derivatized sialic acid precursor may be N-acetylmannosamine. For example, the alkynyl-derivatized sialic acid precursor may be 1,3,4,6-tetra-O-acetyl-N-4-pentynoylmannosamine. In a further exemplary implementation, the alkynyl-derivatized saccharide may be a peracetylated alkynyl-derivatized saccharide.

In an exemplary implementation, the cellular glycoprotein is glycosylated. For example, the cellular glycoprotein may be a N-glycosylated glycoprotein. For example, the cellular glycoprotein may be an O-glycosylated glycoprotein.

In an exemplary implementation, the enzyme digestion is a trypsin digestion which is capable of cleaving peptide bonds that exists between arginine or lysine residues with other amino acids (except praline) within the peptide portion of the tagged cellular glycoprotein. In an exemplary implementation, the enzyme digestion is a peptide-N-glycosidase F (PNGase F) digestion which hydrolyzes an amide bond that exists between the glycan portion of the tagged cellular glycoprotein and an Asn residue of the peptide portion.

The disclosed methods may be carried out on cells that are healthy or abnormal cell. In an exemplary implementation, the abnormal cell is selected from an improperly glycosylated cell, a low functioning cell, a cell having a lysosomal storage disorder and an infected cell (bacterial or viral). In a further aspect, the abnormal cell is a cancerous cell. In an exemplary implementation, the cancerous cell is selected from a cancer stem cell, leukemia cell, lymphoma cell, pancreatic cancer cell, non-small cell lung cancer cell, small cell lung cancer cell, colon cancer cell, central nervous system cancer cell, melanoma cell, ovarian cancer cell, a renal cancer cell, a prostate cancer cell line, and a breast cancer cell.

BRIEF DESCRIPTION OF THE FIGURES

FIG. 3 shows an exemplary implementation of how alkyne-tagged glycans can be labeled with Cu(I)-catalyzed [3+2] azide-alkyne cycloaddition (CuAAC) probes and visualized at the cell surface (A), in glycoprotein lysates (B) and intracellularly (C).

FIG. 6 shows categorization of sialylated N-linked glycoproteomic proteins isolated from prostate cancer (PC-3) cells treated with ManNAcyne and analyzed by the GIDmap method disclosed herein in terms of (a) identification of experimentally known (verified) or unknown (predicted by homology: potential; or never annotated: novel) N-glycosylation sites, (b) glycoprotein function, (c) and glycoprotein cellular location. Glycosylation sites, subcellular location, function and process were assessed by Swiss-Prot annotation.

FIGS. 7A-G show lists of the total individual N-linked glycopeptides from glycoproteomes from PC3 cells treated with ManNAcyne analyzed using the GIDmap method disclosed herein. Sites of glycosylation are starred in peptide sequences (listed under heading peptide) and residue numbers corresponding to glycosylation site are listed (under heading site).

FIG. 8 shows PNGase phase data for sialylated N-linked glycoproteomic proteins isolated from RWPE-I (normal) and PC-3 (cancerous) cells treated with ManNAcyne and analyzed by the GIDmap method disclosed herein. Subcellular location, function and process were assessed by Swiss-Prot annotation.

FIG. 9 shows PNGase phase data for sialylated N-linked glycoproteomic proteins isolated from CL1 (non-invasive) and CL1-5 (invasive) lung cancer cells treated with ManNAcyne and analyzed by the GIDmap method disclosed herein. Subcellular location, function and process were assessed by Swiss-Prot annotation.

FIG. 10 shows expression levels of ECE-1 and NRP-1 proteins in RWPE-I and PC-3 cells.

FIG. 11 shows that sialylation of ECE-1 and NRP-1 proteins is upregulated in prostate cancer (PC-3) cells. Immunoprecipitation (IP) with MALI1, a sialic acid specific lectin, before immunoblotting shows that sialylated proteins only found in samples derived from cancerous cells.

FIGS. 12A-B show lists of the unique sialylated N-linked glycoproteins identified from PC-3 prostate cancer cell line.

FIGS. 13A-B show lists of the unique sialylated N-linked glycoproteins identified from CL1-5 invasive lung cancer cell line.

FIGS. 14A-C show lists of the unique fucosylated N-linked glycoproteins identified from FucT4/6-overexpressing cell lines.

FIG. 15 shows the results from examining protein-expression of plexin B2 by immunoblotting.

DETAILED DESCRIPTION OF THE DISCLOSURE

Figure 1:
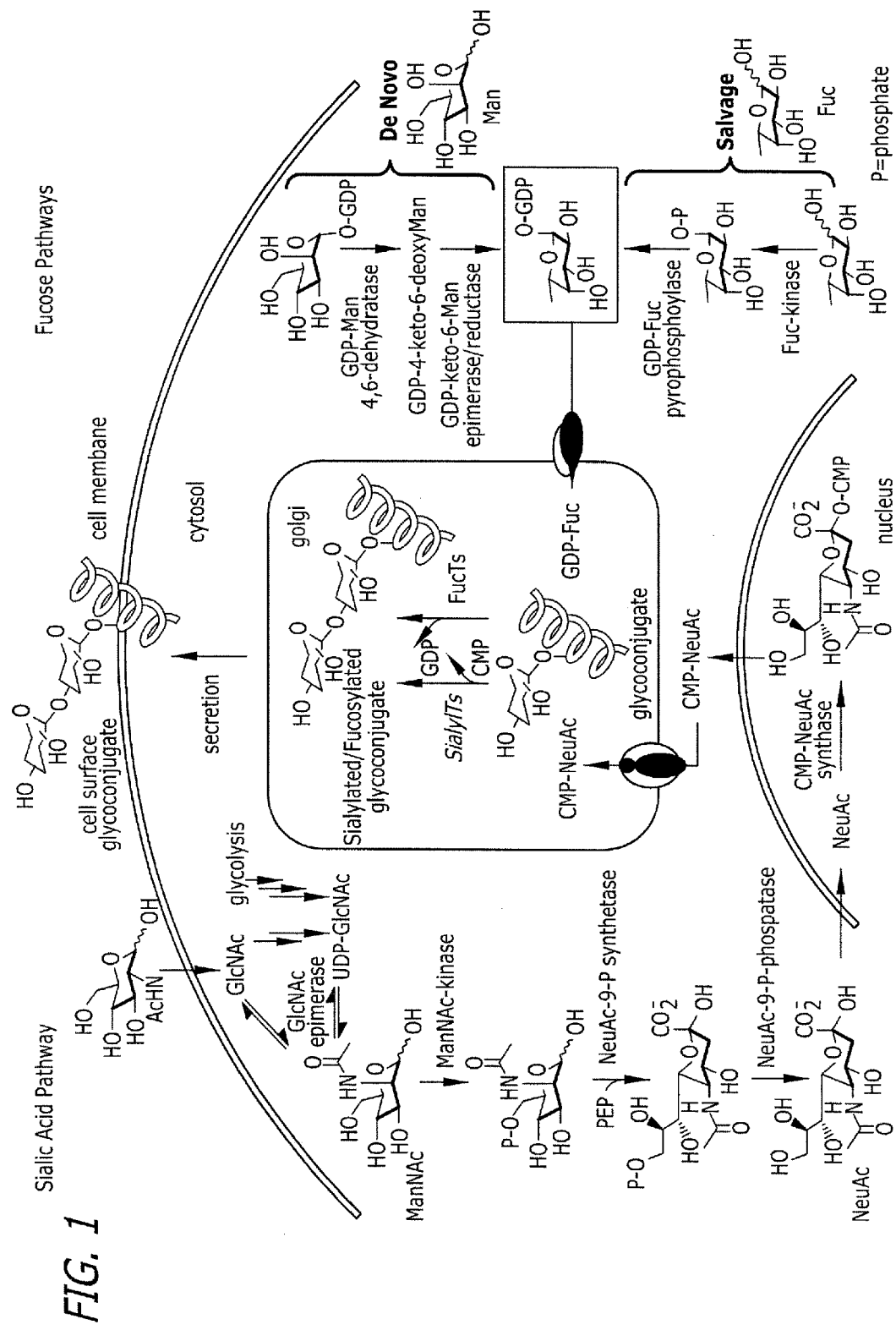
FIG. 1 is a schematic diagram showing biosynthetic pathways for sialylated and fucosylated glycoconjugates.

All scientific terms are to be given their ordinary meanings as understood by those of skill in the art, unless an alternate meaning is set forth below. In case of conflict, the definitions set forth in this specification shall control.

As used herein, the term "proteomics" refers to the study of the proteome, the entire complement of proteins expressed by a genome, cell, tissue or organism. Proteomics has largely been practiced through the separation of proteins by two dimensional gel electrophoresis. In the first dimension, the proteins are separated by isoelectric focusing, which resolves proteins on the basis of charge. In the second dimension, proteins are separated by molecular weight using SDS-PAGE. The gel is dyed with Coomassie Blue or silver to visualize the proteins. Spots on the gel are proteins that have migrated to specific locations. The mass spectrometer has augmented proteomics. Peptide mass fingerprinting identifies a protein by cleaving it into short peptides and then deduces the protein's identity by matching the observed peptide masses against a sequence database. Tandem mass spectrometry, on the other hand, can get sequence information from individual peptides by isolating them, colliding them with a non-reactive gas, and then cataloguing the fragment ions produced.

As used herein, the term "glycoproteomics" refers to a branch of proteomics that identifies, catalogs, and characterizes proteins containing carbohydrates as a post-translational modification. Glycoproteomics also refers to the study of a cell, tissue, or organism's glycan and glycoprotein content at any point in time.

As used herein, the term "glycan" refers to a polysaccharide, or oligosaccharide. Glycan is also used herein to refer to the carbohydrate portion of a glycoconjugate, such as a glycoprotein, glycolipid, glycopeptide, glycoproteome, peptidoglycan, lipopolysaccharide or a proteoglycan. Glycans usually consist solely of O-glycosidic linkages between monosaccharides. For example, cellulose is a glycan (or more specifically a glucan) composed of beta-1,4-linked D-glucose, and chitin is a glycan composed of beta-1,4-linked N-acetyl-D-glucosamine. Glycans can be homo or heteropolymers of monosaccharide residues, and can be linear or branched. Glycans can be found attached to proteins as in glycoproteins and proteoglycans. They are generally found on the exterior surface of cells. O- and N-linked glycans are very common in eukaryotes but may also be found, although less commonly, in prokaryotes. N-Linked glycans are found attached to the R-group nitrogen (N) of asparagine in the sequon. The sequon is a Asn-X-Ser or Asn-X-Thr sequence, where X is any amino acid except proline.

As used herein, the term "glycoprotein" refers to a protein covalently modified with glycan(s). There are four types of glycoproteins: 1) N-linked glycoproteins, 2) O-linked glycoproteins (mucins), 3) glucosaminoglycans (GAGs, which are also called proteoglycans), 4) GPI-anchored. Most glycoproteins have structural micro-heterogeneity (multiple different glycan structures attached within the same glycosylation site), and structural macro-heterogeneity (multiple sites and types of glycan attachment).

As used herein the term "glycosylation" refers to a process or result of addition of saccharides to proteins and lipids. The process is one of four principal co-translational and post-translational modification steps in the synthesis of membrane and secreted proteins and the majority of proteins synthesized in the rough ER undergo glycosylation. It is an enzyme-directed site-specific process, as opposed to the non-enzymatic chemical reaction of glycation. Two types of glycosylation exist: N-linked glycosylation to the amide nitrogen of asparagine side chains and O-linked glycosylation to the hydroxy oxygen of serine and threonine side chains.

As used herein, the term "cellular glycan" or "cell glycan" refers to a glycan (either alone or as part of a glycoconjugate) that may exist at a surface of a cell, within the cell (intracellularly) or within a lysate from a cell. The glycan is produced, actively biosynthesized, by the cell.

As used herein, the term "abnormal cell" refers to cells having, for example, at least one improper glycosylation, low functionality, lysosomal storage disorder, bacterial infection, viral infection. Abnormal cell may also refer to a cancerous cell, for example, a cancer stem cell, leukemia cell, lymphoma cell, pancreatic cancer cell, non-small cell lung cancer cell, small cell lung cancer cell, colon cancer cell, central nervous system cancer cell, melanoma cell, ovarian cancer cell, a renal cancer cell, a prostate cancer cell line, and a breast cancer cell.

As used herein, the terms "alkynyl group" and "alkyne functional group" refer to a terminal alkyne group comprised of a triple bond between two carbon atoms.

As used herein, the term "derivatization" is used to describe a technique used in chemistry which transforms a chemical compound into a product of similar chemical structure, called a derivative. For example, when reference is made to a sugar analog or precursor that has been "derivatized" with an alkyne group, it is meant that the sugar analog is bearing an alkynyl group.

As used herein, the term "alkynyl-derivatized sugars" refers to sugar analogs and/or precursors that have been derivatized with an alkynyl group, the alkynyl group being placed at permissive positions on the sugar analogs and/or precursors. The alkynyl-derivatized sugars are derivatized using chemical synthesis techniques and have been peraceytylated—all free hydroxyl groups bear acytyl protecting groups. These alkynyl-derivatized sugars may then be fed to cells. The acytyl protecting groups increase cellular uptake and are cleaved off in the cell before they are transformed into the nucleotide sugar donor and transferred onto the cellular glycan.

As used herein, the term "analog" means a derivatized version of a naturally-occurring molecule, e.g. by substitution of an azido or alkylyl functional group at a carbon position.

As used herein, the term "Fucose" (Fuc) means a six-carbon deoxy pyran sugar, distinguished from other hexoses by a L-configuration and an unsubstituted carbon at the 6-position.

As used herein, the term "Fucosyltransferase (FucT)" means an enzyme that transfers a fucose from a donor substrate, GDP-fucose (GDP=Guanosine diphosphate), to an acceptor substrate, a glycoconjugate or glycan.

As used herein, the term "GDP analog" means a molecular derivative of Guanosine diphosphate (GDP).

As used herein, the term "fucosylated" means a molecule (typically a glycoconjugate or glycan) that has been covalently appended with a fucose (Fuc) residue (typically by a FucT)

As used herein, the term "sialylated" means a molecule (typically a glycoconjugate or glycan) that has been covalently appended with a sialic acid (NeuAc) residue (typically by a sialyl transferase)

As used herein, the term "alkynyl fucose," "alkynyl Fuc" and "Fucyne" are used interchangeably.

As used herein, the term "alkynyl N-acetylmannosamine," "alkynyl ManNAc" and "ManNAcyne" are used interchangeably.

As used herein, the term "alkynyl sialic acid," "alkynyl NeuAc" and "NeuAcyne" are used interchangeably.

As used herein, the term "alkynyl-tagged glycan" refers to cellular glycans that have been functionalized with the alkynyl-derivatized sugars. The alkyne group is used as a chemical reporting group to specifically tag glycans that are fucosylated and/or sialylated. In an exemplary implementation, an alkynyl-derivatized sugar is incorporated with the cellular glycan through any permissive biosynthetic pathway involved in glycoconjugate synthesis. The alkynyl-tag remains inert until subjected to CuAAC with an appropriate azide bearing probe.

As used herein, the term "bioorthogonal" means chemical reactants and reactions that are compatible with living systems. Bioorthogonal reactions proceed in high yield under physiological conditions and result in covalent bonds between reactants that are otherwise stable in these settings.

As used herein, the term "reporting group" means a molecule that has properties capable of providing detectable feedback about events transpiring in a test system (from a controlled in vitro assay to a complex biological system).

As used herein, the term "bioorthoganal chemical reporting group" means a non-native, non-perturbing, inert chemical functional group, which can be modified in biological systems by chemo-selective reactions with exogenously delivered probes.

As used herein, the term "click-activated" means any reaction that bioorthogonally proceeds in a manner that changes the chemical and/or physical properties of the resultant molecule.

As used herein, the term "cycloaddition" means a chemical cyclization reaction; in which two $\pi$ bonds are lost and two $\sigma$ bonds are gained—the reaction can proceed catalyzed or uncatalyzed or in a concerted or stepwise manner.

As used herein, the term "chemoselective" means the preferential reaction of a chemical reagent with only one out of two or more different available functional groups.

As used herein, the term "Fluorescent Labeled" means derivatizing a molecule with a fluorescent material.

As used herein, the term "Fluorogenic" or "Fluorescent Reporting Group" means a material capable of supporting a chemical reaction dependent on the presence of a particular analyte material. Said analyte-dependent chemical reaction produces a fluorescent reporting molecule.

As used herein, the term "Fluorescent" means a material exhibiting fluorescence.

As used herein, the term "coumarin" means any of a group of fluorogenic compounds related to benzopyrone or 2-chromenone that are capable of fluorescence modulation dependent on position of substitution and identity of functional groups.

As used herein "covalenty displaying" refers to a covalent attachment or covalent appendant.

As used herein, the term "labeled glycoprotein" refers to a glycoprotein covalently attached to a moiety that can facilitate the manipulation of the "labeled glycoprotein," such as the isolation, visualization, detection, and quantification of the labeled glycoprotein. In an exemplary implementation, CuAAC is used to label glycoconjugates with several types of probes.

As used herein, the term "metabolic oligosaccharide engineering" or "MOE" refers to a process that exploits the promiscuous biosynthetic pathways involved in glycan synthesis to tag cellular glycans with a chemical reporting group. Glycan synthesis pathways are comprised of multi-step enzymatic transformations that render free sugars in the cytosol into activated nucleotide-donor sugars. These donor sugars are used by glycosyltransferases in the Golgi to transfer the sugar onto glycan structures. Inconspicuous saccharide analogs can infiltrate glycan synthesis pathways allowing the analog, in place of the natural saccharide, to be incorporated into cellular glycans. By providing the cell with a saccharide equipped with a chemical reporting group, cellular glycans can be functionalized, or tagged, for further manipulation via specific labeling chemistries.

As used herein, the term "isolated" means glycoconjugates that can be selectively separated by secondary detection means.

As used herein, the term "Flow cytometry" or "FACS" means a technique for examining the physical and chemical properties of particles or cells suspended in a stream of fluid, through optical and electronic detection devices.

Amino acid residues in peptides shall hereinafter be abbreviated as follows: Phenylalanine is Phe or F; Leucine is Leu or L; Isoleucine is Ile or I; Methionine is Met or M; Valine is Val or V; Serine is Ser or S; Proline is Pro or P; Threonine is Thr or T; Alanine is Ala or A; Tyrosine is Tyr or Y; Histidine is His or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; and Glycine is Gly or G. For further description of amino acids, please refer to Proteins: Structure and Molecular Properties by Creighton, T. E., W. H. Freeman & Co., New York 1983.

As used herein, "Liquid chromatography-mass spectrometry" or "LC-MS" refers to an analytical chemistry technique that combines the physical separation capabilities of liquid chromatography (aka HPLC) with the mass analysis capabilities of mass spectrometry. LC-MS is a powerful technique used for many applications which has very high sensitivity and specificity. Generally its application is oriented towards the specific detection and potential identification of chemicals in the presence of other chemicals (in a complex mixture). LC-MS is also used in the study of proteomics where components of a complex mixture must be detected and identified in some manner. The bottom-up proteomics LC-MS approach to proteomics generally involves protease digestion (usually Trypsin) followed by LC-MS with peptide mass fingerprinting or LC-MS$^2$ (tandem MS) to derive the sequence of individual peptides.

As used herein, the term "SEQUEST" refers to a tandem mass spectrometry data analysis program used for protein identification. SEQUEST identifies collections of tandem mass spectra to peptide sequences that have been generated from databases of protein sequences.

As used herein, the term Multidimentional Protein Identification Technology or "MudPIT" refers to the characterization of protein mixtures using LC-MS. A peptide mixture that results from digestion of a protein mixture is fractionated by one or two steps of liquid chromatography. The eluent from the chromatography stage can be either directly introduced to the mass spectrometer through electrospray ionization, or laid down on a series of small spots for later mass analysis using MALDI.

GIDmapping

Disclosed herein are tailored glycoproteomic methods for saccharide-selective glycoprotein identification (ID) and glycan mapping (GIDmap). The remarkable complexity of glycans presents major challenges to deciphering the glycans structure and activities on an individual protein, let alone, proteomic scale. These challenges include identifying glycoconjugates, sites of modification (especially for glycoproteins), and determining information about saccharide composition/structure; in addition to, ultimately, understanding the direct roles of glycans/glycoconjugates in cellular function and dysfunction. The global analysis of glycoproteins and glycopeptides by mass spectrometry (MS) is a challenging task. Problematic characteristics associated with the MS of glycans, which include poor ionization, low relative abundance, and extensive heterogeneity, have spurred the development of integral enrichment steps in many glycoproteomic approaches.

A method is disclosed for metabolic oligosaccharide engineering (MOE) which allows cellular glycans to be tagged with chemical reporting groups in vivo, through the incorporation of chemically modified building block analogs that closely resemble natural sugars. The disclosed MOE method provides a powerful glycan enrichment step for proteomic endeavors—the isolation of glycans based on their saccharide composition. In exemplary implementations of the MOE method, sugar analogs based on fucose (Fuc) or the sialic acid (NeuAc) precursor N-acetyl mannosamine (ManNAc) are derivatized with alkyne groups by chemical synthesis to form alkynyl-derivatized precursors. These alkynyl-derivatized precursors are then introduced to cells where they can "tag" fucosylated and sialylated cellular glycans to form tagged cellular glycans. These tagged cellular glycans may be labeled with chemical probes by Copper(I)-catalyzed [3+2] azide-alkyne cycloaddition, CuAAC-based labeling or "click" chemistry. In an exemplary implementation, the chemical probes include click-activated fluorogenic molecules that only become fluorescent upon CuAAC-based labeling. In another exemplary implementation, the chemical probes include azide derivatized affinity labels, for example, a biotin label. The disclosed click-activated fluorogenic probes may be used for selective and specific labeling of modified glycans at the cell surface, intracellularly, or in a cellular extract. The alkynyl sugars also are efficient ligation partners for click-activated fluorogenic and standard click probes. Labeling with click-activated probes is particularly useful because of the generation of an instant signal upon ligation with modified glycans that does not produce any significant background. In an exemplary implementation, cellular imaging, including flow cytometry, confocal microscopy and SDS/PAGE may be used to visualize the labeled/tagged cellular glycans and to monitor differences in glycan dynamics, setting the stage for further proteomic analysis.

A signal generated by the click-activated probes disclosed herein is equivalent to that of the biotin-secondary detection systems known, however, the disclosed probes require one less incubation step and no washing. Furthermore, the click-activated probes disclosed herein are small and hydrophobic, making them more amenable to intracellular penetration and labeling in living cells.

A method is disclosed for saccharide-selective glycoprotein identification and glycan mapping (GIDmap) that includes generating glycans bearing bioorthogonally-tagged alkynyl saccharides; labeling the alkynyl-tagged glycoproteins with an azide derivatized label by Cu(I) catalyzed [3+2] azide-alkyne cycloaddition; capturing labeled glycans from proteomes via affinity capture to a solid support; harvesting non-glycosylated peptides from the solid support by tryptic digest; analysis of the tryptic digest by tandem liquid chromatography-mass spectroscopy (LC-MS$^2$ or MudPIT) to identify the protein; treating the remaining captured glycopeptides with peptide-N-glycosidase F (PNGase) to hydrolyze the amide bond between the biotinylated glycan and Asn residue of the bound peptide; analyzing the PNGase digest by tandem LC-MS$^2$ to sequence the peptides and determine the shift from Asn to Asp at formerly glycosylated sites in the protein; and assigning glycosylation sites by a search algorithm.

The disclosed GIDmap methods have promise for being an encompassing global analysis—concomitant protein identification (ID), glycosylation site mapping, and glycan sequencing. The disclosed method may be further used to obtain information about cellular glycans under different physiological disease states and cellular statuses, such as stress, apoptosis, or inflammation. In an exemplary implementation, the disclosed GIDmap methods may be used to detect glycosylated glycoproteins, such as N-glycosylated glycoproteins and O-glycosylated glycoproteins.

Defining the molecular and structural details of glycan biology is complicated by many factors inherent to glycans, including their underpinning structural complexity and multifaceted mode of action. A long standing obstacle to glycan study has been the lack of effective means to directly manipulate them in vivo. Since glycan structures are not under direct transcriptional control, the powerful molecular biology technologies afforded to proteins, such as making them fluorescent by fusion to GFP or enriching them by engineering in affinity tags are not available. To step past these genetic limitations, several chemical strategies have been developed to probe glycan functions. Among these chemical glycobiology tools, metabolic oligosaccharide engineering (MOE) schemes offer routs to label, isolate, detect, and visualize cellular glycans.

The MOE method disclosed herein makes use of the promiscuous biosynthetic pathways involved in glycan synthesis, as shown schematically in FIG. 1. These pathways are multi-step enzymatic transformations that convert free sugars in the cytosol into activated nucleotide-donor sugars. The nucleotide-sugars are the substrates for glycosyltransferases, enzymes that build up glycan structures in the Golgi. These pathways can be hijacked by inconspicuous saccharide analogs, wherein, the analog, in place of the natural saccharide, is incorporated into cellular glycans. Thus, by providing the cell with a saccharide equipped with a chemical reporting group, cellular glycans can be functionalized, or tagged, for further manipulation via specific ligation chemistries.

Figure 2:
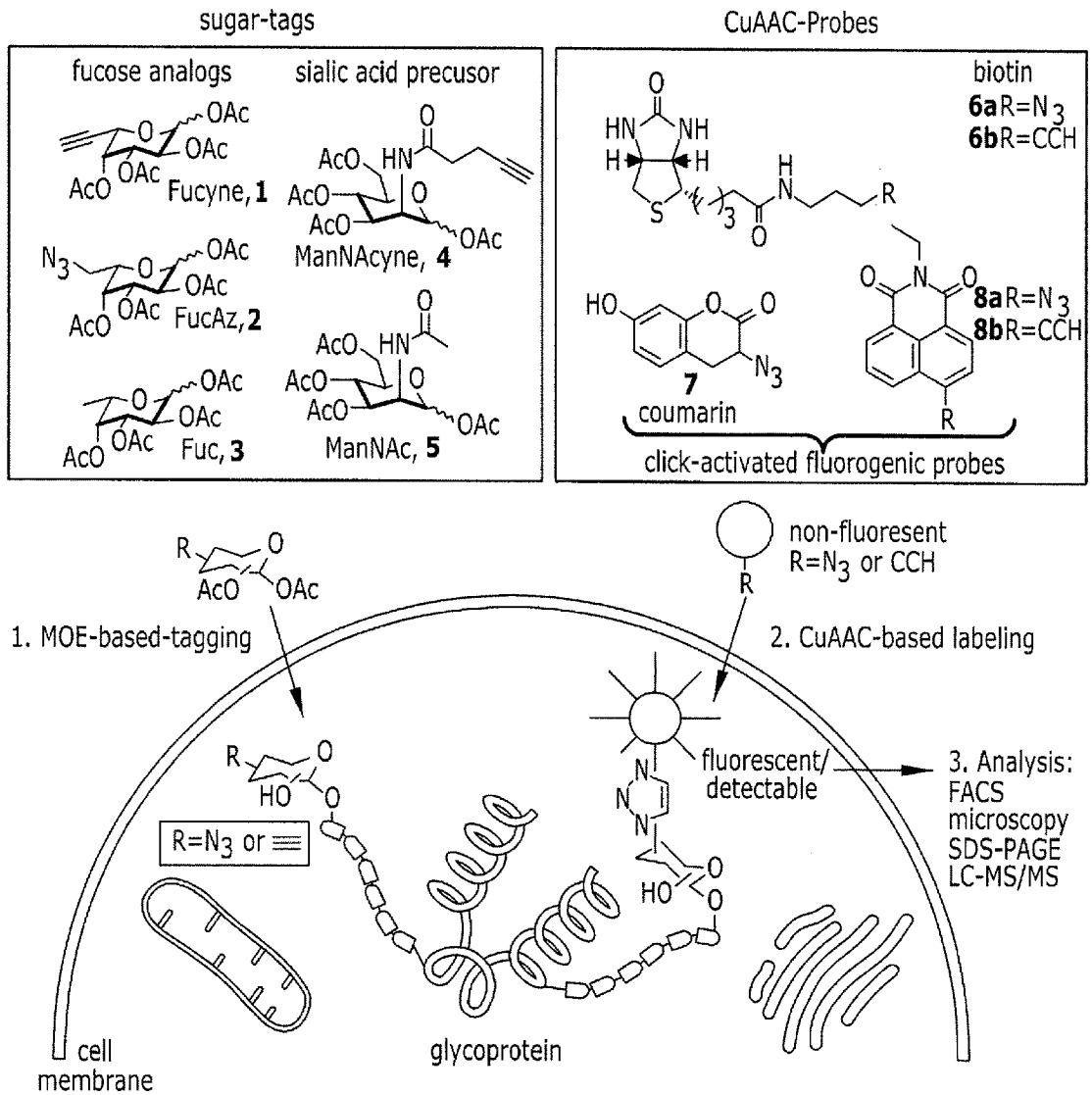
FIG. 2 is a schematic diagram showing an exemplary implementation of a metabolic oligosaccharide engineering (MOE) method of the present disclosure.

FIG. 2 shows a schematic representation of a MOE method according to an exemplary implementation of the present disclosure. The MOE method tags fucosylated and sialylated cellular glycans with alkyne groups and chemoselectively labels them using Cu(I)-catalyzed [3+2] azide-alkyne cycloaddition (CuAAC) or click chemistry. In an exemplary implementation, sugars based on fucose (Fuc) analogs and the sialic acid (NeuAc) precursor N-acetyl mannosamine (ManNAc) are derivatized with an alkyne group by chemical synthesis to yield alkynyl-derivatized precursors. These alkynyl-derivatized precursors are then introduced to cells where they are incorporated into fucosylated and sialylated cellular glycans, thereby tagging them with chemical handles (step 1) yielding "tagged cellular glycans". For the case of alkynyl ManNAc (also referred to as ManNAcyne), the ManNAcyne is first transformed to alkynyl sialic acid (also referred to as NeuAcyne) in the cell before incorporation into the cellular glycans. The tagged cellular glycans may then be labeled with probes by CuAAC-based labeling (step 2) yielding "labeled cellular glycans". The CuAAC-based probes disclosed herein include click-activated fluorogenic molecules that only become fluorescent upon CuAAC-based labeling, and a standard biotin probe derivatized with an azido group. Labeling with probes allows the tagged cellular glycans to be manipulated for analysis (step 3).

The alkynyl saccharides represent a robust platform for tagging and labeling fucosylated and sialylated cellular glycans in vivo, allowing for these cellular glycans to be visualized at the cell-surface (by flow cytometry) and intracellularly (by microscopy), and isolated by techniques such as SDS-PAGE. Having access to multiple chemoselective handles is a useful tool that can allow samples to be doubly labeled (e.g., azide labeled Fuc (FucAz) and NueAcyne bearing cellular glycans, or pulse-chased experiments with Fucyne followed by FucAz), and visualized/isolated by variations of click chemistry, or a combination of CuAAC and Staudinger ligation. The MOE method disclosed herein enables cellular glycans to be labeled in a manner similar to the genetic manipulation of proteins, representing a powerful tool for understanding the roles of cellular glycans by being able to isolate them for proteomic analysis and image their localization, trafficking, and dynamics.

In an exemplary implementation of the MOE method disclosed herein, an appropriate cell growth medium is supplemented with a peracetylated version of the CuAAC competent sugars, 25 µM for sialic acid precursors and 200 µM for fucose precursors (although peracetylation increases cellular uptake of sugars, the acetate groups are cleaved by esterases before it is converted to the nucleotide-sugar donor and incorporated into emerging glycans via glycosyltransferases). As shown by the biosynthetic pathways in FIG. 1, the ManNAc derivatives feed directly into de novo synthesis of NeuAc-CMP, whereas, fucose derivatives are incorporated through a salvage pathway for the synthesis of Fuc-GDP. For labeling, the alkyne-tagged cellular glycans, cells and/or cell lysates are treated with an appropriate CuAAC probe (depicted as 6-8 in FIG. 2). Overall, CuAAC is well-suited for functionalizing cellular glycans since it may be performed in aqueous environments, with high chemoselectivly, to form stable 1,2,3-triazoles in nearly quantitative yield, starting from inconspicuous and inert azide or alkyne reaction partners. In conjunction the triazole ligand, CuAAc reactions can be executed under very mild and biocompatible conditions, requiring ambient temperature and low reactant concentrations. Side-by-side comparison of CuACC with similar bioorthoganol chemistries shows that it is the most robust in terms of kinetics and efficiency of labeling. CuAAC is well-suited for end-point analysis, such as flow cytometry and glycoproteomic purposes. However, in order to allow for imaging in live cells, the toxicity of Cu(I) must be circumvented. Time-course and dose-dependent assays have revealed the optimal conditions to maximize incorporation and minimize toxicity, as listed above. In previous approaches, azido Fuc analogs incorporated into glycans were shown to be toxic to cells at the levels required for efficient uptake (200 µM). One significant advantage of the MOE method disclosed herein is that Fucyne and ManNAcyne analogs show greatly reduced toxicity and yields higher signal and less background.

In an exemplary implementation, synthesis of alkynyl sugars and biotinylated azide probes for the tagging and labeling of fucosylated and sialylated cellular glycans is disclosed.

Peracetylated alkynyl derivatives of Fuc (Fucyne), ManNAc (ManNAcyne) and sialic acid (NeuAcyne), were synthesized in their peracetylated forms, as this modification is known to increase their cellular uptake efficiency. The acetate esters are subsequently hydrolyzed in the cytosol.

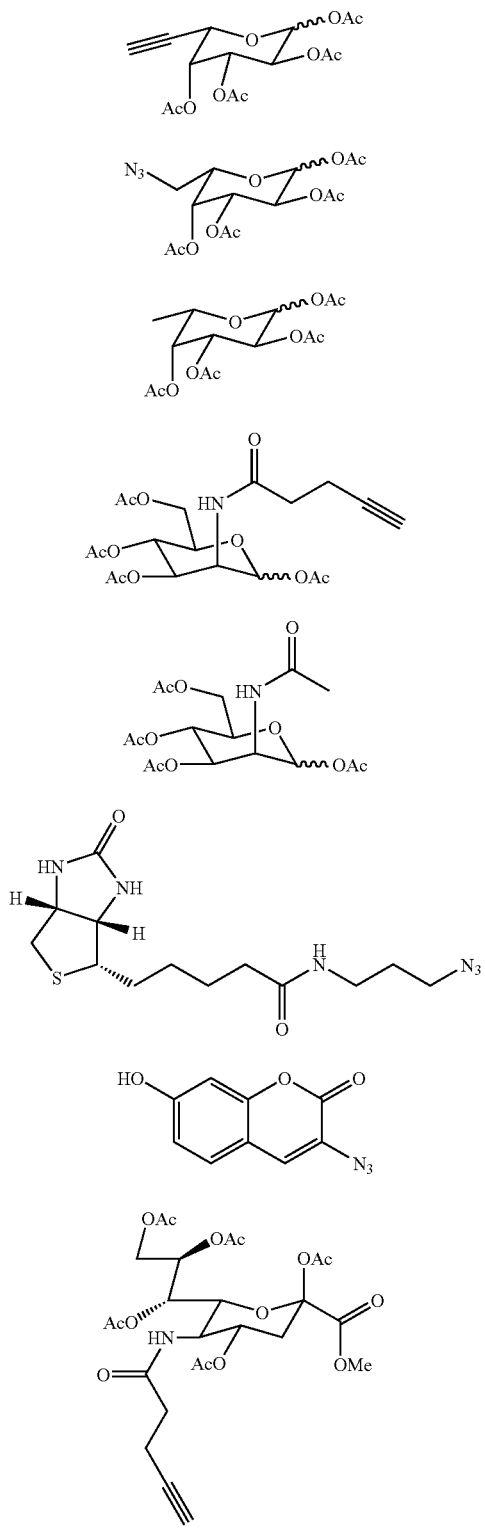

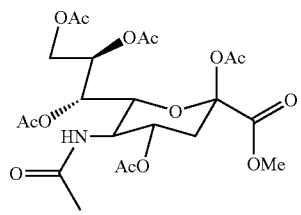

Key:
1: Fucyne
2: FucAz
3: Fuc
4: ManNAcyne
5: ManNAc
6: Biotin Probe
7: Coumarin Probe
11: NeuAcyne
12: NeuAc The synthesis of Fucyne, proceeds from a known four-step transformation, beginning with I-(+)-galactonic acid □-lactone and ending with the alkynyl diisopropylidene-Fuc intermediate (see Scheme 1 and Example 1). Subsequent protecting group removal followed by acetylation of the intermediate yields the desired compound, as a mixture of pyranoside and furanoside forms.

Scheme 1:

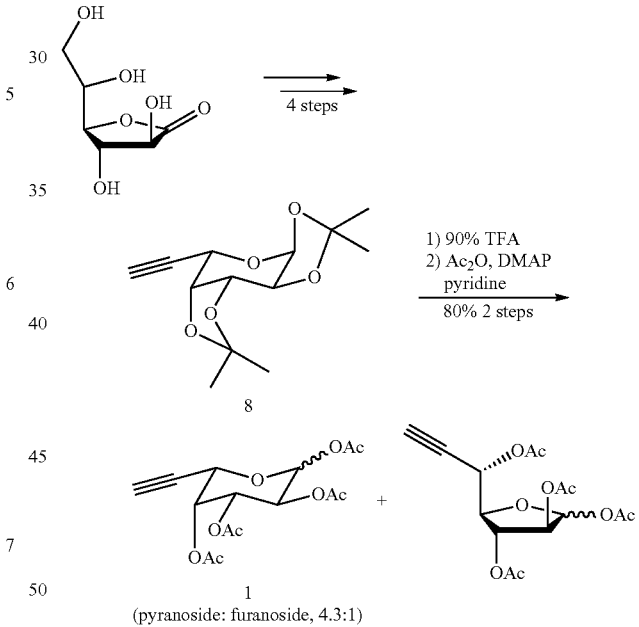

For synthesizing ManNAcyne, D-Mannosamine hydrochloride is reacted with N-succinimidyl 4-pentynoate in triethylamine to yield alkynyl ManNAc derivative (see Scheme 2 and Example 2). The ManNAcyne is subsequently obtained by acetylation.

Scheme 2:

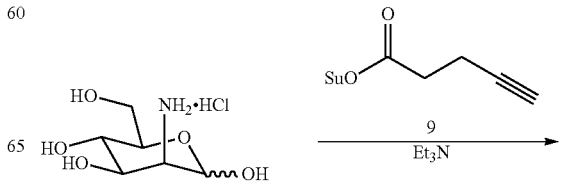

-continued

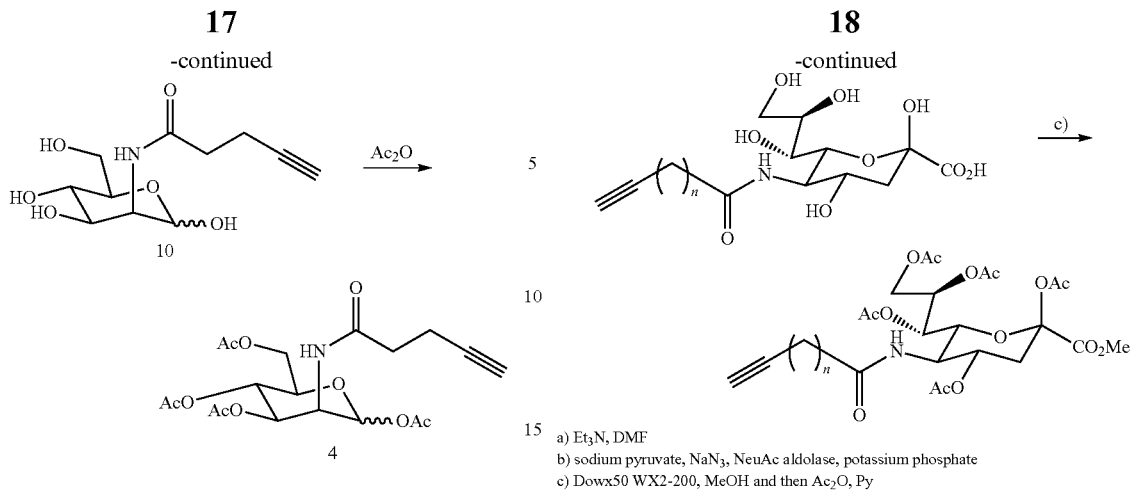

a) Et₃N, DMF
b) sodium pyruvate, NaN₃, NeuAc aldolase, potassium phosphate
c) Dowx50 WX2-200, MeOH and then Ac₂O, Py

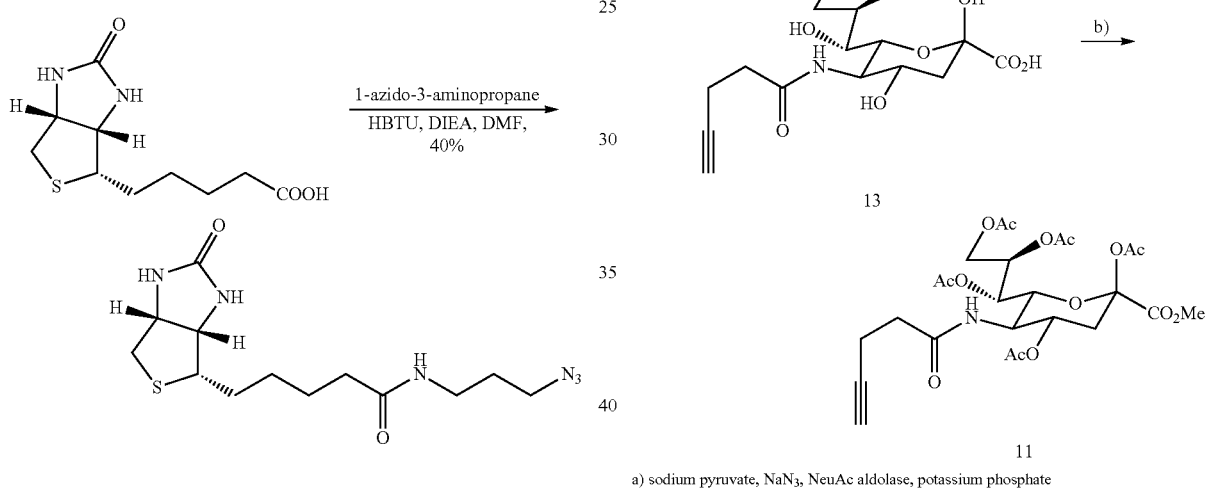

a) sodium pyruvate, NaN₃, NeuAc aldolase, potassium phosphate
b) Dowx50 WX2-200, MeOH and then Ac₂O, Py The coupling partner, biotinylated azido probe is synthesized by coupling of biotin to 1-azido-3-aminopropane (see Scheme 3 and Example 4).

Scheme 3:

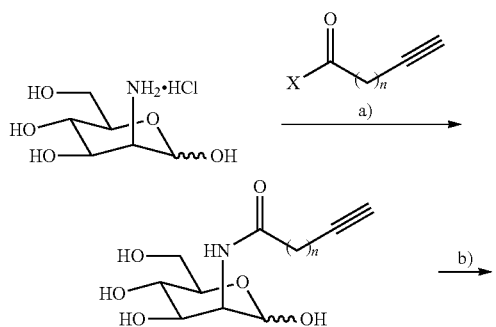

Synthesis of fluorogenic probe, 3-azido-7-hydroxycoumarin, was previously reported. N-5-pentynoyl-D-neuraminic acid 10 is performed via treatment of N-4-pentynoylmannosamine with N-acetylneuraminic acid aldolase as shown in Scheme 4, followed by peracetylation (also see Examples 5 and 6).

Figure 3A:
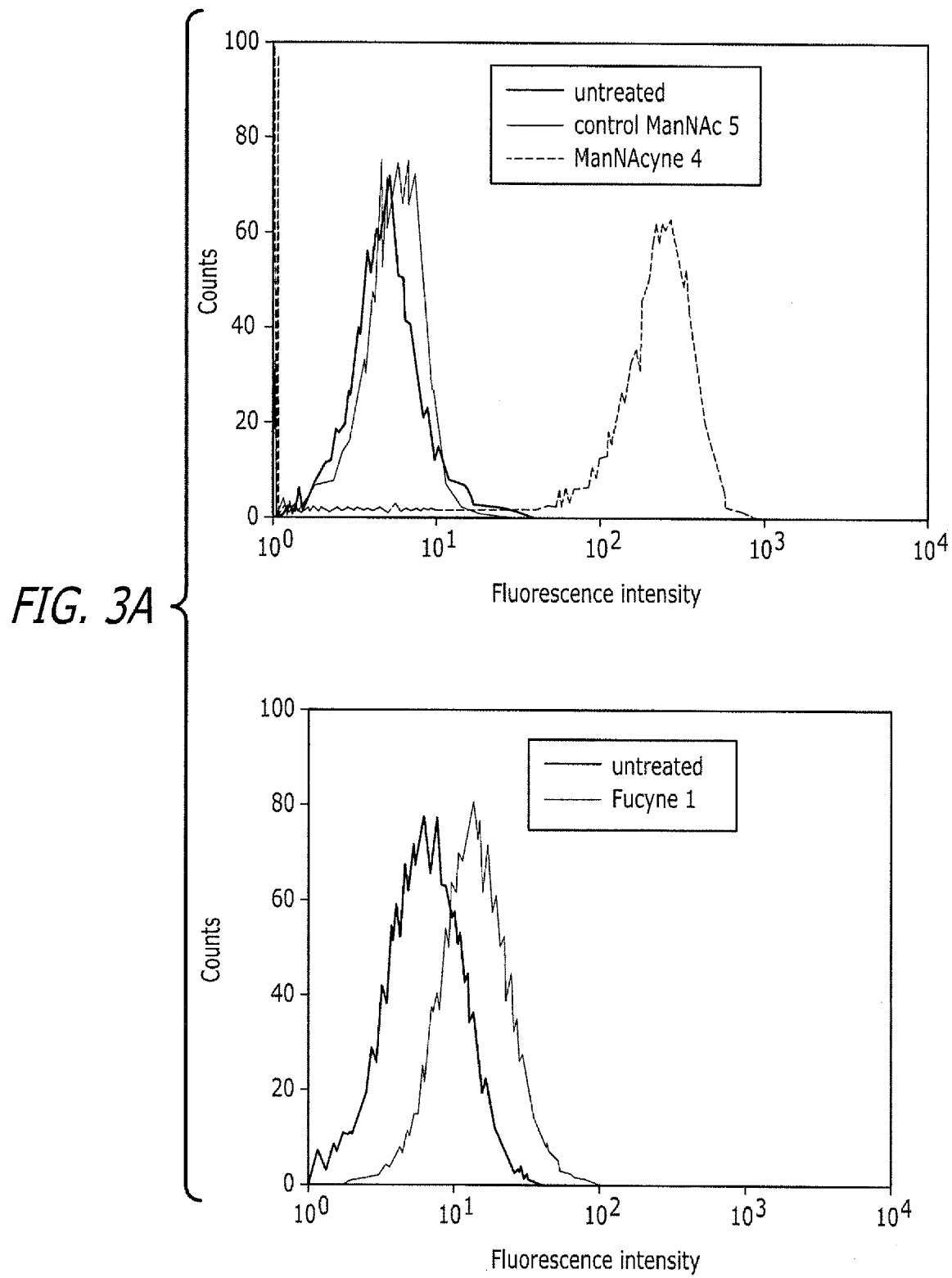
FIG. 3A shows flow cytometry analysis of Jurkat cells treated with ManNAcyne (left, CuAAC-labeled with biotin and detected by fluorescein-conjugated streptavidin, pink lines) and Fucyne (right, CuACC-labeled with click-activated coumarin probe (3-azido-7-hydroxycoumarin), green line) probe.
Figure 3B:
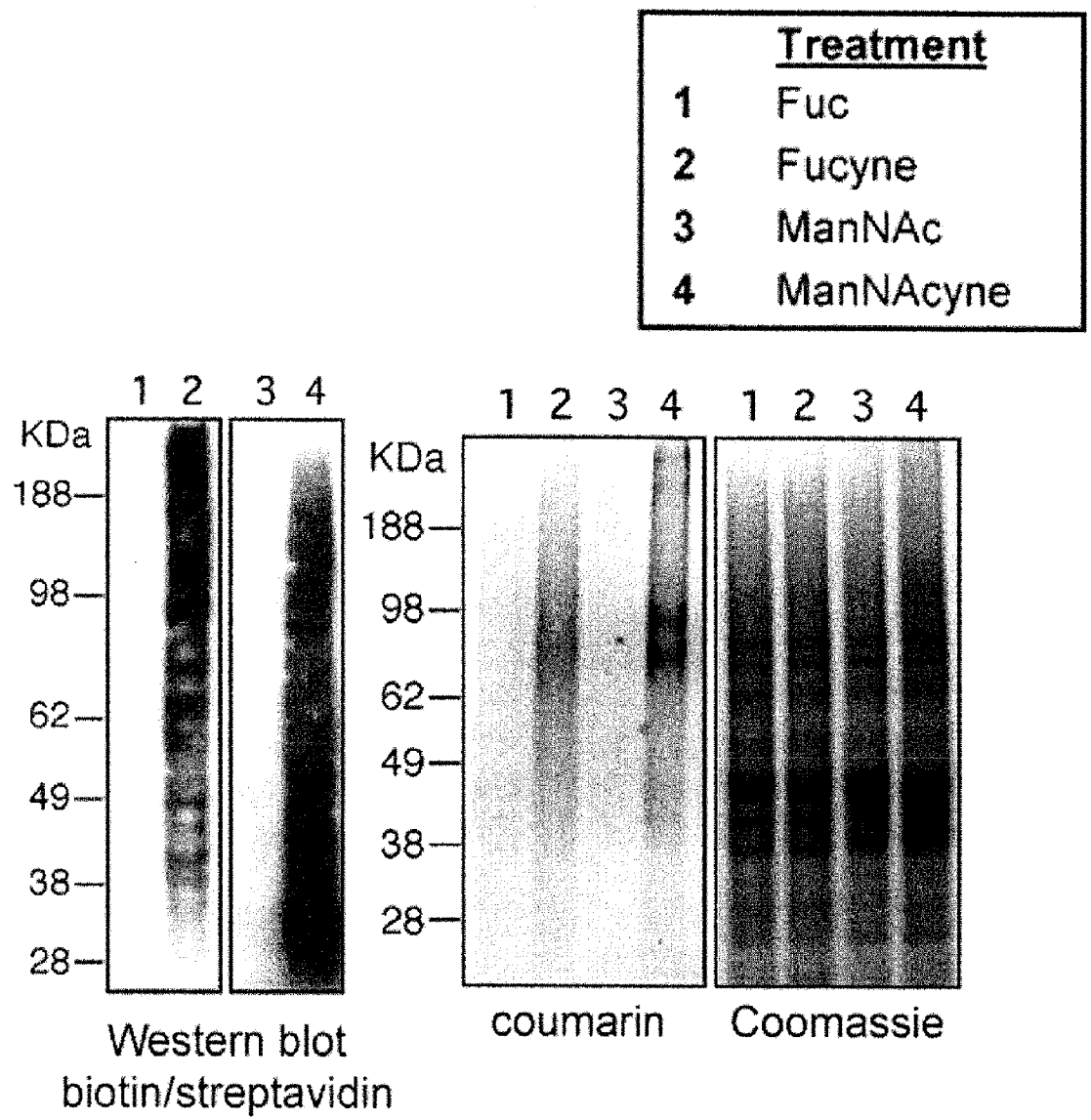
FIG. 3B shows protein lysates separated by SDS-PAGE (lane 1: Fuc; lane 2: Fucyne; lane 3: ManNAc; and lane 4: ManNAcyne) and visualized (left, western blot of CuACC-biotin labeling, detection by: 1) mouse anti-biotin MAb, 2) peroxidase-conjugated goat anti-mouse IgG, 3) SuperSignal® Chemiluminescent Substrate; right, CuACC-coumarin labeling, detection by fluorescence flat-bed scanner) show that alkynyl-tagged glycoproteins are selectively labeled and detected.
Figure 3C:
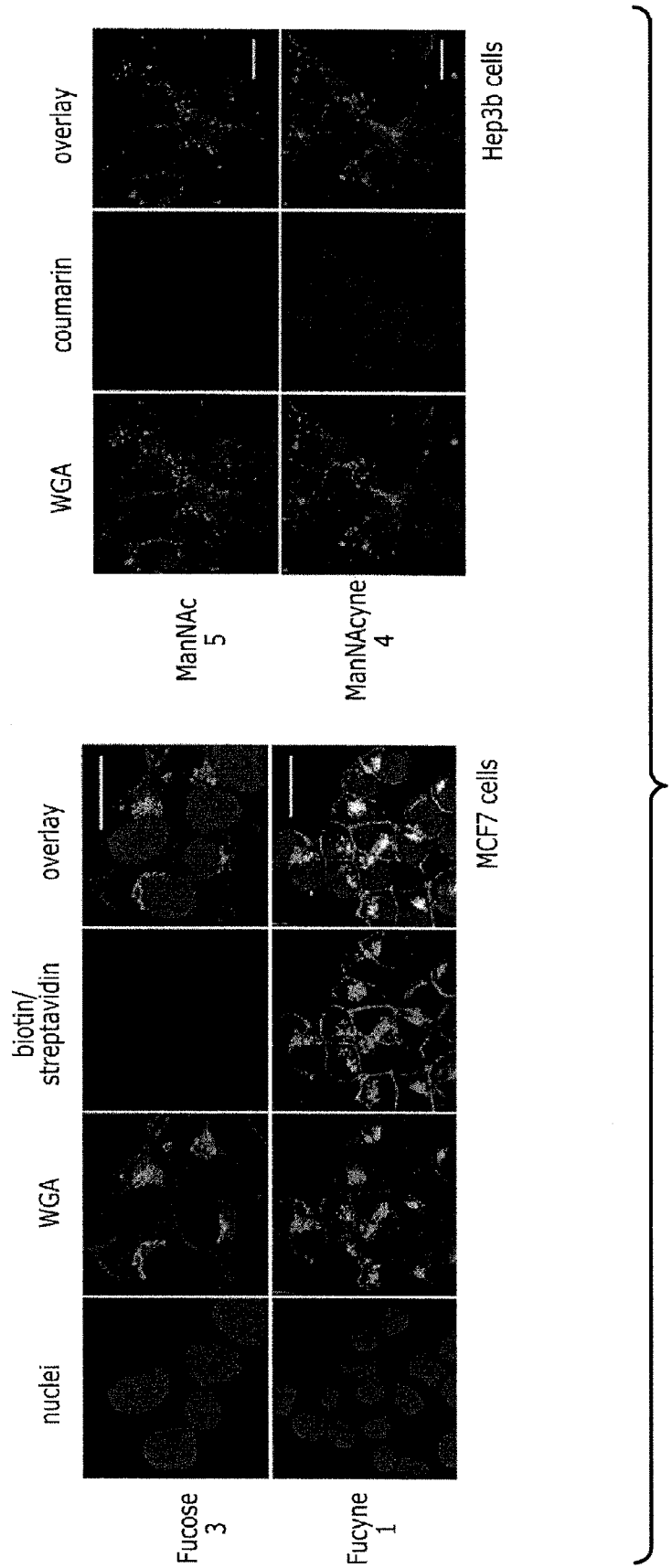
FIG. 3C shows selective labeling of alkynylated-tagged glycans in cancer cells (top panel treated with control sugar, and bottom with alkynyl-derivatized sugar). Confocal microscopy of MCF7 cells (left grouping, treated with Fuc analogs, CuACC with biotin azide, and detection with fluorescein-conjugated streptavidin) and Hep3b cell (right grouping, treated with ManNAc derivatives, CuACC with coumarin probe). Co-stains of nucleus (blue) and Golgi (red, WGA lectin AlexaFluor 594-conjugated), show the alkynyl-tagged glycans co-localize in the Golgi.

Scheme 4:

It is now disclosed that treating cells with ManNAcyne results in alkyne-bearing sialyl glycans. In an exemplary implementation of the MOE method, cells are treated with ManNAcyne at various concentrations for one to 3 days. FIG. 3A-C shows an exemplary implementation of how alkyne-tagged glycans can be labeled with Cu(I)-catalyzed [3+2] azide-alkyne cycloaddition (CuAAC) probes and visualized at the cell surface (A), in glycoprotein lysates (B) and intracellularly (C).

As shown in FIG. 3A, labeling with ManNAcyne yielded a specific signal on the cell surface compared with the control values obtained from cells treated with control ManNAc (left, CuAAC-labeled with biotin and detected by fluorescein-conjugated streptavidin, pink lines) and labeling with Fucyne allowed significant fluorescent labeling after reacting with 3-azido-7-hydroxycoumarin probe, whereas cells treated with control Fuc gave very low background signals (right, CuACC-labeled with click-activated coumarin probe (3-azido-7-hydroxycoumarin), green line).

As shown in FIG. 3B, cell extracts are analyzed after growing cells with alkynyl sugars to demonstrate the detection of individual labeled proteins. Soluble lysate fractions are tagged with biotin probe, fluorogenic coumarin probe, or a standard rhodamine probe used in proteomics before separating proteins by SDS/PAGE. As shown in FIG. 3B, specific biotin-labeling signals were detected by Western blot (mouse anti-biotin MAb) in proteins from cells treated with Fucyne and ManNAcyne (SDS-PAGE gel lane 1: Fuc; lane 2: Fucyne; lane 3: ManNAc; and lane 4: ManNAcyne). Positive fluorescent signal was also detected in alkynyl positive protein lysate when clicked with fluorogenic 3-azido-7-hydroxycoumarin probe and rhodamine-azide probes. Proteins harvested from cells grown with control Fuc and ManNAc and processed under the same click condition, showed little to no signal by Western blot or fluorescence. The labeling patterns for Fuc and ManNAc are notably different, indicating the detection of unique glycoproteins. The data herein presented demonstrate the feasibility and utility of labeling and identifying individual glycoproteins by using this probing system. Moreover, further processing, including an avidin enrichment or gel slice purification, will allow for comparative identification of unknown glycoproteins expressed at different cell status, for instance, un-differentiated verses differentiated cells, normal verses cancer cells, or cells at different stages of cancer.

To visualize the localization of alkyne-tagged glycans, adherent cells were grown on slides in the presence or absence of alkynyl sugar analogs or precursors. After a 3-day-incubation, cells attached to the slides are fixed, permeabilized, and labeled with either a biotin probe or fluorogenic coumarin probe for fluorescent signal analysis with confocal microscopy, as shown in FIG. 3C. For comparison, samples are also stained with wheat germ agglutinin (WGA, a Golgi marker). In one exemplary implementation, cancer cell lines, such as MCF7 (breast adenocarcinoma) cells, are treated with Fucyne to result in a strong punctuate-labeling signal after clicking on the biotin probe and staining with fluorescein-conjugated streptavidin. This signal shows significant overlap with the WGA signal, indicating the labeled fucosylated glycans are localized in Golgi apparatus. Similar results are obtained from cells treated with ManNAcyne, which probes for sialic acid-containing glycans, when labeled by biotin probe and fluorogenic probe. Consistent with the results from flow cytometry, confocal microscopic analysis of cells treated with control sugars Fuc and ManNAc gives very low background after reacting with click probes, confirming the labeling of alkynyl containing glycans is specific and sensitive.

Figures 1, 4:
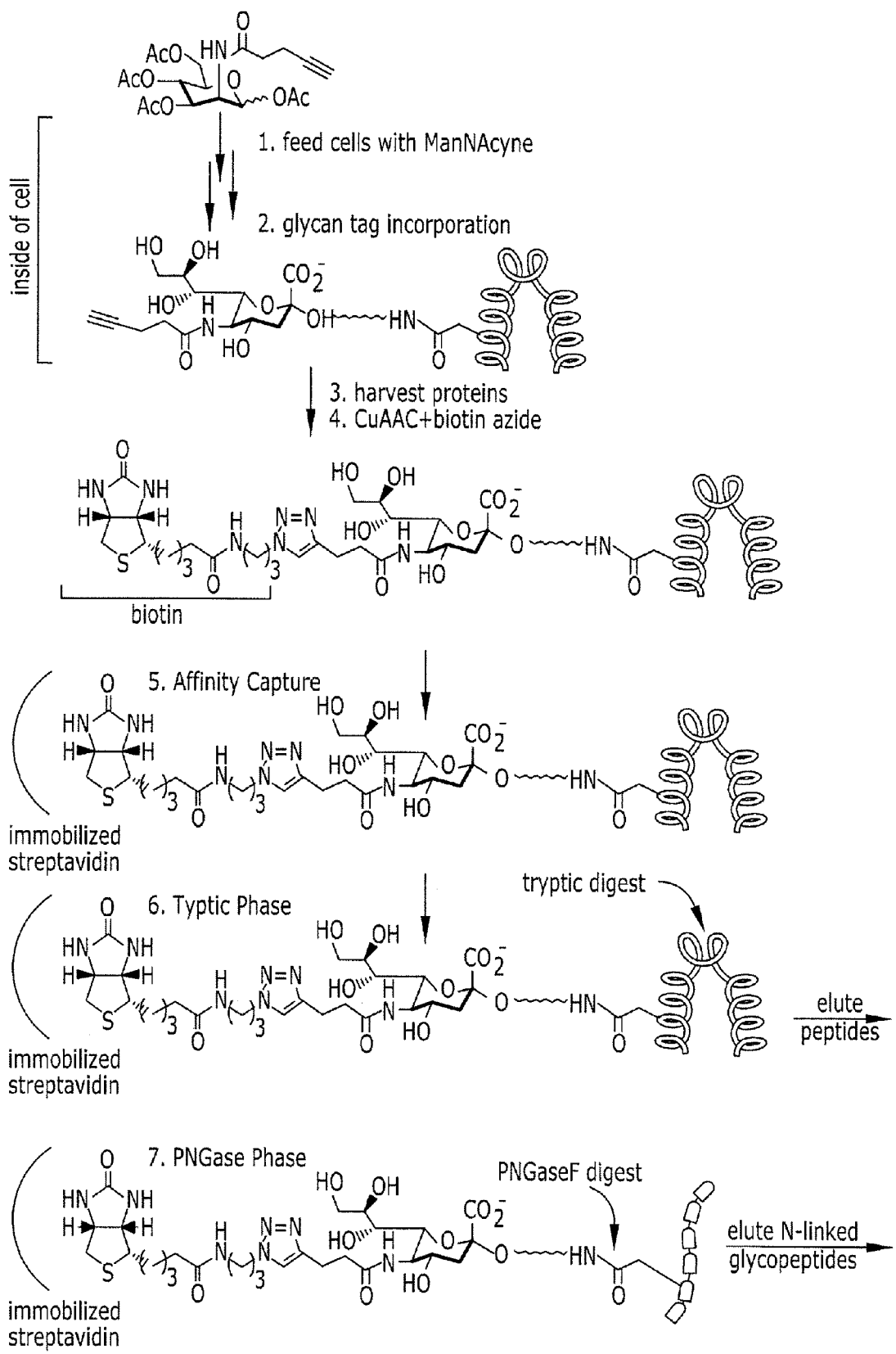
FIG. 4 is a schematic diagram showing an exemplary implementation of a glycoprotein identification and glycan site mapping (GIDmap) method of the present disclosure.

FIG. 4 shows a schematic representation of an exemplary implementation of a GIDmap method of the present disclosure. The GIDmap method is based on a saccharide-selective route to capture specific glycan subpopulations from proteomes based on their unique carbohydrate composition (i.e., those that are tagged by alkynyl derivatives of fucose or sialic acid). The GIDmap method disclosed herein is capable of identifying enriched glycoproteins, identifying N-linked glycoproteins, mapping the type of glycosylation (N-linked or O-linked), mapping the site on the glycoprotein where glycosylation occurs (glycosylation site), and providing information about the saccharide content of the glycan portion at glycosylation sites. In the GIDmap method, the metabolic oligosaccharide engineering (MOE) method disclosed above is employed to insert Fuc analogs and/or NeuAc precursors derivatized with alkynyl groups in place of their native counterparts via promiscuous glycan synthesis pathways in vivo. As depicted in the exemplary implementation shown in FIG. 4, a ManNAc is derivatized with an alkynyl group by chemical synthesis to yield ManNAcyne. The ManNAcyne is then introduced to cells where it is transformed to NeuAcyne. The NeuAcyne is capable of tagging a sialylated glycoprotein (sialylated glycan bound to a protein) within the cell yielding a tagged sialylated glycoprotein. The tagged sialylated glycoprotein may then be labeled by CuAAC or "click" chemistry with an azide derivatized affinity label, yielding a labeled sialylated glycoprotein population, which permits enrichment of the population via solid support affinity capture. Protein identification (ID) and glycan site mapping may then be carried out on the population on-bead by using sequential enzyme treatments to release specific peptide populations, followed by liquid chromatography-mass spectroscopy (LC-MS$^2$) analysis. First, non-glycosylated peptide fragments within the population are harvested by tryptic digestion, allowing for total protein ID. Analysis of the remaining captured N-linked glycopeptides is achieved by treatment with peptide-N-glycosidase F (PNGase), which hydrolyzes an amide bond between the biotinylated glycan and the Asn residue of the bound peptide, yielding a mixture of PNGase peptides. The resulting shift from Asn to Asp at formerly glycosylated sites can be identified as a mass signature by a search algorithm (i.e., by using a differential modification, or diff mod, of +1 Da on Asn in searches of MS data) thus allowing for the site of glycosylation to be mapped. MS$^2$ fragmentation data can be used to show +1 Da mass signature on glycosylated peptides.

The alkynyl sugars (saccharides) used in the GIDmap method are selected from one or more of alkynyl fucose (Fucyne), alkynyl N-acetylmannosamine (ManNAcyne), alkynyl sialic acid (NeuAcyne), and analogs and derivatives thereof. In an exemplary implementation, the alkynyl saccharide is peracetylated. In another exemplary implementation, the alkynyl saccharide is selected from 1,2,3,4-tetraacetyl alkynyl fucose and 2,4,7,8,9-penta-O-acetyl-N-5-pentynoyl-D-neuraminic-1-methyl ester. In an exemplary implementation, the azide derivatized affinity label is an azide derivatized biotin label, for example, 3-azidopropyl biotin amide. In an exemplary implementation, the solid support is an agarose bead solid support, derivatized with streptavidin for affinity capture of the biotin-labeled glycoprotein. In one exemplary implementation, the search algorithm is SEQUEST.

The disclosed methods for saccharide-selective glycoprotein identification (ID) and glycan mapping (GIDmap) may be carried out on both normal and abnormal cells. In an exemplary implementation, the abnormal cell is selected, for example, from an improperly glycosylated cell, a low functioning cell, a cell having a lysosomal storage disorder and an infected cell (bacterial or viral). In a further aspect, the abnormal cell is as a cancerous cell. In an exemplary implementation, the cancerous cell is selected from a cancer stem cell, leukemia cell, lymphoma cell, pancreatic cancer cell, non-small cell lung cancer cell, small cell lung cancer cell, colon cancer cell, central nervous system cancer cell, melanoma cell, ovarian cancer cell, a renal cancer cell, a prostate cancer cell line, and a breast cancer cell.

In an exemplary implementation, the disclosed GIDmap method was used to analyze and inventory sialylated N-linked glycoproteome isolated from prostate cancer (PC-3) cells, which is described in detail in Example 8 below. Briefly, the experiments were performed on 1.5 mg of total cellular protein harvested from PC-3 cells grown in the presence of alkynyl-derivatized N-acetylmannosamine (ManNAcyne), or untagged control ManNAc.

Figure 5:
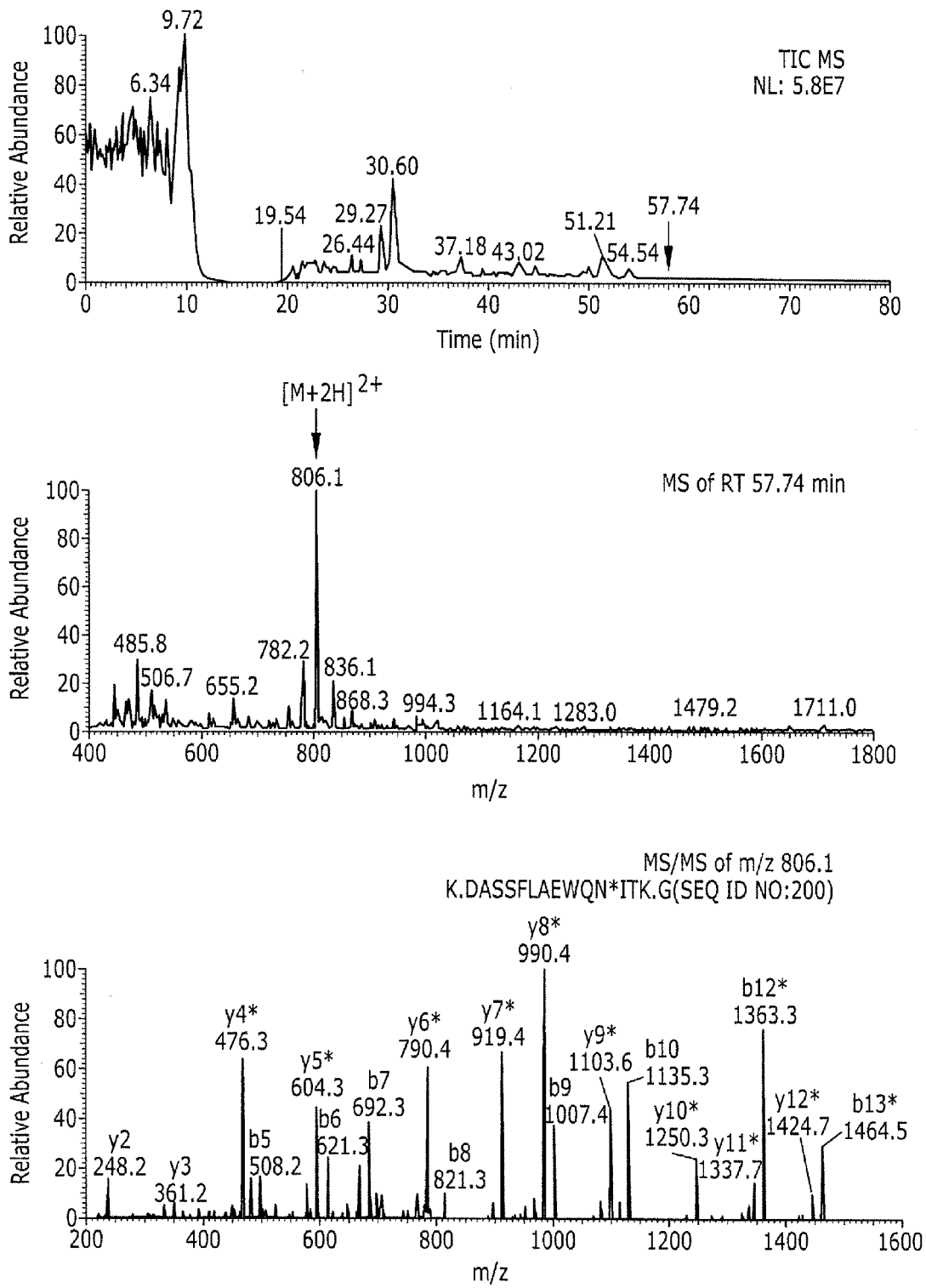
FIG. 5 shows representative LC-MS$^2$ data for a PNGase-treated sample. The total ion chromatogram highlighting a peptide eluting at 57.74 minutes in PNGase step 2 (upper frame). The full MS$^2$ scan of peptides eluting at 57.74 minutes highlighting a specific peptide at $[M+2H]^{2+}=806.1$ (middle frame). The MS² scan (lower frame) of the [M+2H]²⁺=806.1 ion clearly illustrating a mass shift of +1 Da on all b and y ions containing the formerly glycosylated N, as marked by an asterisk *.

In an exemplary embodiment, peptides may be analyzed by multidimensional nano-LC-MS (MudPIT). For samples treated with PNGase, a differential modification (diffmod) of +1 Da on Asn was included in SEQUEST searches. Manual inspection of peptides with an Asn diffmod showed MS spectra where all b and y ions containing the modification were clearly shifted by +1 Da. FIG. 5, shows representative MS² fragmentation data that clearly shows a mass shift of +1 Da for fragment ions containing the diffmod. It must be noted, that in some cases SEQUEST had trouble assigning the particular Asn that was modified. In most cases, these ambiguities were resolved by analyzing the peptides individually and reassigning to the consensus sequon. In a few instances, there are peptides that have more than one glycosylation site (10/219, less than 5%). In these cases, mapping the glycosylation site with absolute certainty was not possible. To do so, a higher resolution MS analysis is required.

In glycoproteomes from ManNAcyne-treated cells, specific enrichment of N-glycopeptides was noted in PNGase-released peptides. In total, GIDmap identified 219 unique N-glycosylated peptides representing 108 non-redundant glycoproteins. PNGase-released peptides showed very specific enrichment of N-glycopeptides, with unique peptide IDs. Of the 219 unique peptide IDs containing a modified Asn within the established N-glycosylation consensus sequence (N-X-T/S, where X is not proline) over 97% of the time. By comparison, bioinformatics analysis predicts that only 12.7% of Asn residues within the searched human proteome fall into a consensus sequon, confirming specific enrichment of N-glycopeptides. Negative control glycoproteomes, showed negligible IDs after PNGase treatment, further demonstrating selectivity for tagged glycopeptides. Of the 219 unique peptides, 75 were also found within tryptic samples. Analysis of the 33 PNGase-only IDs strongly indicates that they are true N-glycopeptides enriched from underrepresented (i.e. low abundance) proteins in the tryptic digest. This set was discriminated by several checks including reproducibility in triplicate runs, coverage by multiple glycopeptides, and/or agreement with experimentally assigned glycosylation sites. The number of N-glycosylation sites found per protein ranged from 1 to 7, with an average of 2. The N-glycosylation site IDs were sorted according to Swiss-Prot database annotation (www.expasy.org), which indicates if sites have associated experimental evidence, 'verified', or whether they have been predicted based on homology and/or computational programs, 'potential'. As depicted in FIG. 6a, out of the 219 mapped sites, only 69 (32%) fell into a verified status. Notably, at least ⅓ of these (23) were only recently found by other glycoproteomic mapping endeavors. The majority of hits represent previously uncharacterized glycosylation sites, 113 (52%) of which were annotated as potential, and 37 (17%) of which are novel sites, previously not annotated (22 are from proteins of unknown function). Consistent with known N-linked glycoprotein distribution, the majority of IDs were membrane-bound receptors, transporters, adhesion molecules, and components of subcellular locations rich in glycoproteins, (lysosome, ER, and golgi) as shown in FIG. 6b. About 26% (28) of the protein IDs had known associations with tumor progression and/or metastasis.

Glycoproteomes (1.5 mg) from PC3 cells treated with ManNAcyne analyzed using the GIDmap method disclosed herein are shown in FIGS. 7A-P. Total spectral counts are provided for each IPI ID from peptides harvested from tryptic (columns 1t, 2t, and 3t) and PNGase (columns 1p, 2p, and 3p) treatment, from triplicate runs 1-3, respectively. Proteins are numbered (#) and PNGase peptide sequences are listed (peptide), where N* indicates a diffmod on Asn of +1 Da assigned by SEQUEST. Protein sequences were searched and glycosylation site numbers were assigned (site). Ambiguous assignments, with multiple potential glycosylation sites are indicated by a shaded "peptide" cell. Identified sites were tallied according to annotation in Swiss-Prot: column headings indicate A=assigned (verified by experimental evidence), P=potential (no biochemical characterization), and N=novel (not annotated). If no information was available regarding glycosylation, the column is starred (*) Modified peptides that did not contain a consensus sequence are grayed out. Peptides are listed in groups according to ID status in tryptic and PNGase runs (A), mostly PNGase runs only (B), and mostly tryptic (C).

In another exemplary implementation, the disclosed GIDmap method was used to examine and compare the fucosyl or sialyl proteomes of different cells, including healthy and cancerous lines of prostate and lung cells, and lung cells over-expressing fucosyltransferases, which is described in detail in Example 9 below. With this method, glycosylation/glycan patterns common to cancers and/or the molecular signatures for disease progression may be revealed. The core group of glycans/glycoproteins that are commonly/progressively hyper-fucosylated/-sialylated in correlation with cancer or other disease progression may be examined for the purpose of discovering glycan-related biomarkers.

Figures 10A, 10B:
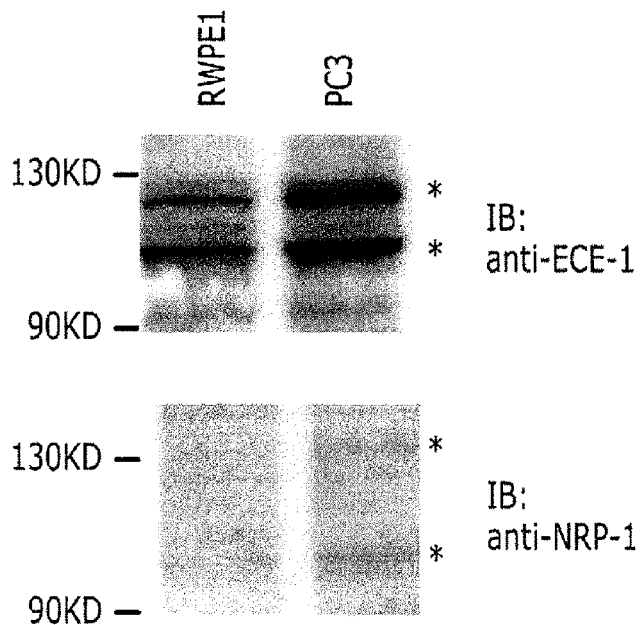
FIG. 10A shows peptide counts from the tryptic and PNGase (png) phase of the GIDmap method disclosed herein.
FIG. 10B shows immunoblotting of ECE-1 and NRP-1. Proteins extracted from RWPE-1 and PC-3 cells (50 μg) were separated by SDS-PAGE and transferred for immunoblotting with specific antibodies (anti-ECE-1 was purchased from R &D Systems; anti-NRP-1 was from Zymed Laboratories). Asterisks indicate specific proteins.
Figure 10C:
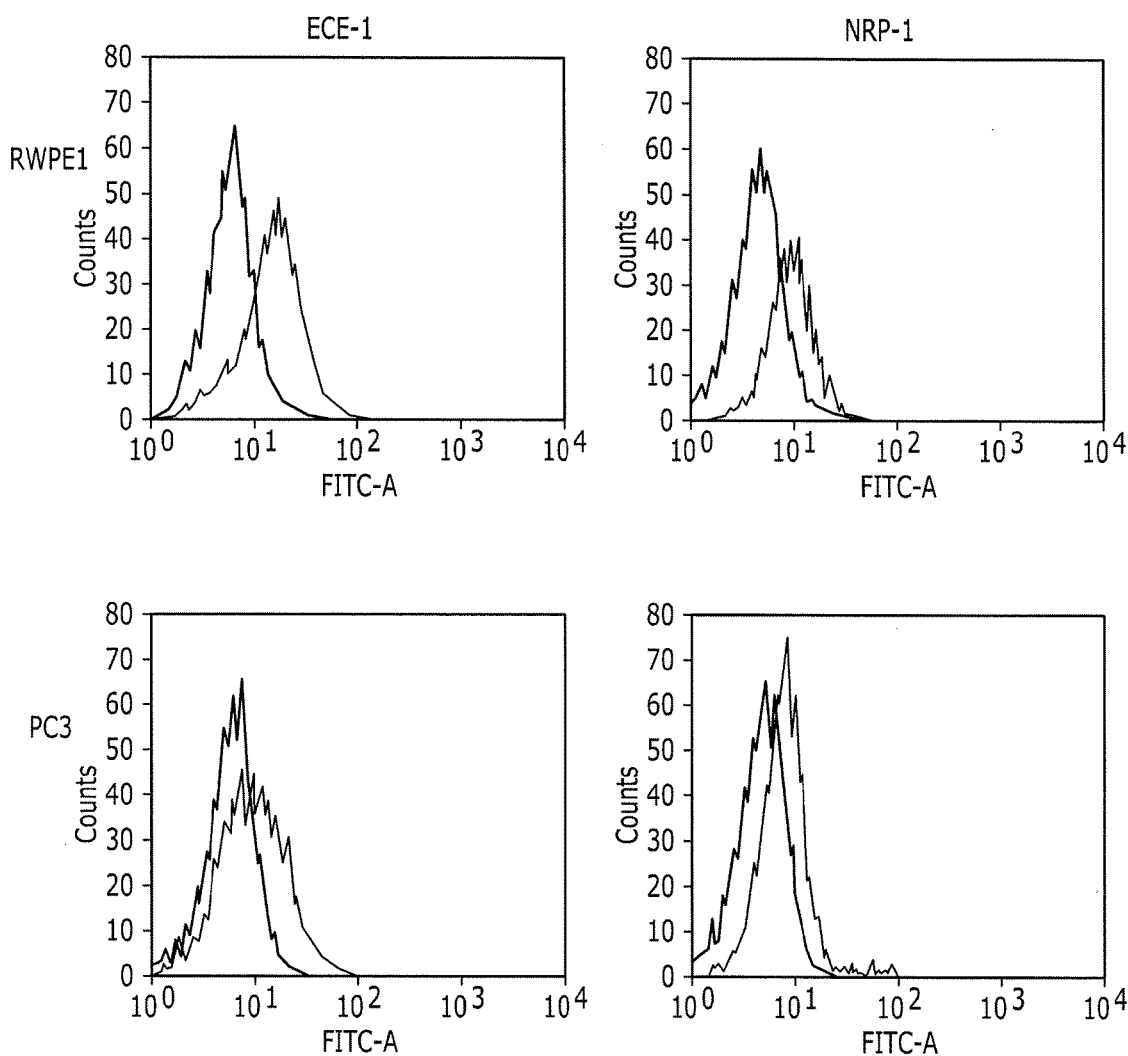
FIG. 10C shows flow cytometric analysis for detecting cells surface ECE-1 and NRP-1 expression by antibody staining.

Profiling of sialylated N-linked glycoproteins in prostate cell lines and lung cancer cell lines was performed by labeling the cells with alkynyl ManNAc. Comparing between the sialylated N-linked glycoproteomes of two prostate cell lines, RWPE-1 vs. PC-3 (i.e., healthy vs. cancerous), about half of the N-sialylated glycoproteins from PC-3 cells were uniquely expressed, while less than 10% of the N-sialylated glycoproteins in the healthy cells were unique (FIG. 8). Of the proteins common to these samples, the majority extracted from the PC-3 cell line had higher counts, consistent with reports that cancerous cells have higher levels of sialylation. Similar results were found for the sialylated N-linked glycoproteins in lung cancer cell lines (FIG. 9). These results provide a host of potential glycoproteins and their glycan structures to examine. The results were verified by selecting several interesting hits (e.g., unique proteins and proteins reporting higher levels of sialylation) for individual analysis by immunoblotting (IB) and flow cytometry. Two examples, endothelin-converting enzyme (ECE-1) and neuropilin-1 (NRP-1), were found to have significant N-linked sialylation only in proteomes of prostate cancer cells by GIDmap (FIG. 10 A). By flow cytometry (10 B) immunobloting (10 C) the protein levels of NRP-1 and ECE-1 seem to be similar in cancerous and non-cancereous cells. However, immunoprecipitation (IP) with the lectin that is specific for sialic acid (*Maackia amurensis* lectin II, MALII) confirmed that sialylated ECE-1 and NRP-1 were only in the PC-3 sample (FIG. 11). This verifys the ability of GIDmap method disclosed herein to discriminate based on glycan composition. Notably, 77% and 85% N-sialylated glycoproteins uniquely identified in prostate cancer cell PC-3 and more invasive lung cancer cell CL1-5, respectively, were either membrane or secreted proteins (FIGS. 8 and 9). This demonstrates the advantage of the GIDmap method disclosed herein in identifying the glycans/glycoproteins that have higher potential to serve as biomarkers. Unique N-sialylated proteins that identified in PC-3 and CL1-5 are listed in FIGS. 12 and 13.

Figure 15A:
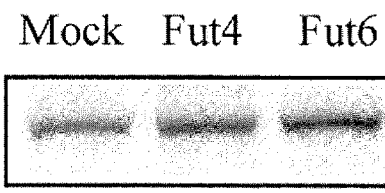
FIG. 15A shows protein expression of plexin B2 in cell lysates. Proteins (50 mg) extracted from mock control cells and stable cell clones that express fucosyltransferases (FucT) 4 or 6 were separated by protein gels, transferred to PVDF membranes and probed with anti-plexin B2 antibody.
Figure 15B:
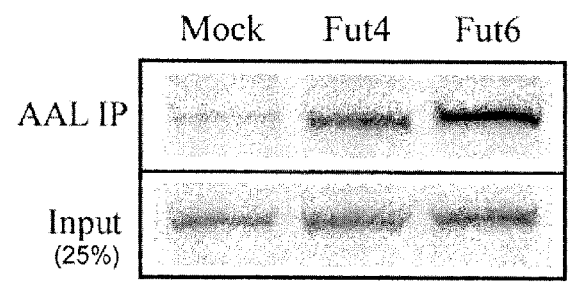
FIG. 15B shows immunoprecipitation (IP) of plexin B2 by fucose lectin AAL.
Figure 16:
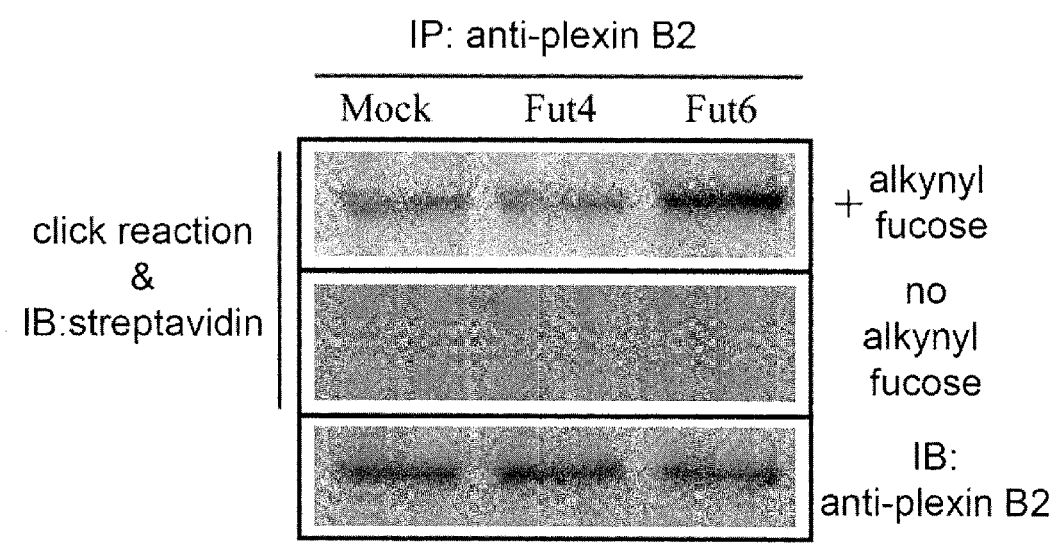
FIG. 16 shows the incorporation of alkynyl fucose to plexin B2 glycans. Total proteins were extracted from untreated or alkynyl fucose-treated mock control, FucT4 and FucT6 stable cell lines. Proteins (200 mg) were dissolved in 500 ml IP buffer (1% NP-40, 150 mM NaCl, 10% glycerol, 50 mM HEPES, pH 7.5 and 1×EDTA-free protease inhibitor cocktail) and precleared with 25 ml protein G beads (GE Healthcare) at 4° C. for 1 h. Precleared proteins extracts were then incubated with 3 mg anti-plexin B2 antibody/25 ml protein G beads at 4° C. for 1 h for overnight. Immunoprecipitates were subjected to SDS-PAGE and the proteins were transferred to PVDF membrane. After blocking with 5% BSA/PBST (0.1% Tween 20/PBS) for 1 h and wash with PBST and PBS sequentially, the protein-side of PVDF membrane was faced down to immerse in click reaction mixture (0.1 mM azido biotin, 0.1 mM Tris-triazoleamine catalyst, 1 mM $CuSO_4$, 2 mM sodium ascorbate; 1 ml for a blot from a mini-gel) and incubated at room temperature for 1 h. After wash with PBST twice, the membrane was probed with peroxidase-conjugated streptavidin for biotin tags on blots.

Comparative profiling of fucosylated N-linked glycoproteins using the GIDmap method disclosed herein was conducted in lung cancer cell line A549 over-expressing either fucosyltransferases (FucT) 4 or 6. Proteins uniquely expressed in FucT4 or FucT6 lines against control (mock) cells are listed in FIG. 14. Among these proteins, plexin B2, a protein linked to cancer metastasis, was examined to confirm that its N-glycans bear fucosylation. Mock (no FucT overexpression), FucT4 and FucT6 lines had similar plexin B2 abundance, while higher levels of fucosylated plexin B2 were observed in FucT4/6-overexpressing lines, as witnessed by immunoprecipitation with the *Aleuria aurantia* lectin (AAL, a fucose-specific lectin) (FIG. 15). To further examine the incorporation of alkynyl fucose into plexin B2 glycan chains, the anti-plexin B2 antibody was used to pull down (immunoprecipitate) plexin B2 from fucose-treated mock, FucT4, and FucT6 cells. Immunoprecipitates were resolved by SDS-PAGE, and transferred onto PVDF membrane for immunoblotting assay. To label the alkynyl fucose residues of plexin B2 glycans with biotin, on-membrane CuAAC reactions were carried out by immersing the PVDF membrane into the a click reaction mix containing azido biotin probe. The biotin signals were then detected by immunoblotting with peroxidase-conjugated streptavidin. As shown in FIG. 16, plexin B2 immunoprecipitated from alkynyl fucose-treated mock, FucT4 and FucT6 cells showed positive signals, with stronger signals in FucT4/6-overexpressing cells, confirming the incorporation of alkynyl fucose onto plexin B2 in FucT4/6-overexpressing cells. In addition, plexin B2 from mock, FucT4 and FucT6 cells without alkynyl fucose treatment showed no signal, indicating a specific reaction with the alkynyl tags of the glycoprotein on PVDF membrane. These results demonstrate the application of using alkynyl sugars for metabolic tagging using overexpressed glycosyltransferases and for detecting the tagged-glycoproteins using CuAAC for analysis by protein blots or GIDmap.

The GIDmap method disclosed herein contributes to the emerging stock of glycoproteome characterization methods that seek to enrich low abundance glycoproteins as a primary step. Previous isolation strategies for secretory glycoproteins have exploited cis-diol chemistry of saccharide chains to immobilize total glycan populations, or immobilized lectins to enrich subpopulations of N-glycosylated proteins and/or peptides after tryptic digestion.

The GIDmap method disclosed herein offers the combined advantage of covalent immobilization and subpopulation enrichment using chemistry that is non-destructive to peptides and glycans. A key benefit to the GIDmap method disclosed herein lies in the ability to tailor isolation of specific glycoproteins based on their unique carbohydrate composition by incorporating alkyne-tagged sugars via the MOE method disclosed herein. This capability not only adds a precise saccharide-selective dimension to traditional glycoprotein isolation, but also relays specific details regarding glycan content. The GIDmap method disclosed herein may be used to provide information about specific glycosylation events, such as sialylation and fucosylation, and different glycosylation events can be directly compared by analyzing cells treated with ManNAcyne and Fucyne, respectively. Such discrimination should prove useful for determining how these saccharides are involved in protein dysfunction. Aberrant glycosylation in the form of terminal sialylation and hyper-fucosylation is documented in several cancers.

In an exemplary implementation of the present GIDmap method, O-glycan site mapping is possible by incorporating established techniques, for example, BEMAD (alkaline induced β-elimination of glycans followed by Michael addition, usually by a thiol).

In a further exemplary implementation of the present GIDmap method, total glycomic analysis may be performed by chemically eluting remaining saccharide moieties and subjecting them to glycan sequencing technology. Notably, this additional step would not be possible using chemical immobilization strategies, since the carbohydrate structure is destroyed and covalently attached to the resin; lectin affinity methods are also not amenable because glycans are cleaved from peptides off-resin, requiring a complex separation of two valuable samples—peptides and glycans.

Disclosed herein is a method for metabolic oligosaccharide engineering that can incorporate alkyne-bearing sugar analogs/precursors into cellular glycans. The utility of the alkynyl system has been demonstrated by incorporating Fuc and ManNAc derivative sugars into cancer cell lines, where they were visualized at the cell surface, intracellularly, and as individual glycoproteins. Sugars were selected that report on Fuc (alkynyl Fuc) and sialic acid (alkynyl ManNAc) because these residues, in particular, have been linked to many aberrant glycans in cancer. Although several epitopes are known, there are likely many other as yet unidentified glycans and activities that contribute.

Disclosed herein is a GIDmap method, which represents a powerful and robust method for analyzing distinct facets of glycoproteins on a proteome-wide scale. The effectivness of GIDmap to compare the glycosylation status of glycoproteoms stage-specific tissues was also demonstrated (i.e., comparison of prostate cells in a healthy verses cancerous lines, and comparison of lung cancer in a less invasive and more invasive cancer cell lines). These experiments show that cancer cells have higher levels of N-linked glycoprotein sialylation. The identified proteins will be investigated for their roles in cancer and to determine if glycosylation influences any pathophysiological behavior. GIDmap also proved to be useful for profiling the glycoprotein targets of fucosyltransferases. In conclusion, the GIDmap method will allow for the determination of glycosylation sites, glycan linkage, and occupancy by specific saccharides, and will also assist to identify glycan substrates for glycosyltransferases and to better understand the role of glycans in temporal- and stage-specific tissues.

EXAMPLES

All chemicals were purchased as reagent grade and used without further purification. Reactions were monitored with analytical thin-layer chromatography (TLC) on silica gel 60 F254 plates and visualized under UV (254 nm) and/or by staining with 5% sulfuric acid or acidic ceric ammonium molybdate. $^1$H- or $^{13}$C-NMR spectra were measured on a Bruker DRX-500 or DRX-600 using $CDCl_3$ or DMSO-$d^6$ as the solvent ($^1$H, 500 or 600 MHz; $^{13}$C, 125 or 150 MHz). Chemical shifts (in ppm) were determined relative to either tetramethylsilane (0 ppm) or deuterated chloroform (77 ppm). Mass spectra were obtained by the analytical services of The Scripps Research Institute. For preparation of samples for mass spectral analysis, the following reagents were used: high purity water (Burdick & Jackson), Optima grade acetone and acetonitrile (ACN), and 99% formic acid (Acros). Peptide-N-glycosidase F (PNGase) enzyme (glycerol free) and 10×G7 reaction buffer were obtained from NEB. PBS and cell culture products used throughout were obtained from Invitrogen. The synthesis of ManNAcyne analogs and biotin azide was reported previously (Hsu et al., Proc Natl Acad Sci USA 2007, 104, 2614-9). Biotin-conjugated *Aleuria Aurantia* Lectin (AAL), FITC-conjugated streptavidin, and fluorescein conjugated *Ulex Europaeus* Agglutinin I (UEA-1) was purchased from Vector laboratories (Burlingame, Calif.). RPMI 1640, DMEM, Alexa Fluor® 594-conjugated WGA lectin, and Hoechst 33342 were purchased from Invitrogen (Carlsbad, Calif.).

SuperBlock® Blocking buffer, peroxidase-conjugated goat anti-mouse IgG, and SuperSignal® Chemiluminescent Substrate were obtained from Pierce (Rockford, Ill.). EDTA-free protease inhibitor cocktail and anti-biotin MAb were purchased from Roche Applied Science (Indianapolis, Ind.).

Example 1

Synthesis of 1,2,3,4-tetraacetyl alkynyl fucose (Fucyne) (1, mixture of anomers; Scheme 1)

To a flask containing compound 8 (0.05 g, 0.2 mmol) (Basak and Lowary, Can. J. Chem., 2002, 80:943-948, Sawa et al., 2006), TFA solution (1 ml, 90% TFA in $H_2O$) was slowly added at 0° C. The reaction was stirred on ice for 1 h and concentrated in vacuo. The resulting residue was treated with pyridine (1 ml), N,Ndimethylaminopyridine (2.0 mg), and acetic anhydride (1 ml), stirred overnight, concentrated, and diluted with dichloromethane. This solution was then sequentially washed with 1 N aqueous HCl, saturated aqueous $NaHCO_3$, and brine. The organic phase was dried over anhydrous $Na_2CO_3$ and concentrated. Silica gel chromatography gave Fucyne (0.055 g, 80%, □-pyranoside:β-pyranoside:□-furanoside:β-furanisude=30:51:11:8) as a colorless gum (FIG. 9). Partial $^1$H-NMR of mixture (500 MHz, $CDCl_3$) □ 5.74 (d, J=8.4 Hz, H-1(βpyr)), 6.24 (s, H-1(□fur)), 6.36 (d, J=4.8 Hz, H-1(βfur)), 6.43(d, J=2.6 Hz, H-1(□pyr)); ESI-TOF-HRMS m/e calculated for $(M+Na)^+$ $C_{15}H_{18}O_9Na$ 365.0843; found 365.0839.

Example 2

Synthesis of N-4-pentynoylmannosamine (10, mixture of anomers; Scheme 2)

A mixture of D-mannosamine hydrochloride (863 mg, 4.0 mmol), N-succinimidyl 4-pentynoate 9 (Salmain M, Vessieres A, Butler I S, Jaouen G (1991) Bioconjug Chem 2:13-15.) (781 mg, 4.0 mmol), triethylamine (1.67 ml, 12.0 mmol) in DMF (31 ml) was stirred at room temperature overnight. The reaction mixture was concentrated in vacuo, and the residue was purified by flash column chromatography ($CHCl_3$/MeOH 8:1) to give N-4-Pentynoylmannosamine, 10 (898 mg, 87%); $^1$H-NMR (500 MHz, $D_2O$)□ 2.37 (t, 2.63H, J=2.5 Hz), 2.48-2.63 (m, 10.5H), 3.38-3.42 (m, 1H), 3.52 (t, 1H, J=10 Hz), 3.63 (t, 1.63H, J=10 Hz), 3.69-3.91 (m, 7.89H), 4.05 (dd, 1.63H, J=4.5 and 10 Hz), 4.35 (dd, 1.63H, J=1.5 and 4.5 Hz), 4.47 (dd, 1H, J=1.5 and 4.5 Hz), 5.03 (d, 1H, J=1.5 Hz), 5.13 (d, 1.63H, J=1.5 Hz); $^{13}$C-NMR (125 MHz, $D_2O$)□ 14.78, 14.91, 34.62, 34.79, 53.67, 54.50, 60.91, 60.93, 67.01, 67.28, 69.25, 70.56, 70.71, 72.47, 72.50, 76.80, 84.04, 84.45, 93.36, 93.67, 175.68, 176.41; ESI-TOF-HRMS m/e calculated for $(M+H)^+$ $C_{11}H_{17}NO_6$ 260.1129; found 260.1120.

Example 3

Synthesis of 1,3,4,6-tetra-O-acetyl-N-4-pentynoylmannosamine (4, mixture of anomers; Scheme 2)

A mixture of 10 (123 mg, 0.500 mmol) and acetic anhydride (0.227 ml, 2.40 mmol) in pyridine (4 ml) was stirred at room temperature overnight. The reaction mixture was concentrated in vacuo, and the residue was dissolved in $CH_2Cl_2$ and washed with water. The organic layer was dried over $Na_2SO_4$ and evaporated. The residue was purified by flash column chromatography (AcOEt/Hexane 1:4) to give 1,3,4,6-tetra-O-acetyl-N-4-pentynoylmannosamine, 4 (183 mg, 86%); $^1$H-NMR (500 MHz, $CDCl_3$) □ 2.00 (s, 9H), 2.06 (s, 9H), 2.097 (s, 3H), 2.10 (s, 3H), 2.11 (s, 3H), 2.14-2.18 (m, 3H), 2.19 (s, 6H), 2.46-2.58 (m, 12H), 3.81-3.87 (m, 1H), 4.00-4.15 (m, 5H), 4.23-4.30 (m, 3H), 4.69 (dd, 2H, J=4.5 and 10 Hz), 4.82 (dd, 1H, J=4.5 and 10 Hz), 5.09 (dd, 1H, J=4.5 and 10 Hz), 5.17 (t, 1H, J=10 Hz), 5.23 (t, 2H, J=10 Hz), 5.33 (dd, 2H, J=4.5 and 10 Hz), 5.90 (s, 1H), 6.03 (s, 2H), 6.36 (d, 1H, J=9.5 Hz), 6.54 (d, 2H, J=9.5 Hz); $^{13}$C-NMR (125 MHz, $CDCl_3$) □ 15.29, 15.40, 20.99, 21.01, 21.06, 21.09, 21.15, 21.21, 35.51, 35.72, 49.56, 49.80, 62.55, 62.70, 65.87, 66.07, 69.25, 70.39, 70.54, 70.63, 71.63, 73.69, 83.07, 83.11, 90.98, 92.08, 168.59, 168.81, 170.07, 170.44, 170.51, 170.98, 171.82, 172.15; ESI-TOF-HRMS m/e calculated for $(M+H)^+$ $C_{19}H_{25}NO_{10}$ 428.1551; found 428.1549.

Example 4

Synthesis of 3-azidopropyl biotin amide (6; Scheme 3)

A mixture of D-(+)-biotin (100 mg, 0.41 mmol), 1-azido-3-aminopropane (82 mg, 0.82 mmol) (Carboni B, Benalil A, Vaultier M (1993) J Org Chem 58:3736-3741), O-(benzotriazol-1-yl)-N,N,N',N'-tetramethyluronium hexafluorophosphate (311 mg, 0.82 mmol) and N,N-diisopropylethylamine (106 mg, 0.82 mmol) in DMF (5 ml) was stirred at room temperature for 2 h. The reaction mixture was concentrated in vacuo, and the residue was purified by flash column chromatography ($CHCl_3$/MeOH 10:1) to give the amide 6 (53 mg, 40%); $^1$H-NMR (400 MHz, DMSO-d$^6$) □ 1.21-1.35 (m, 4H), 1.45-1.55 (m, 3H), 1.60-1.67 (m, 3H), 2.05 (t, 2H, J=7.6 Hz), 2.57 (d, 1H, J=12.6 Hz), 2.82 (dd, 1H, J=4.8 and 12.6 Hz), 3.07-3.10 (m, 3H), 4.10-4.14 (m, 1H), 4.28-4.32 (m, 1H), 6.36 (s, 1H), 6.42 (s, 1H), 7.84 (m, 1H); ESI-TOF-HRMS m/e calculated for $(M+H)^+$ $C_{13}H_{23}N_6O_2S$ 327.1598; found 327.1598.

Example 5

Synthesis of N-5-pentynoyl-D-neuraminic acid (13, Scheme 4)

A mixture of N-4-pentynoylmannosamine (300 mg, 1.16 mmol), sodium pyruvate (2.31 g, 20.0 mmol), $NaN_3$ (1%, 520 □L), and N-acetylneuraminic acid aldolase (63.3 U), in potassium phosphate buffer (pH 7.20, 0.05 mmol/L, 21.0 mL), was incubated at room temperature for 2 days. The solvent was evaporated and the residue was applied to a Bio-RAD AG 1-X8 (formate form, 100-200 mesh) column and eluted with water and formic acid (0.1-1.0 mol/L) sequentially. Fractions containing the desired product were pooled and freeze-dried to obtain the pure product (268 mg, 67%). $^1$H-NMR (500 MHz, $D_2O$) □ 1.82 (dd, 1H, J=13.0, 13.0 Hz), 2.26 (dd, 1H, J=13.0, 4.0 Hz), 2.36 (s, 1H), 2.41-2.53 (m, 4H), 3.55 (dd, 1H, J=11.5, 6.0 Hz), 3.64 (d, 1H, J=8.5 Hz), 3.71 (t, 1H, J=6.0 Hz), 3.77 (d, 1H, J=11.5 Hz) 3.91 (t, 1H, J=10.0 Hz), 3.98-4.08 (m, 2H). $^{13}$C-NMR (125 MHz, $D_2O$) □ 14.99, 35.12, 39.34, 52.47, 63.58, 66.97, 68.66, 70.79, 70.83 (×2), 83.94, 95.95, 174.16, 175.81. ESI m/e calculated for $(M+H)^+$ $C_{14}H_{22}NO_9$ 348; found 348.

Example 6

Synthesis of 2,4,7,8,9-penta-O-acetyl-N-5-pentynoyl-D-neuraminic-1-methyl ester (11, Scheme 4)

A suspension of N-5-pentynoyl-D-neuraminic acid 13 (287.5 mg, 0.828 mmol) and Dowex 50 WX2-200 ($H^+$ form) in methanol (8 mL) was stirred at room temperature for overnight. The resins were filtered, and then washed with methanol. The washings were concentrated to give N-5-pentynoyl-D-neuraminic-1-methyl ester (296 mg, 99%). A mixture of N-5-pentynoly-D-neuraminic-1-methyl ester (150 mg, 0.415 mmol) and $Ac_2O$ (3.0 mL) in pyridine (6.0 mL) was stirred at room temperature for overnight. After evaporating the solvent, the compound was extracted by AcOEt. The AcOEt extract was washed with $H_2O$, dried over $Na_2SO_4$, and evaporated under reduced pressure. The residue was purified by silica chromatography (AcOEt:Hexane 1:4/1:3/1:2/2:3) to give 2,4,7,8,9-Penta-O-acetyl-N-5-pentynoyl-D-neuraminic-1-methyl ester 11 (87.7 mg, 37%). $^1$H-NMR (500 MHz, $CDCl_3$) ☐ 2.037 (s, 3H), 2.042 (s, 3H), 2.06 (s, 3H), 2.14 (s, 3H), 2.16 (s, 3H), 2.52-2.00 (m, 7H), 2.56 (dd, 1H, J=13.5, 5.0 Hz), 3.80 (s, 3H), 4.20-4.10 (m, 3H), 4.51 (dd, 1H, J=12.5, 2.0 Hz), 5.02-5.10 (m, 1H), 5.22-5.30 (m, 1H), 5.41 (d, 1H, J=4.0 Hz), 5.94 (d, 1H, J=8.5 Hz). $^{13}$C-NMR (125 MHz, $CDCl_3$) ☐ 21.11, 21.16 (×2), 21.28, 21.36, 35.72, 36.38, 49.37, 53.59, 62.51, 68.24, 68.66, 69.86, 71.90, 73.11, 83.37, 97.81, 166.79, 168.71, 170.65, 170.79, 171.03, 171.07, 171.25, 171.63. ESI-TOF-HRMS m/e calculated for $(M+H)^+$ $C_{25}H_{34}NO_{14}$ 572.1974; found 572.1957.

Example 7

MOE method for Demonstrating How Alkynyl-Tagged Glycans can be Labeled with CuAAC-Probes and Visualized at the Cell Surface, in Glycoprotein Lysates and Intracellularly Cell culture: Breast cancer MCF-7 and Jurkat cells were cultivated ($2\times10^6$/10 ml) in RPMI 1640 medium (Invitrogen) supplemented with 10% FCS. Peracetylated alkynyl sugars Fucyne (200 uM) and ManNAcyne (25 uM) or native control sugars ManNAc for 1 to 3 days at 37° C.

Flow cytometry analysis: Cells were harvested, washed with 0.1% FCS/PBS, and resuspended ($10^6$ cells for Jurkat cells; $3\times10^5$ cells for other cells) in 100 microliters of click reaction solution (0.1 mM biotin probe, 0.1 mM Tris-triazoleamine catalyst, 0.1 mM $CuSO_4$/0.5 mM sodium ascorbate, in PBS). The reaction was incubated at room temperature for 30 min, and then the cells were washed twice with 0.1% FCS/PBS. Cells treated with biotin probe were subsequently stained with fluorescein-conjugated streptavidin (0.5 microgram per sample in 50 microliters of 1% FCS/PBS) for 30 min at 4° C., and washed three times with 1% FCS/PBS. Data were acquired by BD LSR II with FACSDiva software, and were analyzed by CellQuestPro software (BD Biosciences).

Immunoblotting (IB) and immunoprecipitation (IP): Cells were seeded at $3\times10^6$/8 ml per 10-cm dish and treated with control and test sugars (200 micromolar Fuc vs. Fucyne or 25 micromolar ManNAc vs. ManNAcyne) in growth medium at 37° C. After 3 days, cell extracts were prepared by resuspending the cells in 1 ml of lysis buffer (1% Nonidet P-40/150 mM NaCl/protease inhibitor/100 mM sodium phosphate, pH 7.5). Protein extract (1 mg/ml) was labeled for 1 h at room temperature (0.1 mM biotin probe, or fluorogenic coumarin probe, 0.1 mM tris-triazoleamine catalyst, 1 mM $CuSO_4$, and 2 mM sodium ascorbate, in PBS; the azido rhodamine probe was a gift from Benjamin F. Cravatt, The Scripps Research Institute). Labeled protein lysate was resolved by SDS/PAGE. For immunoblotting of biotin-labeled glycoproteins, electrophoresed proteins were transferred onto PVDF membranes, blocked for 20 min with SuperBlock® Blocking Buffer. Blots were either probed for 1 h with anti-biotin MAb (1 microgram/ml), and incubated with peroxidase-conjugated goat anti-mouse IgG (1:7,500 dilution) for 30 min; or probed for 1 h with peroxidase-conjugated anti-biotin Ab (Calbiochem)(1:5000 in SuperBlock). Each step was followed by a wash with 0.02% Tween 20/PBS (PBST). Signal was developed with SuperSignal Chemiluminescent Substrate and detected by exposure to x-ray film. For detecting the coumarin-labeled glycoproteins, gels were examined under 365 nm UV light with a 535+/−50 nm filter. Images were taken by using a BioDoc-It imaging system (UVP). Rhodamine gels were analyzed as described (Speers A E, Cravatt B F (2004) Chem Biol 11:535-546).

Fluorescent Labeling in Cells: Human hepatocellular carcinoma cells (Hep3B) or breast adenocarcinoma cells (MCF7) were seeded onto six-well plates ($3\times10^5$/2 ml per well) containing glass coverslips, and were cultivated in 10% FCS/DMEM or 10% FCS/RPMI medium 1640. Growth medium was supplemented with a control sugar (200 micromolar Fuc or 25 micromolar ManNAc) and an alkynyl-modified sugar (Fucyne or ManNAcyne at the same concentration as control sugars). After growing for 3 days, cells on coverslips were fixed and permeabilized with acetone for 10 min, then subjected to the probe labeling reaction: 0.1 mM biotin probe or fluorogenic coumarin probe, 0.1 mM Tris-triazoleamine catalyst, 1 mM $CuSO_4$, 2 mM sodium ascorbate, in PBS, at room temperature for 30 min. Subsequently, the fixed and labeled cells were rinsed with PBS and stained with Alexa Fluor 594-conjugated WGA lectin (2 micrograms/ml in 5% BSA/PBS) and/or fluorescein-conjugated streptavidin (2 micrograms/ml in 5% BSA/PBS) at room temperature for 30 min. Hoechst 33342 (10 microgram/ml in PBS) was used to stain nuclei. Fluorescent images were captured by Bio-Rad (Carl Zeiss) Radiance 2100 Rainbow laser scanning confocal microscopy system.

Example 8

GIDmap Method for Analyzing N-Linked Glycoproteome Isolated from Prostate Cancer (PC3) Cells Based on MudPIT Cell culture: In this study prostate cancer (PC3) cells from ATCC were used in order to study their tagged N-glycome after treatment with ManNAcyne. Briefly, PC3 cells ($2\times10^6$ cells/T75 adherent flask) were cultured in RPMI 1640 (12 mL) supplemented with 10% FCS and 25 micromolar sugar, either peracetylated ManNAcyne or control ManNAc, at 37° C. for 2 days. Then, cells were resuspended in 0.5 mL lysis buffer (1% NP-40, 150 mM NaCl, Roche protease inhibitor, and 100 mM sodium phosphate pH 7.5) and homogenized. Cellular debris was removed by centrifugation and cell lysates were analyzed for protein content by BCA assay.

Biotin labeling using click chemistry: Glycoproteome samples (1.5 mg, 1 to 2 mg/mL) were divided into 0.5 mL aliquots and treated sequentially with 100 µM biotin-azide, 1 mM TCEP (prepared fresh), and 100 µM triazole ligand, all diluted from 50× stocks. The reactions were thoroughly mixed, treated with 1 mM $CuSO_4$, mixed again, and incubated for one hour at room temperature, with one additional mixing halfway through. Proteins were then precipitated by adding 125 µL (20% final volume) of an ice-cold TCA:Acetone solution (1:1 w/v), followed by a 30 minute incubation on ice before pelleting by centrifugation (5900×g, 4 min, 4° C.). Pelleted proteins were washed two times by adding 0.5 mL cold acetone, sonicating for 5 s, and repelleting. Protein was finally resuspended in a 1.2% SDS in PBS solution, sonicated for 5 s, and heated at 80° C. for 5 minutes.

Affinity capture: Biotin-labeled glycoproteins were enriched using immunopure streptavidin-agarose beads (Pierce). Beads (50 μL per 1.5 mgs of total proteome) pre-equilibrated in PBS (wash 3×10 mL PBS) were treated with glycoproteomic samples diluted to 0.2% SDS (6 mL) for 1.5 h at room temperature, or overnight at 4° C., with rotation. Beads were washed with 0.2% SDS in PBS (10 mL, 1×), PBS (10 mL, 3×), and water (10 mL, 3×). Centrifugation of beads between steps was carried out using a swinging bucket rotor (1300×g, 3 min).

Trypsin Digestion (on-bead): Affinity captured products were digested on-bead in microtubes by the following procedure. Unless otherwise noted, all incubation steps were carried out at 37° C., with agitation. First, the beads were suspended in a freshly prepared 6 M urea in PBS solution (0.5 mL) containing 10 mM TCEP (Tris(2-carboxyethyl)phosphine hydrochloride), for 30 min. Iodoacetamide (20 mM, prepared fresh) was then added to the solution and alkylation proceeded for 30 min, in the dark. The concentration of urea in solution was then diluted to 2 M with PBS, the beads were sedimented by microfuge, and the supernatant was removed. A fresh premixed trypsin solution, consisting of 10 μg/mL sequence grade modified trypsin (Promega), 1 mM $CaCl_2$, and 2 M urea in PBS, was added to the beads. The digestion was allowed to proceed overnight. The tryptic solution and beads were then transferred into Bio-spin columns (BioRad) from which the tryptic peptides were eluted by microfuge. The beads were washed two times with 50 μL of water. Eluted sample and washes were combined, treated with formic acid (5% final volume), and stored at −20° C.

PNGase Digestion (on-bead): To remove a subset of remaining affinity captured N-linked glycopeptides, an on-bead PNGase digestion procedure was used. After trypsin digestion and elution, streptavidin beads were extensively washed (3×, 0.5 mL PBS and 3×, 0.5 mL water, 1×0.5 mM G7 buffer) and transferred to a new microtube in G7 buffer (200 μL). PNGase (2.5 U/μl) was added and the digestion was carried out overnight, at 37° C., with agitation. PNGase peptides were isolated by filtration as described previously for tryptic peptides.

Mass spectrometry (MS) procedures: LC-$MS^2$ equipment. Briefly, LCMS data was obtained on a quaternary Agilent 1100 series HPLC coupled to an LTQ ion trap mass spectrometer (ThermoElectron) equipped with a nano-LC electrospray ionization source. The LTQ was controlled by Xcalibur data system software (ThermoElectron). LCMS mobile phase buffers were composed in water with 0.1% formic acid with the following additional modifiers: A (5% ACN), B (80% ACN), C (500 mM ammonium acetate, 5% ACN).

LC microcapillary columns: Fused silica microcapillary columns (100 μm i.d.×365 μm o.d.) were pulled to generate 5 μm tips using a Model P-2000 $CO_2$ laser puller (Sutter Instrument). Biphasic columns were packed with 10 cm of 5 μm Aqua C18 reverse phase resin (RP; Phemomenex) followed by 3 cm of Partisphere strong cation exchange resin (SCX; Whatman). Loading/desalting tips were prepared by packing 4 cm of RP resin into a 250 μm silica microcapillary fitted with a 2 μm inline microfilter (Upchurch Scientific). Column packing was performed using a high pressure loading device (600 psi helium). Columns and tips were equilibrated in buffer A shortly before use.

MudPIT analysis: (Washburn et al., Nat Biotechnol 2001, 19, (3), 242-7) The desalting tip was loaded with sample and connected to a biphasic column and equilibrated with buffer A for 10 minutes before connecting to the MS. Peptides were eluted in steps beginning with a salt wash protocol (% C), followed by an ACN gradient. For tryptic samples, five salt-wash steps (0%, 25%, 50%, 80%, and 100% C) were used, see Tables 1 through 5. For PNGase samples five steps were used (0%, 50%, 80%, 100%, 100%), see Tables 6 through 10. The flow rate was set to approximately 0.25 μL/min and the applied distal spray voltage to 2.5-2.7 kV. For tryptic samples, MS2 data was collected using one full scan (400-1800 MW) followed by 7 data dependent $MS^2$ scans of the most abundant ions with dynamic exclusion enabled (repeat count=1; exclusion list size=300, exclusion duration=60). For PNGase samples, $MS^2$ data was collected using one full scan (400-1800 MW) followed by 18 data dependent $MS^2$ scans of the most abundant ions with dynamic exclusion disabled.

Database Searches of $MS^2$ spectra: Tandem mass spectra were searched using a SEQUEST algorithm against the human database (ipi.HUMANv323.fasta) from the European Bioinformatics Institute (EBI). The mass window for peptides searched was given a tolerance of 3 Da between the measured average mass and the calculated average mass, and the b and y ions were included. All samples were searched with a static mod of +57 Da for cys residues, and PNGase samples were also searched with a differential modification (diffmod) of +1 Da Asn, for the catalyzed conversion of a glycan bearing Asn to Asp. For analysis of this diffmod, a sample was searched without it and with it (allowed to occur at 1, or up to 4 positions in the peptide), see analysis of PNGase searches. Data was also searched against a human database with a reversed protein sequence addendum (EBI-IPI_human_3.23_11-022006_con_reversed.fasta) in order to quantify false positive rates that might occur from the diffmod +1 N search. DTASelect was used to render SEQUEST output files. For tryptic rendering, default parameters were used, along with constraints for tryptic ends and exclusion of protein subsets. For PNGase rendering, default values were lowered (Xcorr parameters to 1.0 (+1), 2.0 (+2) 2.0 (+3) and the DeltaCN to 0.06), subsets were excluded, single peptides were included, and tryptic ends, and modification were required. In house software was used to extract modified peptide sequences to compare spectral counts from DTAselect files.

TABLE 1

Tryptic Step 1 (0% ammonium acetate)

| Time (min) | Flow rate (ml/min) | % Buffer A | % Buffer B | % Buffer C |
|---|---|---|---|---|
| 0.00 | 0.1 | 100 | 0 | 0 |
| 5.00 | 0.1 | 100 | 0 | 0 |
| 60.00 | 0.1 | 55 | 45 | 0 |
| 70.00 | 0.1 | 0 | 100 | 0 |
| 80.00 | 0.1 | 0 | 100 | 0 |
| 90.00 | 0.1 | 0 | 100 | 0 |

TABLE 2

Tryptic Step 2 (25% ammonium acetate)

| Time (min) | Flow rate (ml/min) | % Buffer A | % Buffer B | % Buffer C |
|---|---|---|---|---|
| 0.00 | 0.1 | 100 | 0 | 0 |
| 3.00 | 0.1 | 100 | 0 | 0 |
| 3.10 | 0.1 | 70 | 5 | 25 |
| 5.00 | 0.1 | 70 | 5 | 25 |
| 5.10 | 0.1 | 95 | 5 | 0 |
| 15.00 | 0.1 | 85 | 15 | 0 |
| 60.00 | 0.1 | 75 | 25 | 0 |
| 112.00 | 0.1 | 45 | 55 | 0 |

TABLE 3

Tryptic Step 3 (50% ammonium acetate)

| Time (min) | Flow rate (ml/min) | % Buffer A | % Buffer B | % Buffer C |
|---|---|---|---|---|
| 0.00 | 0.1 | 100 | 0 | 0 |
| 3.00 | 0.1 | 100 | 0 | 0 |
| 3.10 | 0.1 | 45 | 5 | 50 |
| 5.00 | 0.1 | 45 | 5 | 50 |
| 5.10 | 0.1 | 95 | 5 | 0 |
| 15.00 | 0.1 | 85 | 15 | 0 |
| 60.00 | 0.1 | 75 | 25 | 0 |
| 112.00 | 0.1 | 45 | 55 | 0 |

TABLE 4

Tryptic Step 4 (80% ammonium acetate)

| Time (min) | Flow rate (ml/min) | % Buffer A | % Buffer B | % Buffer C |
|---|---|---|---|---|
| 0.00 | 0.1 | 100 | 0 | 0 |
| 3.00 | 0.1 | 100 | 0 | 0 |
| 3.10 | 0.1 | 15 | 5 | 80 |
| 5.00 | 0.1 | 15 | 5 | 80 |
| 5.10 | 0.1 | 95 | 5 | 0 |
| 15.00 | 0.1 | 85 | 15 | 0 |
| 60.00 | 0.1 | 75 | 25 | 0 |
| 112.00 | 0.1 | 45 | 55 | 0 |

TABLE 5

Tryptic Step 5 (100% ammonium acetate)

| Time (min) | Flow rate (ml/min) | % Buffer A | % Buffer B | % Buffer C |
|---|---|---|---|---|
| 0.00 | 0.1 | 100 | 0 | 0 |
| 2.00 | 0.1 | 100 | 0 | 0 |
| 2.10 | 0.1 | 0 | 0 | 100 |
| 15.00 | 0.1 | 0 | 0 | 100 |
| 15.10 | 0.1 | 93 | 7 | 0 |
| 23.00 | 0.1 | 85 | 15 | 0 |
| 90.00 | 0.1 | 70 | 30 | 0 |
| 140.00 | 0.1 | 35 | 65 | 0 |
| 150.00 | 0.1 | 100 | 0 | 0 |

TABLE 6

PNGase Step 1 (0% ammonium acetate)

| Time (min) | Flow rate (ml/min) | % Buffer A | % Buffer B | % Buffer C |
|---|---|---|---|---|
| 0.00 | 0.1 | 100 | 0 | 0 |
| 5.00 | 0.1 | 100 | 0 | 0 |
| 60.00 | 0.1 | 55 | 45 | 0 |
| 70.00 | 0.1 | 0 | 100 | 0 |
| 100.00 | 0.1 | 0 | 100 | 0 |

TABLE 7

PNGase Step 2 (50% ammonium acetate)

| Time (min) | Flow rate (ml/min) | % Buffer A | % Buffer B | % Buffer C |
|---|---|---|---|---|
| 0.00 | 0.1 | 100 | 0 | 0 |
| 6.00 | 0.1 | 100 | 0 | 0 |
| 6.10 | 0.1 | 45 | 5 | 50 |
| 8.00 | 0.1 | 45 | 5 | 50 |
| 8.10 | 0.1 | 95 | 5 | 0 |
| 15.00 | 0.1 | 85 | 15 | 0 |
| 35.00 | 0.1 | 75 | 25 | 0 |
| 75.00 | 0.1 | 45 | 55 | 0 |
| 80.00 | 0.1 | 45 | 55 | 0 |

TABLE 8

PNGase Step 3 (80% ammonium acetate)

| Time (min) | Flow rate (ml/min) | % Buffer A | % Buffer B | % Buffer C |
|---|---|---|---|---|
| 0.00 | 0.1 | 100 | 0 | 0 |
| 5.00 | 0.1 | 100 | 0 | 0 |
| 5.10 | 0.1 | 15 | 5 | 80 |
| 8.00 | 0.1 | 15 | 5 | 80 |
| 8.10 | 0.1 | 95 | 5 | 0 |
| 18.00 | 0.1 | 85 | 15 | 0 |
| 63.00 | 0.1 | 75 | 25 | 0 |
| 115.00 | 0.1 | 45 | 55 | 0 |
| 120.00 | 0.1 | 45 | 55 | 0 |

TABLE 9

PNGase Step 4 (100% ammonium acetate)

| Time (min) | Flow rate (ml/min) | % Buffer A | % Buffer B | % Buffer C |
|---|---|---|---|---|
| 0.00 | 0.1 | 100 | 0 | 0 |
| 4.00 | 0.1 | 100 | 0 | 0 |
| 4.10 | 0.1 | 0 | 0 | 100 |
| 20.00 | 0.1 | 0 | 0 | 100 |
| 20.10 | 0.1 | 93 | 7 | 0 |
| 25.00 | 0.1 | 85 | 15 | 0 |
| 100.00 | 0.1 | 70 | 30 | 0 |
| 184.00 | 0.1 | 0 | 100 | 0 |
| 194.00 | 0.1 | 0 | 100 | 0 |
| 195.00 | 0.1 | 100 | 0 | 0 |
| 200.00 | 0.1 | 100 | 0 | 0 |

TABLE 10

PNGase step 5 (100% ammonium acetate)

| Time (min) | Flow rate (ml/min) | % Buffer A | % Buffer B | % Buffer C |
|---|---|---|---|---|
| 0.00 | 0.1 | 100 | 0 | 0 |
| 4.00 | 0.1 | 100 | 0 | 0 |
| 4.10 | 0.1 | 0 | 0 | 100 |
| 14.00 | 0.1 | 0 | 0 | 100 |
| 14.10 | 0.1 | 93 | 7 | 0 |
| 30.00 | 0.1 | 70 | 30 | 0 |
| 50.00 | 0.1 | 0 | 100 | 0 |
| 55.00 | 0.1 | 0 | 100 | 0 |
| 56.00 | 0.1 | 100 | 0 | 0 |
| 60.00 | 0.1 | 100 | 0 | 0 |

Analysis of PNGase searches: The diffmod searches of +1 N were validated by several avenues. First, data was searched without a diffmod (0) and with 1 diffmod (1) and up to 4 diffmods (4) per peptide. Peptides with total counts of 2 or greater were analyzed, only peptides with diffmods were considered in 1 and 4. Good IDs were defined as a peptide with the N-glycosylation motif (N-X-S/T, where X is not proline), whereas Bad IDs did not have motifs. Error is a percentage of Bad IDs/total peptides. As can be seen in Table 11, the diffmod searches had very low error. Moreover, these searches covered 90% percent of the Good IDs in the 0 search, with an average of 1.5 additional peptides covering the same protein. Diffmod searches were also performed against a database with reversed sequences. After rendering data through SEQUESIT as described previously, a false positive rate of 1.72% was determined for all peptide IDs. This error was even lower, at 0.3%, when only modified peptides were considered. In the final analysis of PNGase-treated peptides performed in triplicate, the error was approximately 2.3% (5/219, Bad ID marked in gray in Table 12). Notably, most BadIDs have low spectral counts and were found among stronger Good IDs. FIG. 5, shows representative $MS^2$ fragmentation data that clearly shows a mass shift of +1 Da for fragment ions containing the diffmod. However, it must be noted, that in some cases SEQUEST had trouble assigning the particular Asn that was modified. In most cases, these ambiguities were resolved by analyzing the peptides individually and reassigning to the consensus sequon. In a few instances, there are peptides that have more than one glycosylation site (10/219, less than 5%). In these cases, mapping the glycosylation site with absolute certainty was not possible. To do so, a higher resolution MS analysis is required.

TABLE 11

Analysis of Differential Modification Search

|  | diffmod param | | |
| --- | --- | --- | --- |
|  | 0 | 1 | 4 |
| total peptide | 161 | 125 | 120 |
| Good ID | 59 | 121 | 117 |
| % Error | 66.9% | 3.2% | 2.5% |

Representative LCMS data for a PNGase-treated sample (FIG. 5): The total ion chromatogram highlighting a peptide eluting at 57.74 minutes in PNGase step 2 (upper frame) is shown in FIG. 5. The full MS scan of peptides eluting at 57.74 minutes highlighting a specific peptide at $[M+2H]^{2+}=806.1$ (middle frame). The $MS^2$ scan (lower frame) of the $[M+2H]^{2+}=806.1$ ion clearly illustrating a mass shift of +1 Da on all b and y ions containing the formerly glycosylated N, as marked by asterisk *.

Total N-linked glycopeptides: Glycoproteomes (1.5 mg) from PC3 cells treated with ManNAcyne analyzed using the GIDmap method disclosed herein are shown in FIGS. 7A-G. Total spectral counts are provided for each IPI ID from peptides harvested from tryptic (columns 1t, 2t, and 3t) and PNGase (columns 1p, 2p, and 3p) treatment, from runs 1-3, respectively. Proteins are numbered (# column) and PNGase peptide sequences are listed (peptide sequence column), where N* indicates a diffmod on Asn of +1 Da assigned by SEQUEST. Each peptide sequence fragment is listed has been assigned a SEQ ID. NO. Protein sequences were searched and glycosylation site numbers were assigned (site). Ambiguous assignments, with multiple potential glycosylation sites are indicated by a shaded "peptide" cell. Identified sites were tallied according to annotation in Swiss-Prot: column headings indicate A=assigned (verified by experimental evidence), P=potential (no biochemical characterization), and N=novel (not annotated). In these columns * indicates that no information was available regarding glycosylation. Modified peptides that did not contain a consensus sequence are grayed out. Peptides are listed in groups according to ID status in tryptic and PNGase runs (A), mostly PNGase runs only (B), and mostly tryptic (C).

Example 9

GIDmap Method for Analyzing N-Linked Glycoproteome Isolated from Prostate Cancer (PC3) and Normal (RWPE-1) Cells, and Lung Cancer (CL1-5) and Non-Invasive (CL1) Cells Based on MudPIT Cell culture: Prostate cancer cells PC-3, lung cancer cells CL1 and CL1-5, A549/mock, A549/FucT4, and A549/FucT6 were cultivated in RPMI 1640 (Invitrogen) supplemented with 10% FBS. Non-cancerous prostate cells RWPE-1 were cultivated in Keratinocyte-SFM (Invitrogen) supplemented with human EGF (5 ng/mL) and bovine pituitary extract (50 □g/mL). Peracetylated Fucyne (200 □M) or ManNAcyne (200 □M) were added to culture medium and incubate with cells ($2\times10^6$/ml) for 3 days at 37° C.

On-membrane click reaction: Proteins were separated by SDS-PAGE and transferred onto methanol-activated PVDF membrane. After blocking with 5% BSA/PBST (0.1% Tween 20/PBS) for 1 h and wash with PBST and PBS sequentially, the protein-side of PVDF membrane was faced down to immerse in click reaction mixture (0.1 mM azido biotin, 0.1 mM Tris-triazoleamine catalyst, 1 mM $CuSO_4$, 2 mM sodium ascorbate; 1 ml for a blot from a mini-gel) and incubated at room temperature for 1 h. After wash with PBST twice, the membrane was probed with peroxidase-conjugated streptavidin for biotin labels on blots.

Flow cytometry analysis: Cells were detached by Dissociation buffer (Invitrogen) and washed twice with FACS staining/washing buffer (1% FCS and 0.1% $NaN_3$ in PBS), followed by incubation with anti-NRP-1 and anti-ECE-1 antibodies in 50 staining buffer at 4° C. for 20 min. After washing with FACS staining/washing buffer three times, cells were further incubated at 4° C. for 20 min with 50 FITC-conjugated secondary antibodies diluted (1:200) in FACS staining/washing buffer. Cells were washed and fixed with 1% paraformaldehyde in PBS for 30 min at 4° C. before their fluorescence was analyzed with a FACSCanto® (Becton Dickinson, Mountain View, Calif.).

Immunoblotting (IB) and immunoprecipitation (IP): Protein extracts (50 □g) were separated by SDS-PAGE and transferred for immunoblotting with specific antibodies (anti-ECE-1 was purchased from R &D Systems; anti-NRP-1 was from Zymed Laboratories) and HRP-conjugated secondary antibodies. For IP with MALII, cell lysates (200 µg protein in 500 □l buffer: 0.2% NP-40, 150 mM NaCl, 0.1 mM CaCl2, 10 mM HEPES, pH 7.5, 1×EDTA-free protease inhibitor cocktail from Roche) were precleared with 20 □l Neutravidin beads (Pierce) at 4° C. for 1 h, followed by immunoprecipitation with 5 □g biotinylated MALII (preferentially binds to alpha 2,3-linked sialic acid, purchased from Vector Laboratories) or and 20 □l Neutravidin beads at 4° C. for overnight. After wash three times with IP buffer, immunoprecipitates were resuspended in 1×LDS sample buffer (Invitrogen), boiled for 5 min and subjected to protein gel electrophoresis (4-12% NuPAGE, MOPS running buffer, all purchased from Invitrogen), followed by immunoblotting to detect ECE-1 and NRP-1 by specific primary and HRP-conjugated secondary antibodies. For IP with AAL, fucosylated proteins in cell lysates (200 □g in 500 □l of the buffer: 0.2% NP-40, 150 mM NaCl, 0.1 mM CaCl2, 10 mM HEPES, pH 7.5, 1×EDTA-free protease inhibitor cocktail) were pulled-down by 5 □g biotinylated AAL (Vector Laboratories)/20 □l Neutravidin beads at 4° C. for overnight, and examined by anti-plexin B2 (Santa Cruz) immunoblotting. For IP with anti-plexin B2, proteins (200 μg) were dissolved in 500 μl IP buffer (1% NP-40, 150 mM NaCl, 10% glycerol, 50 mM HEPES, pH 7.5 and 1×EDTA-free protease inhibitor cocktail) and precleared with 25 μl protein G beads (GE Healthcare) at 4° C. for 1 h. Precleared proteins extracts were then incubated with 3 μg anti-plexin B2 antibody/25 μl protein G beads at 4° C. for 1 h for overnight. Immunoprecipitates were subjected to SDS-PAGE and the proteins were transferred to PVDF membrane.

Identification of glycoproteomes by GIDmap: Glycoproteins were harvested in cell lysis buffer (1% NP-40, 150 mM NaCl, Roche protease inhibitor, and 100 mM sodium phosphate pH 7.5) and subjected to the GIDmap method disclosed herein. Subcellular location, function and biological process were assessed by Swiss-Prot annotation.

While various exemplary implementation of the present disclosure have been described in detail, it is apparent that modifications and adaptations of those implementations will occur to those skilled in the art. However, it is to be expressly understood that such modifications and adaptations are within the spirit and scope of the present disclosure.

What is claimed is:

1. A method of harvesting peptide fragments comprising:
presenting an alkynyl-derivatized sugar to a cell;
wherein the alkynyl-derivatized sugar has an alkynyl functional group; and
wherein the cell is capable of producing a glycoprotein;
incorporating the alkynyl-derivatized sugar into the cell;
wherein the alkynyl-derivatized sugar is subsequently used by the cell to produce a tagged glycoprotein; and
wherein the tagged glycoprotein includes a glycan portion, a peptide portion; and the alkynyl functional group;
reacting the tagged glycoprotein with a probe to produce a labeled glycoprotein,
wherein the labeled glycoprotein includes the glycan portion, the peptide portion, the alkynyl functional group and the probe;
capturing the labeled glycoprotein onto a solid support, wherein the solid support is labeled with a binding moiety capable of binding to the probe of the labeled glycoprotein; and
washing the solid support with an enzyme digestion to remove peptide fragments from the peptide portion of the labeled glycoprotein, resulting in the peptide fragments being harvested.

2. The method of claim 1 wherein the alkynyl-derivatized sugar is selected from the group consisting of an alkynyl-derivatized fucose analog, an alkynyl-derivatized sialic acid analog and an alkynyl-derivatized sialic acid precursor.

3. The method of claim 2 wherein the glycoprotein produced by the cell is a fucosylated glycoprotein and the alkynyl-derivatized fucose analog is 1,2,3,4-tetraacetyl alkynyl fucose.

4. The method of claim 2 wherein the glycoprotein produced by the cell is a sialylated glycoprotein and the alkynyl-derivatized sialic acid precursor is N-acetylmannosamine.

5. The method of claim 2 wherein the glycoprotein produced by the cell is a sialylated glycoprotein and the alkynyl-derivatized sialic acid precursor is 1,3,4,6-tetra-O-acetyl-N-4-pentynoylmannosamine.

6. The method of claim 1 wherein the labeled glycoprotein is produced using a Cu(I)-catalyzed [3+2] azide-alkyne cycloaddition technique.

7. The method of claim 1 wherein the probe contains a biotin group.

8. The method of claim 1 wherein the alkynyl-derivatized sugar is a peracetylated alkynyl-derivatized sugar.

9. The method of claim 1 wherein the alkynyl functional group is a terminal alkynyl functional group.

10. The method of claim 1 wherein the glycoprotein produced by the cell is a glycosylated glycoprotein.

11. The method of claim 10 wherein the glycosylated glycoprotein is a N-glycosylated glycoprotein.

12. The method of claim 10 wherein the glycosylated glycoprotein is an o-glycosylated glycoprotein or proteoglycan.

13. The method of claim 1 wherein the cell is a healthy cell.

14. The method of claim 1 wherein the cell is an abnormal cell.

15. The method of claim 1 wherein the solid support includes at least one bead covalently displaying the binding moiety.

16. The method of claim 15 wherein the binding moiety is a streptavidin or avidin protein.

17. The method of claim 1 wherein the enzyme digestion is a trypsin digestion which is capable of cleaving peptide bonds that exist between arginine or lysine residues with other amino acids (except proline) within the peptide portion of the labeled glycoprotein.

18. The method of claim 11 wherein the enzyme digestion is a peptide-N-glycosidase F (PNGase F) digestion which hydrolyzes an amide bond that exists between the glycan portion of the labeled glycoprotein and an Asn residue of the peptide portion of the labeled glycoprotein.

19. The method of claim 1 wherein the washing step is performed more than once using different enzyme digestions.

20. The method of claim 1 wherein the glycoprotein produced by the cell is at a surface of the cell.

21. The method of claim 1 wherein the glycoprotein produced by the cell is intracellular.

22. A method of determining whether sites of glycosylation found on a glycoprotein from an abnormal cell are present in a proteome of a healthy cell comprising:
presenting an alkynyl-derivatized sugar to the abnormal cell;
wherein the alkynyl-derivatized sugar has an alkynyl functional group; and
wherein the abnormal cell is capable of producing a glycoprotein;
incorporating the alkynyl-derivatized sugar into the abnormal cell;
wherein the alkynyl-derivatized sugar is subsequently used by the abnormal cell to produce a tagged glycoprotein; and
wherein the tagged glycoprotein includes a glycan portion, a peptide portion, and the alkynyl functional group;
reacting the tagged glycoprotein with a probe to produce a Labeled glycoprotein;
wherein the labeled glycoprotein includes the glycan portion, the peptide portion, the alkynyl functional group and the probe;
capturing the labeled glycoprotein onto a solid support, wherein the solid support is labeled with a binding moiety capable of binding to the probe of the labeled glycoprotein;
washing the solid support with an enzyme digestion to remove peptide fragments of the glycoprotein from the abnormal cell;
harvesting the peptide fragments of the glycoprotein from the abnormal cell;
analyzing the peptide fragments of the glycoprotein from the abnormal cell using mass spectrometry-based proteomics, resulting in the sites of glycosylation on the glycoprotein from the abnormal cell being determined; presenting an alkynyl-derivatized sugar to the healthy cell;
wherein the alkynyl-derivatized sugar has an alkynyl functional group; and wherein the healthy cell is capable of producing a proteome;
incorporating the alkynyl-derivatized sugar into the healthy cell;
wherein the alkynyl-derivatized sugar is subsequently used by the healthy cell to produce a tagged proteome; and
wherein the tagged proteome includes at least one of a glycan portion, a peptide portion, and the alkynyl functional group;
reacting the tagged proteome with a probe to produce a labeled proteome;
wherein the labeled proteome includes at least one of the glycan portion, the peptide portion, the alkynyl functional group and the probe;
capturing the labeled proteome onto a solid support, wherein the solid support is labeled with a binding moiety capable of binding to the probe of the labeled proteome;
washing the solid support with an enzyme digestion to remove peptide fragments from the peptide portion of the labeled proteome from the healthy cell;
harvesting the peptide fragments of the proteome from the healthy cell;
analyzing the peptide fragments of the proteome from the healthy cell using mass spectrometry-based proteomics, resulting in the peptide fragments being identified; and
determining whether sites of glycosylation found on the glycoprotein from the abnormal cell are present in the proteome of the healthy cell.

23. The method of claim 22 wherein the proteome produced from the healthy cell includes at least one glycoprotein, the glycoprotein including a glycan portion and a peptide portion.

24. The method of claim 22 wherein the proteome produced from the healthy cell includes at least one fucosylated glycoprotein and the alkynyl-derivatized sugar is an alkynyl-derivatized fucose analog.

25. The method of claim 22 wherein the proteome produced from the healthy cell includes at least one sialylated glycoprotein and the alkynyl-derivatized sugar is an alkynyl-derivatized sialic acid analog/precursor.

26. The method of claim 22 wherein the glycoprotein produced from the abnormal cell includes at least one fucosylated glycoprotein and the alkynyl-derivatized sugar is an alkynyl-derivatized fucose analog.

27. The method of claim 22 wherein the glycoprotein produced from the abnormal cell includes at least one sialylated glycoprotein and the alkynyl-derivatized sugar is an alkynyl-derivatized sialic acid analog/precursor.

28. The method of claim 23 wherein the glycoprotein produced from the abnormal cell and the at least one glycoprotein produced from the healthy cell are N-glycosylated glycoproteins.

29. The method of claim 28 wherein the enzyme digestion used on the healthy cell is a peptide-N-glycosidase F (PNGase F) digestion which hydrolyzes an amide bond that exists between the glycan portion of the at least one glycoprotein and an Asn residue of the peptide portion, and the enzyme digestion used on the abnormal cell is also a peptide-N-glycosidase F (PNGase F) digestion which hydrolyzes an amide bond that exists between the glycan portion of the glycoprotein and an Asn residue of the peptide portion.

30. The method of claim 29 wherein the mass spectrometry-based proteomics determines if and where a shift from the Asn residue to an Asp residue at formerly N-glycosylated sites occurs.

31. The method of claim 29 wherein the sites of glycosylation on the glycoprotein from the abnormal cell is deter mined by using a differential modification of +1 Da on the Asn residue and searching a mass spectrometry database.

32. The method of claim 22 wherein determining whether sites of glycosylation found on the glycoprotein from the abnormal cell are present in the proteome of the healthy cell provides information about the abnormal cell.

33. The method of claim 32 wherein the information about the abnormal cell allows for glycan-related targets for biomarker development.

34. The method of claim 22 wherein the abnormal cell is a cancerous version of the healthy cell.

* * * * *

SEQUENCE LISTING

```
<160> NUMBER OF SEQ ID NOS: 282

<210> SEQ ID NO 1
<211> LENGTH: 11
<212> TYPE: PRT
<213> ORGANISM: Human
<220> FEATURE:
<221> NAME/KEY: MISC_FEATURE
<222> LOCATION: (3)..(3)
<223> OTHER INFORMATION: Where Xaa indicates a diffmod on Asn of +1 Da

<400> SEQUENCE: 1

Lys Leu Xaa Tyr Thr Leu Ser Gln Gly His Arg
1               5                   10

<210> SEQ ID NO 2
<211> LENGTH: 11
<212> TYPE: PRT
<213> ORGANISM: Human
<220> FEATURE:
<221> NAME/KEY: MISC_FEATURE
<222> LOCATION: (4)..(4)
<223> OTHER INFORMATION: Where Xaa indicates a diffmod on Asn of +1 Da

<400> SEQUENCE: 2

Ala Glu Phe Xaa Ile Thr Leu Ile His Pro Lys
1               5                   10

<210> SEQ ID NO 3
<211> LENGTH: 22
<212> TYPE: PRT
<213> ORGANISM: Human
<220> FEATURE:
<221> NAME/KEY: MISC_FEATURE
<222> LOCATION: (13)..(13)
<223> OTHER INFORMATION: Where Xaa indicates a diffmod on Asn of +1 Da

<400> SEQUENCE: 3

Gly Pro Ser Thr Pro Leu Pro Glu Asp Pro Asn Trp Xaa Val Thr Glu
1               5                   10                  15

Phe His Thr Thr Pro Lys
            20

<210> SEQ ID NO 4
<211> LENGTH: 22
<212> TYPE: PRT
<213> ORGANISM: Human
<220> FEATURE:
<221> NAME/KEY: MISC_FEATURE
<222> LOCATION: (11)..(13)
<223> OTHER INFORMATION: Where Xaa indicates a diffmod on Asn of +1 Da

<400> SEQUENCE: 4

Gly Pro Ser Thr Pro Leu Pro Glu Asp Pro Xaa Trp Xaa Val Thr Glu
1               5                   10                  15
```

Phe His Thr Thr Pro Lys
            20

<210> SEQ ID NO 5
<211> LENGTH: 17
<212> TYPE: PRT
<213> ORGANISM: Human
<220> FEATURE:
<221> NAME/KEY: MISC_FEATURE
<222> LOCATION: (8)..(9)
<223> OTHER INFORMATION: Where Xaa indicates a diffmod on Asn of +1 Da

<400> SEQUENCE: 5

Val Pro Val Thr Leu Ala Leu Xaa Xaa Thr Leu Phe Leu Ile Glu Glu
1               5                   10                  15

Arg

<210> SEQ ID NO 6
<211> LENGTH: 12
<212> TYPE: PRT
<213> ORGANISM: Human
<220> FEATURE:
<221> NAME/KEY: MISC_FEATURE
<222> LOCATION: (1)..(1)
<223> OTHER INFORMATION: Where Xaa indicates a diffmod on Asn of +1 Da

<400> SEQUENCE: 6

Xaa Ala Thr Leu Val Asn Glu Ala Asp Lys Leu Arg
1               5                   10

<210> SEQ ID NO 7
<211> LENGTH: 17
<212> TYPE: PRT
<213> ORGANISM: Human
<220> FEATURE:
<221> NAME/KEY: MISC_FEATURE
<222> LOCATION: (10)..(10)
<223> OTHER INFORMATION: Where Xaa indicates a diffmod on Asn of +1 Da

<400> SEQUENCE: 7

Asp Phe Glu Asp Leu Tyr Thr Pro Val Xaa Gly Ser Ile Val Ile Val
1               5                   10                  15

Arg

<210> SEQ ID NO 8
<211> LENGTH: 18
<212> TYPE: PRT
<213> ORGANISM: Human
<220> FEATURE:
<221> NAME/KEY: MISC_FEATURE
<222> LOCATION: (11)..(11)
<223> OTHER INFORMATION: Where Xaa indicates a diffmod on Asn of +1 Da

<400> SEQUENCE: 8

Lys Asp Phe Glu Asp Leu Tyr Thr Pro Val Xaa Gly Ser Ile Val Ile
1               5                   10                  15

Val Arg

<210> SEQ ID NO 9
<211> LENGTH: 13
<212> TYPE: PRT
<213> ORGANISM: Human
<220> FEATURE:
<221> NAME/KEY: MISC_FEATURE
<222> LOCATION: (7)..(7)
<223> OTHER INFORMATION: Where Xaa indicates a diffmod on Asn of +1 Da

```
<400> SEQUENCE: 9

Leu Thr Thr Asp Phe Gly Xaa Ala Glu Lys Thr Asp Arg
1               5                   10

<210> SEQ ID NO 10
<211> LENGTH: 16
<212> TYPE: PRT
<213> ORGANISM: Human
<220> FEATURE:
<221> NAME/KEY: MISC_FEATURE
<222> LOCATION: (8)..(8)
<223> OTHER INFORMATION: Where Xaa indicates a diffmod on Asn of +1 Da

<400> SEQUENCE: 10

Asn Pro Cys Thr Ser Glu Gln Xaa Cys Thr Ser Pro Phe Ser Tyr Lys
1               5                   10                  15

<210> SEQ ID NO 11
<211> LENGTH: 30
<212> TYPE: PRT
<213> ORGANISM: Human
<220> FEATURE:
<221> NAME/KEY: MISC_FEATURE
<222> LOCATION: (17)..(17)
<223> OTHER INFORMATION: Where Xaa indicates a diffmod on Asn of +1 Da

<400> SEQUENCE: 11

Ser Cys Gly Glu Cys Ile Gln Ala Gly Pro Asn Cys Gly Trp Cys Thr
1               5                   10                  15

Xaa Ser Thr Phe Leu Gln Glu Gly Met Pro Thr Ser Ala Arg
            20                  25                  30

<210> SEQ ID NO 12
<211> LENGTH: 18
<212> TYPE: PRT
<213> ORGANISM: Human
<220> FEATURE:
<221> NAME/KEY: MISC_FEATURE
<222> LOCATION: (3)..(10)
<223> OTHER INFORMATION: Where Xaa indicates a diffmod on Asn of +1 Da

<400> SEQUENCE: 12

Leu Arg Xaa Pro Cys Thr Ser Glu Gln Xaa Cys Thr Ser Pro Phe Ser
1               5                   10                  15

Tyr Lys

<210> SEQ ID NO 13
<211> LENGTH: 18
<212> TYPE: PRT
<213> ORGANISM: Human
<220> FEATURE:
<221> NAME/KEY: MISC_FEATURE
<222> LOCATION: (10)..(10)
<223> OTHER INFORMATION: Where Xaa indicates a diffmod on Asn of +1 Da

<400> SEQUENCE: 13

Leu Arg Asn Pro Cys Thr Ser Glu Gln Xaa Cys Thr Ser Pro Phe Ser
1               5                   10                  15

Tyr Lys

<210> SEQ ID NO 14
<211> LENGTH: 16
<212> TYPE: PRT
<213> ORGANISM: Human
<220> FEATURE:
<221> NAME/KEY: MISC_FEATURE
<222> LOCATION: (1)..(8)
```

<223> OTHER INFORMATION: Where Xaa indicates a diffmod on Asn of +1 Da

<400> SEQUENCE: 14

Xaa Pro Cys Thr Ser Glu Gln Xaa Cys Thr Ser Pro Phe Ser Tyr Lys
1               5                   10                  15

<210> SEQ ID NO 15
<211> LENGTH: 22
<212> TYPE: PRT
<213> ORGANISM: Human
<220> FEATURE:
<221> NAME/KEY: MISC_FEATURE
<222> LOCATION: (3)..(11)
<223> OTHER INFORMATION: Where Xaa indicates a diffmod on Asn of +1 Da

<400> SEQUENCE: 15

Lys Glu Xaa Ser Ser Glu Ile Cys Ser Asn Xaa Gly Glu Cys Val Cys
1               5                   10                  15

Gly Gln Cys Val Cys Arg
            20

<210> SEQ ID NO 16
<211> LENGTH: 14
<212> TYPE: PRT
<213> ORGANISM: Human
<220> FEATURE:
<221> NAME/KEY: MISC_FEATURE
<222> LOCATION: (11)..(11)
<223> OTHER INFORMATION: Where Xaa indicates a diffmod on Asn of +1 Da

<400> SEQUENCE: 16

Asp Thr Cys Thr Gln Glu Cys Ser Tyr Phe Xaa Ile Thr Lys
1               5                   10

<210> SEQ ID NO 17
<211> LENGTH: 15
<212> TYPE: PRT
<213> ORGANISM: Human
<220> FEATURE:
<221> NAME/KEY: MISC_FEATURE
<222> LOCATION: (12)..(12)
<223> OTHER INFORMATION: Where Xaa indicates a diffmod on Asn of +1 Da

<400> SEQUENCE: 17

Lys Asp Thr Cys Thr Gln Glu Cys Ser Tyr Phe Xaa Ile Thr Lys
1               5                   10                  15

<210> SEQ ID NO 18
<211> LENGTH: 16
<212> TYPE: PRT
<213> ORGANISM: Human
<220> FEATURE:
<221> NAME/KEY: MISC_FEATURE
<222> LOCATION: (11)..(11)
<223> OTHER INFORMATION: Where Xaa indicates a diffmod on Asn of +1 Da

<400> SEQUENCE: 18

Leu Asn Leu Gln Thr Ser Thr Ser Ile Pro Xaa Val Thr Glu Met Lys
1               5                   10                  15

<210> SEQ ID NO 19
<211> LENGTH: 16
<212> TYPE: PRT
<213> ORGANISM: Human
<220> FEATURE:
<221> NAME/KEY: MISC_FEATURE
<222> LOCATION: (2)..(11)
<223> OTHER INFORMATION: Where Xaa indicates a diffmod on Asn of +1 Da

```
<400> SEQUENCE: 19

Leu Xaa Leu Gln Thr Ser Thr Ser Ile Pro Xaa Val Thr Glu Met Lys
1               5                   10                  15

<210> SEQ ID NO 20
<211> LENGTH: 11
<212> TYPE: PRT
<213> ORGANISM: Human
<220> FEATURE:
<221> NAME/KEY: MISC_FEATURE
<222> LOCATION: (2)..(2)
<223> OTHER INFORMATION: Where Xaa indicates a diffmod on Asn of +1 Da

<400> SEQUENCE: 20

Thr Xaa Met Ser Leu Gly Leu Ile Leu Thr Arg
1               5                   10

<210> SEQ ID NO 21
<211> LENGTH: 14
<212> TYPE: PRT
<213> ORGANISM: Human
<220> FEATURE:
<221> NAME/KEY: MISC_FEATURE
<222> LOCATION: (4)..(4)
<223> OTHER INFORMATION: Where Xaa indicates a diffmod on Asn of +1 Da

<400> SEQUENCE: 21

Tyr Phe Phe Xaa Val Ser Asp Glu Ala Ala Leu Leu Glu Lys
1               5                   10

<210> SEQ ID NO 22
<211> LENGTH: 25
<212> TYPE: PRT
<213> ORGANISM: Human
<220> FEATURE:
<221> NAME/KEY: MISC_FEATURE
<222> LOCATION: (2)..(15)
<223> OTHER INFORMATION: Where Xaa indicates a diffmod on Asn of +1 Da

<400> SEQUENCE: 22

Ala Xaa Tyr Thr Gly Gln Ile Val Leu Tyr Ser Val Xaa Glu Xaa Gly
1               5                   10                  15

Asn Ile Thr Val Ile Gln Ala His Arg
            20                  25

<210> SEQ ID NO 23
<211> LENGTH: 12
<212> TYPE: PRT
<213> ORGANISM: Human
<220> FEATURE:
<221> NAME/KEY: MISC_FEATURE
<222> LOCATION: (6)..(6)
<223> OTHER INFORMATION: Where Xaa indicates a diffmod on Asn of +1 Da

<400> SEQUENCE: 23

Thr Ala Ser Cys Ser Xaa Val Thr Cys Trp Leu Lys
1               5                   10

<210> SEQ ID NO 24
<211> LENGTH: 10
<212> TYPE: PRT
<213> ORGANISM: Human
<220> FEATURE:
<221> NAME/KEY: MISC_FEATURE
<222> LOCATION: (6)..(6)
<223> OTHER INFORMATION: Where Xaa indicates a diffmod on Asn of +1 Da

<400> SEQUENCE: 24
```

```
Gly Glu Tyr Phe Val Xaa Val Thr Thr Arg
1               5                   10
```

<210> SEQ ID NO 25
<211> LENGTH: 25
<212> TYPE: PRT
<213> ORGANISM: Human
<220> FEATURE:
<221> NAME/KEY: MISC_FEATURE
<222> LOCATION: (2)..(17)
<223> OTHER INFORMATION: Where Xaa indicates a diffmod on Asn of +1 Da

<400> SEQUENCE: 25

```
Ala Xaa Tyr Thr Gly Gln Ile Val Leu Tyr Ser Val Xaa Glu Xaa Gly
1               5                   10                  15

Xaa Ile Thr Val Ile Gln Ala His Arg
            20                  25
```

<210> SEQ ID NO 26
<211> LENGTH: 15
<212> TYPE: PRT
<213> ORGANISM: Human
<220> FEATURE:
<221> NAME/KEY: MISC_FEATURE
<222> LOCATION: (5)..(5)
<223> OTHER INFORMATION: Where Xaa indicates a diffmod on Asn of +1 Da

<400> SEQUENCE: 26

```
His Leu Leu Glu Xaa Ser Thr Ala Ser Val Ser Glu Ala Glu Arg
1               5                   10                  15
```

<210> SEQ ID NO 27
<211> LENGTH: 16
<212> TYPE: PRT
<213> ORGANISM: Human
<220> FEATURE:
<221> NAME/KEY: MISC_FEATURE
<222> LOCATION: (5)..(5)
<223> OTHER INFORMATION: Where Xaa indicates a diffmod on Asn of +1 Da

<400> SEQUENCE: 27

```
His Leu Leu Glu Xaa Ser Thr Ala Ser Val Ser Glu Ala Glu Arg Lys
1               5                   10                  15
```

<210> SEQ ID NO 28
<211> LENGTH: 12
<212> TYPE: PRT
<213> ORGANISM: Human
<220> FEATURE:
<221> NAME/KEY: MISC_FEATURE
<222> LOCATION: (5)..(5)
<223> OTHER INFORMATION: Where Xaa indicates a diffmod on Asn of +1 Da

<400> SEQUENCE: 28

```
Leu Gly Gly Trp Xaa Ile Thr Gly Pro Trp Ala Lys
1               5                   10
```

<210> SEQ ID NO 29
<211> LENGTH: 11
<212> TYPE: PRT
<213> ORGANISM: Human
<220> FEATURE:
<221> NAME/KEY: MISC_FEATURE
<222> LOCATION: (5)..(5)
<223> OTHER INFORMATION: Where Xaa indicates a diffmod on Asn of +1 Da

<400> SEQUENCE: 29

```
Asp Tyr Tyr Leu Xaa Lys Thr Glu Asn Glu Lys
1               5                   10
```

-continued

<210> SEQ ID NO 30
<211> LENGTH: 15
<212> TYPE: PRT
<213> ORGANISM: Human
<220> FEATURE:
<221> NAME/KEY: MISC_FEATURE
<222> LOCATION: (11)..(11)
<223> OTHER INFORMATION: Where Xaa indicates a diffmod on Asn of +1 Da

<400> SEQUENCE: 30

Glu Tyr Leu Glu Gln Ile Ser Thr Leu Ile Xaa Thr Thr Asp Arg
1               5                   10                  15

<210> SEQ ID NO 31
<211> LENGTH: 7
<212> TYPE: PRT
<213> ORGANISM: Human
<220> FEATURE:
<221> NAME/KEY: MISC_FEATURE
<222> LOCATION: (3)..(3)
<223> OTHER INFORMATION: Where Xaa indicates a diffmod on Asn of +1 Da

<400> SEQUENCE: 31

Phe Phe Xaa Phe Ser Trp Arg
1               5

<210> SEQ ID NO 32
<211> LENGTH: 9
<212> TYPE: PRT
<213> ORGANISM: Human
<220> FEATURE:
<221> NAME/KEY: MISC_FEATURE
<222> LOCATION: (1)..(1)
<223> OTHER INFORMATION: Where Xaa indicates a diffmod on Asn of +1 Da

<400> SEQUENCE: 32

Xaa Ser Ser Val Glu Ala Phe Lys Arg
1               5

<210> SEQ ID NO 33
<211> LENGTH: 11
<212> TYPE: PRT
<213> ORGANISM: Human
<220> FEATURE:
<221> NAME/KEY: MISC_FEATURE
<222> LOCATION: (10)..(10)
<223> OTHER INFORMATION: Where Xaa indicates a diffmod on Asn of +1 Da

<400> SEQUENCE: 33

Glu Leu Ala Val Pro Asp Gly Tyr Thr Xaa Arg
1               5                   10

<210> SEQ ID NO 34
<211> LENGTH: 11
<212> TYPE: PRT
<213> ORGANISM: Human
<220> FEATURE:
<221> NAME/KEY: MISC_FEATURE
<222> LOCATION: (7)..(7)
<223> OTHER INFORMATION: Where Xaa indicates a diffmod on Asn of +1 Da

<400> SEQUENCE: 34

Asp Asp Cys Glu Arg Met Xaa Ile Thr Val Lys
1               5                   10

<210> SEQ ID NO 35
<211> LENGTH: 10
<212> TYPE: PRT

```
<213> ORGANISM: Human
<220> FEATURE:
<221> NAME/KEY: MISC_FEATURE
<222> LOCATION: (1)..(1)
<223> OTHER INFORMATION: Where Xaa indicates a diffmod on Asn of +1 Da

<400> SEQUENCE: 35

Xaa Ile Thr Ile Val Thr Gly Ala Pro Arg
1               5                   10

<210> SEQ ID NO 36
<211> LENGTH: 12
<212> TYPE: PRT
<213> ORGANISM: Human
<220> FEATURE:
<221> NAME/KEY: MISC_FEATURE
<222> LOCATION: (1)..(1)
<223> OTHER INFORMATION: Where Xaa indicates a diffmod on Asn of +1 Da

<400> SEQUENCE: 36

Xaa Ile Thr Leu Ala Tyr Thr Leu Glu Ala Asp Arg
1               5                   10

<210> SEQ ID NO 37
<211> LENGTH: 15
<212> TYPE: PRT
<213> ORGANISM: Human
<220> FEATURE:
<221> NAME/KEY: MISC_FEATURE
<222> LOCATION: (2)..(2)
<223> OTHER INFORMATION: Where Xaa indicates a diffmod on Asn of +1 Da

<400> SEQUENCE: 37

Arg Xaa Ile Thr Leu Ala Tyr Thr Leu Glu Ala Asp Arg Asp Arg
1               5                   10                  15

<210> SEQ ID NO 38
<211> LENGTH: 14
<212> TYPE: PRT
<213> ORGANISM: Human
<220> FEATURE:
<221> NAME/KEY: MISC_FEATURE
<222> LOCATION: (1)..(1)
<223> OTHER INFORMATION: Where Xaa indicates a diffmod on Asn of +1 Da

<400> SEQUENCE: 38

Xaa Ile Thr Leu Ala Tyr Thr Leu Glu Ala Asp Arg Asp Arg
1               5                   10

<210> SEQ ID NO 39
<211> LENGTH: 22
<212> TYPE: PRT
<213> ORGANISM: Human
<220> FEATURE:
<221> NAME/KEY: MISC_FEATURE
<222> LOCATION: (18)..(18)
<223> OTHER INFORMATION: Where Xaa indicates a diffmod on Asn of +1 Da

<400> SEQUENCE: 39

Ala His Cys Val Trp Leu Glu Cys Pro Ile Pro Asp Ala Pro Val Val
1               5                   10                  15

Thr Xaa Val Thr Val Lys
            20

<210> SEQ ID NO 40
<211> LENGTH: 10
<212> TYPE: PRT
<213> ORGANISM: Human
<220> FEATURE:
```

```
<221> NAME/KEY: MISC_FEATURE
<222> LOCATION: (2)..(2)
<223> OTHER INFORMATION: Where Xaa indicates a diffmod on Asn of +1 Da

<400> SEQUENCE: 40

Val Xaa Gly Trp Ala Thr Leu Phe Leu Arg
1               5                   10

<210> SEQ ID NO 41
<211> LENGTH: 11
<212> TYPE: PRT
<213> ORGANISM: Human
<220> FEATURE:
<221> NAME/KEY: MISC_FEATURE
<222> LOCATION: (10)..(10)
<223> OTHER INFORMATION: Where Xaa indicates a diffmod on Asn of +1 Da

<400> SEQUENCE: 41

Thr Ser Ile Pro Thr Ile Asn Met Glu Xaa Lys
1               5                   10

<210> SEQ ID NO 42
<211> LENGTH: 8
<212> TYPE: PRT
<213> ORGANISM: Human
<220> FEATURE:
<221> NAME/KEY: MISC_FEATURE
<222> LOCATION: (2)..(2)
<223> OTHER INFORMATION: Where Xaa indicates a diffmod on Asn of +1 Da

<400> SEQUENCE: 42

Leu Xaa Leu Thr Thr Asp Pro Lys
1               5

<210> SEQ ID NO 43
<211> LENGTH: 14
<212> TYPE: PRT
<213> ORGANISM: Human
<220> FEATURE:
<221> NAME/KEY: MISC_FEATURE
<222> LOCATION: (2)..(2)
<223> OTHER INFORMATION: Where Xaa indicates a diffmod on Asn of +1 Da

<400> SEQUENCE: 43

Gly Xaa Ile Thr Glu Tyr Gln Cys His Gln Tyr Ile Thr Lys
1               5                   10

<210> SEQ ID NO 44
<211> LENGTH: 14
<212> TYPE: PRT
<213> ORGANISM: Human
<220> FEATURE:
<221> NAME/KEY: MISC_FEATURE
<222> LOCATION: (3)..(3)
<223> OTHER INFORMATION: Where Xaa indicates a diffmod on Asn of +1 Da

<400> SEQUENCE: 44

Ala Phe Xaa Ser Thr Leu Pro Thr Met Ala Gln Met Glu Lys
1               5                   10

<210> SEQ ID NO 45
<211> LENGTH: 13
<212> TYPE: PRT
<213> ORGANISM: Human
<220> FEATURE:
<221> NAME/KEY: MISC_FEATURE
<222> LOCATION: (7)..(7)
<223> OTHER INFORMATION: Where Xaa indicates a diffmod on Asn of +1 Da

<400> SEQUENCE: 45
```

```
Leu Val Ile Asn Ser Gly Xaa Gly Ala Val Glu Asp Arg
1               5                   10
```

<210> SEQ ID NO 46
<211> LENGTH: 13
<212> TYPE: PRT
<213> ORGANISM: Human
<220> FEATURE:
<221> NAME/KEY: MISC_FEATURE
<222> LOCATION: (6)..(6)
<223> OTHER INFORMATION: Where Xaa indicates a diffmod on Asn of +1 Da

<400> SEQUENCE: 46

```
Ala Ala Val Pro Lys Xaa Val Ser Val Ala Glu Gly Lys
1               5                   10
```

<210> SEQ ID NO 47
<211> LENGTH: 12
<212> TYPE: PRT
<213> ORGANISM: Human
<220> FEATURE:
<221> NAME/KEY: MISC_FEATURE
<222> LOCATION: (7)..(7)
<223> OTHER INFORMATION: Where Xaa indicates a diffmod on Asn of +1 Da

<400> SEQUENCE: 47

```
Glu Leu Asp Leu Thr Cys Xaa Ile Thr Thr Asp Arg
1               5                   10
```

<210> SEQ ID NO 48
<211> LENGTH: 28
<212> TYPE: PRT
<213> ORGANISM: Human
<220> FEATURE:
<221> NAME/KEY: MISC_FEATURE
<222> LOCATION: (25)..(25)
<223> OTHER INFORMATION: Where Xaa indicates a diffmod on Asn of +1 Da

<400> SEQUENCE: 48

```
Val Ala Glu Ala Val Ser Ser Pro Ala Gly Val Gly Val Thr Trp Leu
1               5                   10                  15

Glu Pro Asp Tyr Gln Val Tyr Leu Xaa Ala Ser Lys
            20                  25
```

<210> SEQ ID NO 49
<211> LENGTH: 9
<212> TYPE: PRT
<213> ORGANISM: Human
<220> FEATURE:
<221> NAME/KEY: MISC_FEATURE
<222> LOCATION: (3)..(3)
<223> OTHER INFORMATION: Where Xaa indicates a diffmod on Asn of +1 Da

<400> SEQUENCE: 49

```
Leu Glu Xaa Trp Thr Asp Ala Ser Arg
1               5
```

<210> SEQ ID NO 50
<211> LENGTH: 13
<212> TYPE: PRT
<213> ORGANISM: Human
<220> FEATURE:
<221> NAME/KEY: MISC_FEATURE
<222> LOCATION: (7)..(7)
<223> OTHER INFORMATION: Where Xaa indicates a diffmod on Asn of +1 Da

<400> SEQUENCE: 50

```
Thr Ala Ser Val Ser Ile Xaa Gln Thr Glu Pro Pro Lys
```

```
<210> SEQ ID NO 51
<211> LENGTH: 15
<212> TYPE: PRT
<213> ORGANISM: Human
<220> FEATURE:
<221> NAME/KEY: MISC_FEATURE
<222> LOCATION: (7)..(7)
<223> OTHER INFORMATION: Where Xaa indicates a diffmod on Asn of +1 Da

<400> SEQUENCE: 51

Thr Ala Ser Val Ser Ile Xaa Gln Thr Glu Pro Pro Lys Val Arg
1               5                   10                  15

<210> SEQ ID NO 52
<211> LENGTH: 18
<212> TYPE: PRT
<213> ORGANISM: Human
<220> FEATURE:
<221> NAME/KEY: MISC_FEATURE
<222> LOCATION: (4)..(4)
<223> OTHER INFORMATION: Where Xaa indicates a diffmod on Asn of +1 Da

<400> SEQUENCE: 52

Thr Ala Ser Xaa Leu Thr Val Ser Val Leu Glu Ala Glu Gly Val Phe
1               5                   10                  15

Glu Lys

<210> SEQ ID NO 53
<211> LENGTH: 12
<212> TYPE: PRT
<213> ORGANISM: Human
<220> FEATURE:
<221> NAME/KEY: MISC_FEATURE
<222> LOCATION: (9)..(9)
<223> OTHER INFORMATION: Where Xaa indicates a diffmod on Asn of +1 Da

<400> SEQUENCE: 53

Thr Gln Asp Glu Ile Leu Phe Ser Xaa Ser Thr Arg
1               5                   10

<210> SEQ ID NO 54
<211> LENGTH: 15
<212> TYPE: PRT
<213> ORGANISM: Human
<220> FEATURE:
<221> NAME/KEY: MISC_FEATURE
<222> LOCATION: (1)..(1)
<223> OTHER INFORMATION: Where Xaa indicates a diffmod on Asn of +1 Da

<400> SEQUENCE: 54

Xaa Tyr Thr Glu Tyr Trp Ser Gly Ser Asn Ser Gly Asn Gln Lys
1               5                   10                  15

<210> SEQ ID NO 55
<211> LENGTH: 12
<212> TYPE: PRT
<213> ORGANISM: Human
<220> FEATURE:
<221> NAME/KEY: MISC_FEATURE
<222> LOCATION: (2)..(2)
<223> OTHER INFORMATION: Where Xaa indicates a diffmod on Asn of +1 Da

<400> SEQUENCE: 55

Ile Xaa Tyr Thr Val Pro Gln Ser Gly Thr Phe Lys
1               5                   10
```

```
<210> SEQ ID NO 56
<211> LENGTH: 16
<212> TYPE: PRT
<213> ORGANISM: Human
<220> FEATURE:
<221> NAME/KEY: MISC_FEATURE
<222> LOCATION: (2)..(2)
<223> OTHER INFORMATION: Where Xaa indicates a diffmod on Asn of +1 Da

<400> SEQUENCE: 56

Ala Xaa Thr Thr Gln Pro Gly Ile Val Glu Gly Gly Gln Val Leu Lys
1               5                   10                  15

<210> SEQ ID NO 57
<211> LENGTH: 19
<212> TYPE: PRT
<213> ORGANISM: Human
<220> FEATURE:
<221> NAME/KEY: MISC_FEATURE
<222> LOCATION: (10)..(10)
<223> OTHER INFORMATION: Where Xaa indicates a diffmod on Asn of +1 Da

<400> SEQUENCE: 57

Ile Ser Ser Leu Gln Thr Thr Glu Lys Xaa Asp Thr Val Ala Gly Gln
1               5                   10                  15

Gly Glu Arg

<210> SEQ ID NO 58
<211> LENGTH: 27
<212> TYPE: PRT
<213> ORGANISM: Human
<220> FEATURE:
<221> NAME/KEY: MISC_FEATURE
<222> LOCATION: (5)..(21)
<223> OTHER INFORMATION: Where Xaa indicates a diffmod on Asn of +1 Da

<400> SEQUENCE: 58

Glu Phe Val Glu Xaa Ser Glu Cys Ile Gln Cys His Pro Glu Cys Leu
1               5                   10                  15

Pro Gln Ala Met Xaa Ile Thr Cys Thr Gly Arg
            20                  25

<210> SEQ ID NO 59
<211> LENGTH: 16
<212> TYPE: PRT
<213> ORGANISM: Human
<220> FEATURE:
<221> NAME/KEY: MISC_FEATURE
<222> LOCATION: (10)..(10)
<223> OTHER INFORMATION: Where Xaa indicates a diffmod on Asn of +1 Da

<400> SEQUENCE: 59

Thr Cys Pro Ala Gly Val Met Gly Glu Xaa Asn Thr Leu Val Trp Lys
1               5                   10                  15

<210> SEQ ID NO 60
<211> LENGTH: 16
<212> TYPE: PRT
<213> ORGANISM: Human
<220> FEATURE:
<221> NAME/KEY: MISC_FEATURE
<222> LOCATION: (10)..(11)
<223> OTHER INFORMATION: Where Xaa indicates a diffmod on Asn of +1 Da

<400> SEQUENCE: 60

Thr Cys Pro Ala Gly Val Met Gly Glu Xaa Xaa Thr Leu Val Trp Lys
1               5                   10                  15
```

```
<210> SEQ ID NO 61
<211> LENGTH: 20
<212> TYPE: PRT
<213> ORGANISM: Human
<220> FEATURE:
<221> NAME/KEY: MISC_FEATURE
<222> LOCATION: (1)..(1)
<223> OTHER INFORMATION: Where Xaa indicates a diffmod on Asn of +1 Da

<400> SEQUENCE: 61

Xaa Ala Thr Tyr Gly Tyr Val Leu Asp Asp Pro Asp Pro Asp Asp Gly
1               5                   10                  15

Phe Asn Tyr Lys
            20

<210> SEQ ID NO 62
<211> LENGTH: 15
<212> TYPE: PRT
<213> ORGANISM: Human
<220> FEATURE:
<221> NAME/KEY: MISC_FEATURE
<222> LOCATION: (12)..(12)
<223> OTHER INFORMATION: Where Xaa indicates a diffmod on Asn of +1 Da

<400> SEQUENCE: 62

Leu Ser Ala Val Asn Ser Ile Phe Leu Ser His Xaa Asn Thr Lys
1               5                   10                  15

<210> SEQ ID NO 63
<211> LENGTH: 13
<212> TYPE: PRT
<213> ORGANISM: Human
<220> FEATURE:
<221> NAME/KEY: MISC_FEATURE
<222> LOCATION: (4)..(4)
<223> OTHER INFORMATION: Where Xaa indicates a diffmod on Asn of +1 Da

<400> SEQUENCE: 63

Gly Asp Lys Xaa Val Thr Met Gly Gln Ser Ser Ala Arg
1               5                   10

<210> SEQ ID NO 64
<211> LENGTH: 16
<212> TYPE: PRT
<213> ORGANISM: Human
<220> FEATURE:
<221> NAME/KEY: MISC_FEATURE
<222> LOCATION: (13)..(13)
<223> OTHER INFORMATION: Where Xaa indicates a diffmod on Asn of +1 Da

<400> SEQUENCE: 64

Arg Leu Ser Ala Val Asn Ser Ile Phe Leu Ser His Xaa Asn Thr Lys
1               5                   10                  15

<210> SEQ ID NO 65
<211> LENGTH: 15
<212> TYPE: PRT
<213> ORGANISM: Human
<220> FEATURE:
<221> NAME/KEY: MISC_FEATURE
<222> LOCATION: (5)..(12)
<223> OTHER INFORMATION: Where Xaa indicates a diffmod on Asn of +1 Da

<400> SEQUENCE: 65

Leu Ser Ala Val Xaa Ser Ile Phe Leu Ser His Xaa Asn Thr Lys
1               5                   10                  15

<210> SEQ ID NO 66
<211> LENGTH: 15
```

```
<212> TYPE: PRT
<213> ORGANISM: Human
<220> FEATURE:
<221> NAME/KEY: MISC_FEATURE
<222> LOCATION: (5)..(13)
<223> OTHER INFORMATION: Where Xaa indicates a diffmod on Asn of +1 Da

<400> SEQUENCE: 66

Leu Ser Ala Val Xaa Ser Ile Phe Leu Ser His Xaa Xaa Thr Lys
1               5                   10                  15

<210> SEQ ID NO 67
<211> LENGTH: 15
<212> TYPE: PRT
<213> ORGANISM: Human
<220> FEATURE:
<221> NAME/KEY: MISC_FEATURE
<222> LOCATION: (5)..(10)
<223> OTHER INFORMATION: Where Xaa indicates a diffmod on Asn of +1 Da

<400> SEQUENCE: 67

Trp Cys Pro Gln Xaa Ser Ser Cys Val Xaa Ala Thr Ala Cys Arg
1               5                   10                  15

<210> SEQ ID NO 68
<211> LENGTH: 13
<212> TYPE: PRT
<213> ORGANISM: Human
<220> FEATURE:
<221> NAME/KEY: MISC_FEATURE
<222> LOCATION: (3)..(3)
<223> OTHER INFORMATION: Where Xaa indicates a diffmod on Asn of +1 Da

<400> SEQUENCE: 68

Val Val Xaa Ser Thr Thr Gly Pro Gly Glu His Leu Arg
1               5                   10

<210> SEQ ID NO 69
<211> LENGTH: 8
<212> TYPE: PRT
<213> ORGANISM: Human
<220> FEATURE:
<221> NAME/KEY: MISC_FEATURE
<222> LOCATION: (4)..(4)
<223> OTHER INFORMATION: Where Xaa indicates a diffmod on Asn of +1 Da

<400> SEQUENCE: 69

Ala Leu Ser Xaa Ile Ser Leu Arg
1               5

<210> SEQ ID NO 70
<211> LENGTH: 15
<212> TYPE: PRT
<213> ORGANISM: Human
<220> FEATURE:
<221> NAME/KEY: MISC_FEATURE
<222> LOCATION: (12)..(12)
<223> OTHER INFORMATION: Where Xaa indicates a diffmod on Asn of +1 Da

<400> SEQUENCE: 70

Ser Cys Val Ala Val Thr Ser Ala Gln Pro Gln Xaa Met Ser Arg
1               5                   10                  15

<210> SEQ ID NO 71
<211> LENGTH: 16
<212> TYPE: PRT
<213> ORGANISM: Human
<220> FEATURE:
<221> NAME/KEY: MISC_FEATURE
<222> LOCATION: (6)..(6)
```

```
<223> OTHER INFORMATION: Where Xaa indicates a diffmod on Asn of +1 Da

<400> SEQUENCE: 71

Leu Ser His Asp Ala Xaa Glu Thr Leu Pro Leu His Leu Tyr Val Lys
1               5                   10                  15

<210> SEQ ID NO 72
<211> LENGTH: 10
<212> TYPE: PRT
<213> ORGANISM: Human
<220> FEATURE:
<221> NAME/KEY: MISC_FEATURE
<222> LOCATION: (7)..(7)
<223> OTHER INFORMATION: Where Xaa indicates a diffmod on Asn of +1 Da

<400> SEQUENCE: 72

Phe Ala Asn Glu Tyr Pro Xaa Ile Thr Arg
1               5                   10

<210> SEQ ID NO 73
<211> LENGTH: 20
<212> TYPE: PRT
<213> ORGANISM: Human
<220> FEATURE:
<221> NAME/KEY: MISC_FEATURE
<222> LOCATION: (3)..(3)
<223> OTHER INFORMATION: Where Xaa indicates a diffmod on Asn of +1 Da

<400> SEQUENCE: 73

Leu Leu Xaa Thr Thr Asp Val Tyr Leu Leu Pro Ser Leu Asn Pro Asp
1               5                   10                  15

Gly Phe Glu Arg
            20

<210> SEQ ID NO 74
<211> LENGTH: 20
<212> TYPE: PRT
<213> ORGANISM: Human
<220> FEATURE:
<221> NAME/KEY: MISC_FEATURE
<222> LOCATION: (3)..(14)
<223> OTHER INFORMATION: Where Xaa indicates a diffmod on Asn of +1 Da

<400> SEQUENCE: 74

Leu Leu Xaa Thr Thr Asp Val Tyr Leu Leu Pro Ser Leu Xaa Pro Asp
1               5                   10                  15

Gly Phe Glu Arg
            20

<210> SEQ ID NO 75
<211> LENGTH: 11
<212> TYPE: PRT
<213> ORGANISM: Human
<220> FEATURE:
<221> NAME/KEY: MISC_FEATURE
<222> LOCATION: (4)..(8)
<223> OTHER INFORMATION: Where Xaa indicates a diffmod on Asn of +1 Da

<400> SEQUENCE: 75

Arg Phe Ala Xaa Glu Tyr Pro Xaa Ile Thr Arg
1               5                   10

<210> SEQ ID NO 76
<211> LENGTH: 12
<212> TYPE: PRT
<213> ORGANISM: Human
<220> FEATURE:
<221> NAME/KEY: MISC_FEATURE
```

```
<222> LOCATION: (8)..(8)
<223> OTHER INFORMATION: Where Xaa indicates a diffmod on Asn of +1 Da

<400> SEQUENCE: 76

Gly Tyr Asn Pro Val Thr Lys Xaa Val Thr Val Lys
1               5                   10

<210> SEQ ID NO 77
<211> LENGTH: 13
<212> TYPE: PRT
<213> ORGANISM: Human
<220> FEATURE:
<221> NAME/KEY: MISC_FEATURE
<222> LOCATION: (6)..(6)
<223> OTHER INFORMATION: Where Xaa indicates a diffmod on Asn of +1 Da

<400> SEQUENCE: 77

Ala Leu Gly Phe Glu Xaa Ala Thr Gln Ala Leu Gly Arg
1               5                   10

<210> SEQ ID NO 78
<211> LENGTH: 11
<212> TYPE: PRT
<213> ORGANISM: Human
<220> FEATURE:
<221> NAME/KEY: MISC_FEATURE
<222> LOCATION: (8)..(8)
<223> OTHER INFORMATION: Where Xaa indicates a diffmod on Asn of +1 Da

<400> SEQUENCE: 78

Asp Ala Gly Val Val Cys Thr Xaa Glu Thr Arg
1               5                   10

<210> SEQ ID NO 79
<211> LENGTH: 19
<212> TYPE: PRT
<213> ORGANISM: Human
<220> FEATURE:
<221> NAME/KEY: MISC_FEATURE
<222> LOCATION: (5)..(5)
<223> OTHER INFORMATION: Where Xaa indicates a diffmod on Asn of +1 Da

<400> SEQUENCE: 79

Glu Pro Gly Ser Xaa Val Thr Met Ser Val Asp Ala Glu Cys Val Pro
1               5                   10                  15

Met Val Arg

<210> SEQ ID NO 80
<211> LENGTH: 12
<212> TYPE: PRT
<213> ORGANISM: Human
<220> FEATURE:
<221> NAME/KEY: MISC_FEATURE
<222> LOCATION: (3)..(3)
<223> OTHER INFORMATION: Where Xaa indicates a diffmod on Asn of +1 Da

<400> SEQUENCE: 80

Gly Leu Xaa Leu Thr Glu Asp Thr Tyr Lys Pro Arg
1               5                   10

<210> SEQ ID NO 81
<211> LENGTH: 13
<212> TYPE: PRT
<213> ORGANISM: Human
<220> FEATURE:
<221> NAME/KEY: MISC_FEATURE
<222> LOCATION: (10)..(10)
<223> OTHER INFORMATION: Where Xaa indicates a diffmod on Asn of +1 Da
```

```
<400> SEQUENCE: 81

Ala Ala Ile Pro Ser Ala Leu Asp Thr Xaa Ser Ser Lys
1               5                   10

<210> SEQ ID NO 82
<211> LENGTH: 15
<212> TYPE: PRT
<213> ORGANISM: Human
<220> FEATURE:
<221> NAME/KEY: MISC_FEATURE
<222> LOCATION: (10)..(10)
<223> OTHER INFORMATION: Where Xaa indicates a diffmod on Asn of +1 Da

<400> SEQUENCE: 82

Thr Val Ile Arg Pro Phe Tyr Leu Thr Xaa Ser Ser Gly Val Asp
1               5                   10                  15

<210> SEQ ID NO 83
<211> LENGTH: 37
<212> TYPE: PRT
<213> ORGANISM: Human
<220> FEATURE:
<221> NAME/KEY: MISC_FEATURE
<222> LOCATION: (5)..(5)
<223> OTHER INFORMATION: Where Xaa indicates a diffmod on Asn of +1 Da

<400> SEQUENCE: 83

Ile Leu Thr Asn Xaa Ser Gln Thr Pro Ile Leu Ser Pro Gln Glu Val
1               5                   10                  15

Val Ser Cys Ser Gln Tyr Ala Gln Gly Cys Glu Gly Gly Phe Pro Tyr
            20                  25                  30

Leu Ile Ala Gly Lys
        35

<210> SEQ ID NO 84
<211> LENGTH: 12
<212> TYPE: PRT
<213> ORGANISM: Human
<220> FEATURE:
<221> NAME/KEY: MISC_FEATURE
<222> LOCATION: (3)..(3)
<223> OTHER INFORMATION: Where Xaa indicates a diffmod on Asn of +1 Da

<400> SEQUENCE: 84

Asp Val Xaa Cys Ser Val Met Gly Pro Gln Glu Lys
1               5                   10

<210> SEQ ID NO 85
<211> LENGTH: 37
<212> TYPE: PRT
<213> ORGANISM: Human
<220> FEATURE:
<221> NAME/KEY: MISC_FEATURE
<222> LOCATION: (4)..(4)
<223> OTHER INFORMATION: Where Xaa indicates a diffmod on Asn of +1 Da

<400> SEQUENCE: 85

Ile Leu Thr Xaa Asn Ser Gln Thr Pro Ile Leu Ser Pro Gln Glu Val
1               5                   10                  15

Val Ser Cys Ser Gln Tyr Ala Gln Gly Cys Glu Gly Gly Phe Pro Tyr
            20                  25                  30

Leu Ile Ala Gly Lys
        35

<210> SEQ ID NO 86
<211> LENGTH: 37
```

```
<212> TYPE: PRT
<213> ORGANISM: Human
<220> FEATURE:
<221> NAME/KEY: MISC_FEATURE
<222> LOCATION: (4)..(5)
<223> OTHER INFORMATION: Where Xaa indicates a diffmod on Asn of +1 Da

<400> SEQUENCE: 86

Ile Leu Thr Xaa Xaa Ser Gln Thr Pro Ile Leu Ser Pro Gln Glu Val
1               5                   10                  15

Val Ser Cys Ser Gln Tyr Ala Gln Gly Cys Glu Gly Gly Phe Pro Tyr
                20                  25                  30

Leu Ile Ala Gly Lys
        35

<210> SEQ ID NO 87
<211> LENGTH: 15
<212> TYPE: PRT
<213> ORGANISM: Human
<220> FEATURE:
<221> NAME/KEY: MISC_FEATURE
<222> LOCATION: (5)..(5)
<223> OTHER INFORMATION: Where Xaa indicates a diffmod on Asn of +1 Da

<400> SEQUENCE: 87

Asp Ser Val Ile Xaa Leu Ser Glu Ser Val Glu Asp Gly Pro Lys
1               5                   10                  15

<210> SEQ ID NO 88
<211> LENGTH: 15
<212> TYPE: PRT
<213> ORGANISM: Human
<220> FEATURE:
<221> NAME/KEY: MISC_FEATURE
<222> LOCATION: (3)..(3)
<223> OTHER INFORMATION: Where Xaa indicates a diffmod on Asn of +1 Da

<400> SEQUENCE: 88

Arg Pro Xaa Gln Ser Gln Pro Leu Pro Pro Ser Ser Leu Gln Arg
1               5                   10                  15

<210> SEQ ID NO 89
<211> LENGTH: 16
<212> TYPE: PRT
<213> ORGANISM: Human
<220> FEATURE:
<221> NAME/KEY: MISC_FEATURE
<222> LOCATION: (3)..(3)
<223> OTHER INFORMATION: Where Xaa indicates a diffmod on Asn of +1 Da

<400> SEQUENCE: 89

Thr Gln Xaa Asp Val Asp Ile Ala Asp Val Ala Tyr Tyr Phe Glu Lys
1               5                   10                  15

<210> SEQ ID NO 90
<211> LENGTH: 23
<212> TYPE: PRT
<213> ORGANISM: Human
<220> FEATURE:
<221> NAME/KEY: MISC_FEATURE
<222> LOCATION: (19)..(19)
<223> OTHER INFORMATION: Where Xaa indicates a diffmod on Asn of +1 Da

<400> SEQUENCE: 90

Phe Ile Thr Ser Ile Leu Tyr Glu Asn Asn Val Ile Thr Ile Asp Leu
1               5                   10                  15

Val Gln Xaa Ser Ser Gln Lys
                20
```

<210> SEQ ID NO 91
<211> LENGTH: 14
<212> TYPE: PRT
<213> ORGANISM: Human
<220> FEATURE:
<221> NAME/KEY: MISC_FEATURE
<222> LOCATION: (5)..(5)
<223> OTHER INFORMATION: Where Xaa indicates a diffmod on Asn of +1 Da

<400> SEQUENCE: 91

Glu Leu Gly Asp Xaa Val Ser Met Ile Leu Val Pro Phe Lys
1               5                   10

<210> SEQ ID NO 92
<211> LENGTH: 22
<212> TYPE: PRT
<213> ORGANISM: Human
<220> FEATURE:
<221> NAME/KEY: MISC_FEATURE
<222> LOCATION: (2)..(13)
<223> OTHER INFORMATION: Where Xaa indicates a diffmod on Asn of +1 Da

<400> SEQUENCE: 92

Phe Xaa Gln Thr Met Gln Pro Leu Leu Thr Ala Gln Xaa Ala Leu Leu
1               5                   10                  15

Glu Asp Asp Thr Tyr Arg
            20

<210> SEQ ID NO 93
<211> LENGTH: 22
<212> TYPE: PRT
<213> ORGANISM: Human
<220> FEATURE:
<221> NAME/KEY: MISC_FEATURE
<222> LOCATION: (2)..(2)
<223> OTHER INFORMATION: Where Xaa indicates a diffmod on Asn of +1 Da

<400> SEQUENCE: 93

Phe Xaa Gln Thr Met Gln Pro Leu Leu Thr Ala Gln Asn Ala Leu Leu
1               5                   10                  15

Glu Asp Asp Thr Tyr Arg
            20

<210> SEQ ID NO 94
<211> LENGTH: 12
<212> TYPE: PRT
<213> ORGANISM: Human
<220> FEATURE:
<221> NAME/KEY: MISC_FEATURE
<222> LOCATION: (8)..(8)
<223> OTHER INFORMATION: Where Xaa indicates a diffmod on Asn of +1 Da

<400> SEQUENCE: 94

Glu Lys Lys Pro Asn Asn Leu Xaa Asp Thr Ile Lys
1               5                   10

<210> SEQ ID NO 95
<211> LENGTH: 21
<212> TYPE: PRT
<213> ORGANISM: Human
<220> FEATURE:
<221> NAME/KEY: MISC_FEATURE
<222> LOCATION: (11)..(11)
<223> OTHER INFORMATION: Where Xaa indicates a diffmod on Asn of +1 Da

<400> SEQUENCE: 95

Thr Gly Val His Asp Ala Asp Phe Glu Ser Xaa Val Thr Ala Thr Leu

Ala Ser Ile Asn Lys
            20

<210> SEQ ID NO 96
<211> LENGTH: 21
<212> TYPE: PRT
<213> ORGANISM: Human
<220> FEATURE:
<221> NAME/KEY: MISC_FEATURE
<222> LOCATION: (11)..(20)
<223> OTHER INFORMATION: Where Xaa indicates a diffmod on Asn of +1 Da

<400> SEQUENCE: 96

Thr Gly Val His Asp Ala Asp Phe Glu Ser Xaa Val Thr Ala Thr Leu
1               5                   10                  15

Ala Ser Ile Xaa Lys
            20

<210> SEQ ID NO 97
<211> LENGTH: 17
<212> TYPE: PRT
<213> ORGANISM: Human
<220> FEATURE:
<221> NAME/KEY: MISC_FEATURE
<222> LOCATION: (12)..(12)
<223> OTHER INFORMATION: Where Xaa indicates a diffmod on Asn of +1 Da

<400> SEQUENCE: 97

Gly Asn Leu Thr Tyr Gly Tyr Val Thr Ile Leu Xaa Gly Ser Asp Ile
1               5                   10                  15

Arg

<210> SEQ ID NO 98
<211> LENGTH: 15
<212> TYPE: PRT
<213> ORGANISM: Human
<220> FEATURE:
<221> NAME/KEY: MISC_FEATURE
<222> LOCATION: (5)..(5)
<223> OTHER INFORMATION: Where Xaa indicates a diffmod on Asn of +1 Da

<400> SEQUENCE: 98

Val Thr Gly Leu Xaa Cys Thr Thr Asn His Pro Ile Asn Pro Lys
1               5                   10                  15

<210> SEQ ID NO 99
<211> LENGTH: 17
<212> TYPE: PRT
<213> ORGANISM: Human
<220> FEATURE:
<221> NAME/KEY: MISC_FEATURE
<222> LOCATION: (2)..(12)
<223> OTHER INFORMATION: Where Xaa indicates a diffmod on Asn of +1 Da

<400> SEQUENCE: 99

Gly Xaa Leu Thr Tyr Gly Tyr Val Thr Ile Leu Xaa Gly Ser Asp Ile
1               5                   10                  15

Arg

<210> SEQ ID NO 100
<211> LENGTH: 20
<212> TYPE: PRT
<213> ORGANISM: Human
<220> FEATURE:
<221> NAME/KEY: MISC_FEATURE
<222> LOCATION: (10)..(10)

<223> OTHER INFORMATION: Where Xaa indicates a diffmod on Asn of +1 Da

<400> SEQUENCE: 100

Leu Gly Gln Ala Pro Ala Asn Trp Tyr Xaa Asp Thr Tyr Pro Leu Ser
1               5                   10                  15
Pro Pro Gln Arg
            20

<210> SEQ ID NO 101
<211> LENGTH: 20
<212> TYPE: PRT
<213> ORGANISM: Human
<220> FEATURE:
<221> NAME/KEY: MISC_FEATURE
<222> LOCATION: (7)..(10)
<223> OTHER INFORMATION: Where Xaa indicates a diffmod on Asn of +1 Da

<400> SEQUENCE: 101

Leu Gly Gln Ala Pro Ala Xaa Trp Tyr Xaa Asp Thr Tyr Pro Leu Ser
1               5                   10                  15
Pro Pro Gln Arg
            20

<210> SEQ ID NO 102
<211> LENGTH: 11
<212> TYPE: PRT
<213> ORGANISM: Human
<220> FEATURE:
<221> NAME/KEY: MISC_FEATURE
<222> LOCATION: (5)..(5)
<223> OTHER INFORMATION: Where Xaa indicates a diffmod on Asn of +1 Da

<400> SEQUENCE: 102

Ile Val Asp Val Xaa Leu Thr Ser Glu Gly Lys
1               5                   10

<210> SEQ ID NO 103
<211> LENGTH: 18
<212> TYPE: PRT
<213> ORGANISM: Human
<220> FEATURE:
<221> NAME/KEY: MISC_FEATURE
<222> LOCATION: (6)..(6)
<223> OTHER INFORMATION: Where Xaa indicates a diffmod on Asn of +1 Da

<400> SEQUENCE: 103

Leu Glu Trp Leu Gly Xaa Cys Ser Gly Leu Asn Asp Glu Thr Tyr Gly
1               5                   10                  15
Tyr Lys

<210> SEQ ID NO 104
<211> LENGTH: 20
<212> TYPE: PRT
<213> ORGANISM: Human
<220> FEATURE:
<221> NAME/KEY: MISC_FEATURE
<222> LOCATION: (12)..(12)
<223> OTHER INFORMATION: Where Xaa indicates a diffmod on Asn of +1 Da

<400> SEQUENCE: 104

Tyr Leu Gln Pro Leu Leu Ala Val Gln Phe Thr Xaa Leu Thr Met Asp
1               5                   10                  15
Thr Glu Ile Arg
            20

<210> SEQ ID NO 105

```
<211> LENGTH: 15
<212> TYPE: PRT
<213> ORGANISM: Human
<220> FEATURE:
<221> NAME/KEY: MISC_FEATURE
<222> LOCATION: (10)..(10)
<223> OTHER INFORMATION: Where Xaa indicates a diffmod on Asn of +1 Da

<400> SEQUENCE: 105

Ser Tyr Ser Thr Thr Tyr Glu Glu Arg Xaa Ile Thr Gly Thr Arg
1               5                   10                  15

<210> SEQ ID NO 106
<211> LENGTH: 15
<212> TYPE: PRT
<213> ORGANISM: Human
<220> FEATURE:
<221> NAME/KEY: MISC_FEATURE
<222> LOCATION: (8)..(8)
<223> OTHER INFORMATION: Where Xaa indicates a diffmod on Asn of +1 Da

<400> SEQUENCE: 106

Asp Leu Gly Pro Thr Leu Ala Xaa Ser Thr His His Asn Val Arg
1               5                   10                  15

<210> SEQ ID NO 107
<211> LENGTH: 24
<212> TYPE: PRT
<213> ORGANISM: Human
<220> FEATURE:
<221> NAME/KEY: MISC_FEATURE
<222> LOCATION: (15)..(15)
<223> OTHER INFORMATION: Where Xaa indicates a diffmod on Asn of +1 Da

<400> SEQUENCE: 107

Thr Tyr Thr Tyr Ala Asp Thr Pro Asp Asp Phe Gln Leu His Xaa Phe
1               5                   10                  15

Ser Leu Pro Glu Glu Asp Thr Lys
            20

<210> SEQ ID NO 108
<211> LENGTH: 9
<212> TYPE: PRT
<213> ORGANISM: Human
<220> FEATURE:
<221> NAME/KEY: MISC_FEATURE
<222> LOCATION: (2)..(2)
<223> OTHER INFORMATION: Where Xaa indicates a diffmod on Asn of +1 Da

<400> SEQUENCE: 108

Ala Xaa Leu Thr Val Val Leu Leu Arg
1               5

<210> SEQ ID NO 109
<211> LENGTH: 15
<212> TYPE: PRT
<213> ORGANISM: Human
<220> FEATURE:
<221> NAME/KEY: MISC_FEATURE
<222> LOCATION: (9)..(9)
<223> OTHER INFORMATION: Where Xaa indicates a diffmod on Asn of +1 Da

<400> SEQUENCE: 109

Leu Asn Pro Thr Val Thr Tyr Gly Xaa Asp Ser Phe Ser Ala Lys
1               5                   10                  15

<210> SEQ ID NO 110
<211> LENGTH: 15
<212> TYPE: PRT
```

```
<213> ORGANISM: Human
<220> FEATURE:
<221> NAME/KEY: MISC_FEATURE
<222> LOCATION: (6)..(6)
<223> OTHER INFORMATION: Where Xaa indicates a diffmod on Asn of +1 Da

<400> SEQUENCE: 110

Gly Val Phe Ile Thr Xaa Glu Thr Gly Gln Pro Leu Ile Gly Lys
1               5                   10                  15

<210> SEQ ID NO 111
<211> LENGTH: 22
<212> TYPE: PRT
<213> ORGANISM: Human
<220> FEATURE:
<221> NAME/KEY: MISC_FEATURE
<222> LOCATION: (19)..(19)
<223> OTHER INFORMATION: Where Xaa indicates a diffmod on Asn of +1 Da

<400> SEQUENCE: 111

Gln Ser Gln Phe Leu Asn Val Thr Ala Thr Glu Asp Tyr Val Asp Pro
1               5                   10                  15

Val Thr Xaa Gln Thr Lys
            20

<210> SEQ ID NO 112
<211> LENGTH: 15
<212> TYPE: PRT
<213> ORGANISM: Human
<220> FEATURE:
<221> NAME/KEY: MISC_FEATURE
<222> LOCATION: (6)..(6)
<223> OTHER INFORMATION: Where Xaa indicates a diffmod on Asn of +1 Da

<400> SEQUENCE: 112

Asn Tyr Lys Asn Pro Xaa Leu Thr Ile Ser Phe Thr Ala Glu Arg
1               5                   10                  15

<210> SEQ ID NO 113
<211> LENGTH: 20
<212> TYPE: PRT
<213> ORGANISM: Human
<220> FEATURE:
<221> NAME/KEY: MISC_FEATURE
<222> LOCATION: (3)..(10)
<223> OTHER INFORMATION: Where Xaa indicates a diffmod on Asn of +1 Da

<400> SEQUENCE: 113

Val Asp Xaa Ile Thr Asp Gln Phe Cys Xaa Ala Ser Val Val Asp Pro
1               5                   10                  15

Ala Cys Val Arg
            20

<210> SEQ ID NO 114
<211> LENGTH: 13
<212> TYPE: PRT
<213> ORGANISM: Human
<220> FEATURE:
<221> NAME/KEY: MISC_FEATURE
<222> LOCATION: (6)..(6)
<223> OTHER INFORMATION: Where Xaa indicates a diffmod on Asn of +1 Da

<400> SEQUENCE: 114

Asp Thr Gly Glu Leu Xaa Val Thr Ser Ile Leu Asp Arg
1               5                   10

<210> SEQ ID NO 115
<211> LENGTH: 9
```

```
<212> TYPE: PRT
<213> ORGANISM: Human
<220> FEATURE:
<221> NAME/KEY: MISC_FEATURE
<222> LOCATION: (4)..(4)
<223> OTHER INFORMATION: Where Xaa indicates a diffmod on Asn of +1 Da

<400> SEQUENCE: 115

Tyr Val Gln Xaa Gly Thr Tyr Asn Lys
1               5

<210> SEQ ID NO 116
<211> LENGTH: 8
<212> TYPE: PRT
<213> ORGANISM: Human
<220> FEATURE:
<221> NAME/KEY: MISC_FEATURE
<222> LOCATION: (4)..(4)
<223> OTHER INFORMATION: Where Xaa indicates a diffmod on Asn of +1 Da

<400> SEQUENCE: 116

Trp Gln Met Xaa Phe Thr Val Arg
1               5

<210> SEQ ID NO 117
<211> LENGTH: 9
<212> TYPE: PRT
<213> ORGANISM: Human
<220> FEATURE:
<221> NAME/KEY: MISC_FEATURE
<222> LOCATION: (5)..(5)
<223> OTHER INFORMATION: Where Xaa indicates a diffmod on Asn of +1 Da

<400> SEQUENCE: 117

Tyr Glu Thr Thr Xaa Lys Thr Tyr Lys
1               5

<210> SEQ ID NO 118
<211> LENGTH: 25
<212> TYPE: PRT
<213> ORGANISM: Human
<220> FEATURE:
<221> NAME/KEY: MISC_FEATURE
<222> LOCATION: (13)..(22)
<223> OTHER INFORMATION: Where Xaa indicates a diffmod on Asn of +1 Da

<400> SEQUENCE: 118

Thr Val Thr Ile Ser Asp His Gly Thr Val Thr Tyr Xaa Gly Ser Ile
1               5                   10                  15

Cys Gly Asp Asp Gln Xaa Gly Pro Lys
            20                  25

<210> SEQ ID NO 119
<211> LENGTH: 25
<212> TYPE: PRT
<213> ORGANISM: Human
<220> FEATURE:
<221> NAME/KEY: MISC_FEATURE
<222> LOCATION: (13)..(13)
<223> OTHER INFORMATION: Where Xaa indicates a diffmod on Asn of +1 Da

<400> SEQUENCE: 119

Thr Val Thr Ile Ser Asp His Gly Thr Val Thr Tyr Xaa Gly Ser Ile
1               5                   10                  15

Cys Gly Asp Asp Gln Asn Gly Pro Lys
            20                  25

<210> SEQ ID NO 120
```

```
<211> LENGTH: 17
<212> TYPE: PRT
<213> ORGANISM: Human
<220> FEATURE:
<221> NAME/KEY: MISC_FEATURE
<222> LOCATION: (14)..(14)
<223> OTHER INFORMATION: Where Xaa indicates a diffmod on Asn of +1 Da

<400> SEQUENCE: 120

Ile Ala Val Gln Phe Gly Pro Gly Phe Ser Trp Ile Ala Xaa Phe Thr
1               5                   10                  15

Lys

<210> SEQ ID NO 121
<211> LENGTH: 19
<212> TYPE: PRT
<213> ORGANISM: Human
<220> FEATURE:
<221> NAME/KEY: MISC_FEATURE
<222> LOCATION: (10)..(10)
<223> OTHER INFORMATION: Where Xaa indicates a diffmod on Asn of +1 Da

<400> SEQUENCE: 121

Val Ala Ser Val Ile Asn Ile Asn Pro Xaa Thr Thr His Ser Thr Gly
1               5                   10                  15

Ser Cys Arg

<210> SEQ ID NO 122
<211> LENGTH: 19
<212> TYPE: PRT
<213> ORGANISM: Human
<220> FEATURE:
<221> NAME/KEY: MISC_FEATURE
<222> LOCATION: (8)..(10)
<223> OTHER INFORMATION: Where Xaa indicates a diffmod on Asn of +1 Da

<400> SEQUENCE: 122

Val Ala Ser Val Ile Asn Ile Xaa Pro Xaa Thr Thr His Ser Thr Gly
1               5                   10                  15

Ser Cys Arg

<210> SEQ ID NO 123
<211> LENGTH: 10
<212> TYPE: PRT
<213> ORGANISM: Human
<220> FEATURE:
<221> NAME/KEY: MISC_FEATURE
<222> LOCATION: (5)..(5)
<223> OTHER INFORMATION: Where Xaa indicates a diffmod on Asn of +1 Da

<400> SEQUENCE: 123

Val Gln Pro Phe Xaa Val Thr Gln Gly Lys
1               5                   10

<210> SEQ ID NO 124
<211> LENGTH: 16
<212> TYPE: PRT
<213> ORGANISM: Human
<220> FEATURE:
<221> NAME/KEY: MISC_FEATURE
<222> LOCATION: (15)..(15)
<223> OTHER INFORMATION: Where Xaa indicates a diffmod on Asn of +1 Da

<400> SEQUENCE: 124

Asn Met Thr Phe Asp Leu Pro Ser Asp Ala Thr Val Val Leu Xaa Arg
1               5                   10                  15
```

-continued

```
<210> SEQ ID NO 125
<211> LENGTH: 19
<212> TYPE: PRT
<213> ORGANISM: Human
<220> FEATURE:
<221> NAME/KEY: MISC_FEATURE
<222> LOCATION: (7)..(7)
<223> OTHER INFORMATION: Where Xaa indicates a diffmod on Asn of +1 Da

<400> SEQUENCE: 125

Ser Ser Cys Gly Lys Glu Xaa Thr Ser Asp Pro Ser Leu Val Ile Ala
1               5                   10                  15

Phe Gly Arg

<210> SEQ ID NO 126
<211> LENGTH: 8
<212> TYPE: PRT
<213> ORGANISM: Human
<220> FEATURE:
<221> NAME/KEY: MISC_FEATURE
<222> LOCATION: (7)..(7)
<223> OTHER INFORMATION: Where Xaa indicates a diffmod on Asn of +1 Da

<400> SEQUENCE: 126

Leu Leu Asn Ile Asn Pro Xaa Lys
1               5

<210> SEQ ID NO 127
<211> LENGTH: 16
<212> TYPE: PRT
<213> ORGANISM: Human
<220> FEATURE:
<221> NAME/KEY: MISC_FEATURE
<222> LOCATION: (1)..(15)
<223> OTHER INFORMATION: Where Xaa indicates a diffmod on Asn of +1 Da

<400> SEQUENCE: 127

Xaa Met Thr Phe Asp Leu Pro Ser Asp Ala Thr Val Val Leu Xaa Arg
1               5                   10                  15

<210> SEQ ID NO 128
<211> LENGTH: 13
<212> TYPE: PRT
<213> ORGANISM: Human
<220> FEATURE:
<221> NAME/KEY: MISC_FEATURE
<222> LOCATION: (5)..(5)
<223> OTHER INFORMATION: Where Xaa indicates a diffmod on Asn of +1 Da

<400> SEQUENCE: 128

Gly Phe Cys Ala Xaa Ser Ser Leu Ala Phe Pro Thr Lys
1               5                   10

<210> SEQ ID NO 129
<211> LENGTH: 13
<212> TYPE: PRT
<213> ORGANISM: Human
<220> FEATURE:
<221> NAME/KEY: MISC_FEATURE
<222> LOCATION: (4)..(4)
<223> OTHER INFORMATION: Where Xaa indicates a diffmod on Asn of +1 Da

<400> SEQUENCE: 129

Leu Tyr Ala Xaa His Thr Ser Leu Pro Ala Ser Ala Arg
1               5                   10

<210> SEQ ID NO 130
<211> LENGTH: 20
<212> TYPE: PRT
```

```
<213> ORGANISM: Human
<220> FEATURE:
<221> NAME/KEY: MISC_FEATURE
<222> LOCATION: (10)..(10)
<223> OTHER INFORMATION: Where Xaa indicates a diffmod on Asn of +1 Da

<400> SEQUENCE: 130

Asn Lys Ala Asn Ile Gln Phe Gly Asp Xaa Gly Thr Thr Ile Ser Ala
1               5                   10                  15

Val Ser Asn Lys
            20

<210> SEQ ID NO 131
<211> LENGTH: 18
<212> TYPE: PRT
<213> ORGANISM: Human
<220> FEATURE:
<221> NAME/KEY: MISC_FEATURE
<222> LOCATION: (8)..(8)
<223> OTHER INFORMATION: Where Xaa indicates a diffmod on Asn of +1 Da

<400> SEQUENCE: 131

Ala Asn Ile Gln Phe Gly Asp Xaa Gly Thr Thr Ile Ser Ala Val Ser
1               5                   10                  15

Asn Lys

<210> SEQ ID NO 132
<211> LENGTH: 18
<212> TYPE: PRT
<213> ORGANISM: Human
<220> FEATURE:
<221> NAME/KEY: MISC_FEATURE
<222> LOCATION: (2)..(8)
<223> OTHER INFORMATION: Where Xaa indicates a diffmod on Asn of +1 Da

<400> SEQUENCE: 132

Ala Xaa Ile Gln Phe Gly Asp Xaa Gly Thr Thr Ile Ser Ala Val Ser
1               5                   10                  15

Asn Lys

<210> SEQ ID NO 133
<211> LENGTH: 22
<212> TYPE: PRT
<213> ORGANISM: Human
<220> FEATURE:
<221> NAME/KEY: MISC_FEATURE
<222> LOCATION: (4)..(19)
<223> OTHER INFORMATION: Where Xaa indicates a diffmod on Asn of +1 Da

<400> SEQUENCE: 133

Asn Gly Thr Xaa Asp Gly Asp Tyr Val Phe Leu Thr Gly Glu Asp Ser
1               5                   10                  15

Tyr Leu Xaa Phe Thr Lys
            20

<210> SEQ ID NO 134
<211> LENGTH: 22
<212> TYPE: PRT
<213> ORGANISM: Human
<220> FEATURE:
<221> NAME/KEY: MISC_FEATURE
<222> LOCATION: (1)..(19)
<223> OTHER INFORMATION: Where Xaa indicates a diffmod on Asn of +1 Da

<400> SEQUENCE: 134

Xaa Gly Thr Asn Asp Gly Asp Tyr Val Phe Leu Thr Gly Glu Asp Ser
1               5                   10                  15
```

```
Tyr Leu Xaa Phe Thr Lys
            20

<210> SEQ ID NO 135
<211> LENGTH: 13
<212> TYPE: PRT
<213> ORGANISM: Human
<220> FEATURE:
<221> NAME/KEY: MISC_FEATURE
<222> LOCATION: (2)..(2)
<223> OTHER INFORMATION: Where Xaa indicates a diffmod on Asn of +1 Da

<400> SEQUENCE: 135

Glu Xaa Ser Thr Asp Tyr Leu Tyr Pro Glu Gln Leu Lys
1               5                   10

<210> SEQ ID NO 136
<211> LENGTH: 10
<212> TYPE: PRT
<213> ORGANISM: Human
<220> FEATURE:
<221> NAME/KEY: MISC_FEATURE
<222> LOCATION: (9)..(9)
<223> OTHER INFORMATION: Where Xaa indicates a diffmod on Asn of +1 Da

<400> SEQUENCE: 136

Tyr Arg Asp Phe Gln His Leu Leu Xaa Arg
1               5                   10

<210> SEQ ID NO 137
<211> LENGTH: 8
<212> TYPE: PRT
<213> ORGANISM: Human
<220> FEATURE:
<221> NAME/KEY: MISC_FEATURE
<222> LOCATION: (7)..(7)
<223> OTHER INFORMATION: Where Xaa indicates a diffmod on Asn of +1 Da

<400> SEQUENCE: 137

Asp Phe Gln His Leu Leu Xaa Arg
1               5

<210> SEQ ID NO 138
<211> LENGTH: 21
<212> TYPE: PRT
<213> ORGANISM: Human
<220> FEATURE:
<221> NAME/KEY: MISC_FEATURE
<222> LOCATION: (18)..(18)
<223> OTHER INFORMATION: Where Xaa indicates a diffmod on Asn of +1 Da

<400> SEQUENCE: 138

Thr Cys Ile Met Glu Ala Ser Thr Asp Phe Leu Pro Gly Leu Asn Phe
1               5                   10                  15

Ser Xaa Cys Ser Arg
            20

<210> SEQ ID NO 139
<211> LENGTH: 17
<212> TYPE: PRT
<213> ORGANISM: Human
<220> FEATURE:
<221> NAME/KEY: MISC_FEATURE
<222> LOCATION: (16)..(16)
<223> OTHER INFORMATION: Where Xaa indicates a diffmod on Asn of +1 Da

<400> SEQUENCE: 139

Gly Gln Thr Glu Ile Gln Val Asn Cys Pro Pro Ala Val Thr Glu Xaa
```

```
1               5                   10                  15
Lys

<210> SEQ ID NO 140
<211> LENGTH: 17
<212> TYPE: PRT
<213> ORGANISM: Human
<220> FEATURE:
<221> NAME/KEY: MISC_FEATURE
<222> LOCATION: (8)..(16)
<223> OTHER INFORMATION: Where Xaa indicates a diffmod on Asn of +1 Da

<400> SEQUENCE: 140

Gly Gln Thr Glu Ile Gln Val Xaa Cys Pro Pro Ala Val Thr Glu Xaa
1               5                   10                  15
Lys

<210> SEQ ID NO 141
<211> LENGTH: 20
<212> TYPE: PRT
<213> ORGANISM: Human
<220> FEATURE:
<221> NAME/KEY: MISC_FEATURE
<222> LOCATION: (13)..(13)
<223> OTHER INFORMATION: Where Xaa indicates a diffmod on Asn of +1 Da

<400> SEQUENCE: 141

Leu Asn Glu Ala Ser Phe Gln Pro Pro Pro Gly Val Xaa Ile Cys Asp
1               5                   10                  15
Val Asn Trp Lys
            20

<210> SEQ ID NO 142
<211> LENGTH: 20
<212> TYPE: PRT
<213> ORGANISM: Human
<220> FEATURE:
<221> NAME/KEY: MISC_FEATURE
<222> LOCATION: (2)..(18)
<223> OTHER INFORMATION: Where Xaa indicates a diffmod on Asn of +1 Da

<400> SEQUENCE: 142

Leu Xaa Glu Ala Ser Phe Gln Pro Pro Pro Gly Val Xaa Ile Cys Asp
1               5                   10                  15
Val Xaa Trp Lys
            20

<210> SEQ ID NO 143
<211> LENGTH: 12
<212> TYPE: PRT
<213> ORGANISM: Human
<220> FEATURE:
<221> NAME/KEY: MISC_FEATURE
<222> LOCATION: (7)..(7)
<223> OTHER INFORMATION: Where Xaa indicates a diffmod on Asn of +1 Da

<400> SEQUENCE: 143

Ile Gly Thr Phe Cys Ser Xaa Gly Thr Val Ser Arg
1               5                   10

<210> SEQ ID NO 144
<211> LENGTH: 9
<212> TYPE: PRT
<213> ORGANISM: Human
<220> FEATURE:
<221> NAME/KEY: MISC_FEATURE
<222> LOCATION: (3)..(3)
```

-continued

<223> OTHER INFORMATION: Where Xaa indicates a diffmod on Asn of +1 Da

<400> SEQUENCE: 144

Glu Ser Xaa Ile Thr Val Leu Ile Lys
1               5

<210> SEQ ID NO 145
<211> LENGTH: 10
<212> TYPE: PRT
<213> ORGANISM: Human
<220> FEATURE:
<221> NAME/KEY: MISC_FEATURE
<222> LOCATION: (1)..(1)
<223> OTHER INFORMATION: Where Xaa indicates a diffmod on Asn of +1 Da

<400> SEQUENCE: 145

Xaa Val Ser Gly Phe Ser Ile Ala Asn Arg
1               5                   10

<210> SEQ ID NO 146
<211> LENGTH: 15
<212> TYPE: PRT
<213> ORGANISM: Human
<220> FEATURE:
<221> NAME/KEY: MISC_FEATURE
<222> LOCATION: (9)..(9)
<223> OTHER INFORMATION: Where Xaa indicates a diffmod on Asn of +1 Da

<400> SEQUENCE: 146

Ala Ser Val Ser Phe Leu Asn Phe Xaa Leu Ser Asn Cys Glu Arg
1               5                   10                  15

<210> SEQ ID NO 147
<211> LENGTH: 16
<212> TYPE: PRT
<213> ORGANISM: Human
<220> FEATURE:
<221> NAME/KEY: MISC_FEATURE
<222> LOCATION: (12)..(12)
<223> OTHER INFORMATION: Where Xaa indicates a diffmod on Asn of +1 Da

<400> SEQUENCE: 147

Leu Gln Phe Gln Val Leu Val Gln His Pro Gln Xaa Glu Ser Asn Lys
1               5                   10                  15

<210> SEQ ID NO 148
<211> LENGTH: 13
<212> TYPE: PRT
<213> ORGANISM: Human
<220> FEATURE:
<221> NAME/KEY: MISC_FEATURE
<222> LOCATION: (5)..(5)
<223> OTHER INFORMATION: Where Xaa indicates a diffmod on Asn of +1 Da

<400> SEQUENCE: 148

Thr Cys Ser Ser Xaa Leu Thr Leu Thr Ser Gly Ser Lys
1               5                   10

<210> SEQ ID NO 149
<211> LENGTH: 23
<212> TYPE: PRT
<213> ORGANISM: Human
<220> FEATURE:
<221> NAME/KEY: MISC_FEATURE
<222> LOCATION: (16)..(16)
<223> OTHER INFORMATION: Where Xaa indicates a diffmod on Asn of +1 Da

<400> SEQUENCE: 149

Asp Ala Thr Gly Asn Val Asn Asp Thr Ile Val Thr Glu Leu Thr Xaa

```
                 1               5                  10                 15
Cys Thr Ser Ala Ala Cys Lys
                20

<210> SEQ ID NO 150
<211> LENGTH: 23
<212> TYPE: PRT
<213> ORGANISM: Human
<220> FEATURE:
<221> NAME/KEY: MISC_FEATURE
<222> LOCATION: (7)..(16)
<223> OTHER INFORMATION: Where Xaa indicates a diffmod on Asn of +1 Da

<400> SEQUENCE: 150

Asp Ala Thr Gly Asn Val Xaa Asp Thr Ile Val Thr Glu Leu Thr Xaa
1               5                  10                 15
Cys Thr Ser Ala Ala Cys Lys
                20

<210> SEQ ID NO 151
<211> LENGTH: 13
<212> TYPE: PRT
<213> ORGANISM: Human
<220> FEATURE:
<221> NAME/KEY: MISC_FEATURE
<222> LOCATION: (9)..(9)
<223> OTHER INFORMATION: Where Xaa indicates a diffmod on Asn of +1 Da

<400> SEQUENCE: 151

Ile Asn Tyr Thr Asp Pro Phe Ser Xaa Gln Thr Val Lys
1               5                  10

<210> SEQ ID NO 152
<211> LENGTH: 13
<212> TYPE: PRT
<213> ORGANISM: Human
<220> FEATURE:
<221> NAME/KEY: MISC_FEATURE
<222> LOCATION: (2)..(9)
<223> OTHER INFORMATION: Where Xaa indicates a diffmod on Asn of +1 Da

<400> SEQUENCE: 152

Ile Xaa Tyr Thr Asp Pro Phe Ser Xaa Gln Thr Val Lys
1               5                  10

<210> SEQ ID NO 153
<211> LENGTH: 17
<212> TYPE: PRT
<213> ORGANISM: Human
<220> FEATURE:
<221> NAME/KEY: MISC_FEATURE
<222> LOCATION: (13)..(13)
<223> OTHER INFORMATION: Where Xaa indicates a diffmod on Asn of +1 Da

<400> SEQUENCE: 153

Ile Val Ser Pro Glu Pro Gly Gly Ala Val Gly Pro Xaa Leu Thr Cys
1               5                  10                 15
Arg

<210> SEQ ID NO 154
<211> LENGTH: 24
<212> TYPE: PRT
<213> ORGANISM: Human
<220> FEATURE:
<221> NAME/KEY: MISC_FEATURE
<222> LOCATION: (14)..(14)
<223> OTHER INFORMATION: Where Xaa indicates a diffmod on Asn of +1 Da
```

```
<400> SEQUENCE: 154

Ile Thr Asn Glu Asn Phe Val Asp Ala Tyr Glu Asn Ser Xaa Ser Thr
1               5                   10                  15

Glu Phe Val Ser Leu Ala Ser Lys
            20

<210> SEQ ID NO 155
<211> LENGTH: 24
<212> TYPE: PRT
<213> ORGANISM: Human
<220> FEATURE:
<221> NAME/KEY: MISC_FEATURE
<222> LOCATION: (12)..(12)
<223> OTHER INFORMATION: Where Xaa indicates a diffmod on Asn of +1 Da

<400> SEQUENCE: 155

Ile Thr Asn Glu Asn Phe Val Asp Ala Tyr Glu Xaa Ser Asn Ser Thr
1               5                   10                  15

Glu Phe Val Ser Leu Ala Ser Lys
            20

<210> SEQ ID NO 156
<211> LENGTH: 24
<212> TYPE: PRT
<213> ORGANISM: Human
<220> FEATURE:
<221> NAME/KEY: MISC_FEATURE
<222> LOCATION: (12)..(14)
<223> OTHER INFORMATION: Where Xaa indicates a diffmod on Asn of +1 Da

<400> SEQUENCE: 156

Ile Thr Asn Glu Asn Phe Val Asp Ala Tyr Glu Xaa Ser Xaa Ser Thr
1               5                   10                  15

Glu Phe Val Ser Leu Ala Ser Lys
            20

<210> SEQ ID NO 157
<211> LENGTH: 18
<212> TYPE: PRT
<213> ORGANISM: Human
<220> FEATURE:
<221> NAME/KEY: MISC_FEATURE
<222> LOCATION: (3)..(3)
<223> OTHER INFORMATION: Where Xaa indicates a diffmod on Asn of +1 Da

<400> SEQUENCE: 157

Val Ile Xaa Gln Thr Thr Cys Glu Asn Leu Leu Pro Gln Gln Ile Thr
1               5                   10                  15

Pro Arg

<210> SEQ ID NO 158
<211> LENGTH: 18
<212> TYPE: PRT
<213> ORGANISM: Human
<220> FEATURE:
<221> NAME/KEY: MISC_FEATURE
<222> LOCATION: (3)..(9)
<223> OTHER INFORMATION: Where Xaa indicates a diffmod on Asn of +1 Da

<400> SEQUENCE: 158

Val Ile Xaa Gln Thr Thr Cys Glu Xaa Leu Leu Pro Gln Gln Ile Thr
1               5                   10                  15

Pro Arg

<210> SEQ ID NO 159
```

```
<211> LENGTH: 10
<212> TYPE: PRT
<213> ORGANISM: Human
<220> FEATURE:
<221> NAME/KEY: MISC_FEATURE
<222> LOCATION: (3)..(3)
<223> OTHER INFORMATION: Where Xaa indicates a diffmod on Asn of +1 Da

<400> SEQUENCE: 159

Arg Gln Xaa Ile Thr Asn Gln Leu Glu Lys
1               5                   10

<210> SEQ ID NO 160
<211> LENGTH: 18
<212> TYPE: PRT
<213> ORGANISM: Human
<220> FEATURE:
<221> NAME/KEY: MISC_FEATURE
<222> LOCATION: (11)..(12)
<223> OTHER INFORMATION: Where Xaa indicates a diffmod on Asn of +1 Da

<400> SEQUENCE: 160

Ser Asn Val Ile Phe Tyr Ile Val Thr Leu Xaa Xaa Thr Ala Asp His
1               5                   10                  15

Leu Arg

<210> SEQ ID NO 161
<211> LENGTH: 9
<212> TYPE: PRT
<213> ORGANISM: Human
<220> FEATURE:
<221> NAME/KEY: MISC_FEATURE
<222> LOCATION: (2)..(2)
<223> OTHER INFORMATION: Where Xaa indicates a diffmod on Asn of +1 Da

<400> SEQUENCE: 161

Gln Xaa Ile Thr Asn Gln Leu Glu Lys
1               5

<210> SEQ ID NO 162
<211> LENGTH: 13
<212> TYPE: PRT
<213> ORGANISM: Human
<220> FEATURE:
<221> NAME/KEY: MISC_FEATURE
<222> LOCATION: (9)..(9)
<223> OTHER INFORMATION: Where Xaa indicates a diffmod on Asn of +1 Da

<400> SEQUENCE: 162

Asp Pro Gln Gly Trp Val Ala Gly Xaa Leu Ser Ala Arg
1               5                   10

<210> SEQ ID NO 163
<211> LENGTH: 13
<212> TYPE: PRT
<213> ORGANISM: Human
<220> FEATURE:
<221> NAME/KEY: MISC_FEATURE
<222> LOCATION: (5)..(5)
<223> OTHER INFORMATION: Where Xaa indicates a diffmod on Asn of +1 Da

<400> SEQUENCE: 163

Ala Val Leu Val Xaa Gly Thr Glu Cys Leu Leu Ala Arg
1               5                   10

<210> SEQ ID NO 164
<211> LENGTH: 15
<212> TYPE: PRT
<213> ORGANISM: Human
```

```
<220> FEATURE:
<221> NAME/KEY: MISC_FEATURE
<222> LOCATION: (11)..(11)
<223> OTHER INFORMATION: Where Xaa indicates a diffmod on Asn of +1 Da

<400> SEQUENCE: 164

Asn Trp Gln Leu Thr Glu Glu Asp Phe Gly Xaa Thr Ser Gly Arg
1               5                   10                  15

<210> SEQ ID NO 165
<211> LENGTH: 8
<212> TYPE: PRT
<213> ORGANISM: Human
<220> FEATURE:
<221> NAME/KEY: MISC_FEATURE
<222> LOCATION: (4)..(5)
<223> OTHER INFORMATION: Where Xaa indicates a diffmod on Asn of +1 Da

<400> SEQUENCE: 165

Leu Cys Leu Xaa Xaa Asp Thr Lys
1               5

<210> SEQ ID NO 166
<211> LENGTH: 10
<212> TYPE: PRT
<213> ORGANISM: Human
<220> FEATURE:
<221> NAME/KEY: MISC_FEATURE
<222> LOCATION: (3)..(3)
<223> OTHER INFORMATION: Where Xaa indicates a diffmod on Asn of +1 Da

<400> SEQUENCE: 166

Ser Tyr Xaa Val Thr Ser Val Leu Phe Arg
1               5                   10

<210> SEQ ID NO 167
<211> LENGTH: 13
<212> TYPE: PRT
<213> ORGANISM: Human
<220> FEATURE:
<221> NAME/KEY: MISC_FEATURE
<222> LOCATION: (8)..(8)
<223> OTHER INFORMATION: Where Xaa indicates a diffmod on Asn of +1 Da

<400> SEQUENCE: 167

Ala Gly Phe Glu Ala Val Glu Xaa Gly Thr Val Cys Arg
1               5                   10

<210> SEQ ID NO 168
<211> LENGTH: 20
<212> TYPE: PRT
<213> ORGANISM: Human
<220> FEATURE:
<221> NAME/KEY: MISC_FEATURE
<222> LOCATION: (12)..(12)
<223> OTHER INFORMATION: Where Xaa indicates a diffmod on Asn of +1 Da

<400> SEQUENCE: 168

Asp Leu Cys Gly Pro Asp Ala Gly Pro Ile Gly Xaa Ala Thr Gly Gln
1               5                   10                  15

Ala Asp Cys Lys
            20

<210> SEQ ID NO 169
<211> LENGTH: 11
<212> TYPE: PRT
<213> ORGANISM: Human
<220> FEATURE:
<221> NAME/KEY: MISC_FEATURE
```

```
<222> LOCATION: (7)..(7)
<223> OTHER INFORMATION: Where Xaa indicates a diffmod on Asn of +1 Da

<400> SEQUENCE: 169

Asn Asn Val Ile Thr Leu Xaa Ile Thr Gly Lys
1               5                   10

<210> SEQ ID NO 170
<211> LENGTH: 11
<212> TYPE: PRT
<213> ORGANISM: Human
<220> FEATURE:
<221> NAME/KEY: MISC_FEATURE
<222> LOCATION: (1)..(7)
<223> OTHER INFORMATION: Where Xaa indicates a diffmod on Asn of +1 Da

<400> SEQUENCE: 170

Xaa Asn Val Ile Thr Leu Xaa Ile Thr Gly Lys
1               5                   10

<210> SEQ ID NO 171
<211> LENGTH: 11
<212> TYPE: PRT
<213> ORGANISM: Human
<220> FEATURE:
<221> NAME/KEY: MISC_FEATURE
<222> LOCATION: (2)..(7)
<223> OTHER INFORMATION: Where Xaa indicates a diffmod on Asn of +1 Da

<400> SEQUENCE: 171

Asn Xaa Val Ile Thr Leu Xaa Ile Thr Gly Lys
1               5                   10

<210> SEQ ID NO 172
<211> LENGTH: 19
<212> TYPE: PRT
<213> ORGANISM: Human
<220> FEATURE:
<221> NAME/KEY: MISC_FEATURE
<222> LOCATION: (6)..(6)
<223> OTHER INFORMATION: Where Xaa indicates a diffmod on Asn of +1 Da

<400> SEQUENCE: 172

Val Glu Asp Glu Gly Xaa Tyr Thr Cys Leu Phe Val Thr Phe Pro Gln
1               5                   10                  15

Gly Ser Arg

<210> SEQ ID NO 173
<211> LENGTH: 10
<212> TYPE: PRT
<213> ORGANISM: Human
<220> FEATURE:
<221> NAME/KEY: MISC_FEATURE
<222> LOCATION: (3)..(3)
<223> OTHER INFORMATION: Where Xaa indicates a diffmod on Asn of +1 Da

<400> SEQUENCE: 173

Arg Gln Xaa Gln Ser Leu Val Tyr Gly Lys
1               5                   10

<210> SEQ ID NO 174
<211> LENGTH: 19
<212> TYPE: PRT
<213> ORGANISM: Human
<220> FEATURE:
<221> NAME/KEY: MISC_FEATURE
<222> LOCATION: (12)..(12)
<223> OTHER INFORMATION: Where Xaa indicates a diffmod on Asn of +1 Da
```

```
<400> SEQUENCE: 174

Gln His Thr Val Thr Thr Thr Lys Gly Glu Xaa Phe Thr Glu Thr
1               5                   10                  15

Asp Val Lys

<210> SEQ ID NO 175
<211> LENGTH: 10
<212> TYPE: PRT
<213> ORGANISM: Human
<220> FEATURE:
<221> NAME/KEY: MISC_FEATURE
<222> LOCATION: (3)..(3)
<223> OTHER INFORMATION: Where Xaa indicates a diffmod on Asn of +1 Da

<400> SEQUENCE: 175

Gly Glu Xaa Phe Thr Glu Thr Asp Val Lys
1               5                   10

<210> SEQ ID NO 176
<211> LENGTH: 16
<212> TYPE: PRT
<213> ORGANISM: Human
<220> FEATURE:
<221> NAME/KEY: MISC_FEATURE
<222> LOCATION: (4)..(4)
<223> OTHER INFORMATION: Where Xaa indicates a diffmod on Asn of +1 Da

<400> SEQUENCE: 176

Glu Ala Gly Xaa His Thr Ser Gly Ala Gly Leu Val Gln Ile Asn Lys
1               5                   10                  15

<210> SEQ ID NO 177
<211> LENGTH: 16
<212> TYPE: PRT
<213> ORGANISM: Human
<220> FEATURE:
<221> NAME/KEY: MISC_FEATURE
<222> LOCATION: (4)..(15)
<223> OTHER INFORMATION: Where Xaa indicates a diffmod on Asn of +1 Da

<400> SEQUENCE: 177

Glu Ala Gly Xaa His Thr Ser Gly Ala Gly Leu Val Gln Ile Xaa Lys
1               5                   10                  15

<210> SEQ ID NO 178
<211> LENGTH: 14
<212> TYPE: PRT
<213> ORGANISM: Human
<220> FEATURE:
<221> NAME/KEY: MISC_FEATURE
<222> LOCATION: (4)..(10)
<223> OTHER INFORMATION: Where Xaa indicates a diffmod on Asn of +1 Da

<400> SEQUENCE: 178

Ile Asp Leu Xaa Ser Thr Ser His Val Xaa Ile Thr Thr Arg
1               5                   10

<210> SEQ ID NO 179
<211> LENGTH: 13
<212> TYPE: PRT
<213> ORGANISM: Human
<220> FEATURE:
<221> NAME/KEY: MISC_FEATURE
<222> LOCATION: (4)..(5)
<223> OTHER INFORMATION: Where Xaa indicates a diffmod on Asn of +1 Da

<400> SEQUENCE: 179

Leu Leu Lys Xaa Xaa Glu Ser Leu Asp Glu Gly Leu Arg
```

<210> SEQ ID NO 180
<211> LENGTH: 13
<212> TYPE: PRT
<213> ORGANISM: Human
<220> FEATURE:
<221> NAME/KEY: MISC_FEATURE
<222> LOCATION: (9)..(9)
<223> OTHER INFORMATION: Where Xaa indicates a diffmod on Asn of +1 Da

<400> SEQUENCE: 180

Gly Glu Thr Ala Ser Leu Leu Cys Xaa Ile Ser Val Arg
1               5                   10

<210> SEQ ID NO 181
<211> LENGTH: 22
<212> TYPE: PRT
<213> ORGANISM: Human
<220> FEATURE:
<221> NAME/KEY: MISC_FEATURE
<222> LOCATION: (12)..(12)
<223> OTHER INFORMATION: Where Xaa indicates a diffmod on Asn of +1 Da

<400> SEQUENCE: 181

Ile Gly Pro Gly Glu Pro Leu Glu Leu Leu Cys Xaa Val Ser Gly Ala
1               5                   10                  15

Leu Pro Pro Ala Gly Arg
            20

<210> SEQ ID NO 182
<211> LENGTH: 9
<212> TYPE: PRT
<213> ORGANISM: Human
<220> FEATURE:
<221> NAME/KEY: MISC_FEATURE
<222> LOCATION: (4)..(4)
<223> OTHER INFORMATION: Where Xaa indicates a diffmod on Asn of +1 Da

<400> SEQUENCE: 182

Thr Met Phe Xaa Ser Thr Asp Ile Lys
1               5

<210> SEQ ID NO 183
<211> LENGTH: 12
<212> TYPE: PRT
<213> ORGANISM: Human
<220> FEATURE:
<221> NAME/KEY: MISC_FEATURE
<222> LOCATION: (3)..(3)
<223> OTHER INFORMATION: Where Xaa indicates a diffmod on Asn of +1 Da

<400> SEQUENCE: 183

Leu Gly Xaa Leu Thr Val Thr Gln Ala Ile Leu Lys
1               5                   10

<210> SEQ ID NO 184
<211> LENGTH: 16
<212> TYPE: PRT
<213> ORGANISM: Human
<220> FEATURE:
<221> NAME/KEY: MISC_FEATURE
<222> LOCATION: (6)..(6)
<223> OTHER INFORMATION: Where Xaa indicates a diffmod on Asn of +1 Da

<400> SEQUENCE: 184

Leu Asp Met Ser Gln Xaa Val Ser Leu Val Thr Ala Glu Leu Ser Lys
1               5                   10                  15

```
<210> SEQ ID NO 185
<211> LENGTH: 18
<212> TYPE: PRT
<213> ORGANISM: Human
<220> FEATURE:
<221> NAME/KEY: MISC_FEATURE
<222> LOCATION: (10)..(10)
<223> OTHER INFORMATION: Where Xaa indicates a diffmod on Asn of +1 Da

<400> SEQUENCE: 185

Gln Gln Met Glu Asn Tyr Pro Lys Asn Xaa His Thr Ala Ser Ile Leu
1               5                   10                  15

Asp Arg

<210> SEQ ID NO 186
<211> LENGTH: 10
<212> TYPE: PRT
<213> ORGANISM: Human
<220> FEATURE:
<221> NAME/KEY: MISC_FEATURE
<222> LOCATION: (2)..(2)
<223> OTHER INFORMATION: Where Xaa indicates a diffmod on Asn of +1 Da

<400> SEQUENCE: 186

Asn Xaa His Thr Ala Ser Ile Leu Asp Arg
1               5                   10

<210> SEQ ID NO 187
<211> LENGTH: 10
<212> TYPE: PRT
<213> ORGANISM: Human
<220> FEATURE:
<221> NAME/KEY: MISC_FEATURE
<222> LOCATION: (1)..(1)
<223> OTHER INFORMATION: Where Xaa indicates a diffmod on Asn of +1 Da

<400> SEQUENCE: 187

Xaa Asn His Thr Ala Ser Ile Leu Asp Arg
1               5                   10

<210> SEQ ID NO 188
<211> LENGTH: 10
<212> TYPE: PRT
<213> ORGANISM: Human
<220> FEATURE:
<221> NAME/KEY: MISC_FEATURE
<222> LOCATION: (1)..(2)
<223> OTHER INFORMATION: Where Xaa indicates a diffmod on Asn of +1 Da

<400> SEQUENCE: 188

Xaa Xaa His Thr Ala Ser Ile Leu Asp Arg
1               5                   10

<210> SEQ ID NO 189
<211> LENGTH: 12
<212> TYPE: PRT
<213> ORGANISM: Human
<220> FEATURE:
<221> NAME/KEY: MISC_FEATURE
<222> LOCATION: (6)..(6)
<223> OTHER INFORMATION: Where Xaa indicates a diffmod on Asn of +1 Da

<400> SEQUENCE: 189

Cys Cys Gly Ala Ala Xaa Tyr Thr Asp Trp Glu Lys
1               5                   10

<210> SEQ ID NO 190
<211> LENGTH: 22
```

```
<212> TYPE: PRT
<213> ORGANISM: Human
<220> FEATURE:
<221> NAME/KEY: MISC_FEATURE
<222> LOCATION: (10)..(20)
<223> OTHER INFORMATION: Where Xaa indicates a diffmod on Asn of +1 Da

<400> SEQUENCE: 190

Asn Arg Val Pro Asp Ser Cys Cys Ile Xaa Val Thr Val Gly Cys Gly
1               5                   10                  15

Ile Xaa Phe Asn Glu Lys
            20

<210> SEQ ID NO 191
<211> LENGTH: 22
<212> TYPE: PRT
<213> ORGANISM: Human
<220> FEATURE:
<221> NAME/KEY: MISC_FEATURE
<222> LOCATION: (1)..(10)
<223> OTHER INFORMATION: Where Xaa indicates a diffmod on Asn of +1 Da

<400> SEQUENCE: 191

Xaa Arg Val Pro Asp Ser Cys Cys Ile Xaa Val Thr Val Gly Cys Gly
1               5                   10                  15

Ile Asn Phe Asn Glu Lys
            20

<210> SEQ ID NO 192
<211> LENGTH: 20
<212> TYPE: PRT
<213> ORGANISM: Human
<220> FEATURE:
<221> NAME/KEY: MISC_FEATURE
<222> LOCATION: (8)..(16)
<223> OTHER INFORMATION: Where Xaa indicates a diffmod on Asn of +1 Da

<400> SEQUENCE: 192

Val Pro Asp Ser Cys Cys Ile Xaa Val Thr Val Gly Cys Gly Ile Xaa
1               5                   10                  15

Phe Asn Glu Lys
            20

<210> SEQ ID NO 193
<211> LENGTH: 17
<212> TYPE: PRT
<213> ORGANISM: Human
<220> FEATURE:
<221> NAME/KEY: MISC_FEATURE
<222> LOCATION: (8)..(8)
<223> OTHER INFORMATION: Where Xaa indicates a diffmod on Asn of +1 Da

<400> SEQUENCE: 193

Gly Gly Gly Asp Pro Trp Thr Xaa Gly Ser Gly Leu Ala Leu Cys Gln
1               5                   10                  15

Arg

<210> SEQ ID NO 194
<211> LENGTH: 14
<212> TYPE: PRT
<213> ORGANISM: Human
<220> FEATURE:
<221> NAME/KEY: MISC_FEATURE
<222> LOCATION: (5)..(5)
<223> OTHER INFORMATION: Where Xaa indicates a diffmod on Asn of +1 Da

<400> SEQUENCE: 194
```

```
Thr Ser Pro Ala Xaa Cys Thr Trp Leu Ile Leu Gly Ser Lys
1               5                   10

<210> SEQ ID NO 195
<211> LENGTH: 9
<212> TYPE: PRT
<213> ORGANISM: Human
<220> FEATURE:
<221> NAME/KEY: MISC_FEATURE
<222> LOCATION: (3)..(3)
<223> OTHER INFORMATION: Where Xaa indicates a diffmod on Asn of +1 Da

<400> SEQUENCE: 195

Gly Phe Xaa Ala Thr Tyr His Val Arg
1               5

<210> SEQ ID NO 196
<211> LENGTH: 14
<212> TYPE: PRT
<213> ORGANISM: Human
<220> FEATURE:
<221> NAME/KEY: MISC_FEATURE
<222> LOCATION: (5)..(5)
<223> OTHER INFORMATION: Where Xaa indicates a diffmod on Asn of +1 Da

<400> SEQUENCE: 196

Ser Val Asn Pro Xaa Asp Thr Cys Leu Ala Ser Cys Val Lys
1               5                   10

<210> SEQ ID NO 197
<211> LENGTH: 14
<212> TYPE: PRT
<213> ORGANISM: Human
<220> FEATURE:
<221> NAME/KEY: MISC_FEATURE
<222> LOCATION: (3)..(5)
<223> OTHER INFORMATION: Where Xaa indicates a diffmod on Asn of +1 Da

<400> SEQUENCE: 197

Ser Val Xaa Pro Xaa Asp Thr Cys Leu Ala Ser Cys Val Lys
1               5                   10

<210> SEQ ID NO 198
<211> LENGTH: 22
<212> TYPE: PRT
<213> ORGANISM: Human
<220> FEATURE:
<221> NAME/KEY: MISC_FEATURE
<222> LOCATION: (6)..(6)
<223> OTHER INFORMATION: Where Xaa indicates a diffmod on Asn of +1 Da

<400> SEQUENCE: 198

Gly Ser Glu Gly Gly Xaa Gly Ser Asn Pro Val Ala Gly Leu Glu Thr
1               5                   10                  15

Asp Asp His Gly Gly Lys
            20

<210> SEQ ID NO 199
<211> LENGTH: 22
<212> TYPE: PRT
<213> ORGANISM: Human
<220> FEATURE:
<221> NAME/KEY: MISC_FEATURE
<222> LOCATION: (6)..(9)
<223> OTHER INFORMATION: Where Xaa indicates a diffmod on Asn of +1 Da

<400> SEQUENCE: 199

Gly Ser Glu Gly Gly Xaa Gly Ser Xaa Pro Val Ala Gly Leu Glu Thr
1               5                   10                  15
```

Asp Asp His Gly Gly Lys
            20

<210> SEQ ID NO 200
<211> LENGTH: 14
<212> TYPE: PRT
<213> ORGANISM: Human
<220> FEATURE:
<221> NAME/KEY: MISC_FEATURE
<222> LOCATION: (11)..(11)
<223> OTHER INFORMATION: Where Xaa indicates a diffmod on Asn of +1 Da

<400> SEQUENCE: 200

Asp Ala Ser Ser Phe Leu Ala Glu Trp Gln Xaa Ile Thr Lys
1               5                   10

<210> SEQ ID NO 201
<211> LENGTH: 20
<212> TYPE: PRT
<213> ORGANISM: Human
<220> FEATURE:
<221> NAME/KEY: MISC_FEATURE
<222> LOCATION: (17)..(17)
<223> OTHER INFORMATION: Where Xaa indicates a diffmod on Asn of +1 Da

<400> SEQUENCE: 201

Asp Ile Glu Asn Leu Lys Asp Ala Ser Ser Phe Leu Ala Glu Trp Gln
1               5                   10                  15

Xaa Ile Thr Lys
            20

<210> SEQ ID NO 202
<211> LENGTH: 22
<212> TYPE: PRT
<213> ORGANISM: Human
<220> FEATURE:
<221> NAME/KEY: MISC_FEATURE
<222> LOCATION: (7)..(7)
<223> OTHER INFORMATION: Where Xaa indicates a diffmod on Asn of +1 Da

<400> SEQUENCE: 202

Leu Leu Ile Ala Gly Thr Xaa Ser Ser Asp Leu Gln Gln Ile Leu Ser
1               5                   10                  15

Leu Leu Glu Ser Asn Lys
            20

<210> SEQ ID NO 203
<211> LENGTH: 22
<212> TYPE: PRT
<213> ORGANISM: Human
<220> FEATURE:
<221> NAME/KEY: MISC_FEATURE
<222> LOCATION: (7)..(21)
<223> OTHER INFORMATION: Where Xaa indicates a diffmod on Asn of +1 Da

<400> SEQUENCE: 203

Leu Leu Ile Ala Gly Thr Xaa Ser Ser Asp Leu Gln Gln Ile Leu Ser
1               5                   10                  15

Leu Leu Glu Ser Xaa Lys
            20

<210> SEQ ID NO 204
<211> LENGTH: 13
<212> TYPE: PRT
<213> ORGANISM: Human
<220> FEATURE:
<221> NAME/KEY: MISC_FEATURE

```
<222> LOCATION: (8)..(8)
<223> OTHER INFORMATION: Where Xaa indicates a diffmod on Asn of +1 Da

<400> SEQUENCE: 204

Ser Leu Val Thr Gln Tyr Leu Xaa Ala Thr Gly Asn Arg
1               5                   10

<210> SEQ ID NO 205
<211> LENGTH: 13
<212> TYPE: PRT
<213> ORGANISM: Human
<220> FEATURE:
<221> NAME/KEY: MISC_FEATURE
<222> LOCATION: (8)..(12)
<223> OTHER INFORMATION: Where Xaa indicates a diffmod on Asn of +1 Da

<400> SEQUENCE: 205

Ser Leu Val Thr Gln Tyr Leu Xaa Ala Thr Gly Xaa Arg
1               5                   10

<210> SEQ ID NO 206
<211> LENGTH: 17
<212> TYPE: PRT
<213> ORGANISM: Human
<220> FEATURE:
<221> NAME/KEY: MISC_FEATURE
<222> LOCATION: (10)..(10)
<223> OTHER INFORMATION: Where Xaa indicates a diffmod on Asn of +1 Da

<400> SEQUENCE: 206

Ala Lys Phe Val Gly Thr Pro Glu Val Xaa Gln Thr Thr Leu Tyr Gln
1               5                   10                  15

Arg

<210> SEQ ID NO 207
<211> LENGTH: 15
<212> TYPE: PRT
<213> ORGANISM: Human
<220> FEATURE:
<221> NAME/KEY: MISC_FEATURE
<222> LOCATION: (8)..(8)
<223> OTHER INFORMATION: Where Xaa indicates a diffmod on Asn of +1 Da

<400> SEQUENCE: 207

Phe Val Gly Thr Pro Glu Val Xaa Gln Thr Thr Leu Tyr Gln Arg
1               5                   10                  15

<210> SEQ ID NO 208
<211> LENGTH: 22
<212> TYPE: PRT
<213> ORGANISM: Human
<220> FEATURE:
<221> NAME/KEY: MISC_FEATURE
<222> LOCATION: (9)..(9)
<223> OTHER INFORMATION: Where Xaa indicates a diffmod on Asn of +1 Da

<400> SEQUENCE: 208

Gln Val Ala Leu Gln Thr Phe Gly Xaa Gln Thr Thr Ile Ile Pro Ala
1               5                   10                  15

Gly Gly Ala Gly Tyr Lys
            20

<210> SEQ ID NO 209
<211> LENGTH: 9
<212> TYPE: PRT
<213> ORGANISM: Human
<220> FEATURE:
<221> NAME/KEY: MISC_FEATURE
```

```
<222> LOCATION: (5)..(5)
<223> OTHER INFORMATION: Where Xaa indicates a diffmod on Asn of +1 Da

<400> SEQUENCE: 209

Ile Ile Phe Ala Xaa Val Ser Val Arg
1               5

<210> SEQ ID NO 210
<211> LENGTH: 10
<212> TYPE: PRT
<213> ORGANISM: Human
<220> FEATURE:
<221> NAME/KEY: MISC_FEATURE
<222> LOCATION: (1)..(1)
<223> OTHER INFORMATION: Where Xaa indicates a diffmod on Asn of +1 Da

<400> SEQUENCE: 210

Xaa Ile Thr Asp Leu Val Glu Gly Ala Lys
1               5                   10

<210> SEQ ID NO 211
<211> LENGTH: 18
<212> TYPE: PRT
<213> ORGANISM: Human
<220> FEATURE:
<221> NAME/KEY: MISC_FEATURE
<222> LOCATION: (7)..(7)
<223> OTHER INFORMATION: Where Xaa indicates a diffmod on Asn of +1 Da

<400> SEQUENCE: 211

Gly Val Leu Met Val Gly Xaa Glu Thr Thr Tyr Glu Asp Gly His Gly
1               5                   10                  15

Ser Arg

<210> SEQ ID NO 212
<211> LENGTH: 11
<212> TYPE: PRT
<213> ORGANISM: Human
<220> FEATURE:
<221> NAME/KEY: MISC_FEATURE
<222> LOCATION: (2)..(2)
<223> OTHER INFORMATION: Where Xaa indicates a diffmod on Asn of +1 Da

<400> SEQUENCE: 212

Lys Xaa Ile Thr Asp Leu Val Glu Gly Ala Lys
1               5                   10

<210> SEQ ID NO 213
<211> LENGTH: 14
<212> TYPE: PRT
<213> ORGANISM: Human
<220> FEATURE:
<221> NAME/KEY: MISC_FEATURE
<222> LOCATION: (11)..(11)
<223> OTHER INFORMATION: Where Xaa indicates a diffmod on Asn of +1 Da

<400> SEQUENCE: 213

Thr Cys Asn Pro Glu Thr Phe Pro Ser Ser Xaa Glu Ser Arg
1               5                   10

<210> SEQ ID NO 214
<211> LENGTH: 11
<212> TYPE: PRT
<213> ORGANISM: Human
<220> FEATURE:
<221> NAME/KEY: MISC_FEATURE
<222> LOCATION: (5)..(5)
<223> OTHER INFORMATION: Where Xaa indicates a diffmod on Asn of +1 Da
```

-continued

```
<400> SEQUENCE: 214

His Val Tyr Asn Xaa Leu Thr Glu Glu Gln Lys
1               5                   10

<210> SEQ ID NO 215
<211> LENGTH: 11
<212> TYPE: PRT
<213> ORGANISM: Human
<220> FEATURE:
<221> NAME/KEY: MISC_FEATURE
<222> LOCATION: (4)..(5)
<223> OTHER INFORMATION: Where Xaa indicates a diffmod on Asn of +1 Da

<400> SEQUENCE: 215

His Val Tyr Xaa Xaa Leu Thr Glu Glu Gln Lys
1               5                   10

<210> SEQ ID NO 216
<211> LENGTH: 16
<212> TYPE: PRT
<213> ORGANISM: Human
<220> FEATURE:
<221> NAME/KEY: MISC_FEATURE
<222> LOCATION: (4)..(4)
<223> OTHER INFORMATION: Where Xaa indicates a diffmod on Asn of +1 Da

<400> SEQUENCE: 216

Thr Ala Val Xaa Cys Ser Ser Asp Phe Asp Ala Cys Leu Ile Thr Lys
1               5                   10                  15

<210> SEQ ID NO 217
<211> LENGTH: 11
<212> TYPE: PRT
<213> ORGANISM: Human
<220> FEATURE:
<221> NAME/KEY: MISC_FEATURE
<222> LOCATION: (6)..(6)
<223> OTHER INFORMATION: Where Xaa indicates a diffmod on Asn of +1 Da

<400> SEQUENCE: 217

Glu Ile Phe Val Ala Xaa Gly Thr Gln Gly Lys
1               5                   10

<210> SEQ ID NO 218
<211> LENGTH: 11
<212> TYPE: PRT
<213> ORGANISM: Human
<220> FEATURE:
<221> NAME/KEY: MISC_FEATURE
<222> LOCATION: (3)..(3)
<223> OTHER INFORMATION: Where Xaa indicates a diffmod on Asn of +1 Da

<400> SEQUENCE: 218

Leu Phe Xaa Val Thr Pro Gln Asp Glu Gln Lys
1               5                   10

<210> SEQ ID NO 219
<211> LENGTH: 21
<212> TYPE: PRT
<213> ORGANISM: Human
<220> FEATURE:
<221> NAME/KEY: MISC_FEATURE
<222> LOCATION: (10)..(10)
<223> OTHER INFORMATION: Where Xaa indicates a diffmod on Asn of +1 Da

<400> SEQUENCE: 219

Phe Val Glu Gln Asn Glu Thr Ala Ile Xaa Ile Thr Thr Tyr Pro Asp
1               5                   10                  15
```

Gln Glu Asn Asn Lys
            20

<210> SEQ ID NO 220
<211> LENGTH: 10
<212> TYPE: PRT
<213> ORGANISM: Human
<220> FEATURE:
<221> NAME/KEY: MISC_FEATURE
<222> LOCATION: (3)..(3)
<223> OTHER INFORMATION: Where Xaa indicates a diffmod on Asn of +1 Da

<400> SEQUENCE: 220

Gly Ser Xaa Tyr Ser Glu Ile Leu Asp Lys
1               5                   10

<210> SEQ ID NO 221
<211> LENGTH: 15
<212> TYPE: PRT
<213> ORGANISM: Human
<220> FEATURE:
<221> NAME/KEY: MISC_FEATURE
<222> LOCATION: (8)..(8)
<223> OTHER INFORMATION: Where Xaa indicates a diffmod on Asn of +1 Da

<400> SEQUENCE: 221

Leu Ala Phe Ala Thr Met Phe Xaa Ser Ser Glu Gln Ser Gln Lys
1               5                   10                  15

<210> SEQ ID NO 222
<211> LENGTH: 12
<212> TYPE: PRT
<213> ORGANISM: Human
<220> FEATURE:
<221> NAME/KEY: MISC_FEATURE
<222> LOCATION: (5)..(5)
<223> OTHER INFORMATION: Where Xaa indicates a diffmod on Asn of +1 Da

<400> SEQUENCE: 222

Glu Leu Leu Leu Xaa Thr Ser Glu Val Thr Val Arg
1               5                   10

<210> SEQ ID NO 223
<211> LENGTH: 14
<212> TYPE: PRT
<213> ORGANISM: Human
<220> FEATURE:
<221> NAME/KEY: MISC_FEATURE
<222> LOCATION: (3)..(3)
<223> OTHER INFORMATION: Where Xaa indicates a diffmod on Asn of +1 Da

<400> SEQUENCE: 223

Leu Leu Xaa Cys Thr Ala Pro Gly Pro Asp Ala Ala Ala Arg
1               5                   10

<210> SEQ ID NO 224
<211> LENGTH: 15
<212> TYPE: PRT
<213> ORGANISM: Human
<220> FEATURE:
<221> NAME/KEY: MISC_FEATURE
<222> LOCATION: (6)..(6)
<223> OTHER INFORMATION: Where Xaa indicates a diffmod on Asn of +1 Da

<400> SEQUENCE: 224

Leu Asn Leu Ser Glu Xaa Tyr Thr Leu Ser Ile Ser Asn Ala Arg
1               5                   10                  15

<210> SEQ ID NO 225

```
<211> LENGTH: 19
<212> TYPE: PRT
<213> ORGANISM: Human
<220> FEATURE:
<221> NAME/KEY: MISC_FEATURE
<222> LOCATION: (14)..(14)
<223> OTHER INFORMATION: Where Xaa indicates a diffmod on Asn of +1 Da

<400> SEQUENCE: 225

Leu Gly Asp Cys Ile Ser Glu Asp Ser Tyr Pro Asp Gly Xaa Ile Thr
1               5                  10                  15

Trp Tyr Arg

<210> SEQ ID NO 226
<211> LENGTH: 12
<212> TYPE: PRT
<213> ORGANISM: Human
<220> FEATURE:
<221> NAME/KEY: MISC_FEATURE
<222> LOCATION: (8)..(8)
<223> OTHER INFORMATION: Where Xaa indicates a diffmod on Asn of +1 Da

<400> SEQUENCE: 226

Asn Ala Ile Lys Glu Gly Asp Xaa Ile Thr Leu Lys
1               5                  10

<210> SEQ ID NO 227
<211> LENGTH: 8
<212> TYPE: PRT
<213> ORGANISM: Human
<220> FEATURE:
<221> NAME/KEY: MISC_FEATURE
<222> LOCATION: (4)..(4)
<223> OTHER INFORMATION: Where Xaa indicates a diffmod on Asn of +1 Da

<400> SEQUENCE: 227

Glu Gly Asp Xaa Ile Thr Leu Lys
1               5

<210> SEQ ID NO 228
<211> LENGTH: 8
<212> TYPE: PRT
<213> ORGANISM: Human
<220> FEATURE:
<221> NAME/KEY: MISC_FEATURE
<222> LOCATION: (1)..(1)
<223> OTHER INFORMATION: Where Xaa indicates a diffmod on Asn of +1 Da

<400> SEQUENCE: 228

Xaa Ala Thr Val Val Trp Met Lys
1               5

<210> SEQ ID NO 229
<211> LENGTH: 21
<212> TYPE: PRT
<213> ORGANISM: Human
<220> FEATURE:
<221> NAME/KEY: MISC_FEATURE
<222> LOCATION: (8)..(8)
<223> OTHER INFORMATION: Where Xaa indicates a diffmod on Asn of +1 Da

<400> SEQUENCE: 229

Ile Ile Ile Ser Pro Glu Glu Xaa Val Thr Leu Thr Cys Thr Ala Glu
1               5                  10                  15

Asn Gln Leu Glu Arg
            20

<210> SEQ ID NO 230
```

```
<211> LENGTH: 21
<212> TYPE: PRT
<213> ORGANISM: Human
<220> FEATURE:
<221> NAME/KEY: MISC_FEATURE
<222> LOCATION: (8)..(17)
<223> OTHER INFORMATION: Where Xaa indicates a diffmod on Asn of +1 Da

<400> SEQUENCE: 230

Ile Ile Ile Ser Pro Glu Glu Xaa Val Thr Leu Thr Cys Thr Ala Glu
1               5                   10                  15

Xaa Gln Leu Glu Arg
            20

<210> SEQ ID NO 231
<211> LENGTH: 26
<212> TYPE: PRT
<213> ORGANISM: Human
<220> FEATURE:
<221> NAME/KEY: MISC_FEATURE
<222> LOCATION: (6)..(6)
<223> OTHER INFORMATION: Where Xaa indicates a diffmod on Asn of +1 Da

<400> SEQUENCE: 231

Thr Val Asn Ser Leu Xaa Val Ser Ala Ile Ser Ile Pro Glu His Asp
1               5                   10                  15

Glu Ala Asp Glu Ile Ser Asp Glu Asn Arg
            20                  25

<210> SEQ ID NO 232
<211> LENGTH: 26
<212> TYPE: PRT
<213> ORGANISM: Human
<220> FEATURE:
<221> NAME/KEY: MISC_FEATURE
<222> LOCATION: (6)..(25)
<223> OTHER INFORMATION: Where Xaa indicates a diffmod on Asn of +1 Da

<400> SEQUENCE: 232

Thr Val Asn Ser Leu Xaa Val Ser Ala Ile Ser Ile Pro Glu His Asp
1               5                   10                  15

Glu Ala Asp Glu Ile Ser Asp Glu Xaa Arg
            20                  25

<210> SEQ ID NO 233
<211> LENGTH: 28
<212> TYPE: PRT
<213> ORGANISM: Human
<220> FEATURE:
<221> NAME/KEY: MISC_FEATURE
<222> LOCATION: (6)..(25)
<223> OTHER INFORMATION: Where Xaa indicates a diffmod on Asn of +1 Da

<400> SEQUENCE: 233

Thr Val Ser Asn Leu Xaa Val Ser Ala Ile Ser Ile Pro Glu His Asp
1               5                   10                  15

Glu Ala Asp Glu Ile Ser Asp Glu Xaa Arg Glu Lys
            20                  25

<210> SEQ ID NO 234
<211> LENGTH: 10
<212> TYPE: PRT
<213> ORGANISM: Human
<220> FEATURE:
<221> NAME/KEY: MISC_FEATURE
<222> LOCATION: (4)..(4)
<223> OTHER INFORMATION: Where Xaa indicates a diffmod on Asn of +1 Da
```

```
<400> SEQUENCE: 234

Leu Phe Gln Xaa Cys Ser Glu Leu Phe Lys
1               5                  10

<210> SEQ ID NO 235
<211> LENGTH: 17
<212> TYPE: PRT
<213> ORGANISM: Human
<220> FEATURE:
<221> NAME/KEY: MISC_FEATURE
<222> LOCATION: (11)..(11)
<223> OTHER INFORMATION: Where Xaa indicates a diffmod on Asn of +1 Da

<400> SEQUENCE: 235

Phe Asp Gly Glu Pro Cys Asp Leu Ser Leu Xaa Ile Thr Trp Tyr Leu
1               5                  10                  15

Lys

<210> SEQ ID NO 236
<211> LENGTH: 12
<212> TYPE: PRT
<213> ORGANISM: Human
<220> FEATURE:
<221> NAME/KEY: MISC_FEATURE
<222> LOCATION: (2)..(2)
<223> OTHER INFORMATION: Where Xaa indicates a diffmod on Asn of +1 Da

<400> SEQUENCE: 236

Glu Xaa Gly Thr Asn Leu Thr Phe Ile Gly Asp Lys
1               5                  10

<210> SEQ ID NO 237
<211> LENGTH: 16
<212> TYPE: PRT
<213> ORGANISM: Human
<220> FEATURE:
<221> NAME/KEY: MISC_FEATURE
<222> LOCATION: (9)..(9)
<223> OTHER INFORMATION: Where Xaa indicates a diffmod on Asn of +1 Da

<400> SEQUENCE: 237

Gln Glu Ala Lys Glu Asn Gly Thr Xaa Leu Thr Phe Ile Gly Asp Lys
1               5                  10                  15

<210> SEQ ID NO 238
<211> LENGTH: 12
<212> TYPE: PRT
<213> ORGANISM: Human
<220> FEATURE:
<221> NAME/KEY: MISC_FEATURE
<222> LOCATION: (5)..(5)
<223> OTHER INFORMATION: Where Xaa indicates a diffmod on Asn of +1 Da

<400> SEQUENCE: 238

Glu Asn Gly Thr Xaa Leu Thr Phe Ile Gly Asp Lys
1               5                  10

<210> SEQ ID NO 239
<211> LENGTH: 16
<212> TYPE: PRT
<213> ORGANISM: Human
<220> FEATURE:
<221> NAME/KEY: MISC_FEATURE
<222> LOCATION: (6)..(9)
<223> OTHER INFORMATION: Where Xaa indicates a diffmod on Asn of +1 Da

<400> SEQUENCE: 239

Gln Glu Ala Lys Glu Xaa Gly Thr Xaa Leu Thr Phe Ile Gly Asp Lys
```

-continued

```
<210> SEQ ID NO 240
<211> LENGTH: 12
<212> TYPE: PRT
<213> ORGANISM: Human
<220> FEATURE:
<221> NAME/KEY: MISC_FEATURE
<222> LOCATION: (2)..(5)
<223> OTHER INFORMATION: Where Xaa indicates a diffmod on Asn of +1 Da

<400> SEQUENCE: 240

Glu Xaa Gly Thr Xaa Leu Thr Phe Ile Gly Asp Lys
1               5                   10

<210> SEQ ID NO 241
<211> LENGTH: 18
<212> TYPE: PRT
<213> ORGANISM: Human
<220> FEATURE:
<221> NAME/KEY: MISC_FEATURE
<222> LOCATION: (8)..(8)
<223> OTHER INFORMATION: Where Xaa indicates a diffmod on Asn of +1 Da

<400> SEQUENCE: 241

Ile Leu Leu Thr Cys Ser Leu Xaa Asp Ser Ala Thr Glu Val Thr Gly
1               5                   10                  15

His Arg

<210> SEQ ID NO 242
<211> LENGTH: 16
<212> TYPE: PRT
<213> ORGANISM: Human
<220> FEATURE:
<221> NAME/KEY: MISC_FEATURE
<222> LOCATION: (11)..(11)
<223> OTHER INFORMATION: Where Xaa indicates a diffmod on Asn of +1 Da

<400> SEQUENCE: 242

Ile Thr Asp Ser Glu Asp Lys Ala Leu Met Xaa Gly Ser Glu Ser Arg
1               5                   10                  15

<210> SEQ ID NO 243
<211> LENGTH: 9
<212> TYPE: PRT
<213> ORGANISM: Human
<220> FEATURE:
<221> NAME/KEY: MISC_FEATURE
<222> LOCATION: (4)..(4)
<223> OTHER INFORMATION: Where Xaa indicates a diffmod on Asn of +1 Da

<400> SEQUENCE: 243

Ala Leu Met Xaa Gly Ser Glu Ser Arg
1               5

<210> SEQ ID NO 244
<211> LENGTH: 11
<212> TYPE: PRT
<213> ORGANISM: Human
<220> FEATURE:
<221> NAME/KEY: MISC_FEATURE
<222> LOCATION: (10)..(10)
<223> OTHER INFORMATION: Where Xaa indicates a diffmod on Asn of +1 Da

<400> SEQUENCE: 244

Asp Ile Tyr Thr Phe Asp Gly Ala Leu Xaa Lys
1               5                   10
```

```
<210> SEQ ID NO 245
<211> LENGTH: 19
<212> TYPE: PRT
<213> ORGANISM: Human
<220> FEATURE:
<221> NAME/KEY: MISC_FEATURE
<222> LOCATION: (9)..(9)
<223> OTHER INFORMATION: Where Xaa indicates a diffmod on Asn of +1 Da

<400> SEQUENCE: 245

Ser Asp Ala Val Ser His Ile Gly Xaa Tyr Thr Cys Glu Val Thr Glu
1               5                   10                  15

Leu Thr Arg

<210> SEQ ID NO 246
<211> LENGTH: 16
<212> TYPE: PRT
<213> ORGANISM: Human
<220> FEATURE:
<221> NAME/KEY: MISC_FEATURE
<222> LOCATION: (12)..(12)
<223> OTHER INFORMATION: Where Xaa indicates a diffmod on Asn of +1 Da

<400> SEQUENCE: 246

Thr Ala Leu Phe Pro Asp Leu Leu Ala Gln Gly Xaa Ala Ser Leu Arg
1               5                   10                  15

<210> SEQ ID NO 247
<211> LENGTH: 14
<212> TYPE: PRT
<213> ORGANISM: Human
<220> FEATURE:
<221> NAME/KEY: MISC_FEATURE
<222> LOCATION: (6)..(6)
<223> OTHER INFORMATION: Where Xaa indicates a diffmod on Asn of +1 Da

<400> SEQUENCE: 247

Val Val Leu Gly Ala Xaa Gly Thr Tyr Ser Cys Leu Val Arg
1               5                   10

<210> SEQ ID NO 248
<211> LENGTH: 21
<212> TYPE: PRT
<213> ORGANISM: Human
<220> FEATURE:
<221> NAME/KEY: MISC_FEATURE
<222> LOCATION: (17)..(17)
<223> OTHER INFORMATION: Where Xaa indicates a diffmod on Asn of +1 Da

<400> SEQUENCE: 248

Val Leu Gly Gln Ser Gln Glu Pro Asn Val Asn Pro Ala Ser Ala Gly
1               5                   10                  15

Xaa Gln Thr Gln Lys
            20

<210> SEQ ID NO 249
<211> LENGTH: 29
<212> TYPE: PRT
<213> ORGANISM: Human
<220> FEATURE:
<221> NAME/KEY: MISC_FEATURE
<222> LOCATION: (7)..(14)
<223> OTHER INFORMATION: Where Xaa indicates a diffmod on Asn of +1 Da

<400> SEQUENCE: 249

Asp Gly Tyr Met Val Val Xaa Val Ser Ser Leu Ser Leu Xaa Glu Pro
1               5                   10                  15

Glu Asp Lys Asp Val Thr Ile Gly Phe Ser Leu Asp Arg
```

-continued

```
                20                  25

<210> SEQ ID NO 250
<211> LENGTH: 17
<212> TYPE: PRT
<213> ORGANISM: Human
<220> FEATURE:
<221> NAME/KEY: MISC_FEATURE
<222> LOCATION: (8)..(8)
<223> OTHER INFORMATION: Where Xaa indicates a diffmod on Asn of +1 Da

<400> SEQUENCE: 250

Arg Gly Pro Glu Cys Ser Gln Xaa Tyr Thr Thr Pro Ser Gly Val Ile
1               5                   10                  15

Lys

<210> SEQ ID NO 251
<211> LENGTH: 16
<212> TYPE: PRT
<213> ORGANISM: Human
<220> FEATURE:
<221> NAME/KEY: MISC_FEATURE
<222> LOCATION: (7)..(7)
<223> OTHER INFORMATION: Where Xaa indicates a diffmod on Asn of +1 Da

<400> SEQUENCE: 251

Gly Pro Glu Cys Ser Gln Xaa Tyr Thr Thr Pro Ser Gly Val Ile Lys
1               5                   10                  15

<210> SEQ ID NO 252
<211> LENGTH: 19
<212> TYPE: PRT
<213> ORGANISM: Human
<220> FEATURE:
<221> NAME/KEY: MISC_FEATURE
<222> LOCATION: (6)..(6)
<223> OTHER INFORMATION: Where Xaa indicates a diffmod on Asn of +1 Da

<400> SEQUENCE: 252

Glu Gly Phe Ser Ala Xaa Tyr Ser Val Leu Gln Ser Ser Val Ser Glu
1               5                   10                  15

Asp Phe Lys

<210> SEQ ID NO 253
<211> LENGTH: 11
<212> TYPE: PRT
<213> ORGANISM: Human
<220> FEATURE:
<221> NAME/KEY: MISC_FEATURE
<222> LOCATION: (5)..(6)
<223> OTHER INFORMATION: Where Xaa indicates a diffmod on Asn of +1 Da

<400> SEQUENCE: 253

Ile Gly Tyr Ser Xaa Xaa Gly Ser Asp Trp Lys
1               5                   10

<210> SEQ ID NO 254
<211> LENGTH: 11
<212> TYPE: PRT
<213> ORGANISM: Human
<220> FEATURE:
<221> NAME/KEY: MISC_FEATURE
<222> LOCATION: (6)..(6)
<223> OTHER INFORMATION: Where Xaa indicates a diffmod on Asn of +1 Da

<400> SEQUENCE: 254

Val Leu Glu Ala Val Xaa Gly Thr Asp Ala Arg
1               5                   10
```

```
<210> SEQ ID NO 255
<211> LENGTH: 12
<212> TYPE: PRT
<213> ORGANISM: Human
<220> FEATURE:
<221> NAME/KEY: MISC_FEATURE
<222> LOCATION: (6)..(6)
<223> OTHER INFORMATION: Where Xaa indicates a diffmod on Asn of +1 Da

<400> SEQUENCE: 255

Ala Leu Lys Gln Tyr Xaa Ser Thr Gly Asp Tyr Arg
1               5                   10

<210> SEQ ID NO 256
<211> LENGTH: 13
<212> TYPE: PRT
<213> ORGANISM: Human
<220> FEATURE:
<221> NAME/KEY: MISC_FEATURE
<222> LOCATION: (2)..(2)
<223> OTHER INFORMATION: Where Xaa indicates a diffmod on Asn of +1 Da

<400> SEQUENCE: 256

Gly Xaa Leu Thr Phe Thr Ala Gln Tyr Leu Ser Tyr Arg
1               5                   10

<210> SEQ ID NO 257
<211> LENGTH: 15
<212> TYPE: PRT
<213> ORGANISM: Human
<220> FEATURE:
<221> NAME/KEY: MISC_FEATURE
<222> LOCATION: (1)..(1)
<223> OTHER INFORMATION: Where Xaa indicates a diffmod on Asn of +1 Da

<400> SEQUENCE: 257

Xaa Gln Ser Ile Gly Leu Ile Gln Pro Phe Ala Thr Asn Gly Lys
1               5                   10                  15

<210> SEQ ID NO 258
<211> LENGTH: 17
<212> TYPE: PRT
<213> ORGANISM: Human
<220> FEATURE:
<221> NAME/KEY: MISC_FEATURE
<222> LOCATION: (9)..(9)
<223> OTHER INFORMATION: Where Xaa indicates a diffmod on Asn of +1 Da

<400> SEQUENCE: 258

Glu Glu Thr Leu Leu Tyr Asp Ser Xaa Thr Ser Ser Met Ala Asp Arg
1               5                   10                  15

Lys

<210> SEQ ID NO 259
<211> LENGTH: 14
<212> TYPE: PRT
<213> ORGANISM: Human
<220> FEATURE:
<221> NAME/KEY: MISC_FEATURE
<222> LOCATION: (5)..(5)
<223> OTHER INFORMATION: Where Xaa indicates a diffmod on Asn of +1 Da

<400> SEQUENCE: 259

Ser Gly Val Ile Xaa Leu Thr Glu Glu Val Leu Trp Val Lys
1               5                   10

<210> SEQ ID NO 260
```

```
<211> LENGTH: 16
<212> TYPE: PRT
<213> ORGANISM: Human
<220> FEATURE:
<221> NAME/KEY: MISC_FEATURE
<222> LOCATION: (9)..(9)
<223> OTHER INFORMATION: Where Xaa indicates a diffmod on Asn of +1 Da

<400> SEQUENCE: 260

Glu Glu Thr Leu Leu Tyr Asp Ser Xaa Thr Ser Ser Met Ala Asp Arg
1               5                   10                  15

<210> SEQ ID NO 261
<211> LENGTH: 12
<212> TYPE: PRT
<213> ORGANISM: Human
<220> FEATURE:
<221> NAME/KEY: MISC_FEATURE
<222> LOCATION: (2)..(2)
<223> OTHER INFORMATION: Where Xaa indicates a diffmod on Asn of +1 Da

<400> SEQUENCE: 261

Asp Xaa Ser Ser Gly Thr Phe Ile Val Leu Ile Arg
1               5                   10

<210> SEQ ID NO 262
<211> LENGTH: 10
<212> TYPE: PRT
<213> ORGANISM: Human
<220> FEATURE:
<221> NAME/KEY: MISC_FEATURE
<222> LOCATION: (4)..(4)
<223> OTHER INFORMATION: Where Xaa indicates a diffmod on Asn of +1 Da

<400> SEQUENCE: 262

Thr Phe Ala Xaa Gly Ser Leu Ala Phe Arg
1               5                   10

<210> SEQ ID NO 263
<211> LENGTH: 13
<212> TYPE: PRT
<213> ORGANISM: Human
<220> FEATURE:
<221> NAME/KEY: MISC_FEATURE
<222> LOCATION: (6)..(6)
<223> OTHER INFORMATION: Where Xaa indicates a diffmod on Asn of +1 Da

<400> SEQUENCE: 263

Ala Gly His Phe Gln Xaa Thr Ser Ser Pro Ser Ala Arg
1               5                   10

<210> SEQ ID NO 264
<211> LENGTH: 11
<212> TYPE: PRT
<213> ORGANISM: Human
<220> FEATURE:
<221> NAME/KEY: MISC_FEATURE
<222> LOCATION: (8)..(8)
<223> OTHER INFORMATION: Where Xaa indicates a diffmod on Asn of +1 Da

<400> SEQUENCE: 264

Thr Gly Ile Tyr Gln Val Leu Xaa Gly Ser Arg
1               5                   10

<210> SEQ ID NO 265
<211> LENGTH: 18
<212> TYPE: PRT
<213> ORGANISM: Human
<220> FEATURE:
<221> NAME/KEY: MISC_FEATURE
```

<222> LOCATION: (7)..(7)
<223> OTHER INFORMATION: Where Xaa indicates a diffmod on Asn of +1 Da

<400> SEQUENCE: 265

Tyr Phe Asn Ile Asp Pro Xaa Ala Thr Gln Ala Ser Gly Asn Cys Gly
1               5                   10                  15

Thr Arg

<210> SEQ ID NO 266
<211> LENGTH: 11
<212> TYPE: PRT
<213> ORGANISM: Human
<220> FEATURE:
<221> NAME/KEY: MISC_FEATURE
<222> LOCATION: (8)..(8)
<223> OTHER INFORMATION: Where Xaa indicates a diffmod on Asn of +1 Da

<400> SEQUENCE: 266

Phe Ser Ala Asp Leu Gly Tyr Xaa Gly Thr Arg
1               5                   10

<210> SEQ ID NO 267
<211> LENGTH: 14
<212> TYPE: PRT
<213> ORGANISM: Human
<220> FEATURE:
<221> NAME/KEY: MISC_FEATURE
<222> LOCATION: (8)..(8)
<223> OTHER INFORMATION: Where Xaa indicates a diffmod on Asn of +1 Da

<400> SEQUENCE: 267

Ser Pro Ile Val Thr His Cys Xaa Val Ser Thr Val Asn Lys
1               5                   10

<210> SEQ ID NO 268
<211> LENGTH: 14
<212> TYPE: PRT
<213> ORGANISM: Human
<220> FEATURE:
<221> NAME/KEY: MISC_FEATURE
<222> LOCATION: (4)..(4)
<223> OTHER INFORMATION: Where Xaa indicates a diffmod on Asn of +1 Da

<400> SEQUENCE: 268

Tyr Gly Glu Xaa Asn Ser Leu Ser Val Glu Gly Phe Arg Lys
1               5                   10

<210> SEQ ID NO 269
<211> LENGTH: 13
<212> TYPE: PRT
<213> ORGANISM: Human
<220> FEATURE:
<221> NAME/KEY: MISC_FEATURE
<222> LOCATION: (4)..(5)
<223> OTHER INFORMATION: Where Xaa indicates a diffmod on Asn of +1 Da

<400> SEQUENCE: 269

Tyr Gly Glu Xaa Xaa Ser Leu Ser Val Glu Gly Phe Arg
1               5                   10

<210> SEQ ID NO 270
<211> LENGTH: 20
<212> TYPE: PRT
<213> ORGANISM: Human
<220> FEATURE:
<221> NAME/KEY: MISC_FEATURE
<222> LOCATION: (3)..(3)
<223> OTHER INFORMATION: Where Xaa indicates a diffmod on Asn of +1 Da

```
<400> SEQUENCE: 270

Gly Pro Xaa Leu Thr Ser Pro Ala Ser Ile Thr Phe Thr Thr Gly Leu
1               5                   10                  15

Glu Ala Pro Arg
            20

<210> SEQ ID NO 271
<211> LENGTH: 14
<212> TYPE: PRT
<213> ORGANISM: Human
<220> FEATURE:
<221> NAME/KEY: MISC_FEATURE
<222> LOCATION: (3)..(3)
<223> OTHER INFORMATION: Where Xaa indicates a diffmod on Asn of +1 Da

<400> SEQUENCE: 271

Ala Phe Xaa Ser Thr Leu Pro Thr Met Ala Gln Met Glu Lys
1               5                   10

<210> SEQ ID NO 272
<211> LENGTH: 25
<212> TYPE: PRT
<213> ORGANISM: Human
<220> FEATURE:
<221> NAME/KEY: MISC_FEATURE
<222> LOCATION: (3)..(3)
<223> OTHER INFORMATION: Where Xaa indicates a diffmod on Asn of +1 Da

<400> SEQUENCE: 272

Tyr Tyr Xaa Gln Ser Glu Ala Gly Ser His Thr Leu Gln Met Met Phe
1               5                   10                  15

Gly Cys Asp Val Gly Ser Asp Gly Arg
            20                  25

<210> SEQ ID NO 273
<211> LENGTH: 26
<212> TYPE: PRT
<213> ORGANISM: Human
<220> FEATURE:
<221> NAME/KEY: MISC_FEATURE
<222> LOCATION: (4)..(4)
<223> OTHER INFORMATION: Where Xaa indicates a diffmod on Asn of +1 Da

<400> SEQUENCE: 273

Gly Tyr Tyr Xaa Gln Ser Glu Asp Gly Ser His Thr Ile Gln Ile Met
1               5                   10                  15

Tyr Gly Cys Asp Val Gly Pro Asp Gly Arg
            20                  25

<210> SEQ ID NO 274
<211> LENGTH: 14
<212> TYPE: PRT
<213> ORGANISM: Human
<220> FEATURE:
<221> NAME/KEY: MISC_FEATURE
<222> LOCATION: (1)..(1)
<223> OTHER INFORMATION: Where Xaa indicates a diffmod on Asn of +1 Da

<400> SEQUENCE: 274

Xaa Leu Thr Glu Val Pro Thr Asp Leu Pro Ala Tyr Val Arg
1               5                   10

<210> SEQ ID NO 275
<211> LENGTH: 17
<212> TYPE: PRT
<213> ORGANISM: Human
<220> FEATURE:
```

```
<221> NAME/KEY: MISC_FEATURE
<222> LOCATION: (4)..(4)
<223> OTHER INFORMATION: Where Xaa indicates a diffmod on Asn of +1 Da

<400> SEQUENCE: 275

Val Leu His Xaa Gly Thr Leu Ala Glu Leu Gln Gly Leu Pro His Ile
1               5                   10                  15

Arg

<210> SEQ ID NO 276
<211> LENGTH: 18
<212> TYPE: PRT
<213> ORGANISM: Human
<220> FEATURE:
<221> NAME/KEY: MISC_FEATURE
<222> LOCATION: (9)..(9)
<223> OTHER INFORMATION: Where Xaa indicates a diffmod on Asn of +1 Da

<400> SEQUENCE: 276

His Arg Pro Thr Ala Gly Ala Phe Xaa His Ser Asp Leu Asp Ala Glu
1               5                   10                  15

Leu Arg

<210> SEQ ID NO 277
<211> LENGTH: 19
<212> TYPE: PRT
<213> ORGANISM: Human
<220> FEATURE:
<221> NAME/KEY: MISC_FEATURE
<222> LOCATION: (9)..(9)
<223> OTHER INFORMATION: Where Xaa indicates a diffmod on Asn of +1 Da

<400> SEQUENCE: 277

His Arg Pro Thr Ala Gly Ala Phe Xaa His Ser Asp Leu Asp Ala Glu
1               5                   10                  15

Leu Arg Arg

<210> SEQ ID NO 278
<211> LENGTH: 13
<212> TYPE: PRT
<213> ORGANISM: Human
<220> FEATURE:
<221> NAME/KEY: MISC_FEATURE
<222> LOCATION: (7)..(7)
<223> OTHER INFORMATION: Where Xaa indicates a diffmod on Asn of +1 Da

<400> SEQUENCE: 278

Val Ile Glu Glu Phe Tyr Xaa Gln Thr Trp Val His Arg
1               5                   10

<210> SEQ ID NO 279
<211> LENGTH: 21
<212> TYPE: PRT
<213> ORGANISM: Human
<220> FEATURE:
<221> NAME/KEY: MISC_FEATURE
<222> LOCATION: (7)..(11)
<223> OTHER INFORMATION: Where Xaa indicates a diffmod on Asn of +1 Da

<400> SEQUENCE: 279

Leu Gly Asp Val Glu Val Xaa Ala Gly Gln Xaa Ala Thr Phe Gln Cys
1               5                   10                  15

Ile Ala Thr Gly Arg
            20

<210> SEQ ID NO 280
```

```
<211> LENGTH: 14
<212> TYPE: PRT
<213> ORGANISM: Human
<220> FEATURE:
<221> NAME/KEY: MISC_FEATURE
<222> LOCATION: (11)..(11)
<223> OTHER INFORMATION: Where Xaa indicates a diffmod on Asn of +1 Da

<400> SEQUENCE: 280

Ile Ala Val Asp Trp Glu Ser Leu Gly Tyr Xaa Ile Thr Arg
1               5                   10

<210> SEQ ID NO 281
<211> LENGTH: 18
<212> TYPE: PRT
<213> ORGANISM: Human
<220> FEATURE:
<221> NAME/KEY: MISC_FEATURE
<222> LOCATION: (2)..(2)
<223> OTHER INFORMATION: Where Xaa indicates a diffmod on Asn of +1 Da

<400> SEQUENCE: 281

Gly Xaa Ser Thr His Gly Cys Ser Ser Glu Glu Thr Phe Leu Ile Asp
1               5                   10                  15

Cys Arg

<210> SEQ ID NO 282
<211> LENGTH: 21
<212> TYPE: PRT
<213> ORGANISM: Human
<220> FEATURE:
<221> NAME/KEY: MISC_FEATURE
<222> LOCATION: (18)..(18)
<223> OTHER INFORMATION: Where Xaa indicates a diffmod on Asn of +1 Da

<400> SEQUENCE: 282

Phe Thr Phe Thr Ser His Thr Pro Gly Glu His Gln Ile Cys Leu His
1               5                   10                  15

Ser Xaa Ser Thr Lys
            20
```